United States Patent
Bischof et al.

(10) Patent No.: US 12,102,992 B2
(45) Date of Patent: Oct. 1, 2024

(54) MACHINE LEARNING AND STATISTICAL ANALYSIS FOR CATALYST STRUCTURE PREDICTION AND DESIGN

(71) Applicant: Chevron Phillips Chemical Company, LP, The Woodlands, TX (US)

(72) Inventors: Steven M. Bischof, Humble, TX (US); Uriah J. Kilgore, Kennewick, WA (US); Orson L. Sydora, Houston, TX (US); Daniel H. Ess, Provo, UT (US); Doo-Hyun Kwon, Draper, UT (US); Nicholas K. Rollins, Provo, UT (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 14 days.

(21) Appl. No.: 18/001,037

(22) PCT Filed: Jun. 9, 2021

(86) PCT No.: PCT/US2021/036610
§ 371 (c)(1),
(2) Date: Dec. 7, 2022

(87) PCT Pub. No.: WO2021/252624
PCT Pub. Date: Dec. 16, 2021

(65) Prior Publication Data
US 2023/0330652 A1    Oct. 19, 2023

(51) Int. Cl.
*B01J 31/18*    (2006.01)
*B01J 31/12*    (2006.01)
(Continued)

(52) U.S. Cl.
CPC .......... *B01J 31/189* (2013.01); *B01J 31/122* (2013.01); *C07C 2/32* (2013.01); *G16C 20/30* (2019.02);
(Continued)

(58) Field of Classification Search
CPC .... B01J 31/189; B01J 31/122; B01J 2231/20; B01J 2531/62; B01J 31/143; C07C 2/32;
(Continued)

(56) References Cited

U.S. PATENT DOCUMENTS 7,300,904 B2   11/2007   Dixon
7,361,623 B2    4/2008   Dixon
(Continued)

FOREIGN PATENT DOCUMENTS

WO   2010051415 A1   5/2010
WO   2017010998 A1   1/2017

OTHER PUBLICATIONS

Tang et al. ("2D-QSPR/DFT studies of aryl-substituted PNP-Cr-based catalyst systems for highly selective ethylene oligomerization", J Mol Model (2014) 20:2129). (Year: 2014).*
(Continued)

*Primary Examiner* — Ali Z Fadhel
(74) *Attorney, Agent, or Firm* — Eversheds Sutherland (US) LLP

(57) ABSTRACT

Disclosed is a heteroatomic ligand-metal compound complex transition-state model which has been developed for activity, purity, and/or selectivity for selective ethylene oligomerizations, and density functional theory calculations for determining heteroatomic ligand-metal compound complex reactivity, product purity, and/or selectivity for ethylene trimerizations and/or tetramerizations. Using reaction ground states and transition states, and/or reaction ground states and transition states in combination with the energetic span model, this disclosure reveals that a chromium chromacycle mechanism, there are multiple ground states and multiple transition states, which can account for activity, purity, and/or selectivity for selective ethylene oligomerizations. Based on the reaction ground states and transition
(Continued)

states, and/or reaction ground states and transition states in combination with the energetic span model, the methods disclosed herein can qualitatively and semi-quantitatively used to predict relative heteroatomic ligand-metal compound complex activity, purity, and/or selectivity and lead to a successful process for catalyst design and implementation, in which new ligands can be successfully identified and experimentally validated.

46 Claims, 29 Drawing Sheets

(51) Int. Cl.
    *C07C 2/32*     (2006.01)
    *G16C 20/30*     (2019.01)
    *G16C 20/70*     (2019.01)

(52) U.S. Cl.
    CPC ........... *G16C 20/70* (2019.02); *B01J 2231/20* (2013.01); *B01J 2531/62* (2013.01); *C07C 2531/22* (2013.01)

(58) Field of Classification Search
    CPC .... C07C 2531/22; G16C 20/30; G16C 20/70; G16C 20/50; Y02P 20/52
    See application file for complete search history.

(56) References Cited

U.S. PATENT DOCUMENTS

| | | |
|---|---|---|
| 7,554,001 B2 | 6/2009 | Dixon |
| 7,910,670 B2 | 3/2011 | Knudsen |
| 7,994,363 B2 | 8/2011 | Gao |
| 8,252,956 B2 | 8/2012 | Gao |
| 8,680,003 B2 | 3/2014 | Sydora |
| 8,865,610 B2 | 10/2014 | Sydora |
| 10,183,960 B1 | 1/2019 | Bischof |
| 10,196,328 B2 | 2/2019 | Kilgore |
| 10,294,171 B2 | 5/2019 | Bischof |
| 10,435,336 B2 | 10/2019 | Kreischer |
| 10,493,442 B2 | 12/2019 | Bischof |
| 11,117,845 B2 | 9/2021 | Kilgore |
| 2010/0274065 A1 | 10/2010 | Sydora |
| 2019/0092708 A1* | 3/2019 | Bischof ..................... C07C 2/36 |

OTHER PUBLICATIONS

Agapie, et al., "Mechanistic Studies of Olefin and Alkyne Trimerization with Chromium Catalysts: Deuterium Labeling and Studies of Regiochemistry Using a Model Chromacyclopentane Complex." J. Am. Chem. Soc., 2007, 129, 14281-14295.

Beh, et al., "Synthesis of 5,5-Bicyclic Amidines as Ligands for Thermally Stable Vapor Deposition Precursors." Organometallics, 2017, 36, 1453.

Bollmann, et al., "Ethylene Tetramerization: A New Route to Produce 1-Octene in Exceptionally High Selectives." J. Am. Chem. Soc., 2004, 126, 14712-14713.

Carter, et al., "High Activity Ethylene Trimerisation Catalysts Based on Diphosphine Ligands." Chem. Commun., 2002, 858-859.

Ess et al., "Introduction: Computational Design of Catalysts from Molecules to Materials," ACS Publications, Chem. Rev., 119, 2019, pp. 6507-6508.

International Search Report and Written Opinion for PCT/US2021/03661, Sep. 6, 202, 1-22.

Kwon et al., "Computational Transition-State Design Provides Experimentally Verified Cr(P,N) Catalysts for Control of Ethylene Trimerization and Tetramerization," ACS Catalysis, 8, 2018, pp. 1138-1142.

Maley, et al., "Quantum-mechanical transition-state model combined with machine learning provides catalyst design features for selective Cr olefin oligomerization", Chemical Science, 2020, 11, 9665, https://doi.org/10.1039/D0SC03552A.

Morgan, et al., Journal of Organometallic Chemistry, 961, 2022. https://doi.org/10.1016/j.jorganchem.2021.122251.

Parveen, et al. "DFT and QSAR Studies of Ethylene Polymerization by Zirconocene Catalysts", ACS Catalysis, 2019, 9, 9339-9349.

Sydora, "Selective Ethylene Oligomerization," Organometallics, 38, 2019, pp. 997-1010.

Sydora, et al., "Selective Ethylene Tri-/Tetramerization Catalysts." ACS Catal., 2012, 2, 2452.

Tang, et al. "2D-QSPR/DFT Studies of Aryl-Substituted PNP-Cr-Based Catalyst Systems for Highly Selective Ethylene Oligomerization", Journal of Molecular Modeling, 2014, 20, 2129.

* cited by examiner

*Generation 1*

| L1 | L2 | L3 | L4 | L5 |
| 99:1 | 90:10 | 84:16 | 66:34 | 63:37 |

*Generation 2*

| L6 | L7 | L8 |
| 44:56 | 49:51 | 62:38 |

*Generation 3*

| L9 | L10 | L11 | L12 | L13 | L14 | L15 |
| 3:97 | 3:97 | 1:99 | 5:95 | 5:95 | 4:96 | 4:96 |

MACHINE LEARNING AND STATISTICAL ANALYSIS FOR CATALYST STRUCTURE PREDICTION AND DESIGN

CROSS REFERENCE TO RELATED APPLICATION(S)

This application claims priority to and the benefit of U.S. Provisional Patent Application No. 63/037,405, filed Jun. 10, 2020, which is incorporated by reference in its entirety. This application also claims priority to and the benefit of PCT Patent Application No. PCT/US2021/036610, filed Jun. 9, 2021, which is incorporated by reference in its entirety.

TECHNICAL FIELD OF THE DISCLOSURE

This disclosure relates to computational methods for developing new catalyst systems, including chromium-based catalyst systems for the selective conversion of ethylene to alpha-olefins.

BACKGROUND OF THE DISCLOSURE

Selective ethylene oligomerization can produce short-chain linear α-olefins (LAOS) used in the manufacturing of plasticizers, lubricants, detergents, and linear-low density polyethylene. Chromium based complexes (e.g., (Cr)-phosphine molecular catalysts) have emerged as being well-suited for industrial large-scale use Chromium complex reactivity, herein used synonymously with activity, is highly dependent on the exact ligand (e.g., phosphine ligand) coordinated to the Cr. However, there is currently no simple set of empirical parameters or design principles that allow the reliable prediction of a chromium complex with high activity, high product purity, and/or high selectivity for ethylene trimerization and/or tetramerization. Additionally, general strategies for computational homogeneous, molecular catalyst design have remained elusive.

Therefore, there remains a need for new methods including new computational methods for the design and development of ethylene oligomerization chromium complexes with improved activity, improved product purity, and/or improved selectivity for 1-hexene and/or 1-octene production. There is also a need for new computational methods that can be experimentally verified to better design new chromium based complexes for selective ethylene oligomerization, specifically to increase catalyst activity/productivity, increase product purity, and/or increase 1-octene selectivity.

SUMMARY OF THE DISCLOSURE

This disclosure provides new methods for the design and development of ethylene oligomerization catalysts with improved activity/productivity, improved selectivity for 1-hexene or 1-octene, and/or improved product purity (e.g., 1-hexene product purity and/or 1-octene product purity). The methods provided herein can be experimentally verified and iteratively enhanced for designing and improving new heteroatomic ligand-metal compound complexes for selective ethylene oligomerization, including to increase 1-octene selectivity, among other properties. The heteroatomic ligand-metal compound complexes (e.g., heteroatomic ligand-chromium compound complexes such as Cr N-phosphinamidine (Cr(P,N)) or ((P,N)Cr) catalysts and others described herein) have been examined and designed using a transition-state model for activity/productivity, product purity, and/or selectivity, as calculated by various methods.

Heteroatomic ligand-metal compound complexes (e.g., heteroatomic ligand-chromium compound complexes such as Cr N-phosphinamidine (Cr(P,N)) complexes, among others disclosed herein) can provide a high selectivity (ca. 99%) for 1-hexene. In designing new heteroatomic ligand-metal compound complexes (e.g., heteroatomic ligand-chromium compound complexes) which have increased activity/productivity, increased product purity, and/or are more selective to 1-hexene and/or 1-octene, the design process can involve an iterative method of identifying and adjusting key structural or electronic features of "training" (also termed "instructive") heteroatomic ligand-metal compound complexes (e.g., heteroatomic ligand-chromium compound complexes such as Cr N-phosphinamidine (Cr(P,N)) complexes, among others disclosed herein) that affect the relative energies of ground states and transition states which impact productivity, product purity, and/or 1-octene and/or 1-hexene selectivity. The same design process can also be utilized to improve the selectivity of the trimerization catalytic cycle to 1-hexene (also referred to as the trimerization cycle selectivity to 1-hexene), the selectivity of the tetramerization catalytic cycle to 1-octene, and/or the 1-octene efficiency of the fourth ethylene addition. These key structural or electronic features can be used as input variables for the development of a computational design which examines their relative significance in affecting the relative energies of the ground states and transition states and hence the overall activity/productivity, purity, and/or selectivity of the oligomerization process. Based on this computational design, "target" heteroatomic ligand-metal compound complexes (e.g., heteroatomic ligand-chromium compound complexes such as Cr(P,N) complexes among others disclosed herein) can be identified according to desired adjustments of the structural or electronic features, and these target complexes can be synthesized and experimentally verified. Based upon these results, a computational redesign or iteration can be used to identify next generation target complexes which also may be experimentally verified and subjected to further testing and re-design. In this manner, heteroatomic ligand-metal compound complex (e.g., heteroatomic ligand-chromium compound complexes) performance can be predicted and improved.

In an aspect, for example, the heteroatomic ligand-metal compound complex (e.g., heteroatomic ligand-chromium compound complexes such as Cr N-phosphinamidine complexes among others disclosed herein) transition-state model has been developed for activity/productivity, product purity, and/or selectivity, and density functional theory calculations can be used to address complex activity/productivity, product purity, and/or reactivity for ethylene trimerization and tetramerization. Using ground states and transition states and/or using ground states and transition states in combination with the energetic span model, this disclosure reveals that a mechanism including metal cyclic intermediates can be utilized to predict heteroatomic ligand-metal compound complex activity/productivity, product purity, and/or selectivity. For example, in a non-limiting aspect, heteroatomic ligand-chromium compound complexes can utilize a high-spin $Cr^{I/III}$ chromacycle mechanism where there are multiple $Cr^I$ ethylene coordinated ground states and multiple transition states, which can be utilized to predict and/or estimate heteroatomic ligand-metal compound complex activity/productivity, product purity, and/or selectivity account. Based on the calculated energy landscape, the calculated heteroatomic ligand-metal compound complex activity/productivity, product purity, and/or selectivity can be correlated to the experimental values and the correlation used to predict the heteroatomic ligand-metal compound complex activity/productivity, product purity, and/or selectivity of new complexes. This analysis can thus calculate and compare the activity productivity, product purity, and/or selectivity of other heteroatomic ligand-metal compound complexes. Based on the heteroatomic ligand-metal compound complex catalytic energy spans, the calculations disclosed herein can qualitatively and semi-quantitatively replicate relative heteroatomic ligand-chromium compound complex activity/productivity, product/purity, and/or selectivity and lead us to a successful process for heteroatomic ligand-metal compound complex (e.g., heteroatomic ligand-chromium compound complex design and implementation, in which new heteroatomic ligands can be successfully identified and experimentally validated.

Among other things, this disclosure provides methods for designing heteroatomic ligand-metal compound complexes for olefin oligomerization, which identifies and examines a number of possible ground states and transition states in the oligomerization process, including ground states which surmount different transition states leading to a desired oligomer product (e.g., an olefin trimer and/or olefin tetramer versus other olefin oligomerization products). This method allows the identification of the key structural and electronic features of the identified ground states and transition states that influence activity/productivity, product purity, and/or selectivity, and provides information for how to adjust these features in the next generation design to enhance activity/productivity, product purity, and selectivity.

In an aspect, heteroatomic ligand-metal compound complex can be a heteroatomic ligand-chromium compound complex having a general formula $[(HetLig)CrX_qL_r]^{3-q}$ (A), wherein: HetLig represents a training heteroatomic ligand that can be examined and subject to adjustments to alter the electronic and/or structural features of the ligand; X is an anionic ligand, and q is an integer; L is a neutral ligand; and r is an integer; wherein any two or more of the X and L ligands may be linked to form a multidentate ligand. This disclosure examines the detailed features of the heteroatomic ligand and its complex with a metal compound (e.g., chromium compound) and how such features influence the energetics of ground states and transition states.

Therefore, in one aspect, this disclosure provides a method for designing a heteroatomic ligand-metal compound complex for olefin oligomerization, the method comprising:
  (a) selecting n input variables $I^1, I^2, \ldots I^n$ (n is an integer), each input variable corresponding to a structural property or an electronic property of one or more ground state model structures $GS^{A1}, \ldots GS^{Ap}$ (p is an integer) and a plurality of transition state model structures $TS^{A1}, TS^{A2}, \ldots TS^{Am}$ (m is an integer) associated with the one or more ground state model structures,
    wherein each of the one or more ground state model structures $GS^{A1}, \ldots GS^{Ap}$ and each of the plurality of transition state model structures $TS^{A1}, TS^{A2}, \ldots TS^{Am}$ are derived from one or more first training heteroatomic ligand-metal compound complexes, each complex comprising a first training heteroatomic ligand;
  (b) assigning a quantitative value to each n input variable $I^1, I^2, \ldots I^n$, for each of the ground state model structures $GS^{A1}, \ldots GS^{Ap}$ and each of the transition state model structures $TS^{A1}, TS^{A2}, \ldots TS^{Am}$;
  (c) determining, by at least one processor of a device, the relative energies of each of the ground state model structures $GS^{A1}, \ldots GS^{Ap}$ and each of the transition state model structures $TS^{A1}, TS^{A2}, \ldots TS^{Am}$;
  (d) generating a machine learning model based upon correlating the quantitative value of each n input variable $I^1, I^2, \ldots I^n$ with the relative energies of each of the ground state model structures $GS^{A1}, \ldots GS^{Ap}$ and each of the transition state model structures $TSA^1, TS^{A2}, \ldots TS^{Am}$.
  (e) identifying, based on the machine learning model, one or more of the n input variables $I^1, I^2, \ldots I^n$ associated with [1] the difference in energies between one of the ground state model structures $GS^{A1}, \ldots GS^{Ap}$ and at least one of the plurality of transition state model structures $TS^{A1}, TS^{A2}, \ldots TS^{Am}$ [$\Delta G(TS-GS)$ or $\Delta\Delta G(TS-GS)$] or [2] the difference in energies between any two or more of the plurality of transition state model structures $TS^{A1}, TS^{A2}, \ldots TS^{Am}$ [$\Delta G(TS-TS)$ or $\Delta\Delta G(TS-TS)$];
  (f) generating, based upon the one or more n input variables $I^1, I^2, \ldots I^n$ identified from step (e), a first target heteroatomic ligand-metal compound complex for olefin oligomerization and comprising a first target heteroatomic ligand, wherein the first target heteroatomic ligand-metal compound complex is characterized by n output variables $O^1, O^2, \ldots O^n$, each having a quantitative value corresponding to a structural property or an electronic property of one or more ground state model structures $GS^{B1}, \ldots GS^{Bx}$ (x is an integer) or any of a plurality of transition state model structures $TS^{B1}, TS^{B2}, \ldots TS^{By}$ (y is an integer) associated with the one or more ground state model structures,
    wherein each of the one or more ground state model structures $GS^{B1}, \ldots GS^{Bx}$ and each of the plurality of transition state model structures $TS^{B1}, TS^{B2}, \ldots TS^{By}$ are derived from the first target heteroatomic ligand-metal compound complex, each complex comprising a first target heteroatomic ligand;
  (g) identifying one or more performance parameters associated with an olefin oligomerization reaction and the value of the performance parameters for the one or more first training heteroatomic ligand-metal compound complexes and the first target heteroatomic ligand-metal compound complex; and
  (h) repeating steps (a)-(f) one or more times using the quantitative values of the n output variables $O^1, O^2, \ldots O^n$ of the first target heteroatomic ligand-metal compound complex as an input dataset of new n input variables $I^{1.1}, I^{2.1}, \ldots I^{n.1}$ derived from one or more second training heteroatomic ligand-metal compound complexes for olefin oligomerization and comprising a second training heteroatomic ligand, which is computationally evaluated against the machine learning model to generate a second target heteroatomic ligand-metal compound complex comprising a second target heteroatomic ligand, wherein the second target heteroatomic ligand-metal compound complex is characterized by quantitative values of an output dataset of new n output variables $O^{1.1}, O^{2.1}, \ldots O^{n.1}$, and having one or more second target heteroatomic ligand-metal compound complex performance parameter values.

In this aspect, in step (b), assigning a quantitative value to each n input variable $I^1, I^2, \ldots I^n$, for each of the ground state model structures $GS^{A1}, \ldots GS^{Ap}$ and each of the transition state model structures $TS^{A1}, TS^{A2}, \ldots TS^{Am}$, these assigned quantitative values can be independently assigned a raw value or a normalized value. Also in this aspect, in step (c), determining, by at least one processor of a device, the relative energies of each of the ground state model structures $GS^{A1}, \ldots GS^{Ap}$ and each of the transition state model structures $TS^{A1}, TS^{A2}, \ldots TS^{Am}$, these determined relative energies can be independently the relative energies of a possible ensemble of conformations or one specific conformation of the ground state model structures and the transition state model structures.

Further in this aspect, in step (d), the machine learning model of step (e) may correlate the quantitative value of each n input variable $I^1, I^2, \ldots I^n$ and the relative energies of each of the ground state model structures $GS^{A1}, \ldots GS^{Ap}$ and each of the transition state model structures $TS^{A1}, TS^{A2}, \ldots TS^{Am}$. In this manner, there may be a relationship between the value of each n input variable $I^1, I^2, \ldots I^n$ and the relative energies of the ground state model structures $GS^{A1}, \ldots GS^{Ap}$, and there may be a relationship between the value of each n input variable $I^1, I^2, \ldots I^n$ and the relative energies of the transition state model structures $TS^{A1}, TS^{A2}, \ldots TS^{Am}$. Some of the n input variable $I^1, I^2, \ldots I^n$ are shown in FIG. 1 as examples.

Further in this aspect, in step (e), the relationships in step (d) may allow for mapping one or more of the n input variables $I^1, I^2, \ldots I^n$ to [1] the difference in energies between one of the ground state model structures $GS^{A1}, \ldots GS^{Ap}$ and at least one of the plurality of transition state model structures $TS^{A1}, TS^{A2}, \ldots TS^{Am}$ [$\Delta G(TS\text{-}GS)$ or $\Delta\Delta G(TS\text{-}GS)$] or [2] the difference in energies between any two or more of the plurality of transition state model structures $TS^{A1}, TS^{A2}, \ldots TS^{Am}$ [$\Delta G(TS\text{-}TS)$ or $\Delta\Delta G(TS\text{-}TS)$]. In particular, identifying the one or more of the n input variables $I^1, I^2, \ldots I^n$ associated with [1] $\Delta G(TS\text{-}GS)$ or $\Delta\Delta G(TS\text{-}GS)$ or [2] $\Delta G(TS\text{-}TS)$ or $\Delta\Delta G(TS\text{-}TS)$, these $\Delta G$ or $\Delta\Delta G$ energy differences can be based upon a Boltzmann ensemble $\Delta G$ or $\Delta\Delta G$ values.

Further to this aspect, the machine learning model of steps (d), (e), and (h) may include one or more neural networks. The machine learning model may be applied iteratively to identify and adjust key structural or electronic features of heteroatomic ligand-metal compound complexes that affect the relative energies of ground states and transition states for activity/productivity, selectivity (1-octene versus 1-hexene production), and product purity (1-hexene versus other $C_6$ products and/or 1-octene versus other $C_8$ products). These key structural or electronic features can be used as the n input variables $I^1, I^2, \ldots I^n$ to the machine learning model to train the machine learning model to examine their relative significance in affecting the relative energies of the ground states and transition states, and hence the overall activity/productivity, product purity, and selectivity of the oligomerization process. In this manner, the machine learning model may be trained to assess the effect that a structure or electronic feature may have on the relative energies of the ground states and transition states, and hence the overall activity/productivity, product purity, and selectivity of the oligomerization process. Based on this computational design, "target" heteroatomic ligand-metal compound complexes (e.g., heteroatomic ligand-chromium compound complexes) can be identified according to desired adjustments of the structural or electronic features, and these target complexes can be synthesized and experimentally verified. Based upon these results, a computational redesign or iteration can be used to identify next generation target complexes which also may be experimentally verified and subjected to further testing and re-design of the machine learning model.

Further to this aspect, step (f) may use the mapping generated by step (e) as an input to generate an output that includes a first target heteroatomic ligand-metal compound complex for olefin oligomerization and comprising a first target heteroatomic ligand, wherein the first target heteroatomic ligand-metal compound complex is characterized by n output variables $O^1, O^2, \ldots O^n$, each having a quantitative value corresponding to a structural property or an electronic property of one or more ground state model structures $GS^{B1}, \ldots GS^{Bx}$ (x is an integer) or any of a plurality of transition state model structures $TS^{B1}, TS^{B2}, \ldots TS^{By}$ (y is an integer) associated with the one or more ground state model structures. Each of the one or more ground state model structures $GS^{B1}, \ldots GS^{Bx}$ and each of the plurality of transition state model structures $TS^{B1}, TS^{B2}, \ldots TS^{By}$ are generated from the first target heteroatomic ligand-metal compound complex, each complex comprising a first target heteroatomic ligand. In this manner, the n output variables $O^1, O^2, \ldots O^n$ are reused as new n input variables $I^{1.1}, I^{2.1}, \ldots I^{n.1}$ to the machine learning model, which may assess the input variables for their respective effects on the relative energies of the ground states and transition state.

Further to this aspect, step (h) may involve an iterative repetition of steps (a)-(f) one or more times using the quantitative values of the n output variables $O^1, O^2, \ldots O^n$ of the first target heteroatomic ligand-metal compound complex as an input dataset of the new n input variables $I^{1.1}, I^{2.1}, \ldots I^{n.1}$, the new n input variables $I^{1.1}, I^{2.1}, \ldots I^{n.1}$ derived from one or more second training heteroatomic ligand-metal compound complexes for olefin oligomerization and comprising a second training heteroatomic ligand, which is input the machine learning model to generate a second target heteroatomic ligand-metal compound complex comprising a second target heteroatomic ligand, wherein the second target heteroatomic ligand-metal compound complex is characterized by quantitative values of an output dataset of new n output variables $O^{1.1}, O^{2.1}, \ldots O^{n.1}$, and having one or more second target heteroatomic ligand-metal compound complex performance parameter values. In this manner, the machine learning model may continue to learn which structural or electronic features of heteroatomic ligand-metal compound complexes affect the relative energies of ground states and transition states, and how significantly, in order to identify target heteroatomic ligand-metal compound complexes.

Further to this aspect, the disclosed method may further comprise the step of:

(i) [1] synthesizing the first target heteroatomic ligand and/or the second target heteroatomic ligand; or [2] synthesizing the first target heteroatomic ligand and/or the second target heteroatomic ligand, followed by synthesizing the first target heteroatomic ligand-metal compound complex or the second target heteroatomic ligand-metal compound complex.

Also in this aspect, the disclosed method also can further comprise the step of:

(j) performing the olefin oligomerization reaction by: [1] contacting the first target heteroatomic ligand or the second target heteroatomic ligand, a metal compound, an organometal compound, and an olefin; or [2] contacting the first target heteroatomic ligand-metal compound complex or the second target heteroatomic ligand-metal compound complex, an organometal compound, and an olefin.

These and other embodiments and aspects of the processes, methods, and compositions including catalyst compositions are described more fully in the Detailed Description and claims and further disclosure such as the Examples provided herein.

BRIEF DESCRIPTION OF THE DRAWINGS

FIG. 2A provides geometric descriptors and electrostatic charges.

FIG. 2B illustrates the definition of percent volume buried. FIG. 2C demonstrates the definition of distance out of pocket.

DETAILED DESCRIPTION OF THE DISCLOSURE

Figure 1:
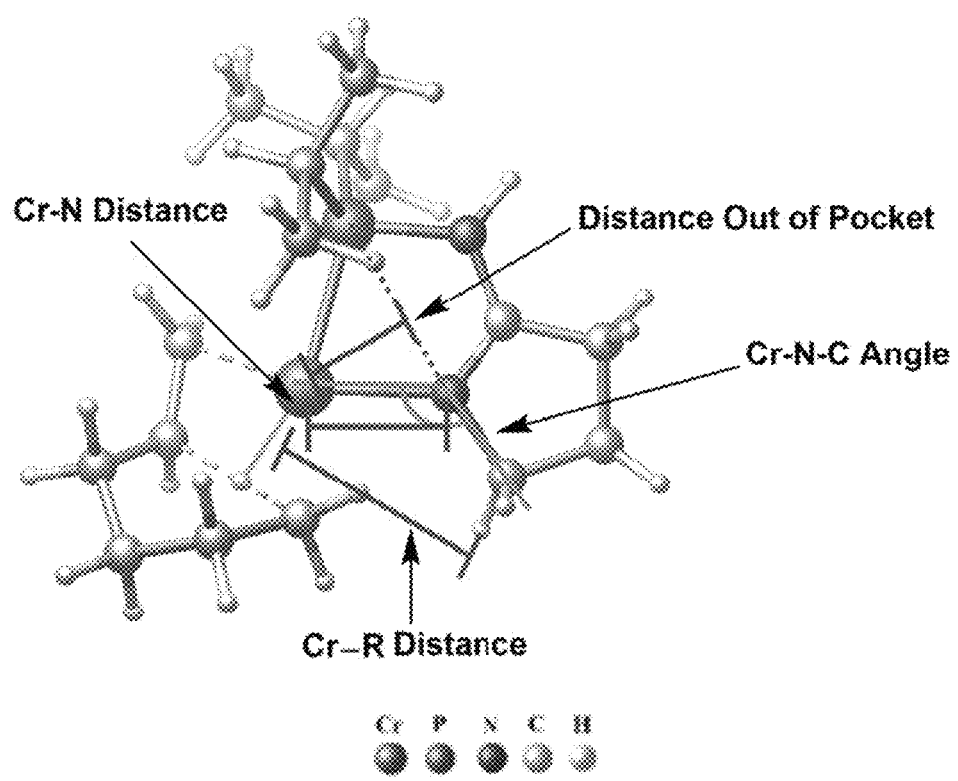
FIG. 1 illustrates some of the geometric input variables used according to aspects of the methods of the present disclosure.

Among other things, this disclosure provides methods for determining and modifying the reactivity (activity/productivity, product purity, and/or selectivity for heteroatomic ligand-metal compound complex (e.g., heteroatomic ligand-chromium compound complex) based ethylene oligomerization catalyst systems. The methods include methods with a view to the activity/productivity, increasing the proportion of 1-octene or 1-hexene in the product, and/or increasing the 1-olefin content of the C6 and/or C8 oligomerization products. The methods also include methods with a view to decrease the proportion of by-products produced. It has been found that density functional theory (DFT) calculations can be used to address activity/productivity, product purity, and/or selectivity for selective ethylene oligomerization using a heteroatomic ligand-metal compound complex transition-state model. This aspect of the disclosure demonstrates the use of ground states and transition states and/or ground states and transition states in combination with the energetic span model, which allows for the discovery of empirical parameters or design principles that provide prediction of high heteroatomic ligand-metal compound complex activity/productivity, product purity, and/or product selectivity.

In an aspect, it is also demonstrated here that combining machine learning computational methods with quantum mechanical transition state models can identify specific design features for selective olefin oligomerization using heteroatomic ligand-metal compound complexes. No useful general strategy for virtual catalyst design or improvement has been developed, and it is difficult to identify simple chemical features that control ethylene oligomerization catalysis, where small energy differences can impart significant influence. In one aspect, this disclosure provides the development of a density functional theory (DFT) transition-state model, in combination with a heteroatomic ligand-metal compound complex design workflow that combines quantum-mechanical transition state modeling with machine learning to reveal specific heteroatomic ligand-chromium compound complex design features with targets of producing 1-hexene and/or 1-octene.

Definitions

To define more clearly the terms used herein, the following definitions are provided, and unless otherwise indicated or the context requires otherwise, these definitions are applicable throughout this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Regarding claim transitional terms or phrases, the transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Unless specified to the contrary, describing a compound or composition "consisting essentially of" is not to be construed as "comprising," but is intended to describe the recited component that includes materials which do not significantly alter composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of, apply only to feature class to which is utilized and it is possible to have different transitional terms or phrases utilized with different features within a claim. For example, a method can comprise several recited steps (and other non-recited steps) but utilize a catalyst composition preparation consisting of specific steps but utilize a catalyst composition comprising recited components and other non-recited components. While compositions, processes, and computational methods are described in terms of "comprising" various components or steps, the compositions, processes, and computational methods can also "consist essentially of" or "consist of" the various components or steps.

The terms "a," "an," and "the" are intended, unless specifically indicated otherwise, to include plural alternatives, e.g., at least one. For instance, the disclosure of "an organoaluminum compound" is meant to encompass one organoaluminum compound, or mixtures or combinations of more than one organoaluminum compound unless otherwise specified.

For any particular compound disclosed herein, a general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to pentane includes n-pentane, 2-methyl-butane, and 2,2-dimethyl-propane, while a general reference to a butyl group includes an n-butyl group, a sec-butyl group, an iso-butyl group, and a tert-butyl group. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

Unless otherwise specified, any carbon-containing group for which the number of carbon atoms is not specified can have, according to proper chemical practice, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, or any range or combination of ranges between these values. For example, unless otherwise specified or unless the context requires otherwise, any carbon-containing group can have from 1 to 30 carbon atoms, from 1 to 25 carbon atoms, from 1 to 20 carbon atoms, from 1 to 15 carbon atoms, from 1 to 10 carbon atoms, or from 1 to 5 carbon atoms, and the like. In an aspect, the context could require other ranges or limitations, for example, when the subject carbon-containing group is an aryl group or an alkenyl group, the lower limit of carbons in these subject groups is six carbon atoms and two carbon atoms, respectively. Moreover, other identifiers or qualifying terms may be utilized to indicate the presence or absence of a particular substituent, a particular regiochemistry and/or stereochemistry, or the presence of absence of a branched underlying structure or backbone, and the like.

Various numerical ranges are disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. For example, by disclosing that a bond angle can be from 90° to 100°, Applicant's intent is to recite individually 90°, 91°, 92°, 93°, 94°, 95°, 96°, 99° 98°, 99° and 100°, including any sub-ranges and combinations of sub-ranges encompassed therein, and these methods of describing such ranges are interchangeable. Moreover, all numerical end points of ranges disclosed herein are approximate, unless excluded by proviso. As a representative example, if Applicant states that one or more steps in the processes disclosed herein can be conducted at a temperature in a range from 10° C. to 75° C., this range should be interpreted as encompassing temperatures in a range from "about" 10° C. to "about" 75° C.

Values or ranges may be expressed herein as "about", from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In another aspect, use of the term "about"

means±15% of the stated value, ±10% of the stated value, ±5% of the stated value, or ±3% of the stated value.

Applicant reserves the right to proviso out or exclude any individual members of any such group of values or ranges, including any sub-ranges or combinations of sub-ranges within the group, that can be claimed according to a range or in any similar manner, if for any reason Applicant chooses to claim less than the full measure of the disclosure, for example, to account for a reference that Applicant may be unaware of at the time of the filing of the application. Further, Applicant reserves the right to proviso out or exclude any individual substituents, analogs, compounds, ligands, structures, or groups thereof, or any members of a claimed group, if for any reason Applicant chooses to claim less than the full measure of the disclosure, for example, to account for a reference or prior disclosure that Applicant may be unaware of at the time of the filing of the application.

The term "substituted" when used to describe a group, for example, when referring to a substituted analog of a particular group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. Unless otherwise specified, "substituted" is intended to be non-limiting and include inorganic substituents or organic substituents as understood by one of ordinary skill in the art.

Specific chemical groups may be specified according to the atom which is bonded to the metal or bonded to another chemical moiety as a substituent, such as an "oxygen-bonded group," which is also called an "oxygen group." For example, an oxygen-bonded group includes species such as hydrocarbyloxide (—OR where R is a hydrocarbyl group, also termed hydrocarboxy), alkoxide (—OR where R is an alkyl group), aryloxide (—OAr where Ar is an aryl group), or substituted analogs thereof, which function as ligands or substituents in the specified location. Therefore, an alkoxide group and an aryloxide group are each a subgenus of a hydrocarbyloxide (hydrocarbyloxy) group. A similar definition applies to chemical groups which may be specified according to the atom which is bonded to the metal or bonded to another chemical moiety as a substituent, in which the free valence is situated on a heteroatom (non-carbon atom), such as a "sulfur group," "nitrogen group," "phosphorus group," "arsenic group," "silicon group," "germanium group," "tin group," "lead group," "boron group," "aluminum group," and the like.

A chemical "group" also may be described according to how that group is formally derived from a reference or "parent" compound, for example, by the number of hydrogen atoms formally removed from the parent compound to generate the group, even if that group is not literally synthesized in this manner. These groups can be utilized as substituents or coordinated or bonded to metal atoms. For example, an "alkyl group" formally can be derived by removing one hydrogen atom from an alkane, while an "alkanediyl group" (also referred to as a "alkylene group") formally can be derived by removing two hydrogen atoms from an alkane. Moreover, a more general term can be used to encompass a variety of groups that formally are derived by removing any number ("one or more") of hydrogen atoms from a parent compound, which in this example can be described as an "alkane group," which encompasses an "alkyl group," an "alkanediyl group," and materials have three or more hydrogen atoms, as necessary for the situation, removed from the alkane. The disclosure that a substituent, ligand, or other chemical moiety can constitute a particular "group" implies that the known rules of chemical structure and bonding are followed when that group is employed as described. When describing a group as being "derived by," "derived from," "formed by," or "formed from," such terms are used in a formal sense and are not intended to reflect any specific synthetic method or procedure, unless specified otherwise or the context requires otherwise.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group that can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, and phosphines, and so forth. In one aspect, the hydrogen atom(s) removed to form the "organyl group," "organylene group," or "organic group" can be attached to a carbon atom belonging to a functional group, for example, an acyl group (—C(O)R), a formyl group (—C(O)H), a carboxy group (—C(O)OH), a hydrocarboxycarbonyl group (—C(O)OR), a cyano group (—C≡N), a carbamoyl group (—C(O)NH$_2$), a N-hydrocarbylcarbamoyl group (—C(O)NHR), or N,N'-dihydrocarbylcarbamoyl group (—C(O)NR$_2$), among other possibilities. In another aspect, the hydrogen atom(s) removed to form the "organyl group," "organylene group," or "organic group" can be attached to a carbon atom not belonging to, and remote from, a functional group, for example, —CH$_2$C(O)CH$_3$, —CH$_2$NR$_2$, and the like. An "organyl group," "organylene group," or "organic group" can be aliphatic, inclusive of being cyclic or acyclic, or can be aromatic. "Organyl groups," "organylene groups," and "organic groups" also encompass heteroatom-containing rings, heteroatom-containing ring systems, heteroaromatic rings, and heteroaromatic ring systems. "Organyl groups," "organylene groups," and "organic groups" can be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, (among others known to those having ordinary skill in the art) as members. When bonded to a transition metal, an "organyl group," "organylene group," or "organic group" can be further described according to the usual $\eta^x$ (eta-x) nomenclature, in which x is an integer corresponding to the number of atoms which are coordinated to the transition metal or are expected to be coordinated to the transition metal, for example, according to the 18-electron rule.

A formamidine group is a group having the general structure

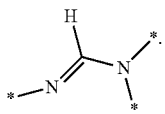

Within the formamidine group the nitrogen participating in a double bond with the central carbon atom is referred to as the $N^1$ nitrogen and the nitrogen atom participating in a single bond with the central carbon atom is referred to as the $N^2$ nitrogen. Similarly, the groups attached to the $N^1$ and $N^2$ nitrogen atoms are referred to as the $N^1$ group and $N^2$ group respectively. An $N^2$-phosphinyl formamidine group has the general structure

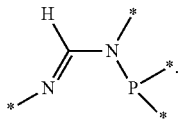

Within the $N^2$-phosphinyl formamidine group the $N^1$ and $N^2$ nitrogen atoms and $N^1$ and $N^2$ groups have the same meaning as described for the formamidine group. Consequently, an $N^2$-phosphinyl formamidine group has the phosphinyl group is attached to the $N^2$ nitrogen atom. An amidine group is a group having the general structure

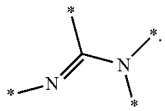

Within the amidine group the nitrogen participating in a double bond with the central carbon atom is referred to as the $N^1$ nitrogen and the nitrogen atom participating in a single bond with the central carbon atom is referred to as the $N^2$ nitrogen. Similarly, the groups attached to the $N^1$ and $N^2$ nitrogen atoms are referred to as the $N^1$ group and $N^2$ group, respectively. An $N^2$-phosphinyl amidine group has the general structure

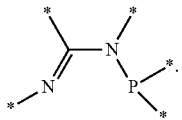

Within the $N^2$-phosphinyl amidine group the $N^1$ and $N^2$ nitrogen atoms and $N^1$ and $N^2$ groups have the same meaning as described for the amidine group. Consequently, an $N^2$-phosphinyl amidine group has the phosphinyl group attached to the $N^2$ nitrogen atom. Within the amidine group and $N^2$-phosphinyl amidine group the carbon atom between the two nitrogen atoms is the central carbon atom and any substituent attached to it is referred to as the central carbon group.

A guanidine group is a group having the general structure

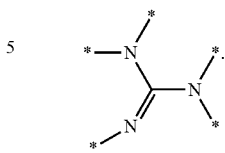

Within the guanidine core, the nitrogen participating in a double bond with the central carbon atom is referred to as the $N^1$ nitrogen and the two nitrogen atoms participating in a single bond with the central carbon atom are referred to as the $N^2$ nitrogen and the $N^3$ nitrogen. Similarly, the groups attached to the $N^1$, $N^2$ and $N^3$ nitrogen atoms are referred to as the $N^1$ group, $N^2$ group, and $N^3$ group respectively. An $N^2$-phosphinyl guanidine group has the general structure

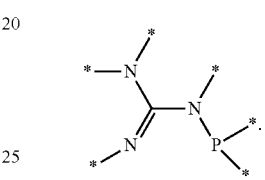

Within an $N^2$-phosphinyl guanidine group, the nitrogen participating in a double bond with the central carbon atom of the guanidine core is referred to as the $N^1$ nitrogen, the nitrogen atom participating in a single bond with the central carbon atom of the guanidine core and a bond with the phosphorus atom of the phosphinyl group is referred to as the $N^2$ nitrogen, and the remaining nitrogen atom participating in a single bond with the central carbon atom of the guanidine core is referred to as the $N^3$ nitrogen. It should be noted that a guanidine core or an $N^2$-phosphinyl guanidine group can be a portion of a larger group (or compound) which does not contain guanidine in it name. For example, while the compound 7-dimethylphosphinylimidazo[1,2-a]imidazole could be classified as a compound having an imidazo[1,2-a]imidazole core (or a compound having a phosphinylimidazo[1,2-a]imidazole group), 7-dimethylphosphinylimidazo[1,2-a]imidazole would still be classified as a compound having a guanidine core (or as a compound having an $N^2$-phosphinyl guanidine group) since it contains the defined general structure of the guanidine core (or the $N^2$-phosphinyl guanidine group).

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates that the presence of one or more halogen atoms replacing an equivalent number of hydrogen atoms in the hydrocarbon).

For purposes of this application, an "inert functional group" is a group which does not substantially interfere with the process described herein in which the material having an inert functional group takes part and/or does not complex with the metal compound of the metal complex. The term "does not complex with the metal compound" can include groups that could complex with a metal compound but in particular molecules described herein may not complex with a metal compound due to its positional relationship within a ligand. For example, while an ether group can complex with a metal compound, an ether group located at a para position of a substituted phenyl phosphinyl group in an $N^2$-phosphinyl amidine can be an inert functional group because a single metal compound cannot complex with both the para ether group and the $N^2$-phosphinyl amidine group of the same metal complex molecule. Thus, the inertness of a particular functional group is not only related to the functional group's inherent inability to complex the metal compound but can also be related to the functional group's position within the metal complex. Non-limiting examples of inert functional groups which do not substantially interfere with processes described herein can include halo (fluoro, chloro, bromo, and iodo), nitro, hydrocarboxy groups (e.g., alkoxy, and/or aroxy, among others), sulfidyl groups, and/or hydrocarbyl groups, among others.

The term "hydrocarbyl" group is used herein in accordance with the definition specified by IUPAC as follows: a univalent group formed by removing a hydrogen atom from a hydrocarbon (that is, a group containing only carbon and hydrogen). Non-limiting examples of hydrocarbyl groups include ethyl, phenyl, tolyl, propenyl, cyclopentyl, and the like. The term "hydrocarbylene" group is also used herein in accordance with the definition specified by IUPAC as follows: a "hydrocarbylene" group refers to a divalent group formed by removing two hydrogen atoms from a hydrocarbon or a substituted hydrocarbon, the free valencies of which are not engaged in forming a double bond. By way of example and comparison, examples of hydrocarbyl and hydrocarbylene groups include, respectively: aryl and arylene; alkyl and alkanediyl (or "alkylene"); cycloalkyl and cycloalkanediyl (or "cycloalkylene"); aralkyl and aralkanediyl (or "aralkylene"); and so forth. For example, an "arylene" group is used in accordance with IUPAC definition to refer to a bivalent group derived from arenes by removal of a hydrogen atom from two ring carbon atoms, which may also be termed an "arenediyl" group. Examples of hydrocarbylene groups include but are not limited to: 1,2-phenylene; 1,3-phenylene; 1,2-propandiyl; 1,3-propandiyl; 1,2-ethandiyl; 1,4-butandiyl; 2,3-butandiyl; and methylene (—CH$_2$—).

The term "heterohydrocarbyl" group is used herein to refer to a univalent group, which can be linear, branched or cyclic, formed by removing a single hydrogen atom from a heteroatom of a parent "heterohydrocarbon" molecule, the heterohydrocarbon molecule being one in which at least one carbon atom is replaced by a heteroatom. Therefore, a "heteroatom" refers to a non-carbon atom such as oxygen, sulfur, nitrogen, phosphorus, silicon, and the like. Examples of "heterohydrocarbyl" groups formed by removing a single hydrogen atom from a heteroatom of a heterohydrocarbon molecule include, for example: [1] a hydrocarbyloxide group, for example, an alkoxide (—OR) group such as tert-butoxide or aryloxide (—OAr) group such as a substituted or unsubstituted phenoxide formed by removing the hydrogen atom from the hydroxyl (OH) group of a parent alcohol or a phenol molecule; [2] a hydrocarbylsulfide group, for example, an alkylthiolate (—SR) group or arylthiolate (—SAr) group formed by removing the hydrogen atom from the hydrogensulfide (—SH) group of an alkylthiol or arylthiol; [3] a hydrocarbylamino group, for example, an alkylamino (—NHR) group or arylamino (—NHAr) group formed by removing a hydrogen atom from the amino (—NH$_2$) group of an alkylamine or arylamine molecule; and [4] a trihydrocarbylsilyl group such as trialkylsilyl (—SiR$_3$) or triarylsilyl (—SiAr$_3$) group.

A "heteroatomic ligand" which may be abbreviated "Het-Lig" is a ligand which includes a heteroatom (non-carbon atom) such as oxygen, sulfur, nitrogen, phosphorus, silicon, and the like. Various heteroatomic ligands which can be utilized in the computational and synthetic aspects of this disclosure are disclosed herein.

An "aliphatic" compound is a class of acyclic or cyclic, saturated or unsaturated, carbon compounds, excluding aromatic compounds, e.g., an aliphatic compound is a non-aromatic organic compound. An "aliphatic group" is a generalized group formed by removing one or more hydrogen atoms (as necessary for the particular group) from a carbon atom of an aliphatic compound. Aliphatic compounds and therefore aliphatic groups can contain organic functional group(s) and/or atom(s) other than carbon and hydrogen.

The term "alkane" whenever used in this specification and claims refers to a saturated hydrocarbon compound. Other identifiers can be utilized to indicate the presence of particular groups in the alkane (e.g., halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic and/or linear or branched unless otherwise specified. Primary, secondary, and tertiary alkyl groups are derived by removal of a hydrogen atom from a primary, secondary, and tertiary carbon atom, respectively, of an alkane. The n-alkyl group can be derived by removal of a hydrogen atom from a terminal carbon atom of a linear alkane. The groups of the form RCH$_2$ (R≠H), R$_2$CH (R≠H), and R$_3$C (R≠H) are primary, secondary, and tertiary alkyl groups, respectively, wherein R is itself alkyl group.

The term "carbocyclic" group is used herein to refer to a group in which a carbocyclic compound is the parent compound, that is, a cyclic compound in which all the ring members are carbon atoms. The carbocyclic group is formed by removing one or more hydrogen atoms from the carbocyclic compound. For example, a carbocyclic group can be a univalent group formed by removing a hydrogen atom from a carbocyclic compound. Non-limiting examples of carbocyclic groups include, for example, cyclopentyl, cyclohexyl, phenyl, tolyl, naphthyl and the like.

A "cycloalkane" is a saturated cyclic hydrocarbon, with or without side chains, for example, cyclobutane. Other identifiers can be utilized to indicate the presence of particular groups in the cycloalkane (e.g., halogenated cycloalkane indicates that the presence of one or more halogen atoms replacing an equivalent number of hydrogen atoms in the cycloalkane). Unsaturated cyclic hydrocarbons having one endocyclic double or one triple bond are called cycloalkenes and cycloalkynes, respectively. Those having more than one such multiple bond are cycloalkadienes, cycloalkatrienes, and so forth. Other identifiers can be utilized to indicate the presence of particular groups in the cycloalkenes, cycloalkadienes, cycloalkatrienes, and so forth.

A "cycloalkyl" group is a univalent group derived by removing a hydrogen atom from a ring carbon atom from a cycloalkane. Examples of cycloalkyl groups include cyclobutyl, cyclopentyl, cyclohexyl, and cycloheptyl groups. For clarity, other examples of cycloalkyl groups include a 1-methylcyclopropyl group and a 2-methylcyclopropyl group are illustrated as follows.

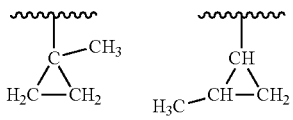

A "cycloalkane group" refers to a generalized group formed by removing one or more hydrogen atoms (as necessary for the particular group and at least one of which is a ring carbon) from a cycloalkane.

The term "alkene" whenever used in this specification and claims refers to an olefin that has at least one carbon-carbon double bond. The term "alkene" includes aliphatic or aromatic, cyclic or acyclic, and/or linear and branched alkene unless expressly stated otherwise. The term "alkene," by itself, does not indicate the presence or absence of heteroatoms and/or the presence or absence of other carbon-carbon double bonds unless explicitly indicated. Other identifiers may be utilized to indicate the presence or absence of particular groups within an alkene. Alkenes may also be further identified by the position of the carbon-carbon double bond. Alkenes, having more than one such multiple bond are alkadienes, alkatrienes, and so forth, and may be further identified by the position of the carbon-carbon double bond.

An "alkenyl group" is a univalent group derived from an alkene by removal of a hydrogen atom from any carbon atom of the alkene. Thus, "alkenyl group" includes groups in which the hydrogen atom is formally removed from an sp$^2$ hybridized (olefinic) carbon atom and groups in which the hydrogen atom is formally removed from any other carbon atom such as an sp$^3$ hybridized carbon atom. For example and unless otherwise specified, 1-propenyl (—CH=CHCH$_3$), 2-propenyl [(CH$_3$)C=CH$_2$], and 3-propenyl (—CH$_2$CH=CH$_2$) groups are all encompassed with the term "alkenyl group." In this aspect, the 3-propenyl (—CH$_2$CH=CH$_2$) group is considered an alkenyl group having a terminal C=C double bond, as is 4-butenyl (—CH$_2$CH$_2$CH=CH$_2$). Other identifiers may be utilized to indicate the presence or absence of particular groups within an alkene group. Alkene groups may also be further identified by the position of the carbon-carbon double bond. Similarly, a "cycloalkenyl" group is a univalent group derived from a cycloalkene by removal of a hydrogen atom from any carbon atom of the cycloalkene, whether that carbon atom is sp$^2$ hybridized (olefinic) or sp$^3$ hybridized carbon atom.

The term "olefin" is used herein in accordance with the definition specified by IUPAC: acyclic and cyclic hydrocarbons having one or more carbon-carbon double bonds apart from the formal ones in aromatic compounds. Thus, the term "olefin" includes aliphatic and aromatic, acyclic and cyclic, and/or linear and branched compounds having at least one carbon-carbon double bond that is not part of an aromatic ring or ring system unless specifically stated otherwise. The class "olefins" subsumes alkenes and cycloalkenes and the corresponding polyenes. Ethylene, propylene, 1-butene, 2-butene, 1-hexene and the like are non-limiting examples of olefins. The term "alpha olefin" as used in this specification and claims refers to an olefin that has a double bond between the first and second carbon atom of the longest contiguous chain of carbon atoms. The term "alpha olefin" includes linear and branched alpha olefins unless expressly stated otherwise. With respect to the olefin oligomerization reactions of this disclosure, the computational and reaction studies are conducted with ethylene, so use of the term "olefin" generally refers to ethylene, unless the context of the disclosure allows or requires otherwise.

According to the context of the disclosure, and unless otherwise specified, the abbreviations "C6" or "C$_6$" can be used to refer to all hydrocarbon compounds having six carbon atoms, and the abbreviations "C8" or "C$_8$" can be used to refer to all hydrocarbon compounds having eight carbon atoms.

An "aromatic group" refers to a generalized group formed by removing one or more hydrogen atoms (as necessary for the particular group and at least one of which is an aromatic ring carbon atom) from an aromatic compound. Thus, an "aromatic group" as used herein refers to a group derived by removing one or more hydrogen atoms from an aromatic compound, that is, a compound containing a cyclically conjugated hydrocarbon that follows the Hückel (4n+2) rule and containing (4n+2) pi-electrons, where n is an integer from 1 to about 5. Aromatic compounds and hence "aromatic groups" may be monocyclic or polycyclic unless otherwise specified. Aromatic compounds include "arenes" (hydrocarbon aromatic compounds) and "heteroarenes," also termed "hetarenes" (heteroaromatic compounds formally derived from arenes by replacement of one or more methine (—C=) carbon atoms by trivalent or divalent heteroatoms, in such a way as to maintain the continuous pi-electron system characteristic of aromatic systems and a number of out-of-plane pi-electrons corresponding to the Hückel rule (4n+2)). While arene compounds and heteroarene compounds are mutually exclusive members of the group of aromatic compounds, a compound that has both an arene group and a heteroarene group that compound generally is considered a heteroarene compound. Aromatic compounds, arenes, and heteroarenes may be mono- or polycyclic unless otherwise specified. Examples of arenes include, but are not limited to, benzene, naphthalene, and toluene, among others. Examples of heteroarenes include, but are not limited to furan, pyridine, and methylpyridine, among others. As disclosed herein, the term "substituted" may be used to describe an aromatic group wherein any non-hydrogen moiety formally replaces a hydrogen in that group, and is intended to be non-limiting.

An arene is an aromatic hydrocarbon, with or without side chains (e.g., benzene, toluene, or xylene, among others). An "aryl group" is a group derived from the formal removal of a hydrogen atom from an aromatic hydrocarbon ring carbon atom from an arene compound. One example of an "aryl group" is ortho-tolyl (o-tolyl), the structure of which is shown here.

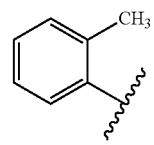 [SMILES: *c1ccccc1C]

The arene can contain a single aromatic hydrocarbon ring (e.g., benzene or toluene), contain fused aromatic rings (e.g., naphthalene or anthracene), and contain one or more isolated aromatic rings covalently linked via a bond (e.g., biphenyl) or non-aromatic hydrocarbon group(s) (e.g., diphenylmethane).

A "heterocyclic compound" is a cyclic compound having at least two different elements as ring member atoms. For example, heterocyclic compounds may comprise rings containing carbon and nitrogen (for example, tetrahydropyrrole), carbon and oxygen (for example, tetrahydrofuran), or carbon and sulfur (for example, tetrahydrothiophene), among others. Heterocyclic compounds and heterocyclic groups may be either aliphatic or aromatic.

An "aralkyl group" is an aryl-substituted alkyl group having a free valance at a non-aromatic carbon atom, for example, a benzyl group and a 2-phenylethyl group are examples of an "aralkyl" group.

A "halide" has its usual meaning; therefore, examples of halides include fluoride, chloride, bromide, and iodide The term "co-catalyst" is used generally herein to refer to compounds such as organoaluminum compounds, organoboron compounds, organozinc compounds, organomagnesium compounds, organolithium compounds, and the like, that can constitute one component of a catalyst composition, when used, for example, with the chromium based catalyst compounds of the disclosure. The term "co-catalyst" is used regardless of the actual function of the compound or any chemical mechanism by which the compound may operate.

The terms "catalyst composition," "catalyst mixture," "catalyst system," and the like, do not depend upon the actual product or composition resulting from the contact or reaction of the initial components of the claimed catalyst composition/mixture/system, the nature of the active catalytic site, or the fate of the co-catalyst, the transition metal catalyst compound(s), any olefin monomer used in the catalytic reaction, and the like. Therefore, the terms "catalyst composition," "catalyst mixture." "catalyst system," and the like, encompass the initial starting components of the composition, as well as whatever product(s) may result from contacting these initial starting components, and this is inclusive of both heterogeneous and homogenous catalyst systems or compositions. The terms "catalyst composition," "catalyst mixture," "catalyst system," and the like, are used interchangeably throughout this disclosure.

An "organoaluminum compound," is used to describe any compound that contains an aluminum-carbon bond. Thus, organoaluminum compounds include, but are not limited to, hydrocarbyl aluminum compounds such as trihydrocarbyl-, dihydrocarbyl-, or monohydrocarbylaluminum compounds; hydrocarbylaluminum halide compounds; hydrocarbylalumoxane compounds; and aluminate compounds which contain an aluminum-organyl bond such as tetrakis(p-tolyl) aluminate salts. An "organoboron" compound, an "organozinc compound," an "organomagnesium compound," and an "organolithium compound" are used in an analogous fashion to describe any compound that contains a direct metal-carbon bond between an organic group and the recited metal.

References to gaseous, liquid, and/or solid materials refer to the physical state of the material at 25° C. and atmospheric pressure.

Features within this disclosure that are provided as minimum values can be alternatively stated as "at least" or "greater than or equal to" any recited minimum value for the feature disclosed herein. Features within this disclosure that are provided as maximum values can be alternatively stated as "less than or equal to" for the feature disclosed herein.

Within this disclosure, the normal rules of organic nomenclature will prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. By way of another example, reference to a 3-substituted naphth-2-yl indicates that there is a non-hydrogen substituent located at the 3 position and hydrogens located at the 1, 4, 5, 6, 7, and 8 positions. References to compounds or groups having substitutions at positions in addition to the indicated position will be referenced using comprising or some other alternative language. For example, a reference to a phenyl group comprising a substituent at the 4 position refers to a group having a non-hydrogen atom at the 4 position and hydrogen or any non-hydrogen group at the 2, 3, 5, and 6 positions.

Processes for forming oligomer products are described herein. Such processes generally comprise contacting ethylene and a catalyst system (or alternatively, contacting ethylene and the components of the catalyst system) to form an oligomer product under oligomerization conditions.

The term "oligomerization," and its derivatives, refers to processes which produce a mixture of products containing at least 70 weight percent products containing from 2 to 30 ethylene units. Similarly, as used herein an "oligomer" is a product that contains from 2 to 30 ethylene units while an "oligomerization product" or "oligomer product" includes all products made by the process including the "oligomers" and products which are not "oligomers" (e.g., products which contain more than 30 ethylene units). Further the terms "oligomer product" and "oligomerization product" can be used interchangeably.

The term "trimerization," and its derivatives, refers to a process which produces a mixture of products containing at least 70 weight percent products containing three and only three ethylene units. A "trimer" is a product which contains three and only three ethylene units while a "trimerization product" includes all products made by the trimerization process including trimers and products which are not trimer (e.g., dimers or tetramers). Generally, a "trimerization" process using ethylene produces an oligomer product containing at least 70 weight percent hexene(s).

The term "tetramerization," and its derivatives, refers to a process which produces a mixture of products containing at least 70 weight percent products containing four and only four ethylene units. A "tetramer" is a product which contains four and only four ethylene units while a "tetramerization product" includes all products made by the tetramerization process including tetramers and products which are not tetramers (e.g., dimers or trimer). Generally, a "tetramerization" process using ethylene produces an oligomer product containing at least 70 weight percent octene(s).

The term "trimerization and tetramerization," and its derivatives, refers to a process which produces a mixture of products containing at least 70 weight percent products containing three and/or four and only three and/or four ethylene units. A "trimerization and tetramerization product" includes all products made by the "trimerization and tetramerization" process including trimers, tetramers, and products which are not tetramers (e.g., dimers). Generally, a "trimerization and tetramerization" process using ethylene produces an oligomer product containing at least 70 weight percent hexene(s) and/or octene(s).

Unless otherwise specified, the terms contacted, combined, and "in the presence of" refer to any addition sequence, order, or concentration for contacting or combining two or more components of the oligomerization process. Combining or contacting of oligomerization components, according to the various methods described herein, can occur in one or more contact zones under suitable contact conditions such as temperature, pressure, contact time, flow rates, etc. The contact zone can be disposed in a vessel (e.g., storage tank, tote, container, mixing vessel, reactor, etc.), a length of pipe (e.g., tee, inlet, injection port, or header for combining component feed lines into a common line), or any other suitable apparatus for bringing the components into contact. The processes can be carried out in a batch or continuous process as can be suitable for a given embodiment.

Use of the term "optionally" with respect to any element of a claim is intended to mean that the subject element is required, or alternatively, is not required. Both alternatives are intended to be within the scope of the claim.

While, the present disclosure utilizes Gibbs free energies for many of its calculation, one can also utilize enthalpies and/or Helmholtz energies as approximations for the Gibbs free energies.

Processes described herein can utilize steps, features, compounds and/or equipment which are independently described herein. The processes described herein may or may not utilize step identifiers (e.g., 1), 2), etc., a), b), etc., i), ii), etc., or first, second etc., among others), feature identifiers (e.g., 1), 2), etc., a), b), etc., i), ii), etc., or first, second etc., among others), and/or compound and/or composition identifiers (e.g., 1), 2), etc., a), b), etc., i), ii), etc., or first, second etc., among others). However, it should be noted that processes described herein can have multiple steps, features (e.g., reagent ratios, formation conditions, among other considerations), and/or multiple compounds and/or compositions using no descriptor or sometimes having the same general identifier. Consequently, it should be noted that the processes described herein can be modified to use an appropriate step or feature identifier (e.g., 1), 2), etc., a), b), etc., i), ii), etc., or first, second etc., among others), feature identifier (e.g., 1), 2), etc., a), b), etc., i), ii), etc., or first, second etc., among others), and/or compound identifier (e.g., first, second, etc.) regardless of step, feature, and/or compound identifier utilized in a particular aspect and/or embodiment described herein and that step or feature identifiers can be added and/or modified to indicate individual different steps/features/compounds utilized within the processes without detracting from the general disclosure.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

General Method Description

In designing new heteroatomic ligand-metal compound complex (e.g., heteroatomic ligand-chromium compound complex) catalyst systems which can produce product with enhanced activity/productivity, product purity, and selectivity (e.g., increased selectivity for 1-hexene or 1-octene), the design process can involve an iterative method of identifying and adjusting key structural or electronic features of "training" heteroatomic ligand-metal compound complexes that affect the relative energies of ground states and transition states for activity/productivity, selectivity (1-octene versus 1-hexene production), and product purity (1-hexene versus other $C_6$ products and/or 1-octene versus other $C_8$ products). The design process can also be utilized to improve the selectivity of the trimerization catalytic cycle to 1-hexene (also referred to as the trimerization cycle selectivity to 1-hexene), the selectivity of the tetramerization catalytic cycle to 1-octene, and/or the 1-octene efficiency for the fourth ethylene addition. These key structural or electronic features can be used as input variables for the development of a computational design which examines their relative significance in affecting the relative energies of the ground states and transition states and hence the overall activity/productivity, product purity, and selectivity of the oligomerization process. Based on this computational design, "target" heteroatomic ligand-metal compound complexes (e.g., heteroatomic ligand-chromium compound complexes) can be identified according to desired adjustments of the structural or electronic features, and these target complexes can be synthesized and experimentally verified. Based upon these results, a computational redesign or iteration can be used to identify next generation target complexes which also may be experimentally verified and subjected to further testing and re-design.

Therefore, in one aspect, this disclosure provides a method for designing a heteroatomic ligand-metal compound complex for olefin oligomerization, the method comprising:

(a) selecting n input variables $I^1, I^2, \ldots I^n$ (n is an integer), each input variable corresponding to a structural property or an electronic property of one or more ground state model structures $GS^{A1}, \ldots GS^{Ap}$ (p is an integer) and a plurality of transition state model structures $TS^{A1}, TS^{A2}, \ldots TS^{Am}$ (m is an integer) associated with the one or more ground state model structures, wherein each of the one or more ground state model structures $GS^{A1}, \ldots GS^{Ap}$ and each of the plurality of transition state model structures $TS^{A1}, TS^{A2}, \ldots TS^{Am}$ are derived from one or more first training heteroatomic ligand-metal compound complexes, each complex comprising a first training heteroatomic ligand;

(b) assigning a quantitative value to each n input variable $I^1, I^2, \ldots I^n$, for each of the ground state model structures $GS^{A1}, \ldots GS^{Ap}$ and each of the transition state model structures $TS^{A1}, TS^{A2}, \ldots TS^{Am}$;

(c) determining, by at least one processor of a device, the relative energies of each of the ground state model structures $GS^{A1}, \ldots GS^{Ap}$ and each of the transition state model structures $TS^{A1}, TS^{A2}, \ldots TS^{Am}$;

(d) generating a machine learning model based upon correlating the quantitative value of each n input variable $I^1, I^2, \ldots I^n$ with the relative energies of each of the ground state model structures $GS^{A1}, \ldots GS^{Ap}$ and each of the transition state model structures $TSA^1, TS^{A2}, \ldots TS^{Am}$.

(e) identifying, based on the machine learning model, one or more of the n input variables $I^1, I^2, \ldots I^n$ associated with [1] the difference in energies between one of the ground state model structures $GS^{A1}, \ldots GS^{Ap}$ and at least one of the plurality of transition state model structures $TS^{A1}, TS^{A2}, \ldots TS^{Am}$ [$\Delta G(TS\text{-}GS)$ or $\Delta\Delta G(TS\text{-}GS)$] or [2] the difference in energies between any two or more of the plurality of transition state model structures $TS^{A1}, TS^{A2}, \ldots TS^{Am}$ [$\Delta G(TS\text{-}TS)$ or $\Delta\Delta G(TS\text{-}TS)$];

(f) generating, based upon the one or more n input variables $I^1, I^2, \ldots I^n$ identified from step (e), a first target heteroatomic ligand-metal compound complex for olefin oligomerization and comprising a first target heteroatomic ligand, wherein the first target heteroatomic ligand-metal compound complex is characterized by n output variables $O^1, O^2, \ldots O^n$, each having a quantitative value corresponding to a structural property or an electronic property of one or more ground state model structures $GS^{B1}, \ldots GS^{Bx}$ (x is an integer) or any of a plurality of transition state model structures $TS^{B1}, TS^{B2}, \ldots TS^{By}$ (y is an integer) associated with the one or more ground state model structures, wherein each of the one or more ground state model structures $GS^{B1}, \ldots GS^{Bx}$ and each of the plurality of transition state model structures $TS^{B1}, TS^{B2}, \ldots TS^{By}$ are derived from the first target heteroatomic ligand-metal compound complex, each complex comprising a first target heteroatomic ligand;

(g) identifying one or more performance parameters associated with an olefin oligomerization reaction and the value of the performance parameters for the one or more first training heteroatomic ligand-metal compound complexes and the first target heteroatomic ligand-metal compound complex; and (h) repeating steps (a)-(f) one or more times using the quantitative values of the n output variables $O^1, O^2, \ldots O^n$ of the first target heteroatomic ligand-metal compound complex as an input dataset of new n input variables $I^{1.1}, I^{2.1}, \ldots I^{n.1}$ derived from one or more second training heteroatomic ligand-metal compound complexes for olefin oligomerization and comprising a second training heteroatomic ligand, which is computationally evaluated against the machine learning model to generate a second target heteroatomic ligand-metal compound complex comprising a second target heteroatomic ligand, wherein the second target heteroatomic ligand-metal compound complex is characterized by quantitative values of an output dataset of new n output variables $O^{1.1}, O^{2.1}, \ldots O^{n.1}$, and having one or more second target heteroatomic ligand-metal compound complex performance parameter values.

In this aspect, in step (b) of assigning a quantitative value to each n input variable $I^1, I^2, \ldots I^n$, these assigned quantitative values can be independently assigned a raw value or a normalized value. Also in this aspect, in step (c) of determining the relative energies of each of the ground state model structures $GS^{A1}, \ldots GS^{Ap}$ and each of the transition state model structures $TS^{A1}, TS^{A2}, \ldots TS^{Am}$, these determined relative energies can be independently the relative energies of a possible ensemble of conformations or one specific conformation of the ground state model structures and the transition state model structures. Further in this aspect, in step (e), identifying the one or more of the n input variables $I^1, I^2, \ldots I^n$ associated with [1] $\Delta G(TS\text{-}GS)$ or $\Delta \Delta G(TS\text{-}GS)$ or [2] $\Delta G(TS\text{-}TS)$ or $\Delta \Delta G(TS\text{-}TS)$, these $\Delta G$ or $\Delta \Delta G$ energy differences can be based upon a Boltzmann ensemble $\Delta G$ or $\Delta \Delta G$ values.

For convenience, this above-described method may be referred to generally as the "computational" method of this disclosure. In a further aspect, the above-described computational method can further comprise the step of:

(i) [1] synthesizing the first target heteroatomic ligand and/or the second target heteroatomic ligand; or [2] synthesizing the first target heteroatomic ligand and/or the second target heteroatomic ligand, followed by synthesizing the first target heteroatomic ligand-metal compound complex or the second target heteroatomic ligand-metal compound complex.

In still a further aspect, following the synthesizing step (i), the above-described method can further comprise the step of:

(j) performing the olefin oligomerization reaction by: [1] contacting the first target heteroatomic ligand or the second target heteroatomic ligand, a metal compound, an organometal compound, and an olefin; or [2] contacting the first target heteroatomic ligand-metal compound complex or the second target heteroatomic ligand-metal compound complex, an organometal compound, and an olefin.

Regarding the input variables, in the above-disclosed computational method, at least one input variable $I^1, I^2, \ldots I^n$ may correspond to a structural property or an electronic property of at least one of the one or more ground state model structures $GS^{A1}, \ldots GS^{Ap}$ set out in the computational method. The at least one input variable $I^1, I^2, \ldots I^n$ may also correspond to a structural property or an electronic property of at least one of the plurality of transition state model structures $TS^{A1}, TS^{A2}, \ldots TS^{Am}$ set out in the computational method. The quantitative value assigned to each n input variable $I^1, I^2, \ldots I^n$, for each of the one or more ground state model structures $GS^{A1}, \ldots GS^{Ap}$ and each of the plurality of transition state model structures $TS^{A1}, TS^{A2}, \ldots TS^{Am}$ derived from the one or more first training heteroatomic ligand-metal compound complexes can be assigned on the basis of calculated, measured, or estimated values, or any combination thereof, and these assigned quantitative values can be independently a raw value or a normalized value.

According to an aspect, the step (e) of the computational method above can identify, based on the machine learning model, one or more of the n input variables $I^1, I^2, \ldots I^n$ associated with the difference in energies between any of the one or more ground state model structures $GS^{A1}, \ldots GS^{Ap}$ and at least one of the plurality of transition state model structures $TS^{A1}, TS^{A2}, \ldots TS^{Am}$ [$\Delta G(TS\text{-}GS)$ or $\Delta \Delta G(TS\text{-}GS)$]. The step (e) of the computational method disclosed above can also identify, based on the machine learning model, one or more of the n input variables $I^1, I^2, \ldots I^n$ associated with the difference in energies between any two or more of the plurality of transition state model structures $TS^{A1}, TS^{A2}, \ldots TS^{Am}$ [$\Delta \Delta G(TS\text{-}TS)$].

Therefore, in one aspect, this method can identify and select one or more of the n input variables $I^1, I^2, \ldots I^n$ which impart the greatest or most significant differences in energies between any of the one or more ground state models and at least one of the plurality of transition state model structures, which can afford efficiency to the method and can guide the design of the next generation compounds, in both synthetic and computational aspects, to deliver improved performance of a desired parameter (e.g., activity/productivity, product purity, and/or selectivity). For example, the one or more of the n input variables $I^1, I^2, \ldots I^n$ identified in step (e) can be identified based upon the greater percentage changes in [1] the difference in energies between any of the one or more ground state model structures $GS^{A1}, \ldots GS^{Ap}$ and at least one of the plurality of transition state model structures $TS^{A1}, TS^{A2}, \ldots TS^{Am}$ [$\Delta G(TS\text{-}GS)$ or $\Delta \Delta G(TS\text{-}GS)$] or [2] the difference in energies between any two or more of the plurality of transition state model structures $TS^{A1}, TS^{A2}, \ldots TS^{Am}$ [$\Delta G(TS\text{-}TS)$ or $\Delta \Delta G(TS\text{-}TS)$], for each percentage change in the one or more of the n input variables $I^1, I^2, \ldots I^n$ which influence $\Delta G(TS\text{-}GS)$, $\Delta \Delta G(TS\text{-}GS)$, or $\Delta \Delta G(TS\text{-}TS)$.

Model Ground State Structures and Model Transition State Structures in Heteroatomic Ligand-Metal Compound Complexes The particular heteroatomic ligand-metal compound complexes (e.g., heteroatomic ligand-chromium compound complexes) that can be utilized in this study for computation and synthetic purposes, for example, the one or more first training heteroatomic ligand-metal compound complexes, can have a general formula independently selected from: [(HetLig)CrX$_q$L$_r$]$^{3-q}$ (A); wherein:
- HetLig represents the one or more first training heteroatomic ligands;
- X is an anionic ligand, and q is an integer;
- L is a neutral ligand, and r is an integer,
- wherein any two or more of the X and L ligands may be linked to form a multidentate ligand.

In an aspect,
- each selected n input variable I$^1$, I$^2$, ... I$^n$, corresponds to a structural property or an electronic property of any of the one or more ground state model structures GS$^{A1}$, ... GS$^{Ap}$ or any of the plurality of transition state model structures TS$^{A1}$, TS$^{A2}$, ... TS$^{Am}$ associated with the one or more ground state model structures of formula (A).

As explained herein, the specific input variables that can be utilized in the computational method can include or can be selected from structural and electronic features of the heteroatomic ligand-metal compound complexes (e.g., heteroatomic ligand-chromium compound complexes) of Formula (A) including: various atomic distances (e.g., chromium to heteroatom of the heteroatomic ligand distances); certain chromium heteroatomic ligand bond angles; various chromium heteroatomic ligand atom dihedral angles; the atomic charges on the Cr and/or the heteroatomic atoms of the heteroatomic ligand chromium compound complex; and/or specific parameters such as the distance out of pocket (Å) and the percent volume buried. These structural feature, electronic feature, and parameters are further provided herein.

In an aspect of the computational method described herein, the method employs a range of model structures to which the method is applied and from which new structures are derived. These structures are delineated according to:
[1] ground state model structures GS$^{A1}$, ... GS$^{Ap}$ derived from the one or more first training heteroatomic ligand-metal compound complexes;
[2] ground state model structures GS$^{B1}$, ... GS$^{Bx}$ derived from the one or more first target heteroatomic ligand-metal compound complexes;
[3] transition state model structures TS$^{A1}$, TS$^{A2}$, ... TS$^{Am}$ derived from the one or more first training heteroatomic ligand-metal compound complexes; and
[4] transition state model structures TS$^{A1}$, TS$^{A2}$, ... TS$^{Am}$ derived from the one or more first training heteroatomic ligand-metal compound complexes.

Each of these model structures comprises a heteroatomic ligand, which may be designated according to the particular complex. For example, the heteroatomic ligand in each complex can be designated as a first training heteroatomic ligand in model structures [1] and [3] listed herein, or a first target heteroatomic ligand in model structures [2] and [4] listed herein.

In an aspect, the one or more ground state model structures GS$^{A1}$, ... GS$^{Ap}$ derived from the one or more first training heteroatomic ligand-metal compound complexes can be selected from any of the following model structures:

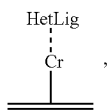

(GS$^I$-I)

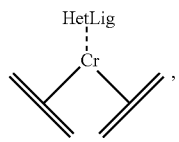

(GS$^I$-II)

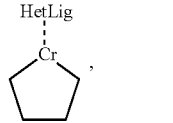

(GS$^I$-III)

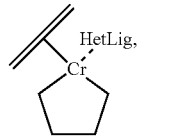

(GS$^I$-IV)

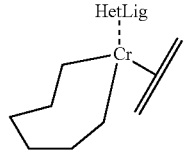

(GS$^I$-V)

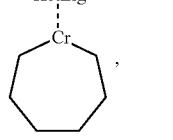

(GS$^I$-VI)

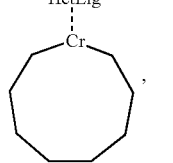

(GS$^I$-VII)

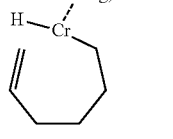

(GS$^I$-VIII)

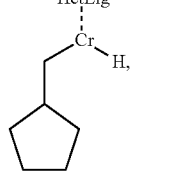

(GS$^I$-IX)

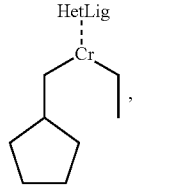

(GS$^I$-X)

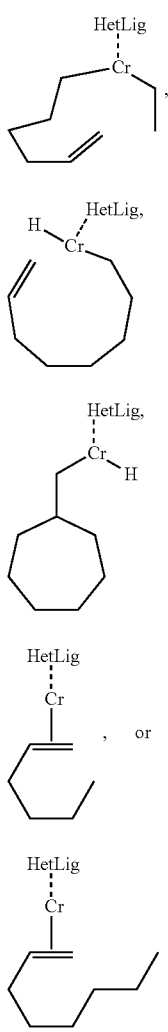

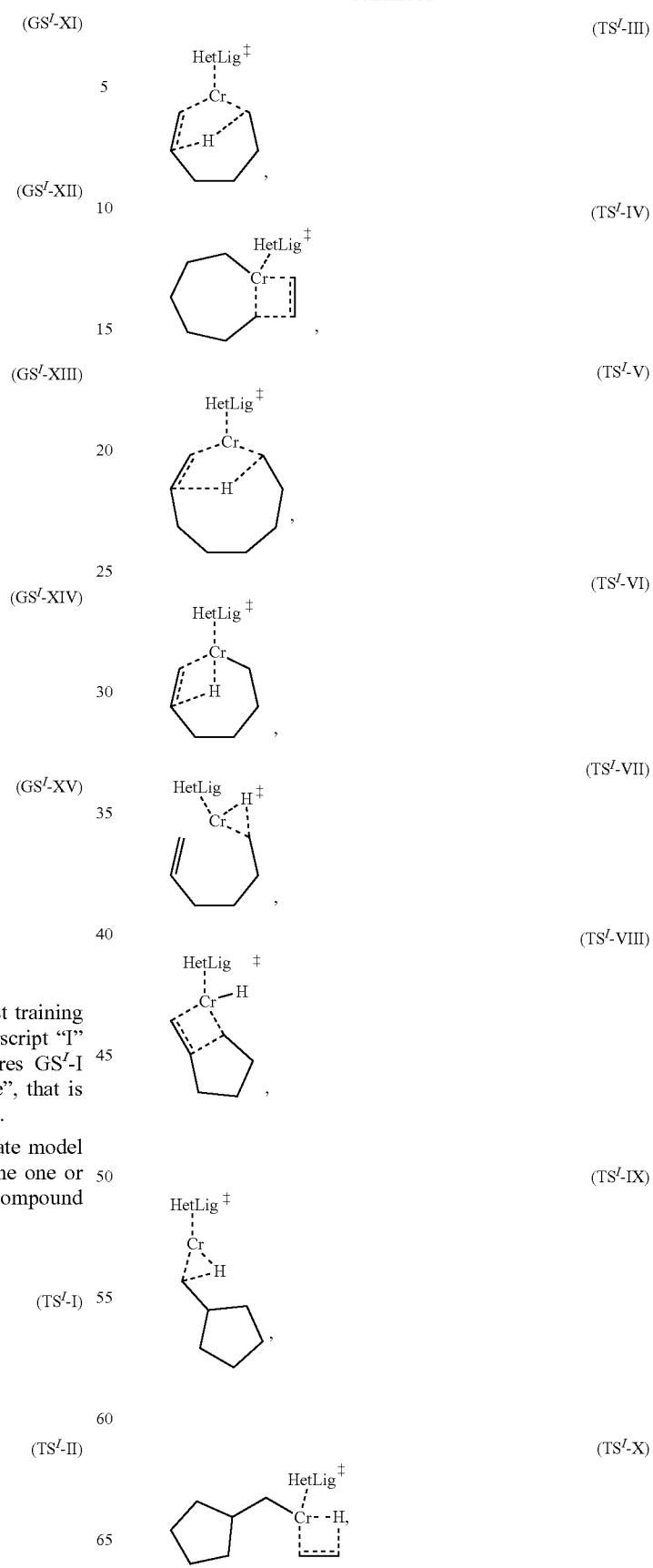

wherein HetLig represents the one or more first training heteroatomic ligands, and wherein the superscript "I" in each of the model ground state structures $GS^I$-I through $GS^I$-XIII designates the "instructive", that is the "training", model ground state structures.

In another aspect, the plurality of transition state model structures $TS^{A1}$, $TS^{A2}$, ... $TS^{Am}$ derived from the one or more first training heteroatomic ligand-metal compound complexes can be selected independently from:

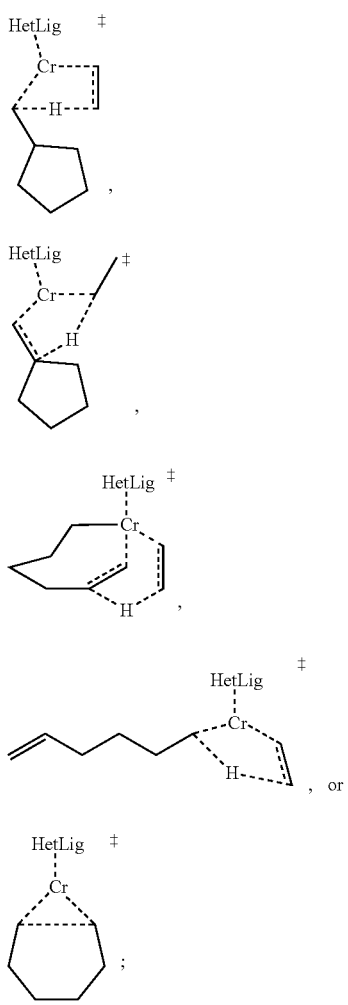

wherein HetLig represents the one or more first training heteroatomic ligands, and wherein the superscript "I" in in each of the model transition state structures $TS^I$-I through $TS^I$-XV designates the "instructive", that is the "training", model transition state structures.

A similar set of model ground state and model transition state structures can be employed as the target heteroatomic ligand-metal compound complexes. Therefore, the one or more ground state model structures $GS^{B1}, \ldots GS^{Bx}$ derived from the one or more first target heteroatomic ligand-metal compound complexes can be selected independently from.

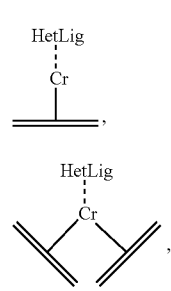

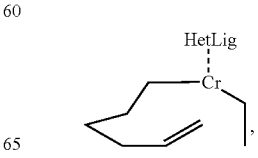

(GS$^T$-XII)

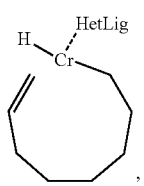

(GS$^T$-XIII)

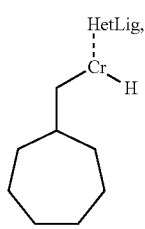

(GS$^T$-XIV)

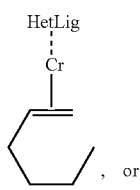, or (GS$^T$-XV)

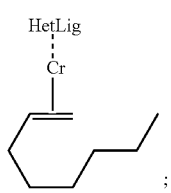;

wherein HetLig represents the one or more first target heteroatomic ligands, and wherein the superscript "T" in each of the model ground state structures GS$^T$-I through GS$^T$-XIII designates the target model ground state structures.

In a further aspect, the plurality of transition state model structures TS$^{A1}$, TS$^{A2}$, ... TS$^{Am}$ derived from the one or more first target heteroatomic ligand-metal compound complexes can be selected independently from:

(TS$^T$-I)

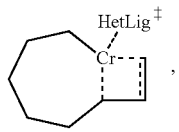

(TS$^T$-II)

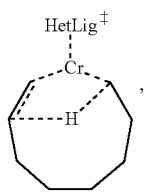

(TS$^T$-III)

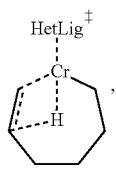

(TS$^T$-IV)

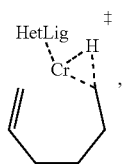, (TS$^T$-V)

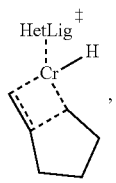, (TS$^T$-VI)

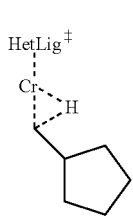, (TS$^T$-VII)

(TS$^T$-VIII)

(TS$^T$-IX)

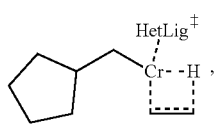

(TS$^T$-X)

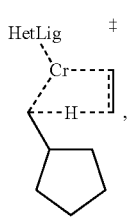, (TS$^T$-XI)

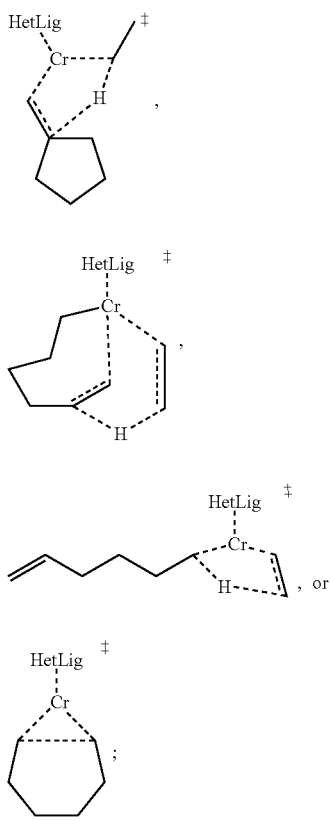

(TS^T-XII)

(TS^T-XIII)

(TS^T-XIV)

(TS^T-V)

wherein HetLig represents the one or more first target heteroatomic ligands, and wherein the superscript "T" in each of the model transition state structures TS$^T$-I through TS$^T$-XV designates the target model transition state structures.

The Heteroatomic Ligand and the Heteroatomic Ligand-Metal Compound Complex

Generally, the heteroatomic ligand or the heteroatomic ligand of the heteroatomic ligand-metal compound complex (e.g., a heteroatomic ligand-chromium compound complex) can be any heteroatomic ligand, which when utilized in the catalyst systems (or catalyst system mixtures) described herein for the processes and/or reaction systems described herein, can form an oligomer product in the reaction zone. In an aspect, the heteroatomic ligand or the heteroatomic ligand of the heteroatomic ligand-metal compound complex (e.g., a heteroatomic ligand-chromium compound complex) can be a neutral heteroatomic ligand or an anionic heteroatomic ligand; alternatively, a neutral heteroatomic ligand; or alternatively, an anionic heteroatomic ligand. In an aspect, the neutral heteroatomic ligand can comprise one or more heteroatomic complexing moieties; alternatively, two heteroatomic complexing; or alternatively, three heteroatomic complexing moieties. In an aspect, the anionic heteroatomic ligand can also comprise one or more neutral heteroatomic complexing moieties; alternatively, two heteroatomic complexing; or alternatively, three heteroatomic complexing moieties. In an aspect, the each neutral heteroatomic complexing moiety of the neutral ligand or the anionic ligand comprising a neutral heteroatomic complexing moiety independently can be an ether group, a sulfide group, an amine group, an imine group, a phosphine group, a phosphinite group, a phosphonite group, or a phosphite group; alternatively, an ether group, a sulfide group, an amine group, an imine group, or a phosphine group; alternatively, an ether group; alternatively, a sulfide group; alternatively, an amine group; alternatively, an imine group; or alternatively, a phosphine group. In an aspect, the anion atom of the anionic heteroatomic ligand (which forms a covalent or ionic bond with the chromium of the chromium compound) can be an anionic carbon atom, an anionic oxygen atom, or an anion nitrogen atom; alternatively, an anionic carbon atom; alternatively, an anionic oxygen atom; or alternatively, an anion nitrogen atom.

In an aspect, for example, the heteroatomic ligand-metal compound complex can be heteroatomic ligand chromium compound complex and can have the general formula [(HetLig)CrX$_q$L$_r$]$^{3-q}$ (A); wherein HetLig represents the one or more first training heteroatomic ligands, X is an anionic ligand and q is an integer, L is a neutral ligand and r is an integer, and wherein any two or more of the X and L ligands may be linked to form a multidentate ligand. Therefore, for the general and specific structures disclosed hereinbelow, it is envisioned that any two or more of the X and L ligands can form a chelating ligand in which a bridging moiety links X ligands, L ligands, or a combination of X and L ligands.

In any aspect, the heteroatomic ligand or the heteroatomic ligand of the heteroatomic ligand chromium compound complex can comprise, can consist essentially of, or can be, an N$^2$-phosphinyl formamidine, an N$^2$-phosphinyl amidine, an N$^2$-phosphinyl guanidine, a heterocyclic 2-[(phosphinyl) aminyl]imine, or any combination thereof; alternatively, an N$^2$-phosphinyl formamidine; alternatively, an N$^2$-phosphinyl amidine; alternatively, an N$^2$-phosphinyl guanidine; or alternatively, a heterocyclic 2-[(phosphinyl)aminyl]imine. Generally, the an N$^2$-phosphinyl formamidine can have Structure NPF-1, the N$^2$-phosphinyl amidine can have Structure NPA-1, the N$^2$-phosphinyl guanidine can have Structure Gu-1, Structure Gu-2, Structure Gu-3, Structure Gu-4, or Structure Gu-5, and the heterocyclic 2-[(phosphinyl)aminyl]imine can have structure HCPA-1. In some aspects, the N$^2$-phosphinyl guanidine have Structure Gu-2, Structure Gu-3, or Structure Gu-4; alternatively, Structure Gu-1; alternatively, Structure Gu-2; alternatively, Structure Gu-3; alternatively, Structure Gu-4; or alternatively Structure Gu-5.

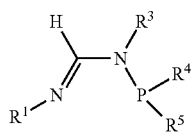

Structure NPF-1

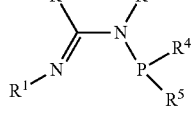

Structure NPA-1

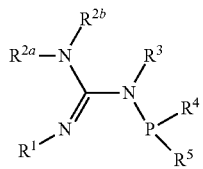

Structure Gu-1

Structure Gu-2

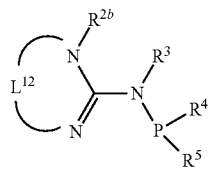

Structure Gu-3

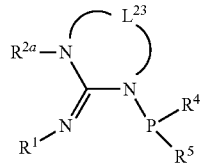

Structure Gu-4

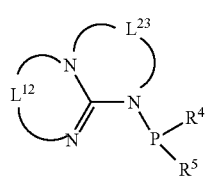

Structure Gu-5

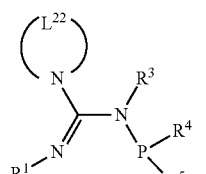

Structure HCPA-1

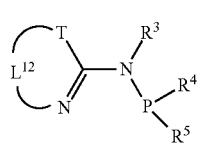

Structure NPFCr-1

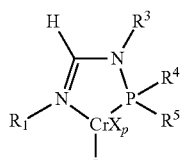

Structure NPACr-1

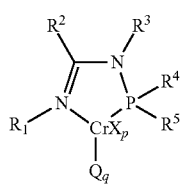

Structure GuCr-1

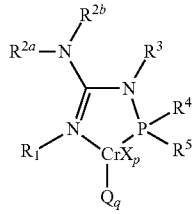

Structure GuCr-2

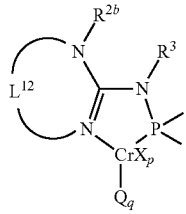

Structure GuCr-3

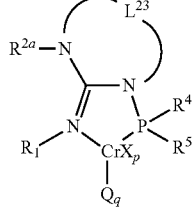

Structure GuCr-4

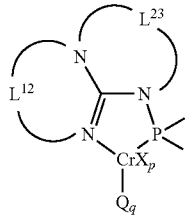

Structure GuCr-5

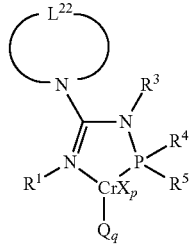

In any aspect, the heteroatomic ligand chromium compound complex can comprise, can consist essentially of, or can be, an $N^2$-phosphinyl formamidine chromium compound complex, an $N^2$-phosphinyl amidine chromium compound complex, an $N^2$-phosphinyl guanidine chromium compound complex, a heterocyclic 2-[(phosphinyl)aminyl]imine chromium compound complex, or any combination thereof; alternatively, an $N^2$-phosphinyl formamidine chromium compound complex; alternatively, an $N^2$-phosphinyl amidine chromium compound complex; alternatively, an $N^2$-phosphinyl guanidine chromium compound complex; alternatively, an $N^2$-phosphinyl guanidine chromium compound complex; or alternatively, a heterocyclic 2-[(phosphinyl)aminyl]imine chromium compound complex. Generally, the an $N^2$-phosphinyl formamidine chromium compound complex can have Structure NPFCr-1, the $N^2$-phosphinyl amidine chromium compound complex can have Structure NPACr-1, the $N^2$-phosphinyl guanidine chromium compound complex can have Structure GuCr-1, Structure GuCr-2, Structure GuCr-3, Structure GuCr-4, or Structure GuCr-5, and the heterocyclic 2-[(phosphinyl)aminyl]imine chromium compound complex can have Structure HCPACr-1. In some aspects, the $N^2$-phosphinyl guanidine chromium compound complex have Structure GuCr-2, Structure GuCr-3, or Structure GuC-4; alternatively, Structure GuC-r1; alternatively, Structure GuCr-2; alternatively, Structure GuCr-3; alternatively, Structure GuCr-4; or alternatively Structure GuCr-5.

Structure HCPACr-2

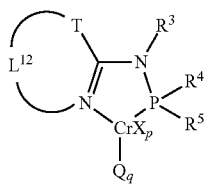

Within the $N^2$-phosphinyl formamidines, the $N^2$-phosphinyl formamidine chromium compound complexes, the $N^2$-phosphinyl amidines, the $N^2$-phosphinyl amidine chromium compound complexes, and the heterocyclic 2-[(phosphinyl)aminyl]imine chromium compound complexes the nitrogen participating in a double bond with the central carbon atom is referred to as the $N^1$ nitrogen and the nitrogen atom participating in a single bond with the central carbon atom is referred to as the $N^2$ nitrogen. Similarly, within the $N^2$-phosphinyl guanidines and the $N^2$-phosphinyl guanidine chromium compound complexes, the nitrogen participating in a double bond with the central carbon atom of the guanidine core is referred to as the $N^1$ nitrogen, the nitrogen atom participating in a single bond with the central carbon atom of the guanidine core and a bond with the phosphorus atom of the phosphinyl group is referred to as the $N^2$ nitrogen, and the remaining nitrogen atom participating in a single bond with the central carbon atom of the guanidine core is referred to as the $N^3$ nitrogen. It should be noted that the guanidine group of the guanidine in the $N^2$-phosphinyl guanidines and the $N^2$-phosphinyl guanidine chromium complexes can be a portion of a larger group which does not contain guanidine in it name. For example, while the compound 7-dimethylphosphinylimidazo[1,2-a]imidazole could be classified as a compound having an imidazo[1,2-a]imidazole core (or a compound having a phosphinylimidazo[1,2-a]imidazole group), 7-dimethylphosphinylimidazo[1,2-a]imidazole would still be classified as a compound having a guanidine core (or as a compound having an guanidine group) since it contains the defined general structure of the guanidine compound.

The $R^1$, $R^3$, $R^4$, and $R^5$ groups within the $N^2$-phosphinyl formamidine structures and the $N^2$-phosphinyl formamidine chromium compound complex structures, $R^1$, $R^2$, $R^3$, $R^4$, and $R^5$ within the $N^2$-phosphinyl amidine structures and the $N^2$-phosphinyl amidine chromium compound complex structures, $R^1$, $R^{2a}$, $R^{2b}$, $R^3$, $R^4$, $R^5$, $L^{12}$, $L^{22}$, and $L^{23}$ within the $N^2$-phosphinyl guanidine structures and the $N^2$-phosphinyl guanidine chromium compound complex structures, and $L^{12}$, T, $R^3$, $R^4$, and $R^5$ within the heterocyclic 2-[(phosphinyl)aminyl]imine structures and heterocyclic 2-[(phosphinyl)aminyl]imine chromium compound complex structures are independently described herein and can be utilized in any combination and without limitation to further describe the $N^2$-phosphinyl formamidine structures, the $N^2$-phosphinyl formamidine chromium compound complex structures, the $N^2$-phosphinyl amidine structures, the $N^2$-phosphinyl amidine chromium compound complex structures, the $N^2$-phosphinyl guanidine structures, the $N^2$-phosphinyl guanidine chromium compound complex structures, the heterocyclic 2-[(phosphinyl)aminyl]imine structures, and the heterocyclic 2-[(phosphinyl)aminyl]imine chromium compound complex structures disclosed herein. $X_p$, Q, and q of the $N^2$-phosphinyl formamidine chromium compound complex structures, the $N^2$-phosphinyl amidine chromium compound complex structures, the $N^2$-phosphinyl guanidine chromium compound complex structures, and the heterocyclic 2-[(phosphinyl)aminyl]imine chromium compound complex structures are independently described herein and can be utilized in any combination, and without limitation, to further describe the $N^2$-phosphinyl formamidine chromium compound complex structures, the $N^2$-phosphinyl amidine chromium compound complex structures, the $N^2$-phosphinyl guanidine chromium compound complex structures, and the heterocyclic 2-[(phosphinyl)aminyl]imine chromium compound complex structures disclosed herein.

Additionally, the independent descriptions of $X_p$, Q, and q can be combined, without limitation, with the independently described $R^1$, $R^2$, $R^{2a}$, $R^{2b}$, $R^3$, $R^4$, $R^5$, $L^{12}$, $L^{22}$, and $L^{23}$ to further describe the appropriate $N^2$-phosphinyl formamidine chromium compound complex structures, the $N^2$-phosphinyl amidine chromium compound complex structures, the $N^2$-phosphinyl guanidine chromium compound complex structures, and the heterocyclic 2-[(phosphinyl)aminyl]imine chromium compound complex structures contemplated herein.

Generally, $R^1$ of the $N^2$-phosphinyl formamidines, the $N^2$-phosphinyl formamidine chromium compound complexes, the $N^2$-phosphinyl amidines, the $N^2$-phosphinyl amidine chromium compound complexes, the $N^2$-phosphinyl guanidines, and/or the $N^2$-phosphinyl guanidine chromium compound complexes which have an $R^1$ group can be an organyl group; alternatively, an organyl group consisting of inert functional groups; or alternatively, a hydrocarbyl group. In an aspect, the $R^1$ organyl group can be a $C_1$ to $C_{20}$, a $C_1$ to $C_{15}$, a $C_1$ to $C_{10}$, or a $C_1$ to $C_5$ organyl group. In an aspect, the $R^1$ organyl group consisting of inert functional groups can be a $C_1$ to $C_{20}$, a $C_1$ to $C_{15}$, a $C_1$ to $C_{10}$, or a $C_1$ to $C_5$ organyl group consisting of inert functional groups. In an aspect, the $R^1$ hydrocarbyl group can be a $C_1$ to $C_{20}$, a $C_1$ to $C_{15}$, a $C_1$ to $C_{10}$, or a $C_1$ to $C_5$ hydrocarbyl group.

In an aspect, $R^1$ of the $N^2$-phosphinyl formamidines, the $N^2$-phosphinyl formamidine chromium compound complexes, the $N^2$-phosphinyl amidines, the $N^2$-phosphinyl amidine chromium compound complexes, the $N^2$-phosphinyl guanidines, and/or the $N^2$-phosphinyl guanidine chromium compound complexes which have an $R^1$ group can be an alkyl group, a substituted alkyl group, a cycloalkyl group, a substituted cycloalkyl group, an aryl group, a substituted aryl group, an aralkyl group, or a substituted aralkyl group; alternatively an alkyl group or a substituted alkyl group; alternatively, a cycloalkyl group or a substituted cycloalkyl group; alternatively, an aryl group or a substituted aryl group; alternatively, an aralkyl group or a substituted aralkyl group; alternatively, an alkyl group, a cycloalkyl group, an aryl group, or an aralkyl group; alternatively, an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group. In any aspect disclosed herein, the $R^1$ alkyl group can be a $C_1$ to $C_{20}$, a $C_1$ to $C_{10}$, or a $C_1$ to $C_5$ alkyl group. In any aspect disclosed herein, the $R^1$ substituted alkyl group can be a $C_1$ to $C_{20}$, a $C_1$ to $C_{10}$, or a $C_1$ to $C_5$ substituted alkyl group. In any aspect disclosed herein, the $R^1$ cycloalkyl group can be a $C_4$ to $C_{20}$, a $C_4$ to $C_{15}$, or a $C_4$ to $C_{10}$ cycloalkyl group. In any aspect disclosed herein, the $R^1$ substituted cycloalkyl group can be a $C_4$ to $C_{20}$, a $C_4$ to $C_{15}$, or a $C_4$ to $C_{10}$ substituted cycloalkyl group. In any aspect disclosed herein, the $R^1$ aryl group can be a $C_6$ to $C_{20}$, a $C_6$ to $C_{15}$, or a $C_6$ to $C_{10}$ aryl group. In any aspect disclosed herein, the $R^1$ substituted aryl group can be a $C_6$ to $C_{20}$, a $C_6$ to $C_{15}$, or a $C_6$ to $C_{10}$ substituted aryl group. In any aspect disclosed herein, the $R^1$ aralkyl group can be a $C_7$ to $C_{20}$, a $C_7$ to $C_{15}$, or a $C_7$ to $C_{10}$ aralkyl group. In any aspect disclosed herein, the $R^1$ substituted aralkyl group can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted $R^1$ group.

In an aspect, $R^1$ can be a methyl group, an ethyl group, a propyl group, a butyl group, a pentyl group, a hexyl group, a heptyl group, or an octyl group; or alternatively, a methyl group, an ethyl group, a n-propyl (1-propyl) group, an iso-propyl (2-propyl) group, a tert-butyl (2-methyl-2-propyl) group, or a neopentyl (2,2-dimethyl-1-propyl) group. In some aspects, the alkyl groups which can be utilized as $R^1$ can be substituted. Each substituent of a substituted alkyl group (general or specific) independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group which can be utilized as $R^1$.

In an aspect, $R^1$ can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group. In an aspect, the substituted cycloalkyl group, which can be utilized as $R^1$, can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; or alternatively, a 2,6-disubstituted cyclohexyl group or a 2,5-disubstituted cyclopentyl group. In an aspect, one or more substituents of a multi-substituted cycloalkyl group utilized as $R^1$ can be the same or different; alternatively, all the substituents of a multi-substituted cycloalkyl group can be the same; or alternatively, all the substituents of a multi-substituted cycloalkyl group can be different. Each substituent of a substituted cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy (general and specific) groups are independently disclosed herein. These substituent halogens, substituent hydrocarbyl groups, and substituent hydrocarboxy groups can be utilized without limitation to further describe a substituted cycloalkyl group (general or specific) which can be utilized as $R^1$.

In a non-limiting aspect, $R^1$ can be a cyclohexyl group, a 2-alkylcyclohexyl group, or a 2,6-dialkylcyclohexyl group; or alternatively, a cyclopentyl group, a 2-alkylcyclopentyl group, or a 2,5-dialkylcyclopentyl group. Alkyl substituent groups (general and specific) are independently described herein and these alkyl substituent groups can be utilized, without limitation, to further describe alkylcyclohexyl groups (general and specific), dialkylcyclohexyl groups (general and specific), alkylcyclopentyl groups (general or specific), and/or dialkylcyclopentyl groups (general and specific) which can be utilized as $R^1$. Generally, the alkyl substituents of a dialkylcyclohexyl group or a dialkylcyclopentyl group can be the same; or alternatively, the alkyl substituents of a dialkylcyclohexyl group or a dialkylcyclopentyl group can be different. In some non-limiting aspects, $R^1$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting aspects, $R^1$ can be a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an aspect, $R^1$ can be a phenyl group, a substituted phenyl group; alternatively, a phenyl group; or alternatively, a substituted phenyl group. In an aspect, the substituted phenyl group, which can be utilized as $R^1$, can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; or alternatively, a 2,4,6-trisubstituted phenyl group. In an aspect, one or more substituents of a multi-substituted phenyl group utilized as $R^1$ can be the same or different; alternatively, all the substituents of a multi-substituted cycloalkyl group can be the same; or alternatively, all the substituents of a multi-substituted cycloalkyl group different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^1$.

In a non-limiting aspect, $R^1$ can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^1$. Generally, the alkyl substituents of a dialkylphenyl group (general or specific) or a trialkylphenyl group (general or specific) can be the same; or alternatively, the alkyl substituents of a dialkylphenyl group or trialkylphenyl group can be different. In some non-limiting aspects, $R^1$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In an aspect, $R^1$ can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group (general or specific) which can be utilized as $R^1$.

Generally, $R^2$ of the $N^2$-phosphinyl amidines and/or the $N^2$-phosphinyl amidine chromium compound complexes can be an organyl group; alternatively, an organyl group consisting of inert functional groups; or alternatively, a hydrocarbyl group. In an aspect, the $R^2$ organyl group can be a $C_1$ to $C_{20}$, a $C_1$ to $C_{15}$, a $C_1$ to $C_{10}$, or a $C_1$ to $C_5$ organyl group. In an aspect, $R^2$ organyl group consisting of inert functional groups can be a $C_1$ to $C_{20}$, a $C_1$ to $C_{15}$, a $C_1$ to $C_{10}$, or a $C_1$ to $C_5$ organyl group consisting of inert functional groups. In an aspect, $R^2$ hydrocarbyl group can be a $C_1$ to $C_{20}$, a $C_1$ to $C_{15}$, a $C_1$ to $C_{10}$, or a $C_1$ to $C_5$ hydrocarbyl group.

In an aspect, $R^2$ of the $N^2$-phosphinyl amidines and/or the $N^2$-phosphinyl amidine chromium compound complexes can be an acyl group or a substituted acyl group; an acyl group; or alternatively, a substituted acyl group. In an aspect, the acyl group can be a $C_1$ to $C_{20}$, a $C_1$ to $C_{15}$, a $C_1$ to $C_{10}$, or a $C_1$ to $C_5$ acyl group. In an aspect, the substituted acyl group can be a $C_1$ to $C_{20}$, a $C_1$ to $C_{15}$, a $C_1$ to $C_{10}$, or a $C_1$ to $C_5$ substituted acyl group. In some aspects, $R^2$ of the $N^2$-phosphinyl amidines and/or the $N^2$-phosphinyl amidine chromium compound complexes can be an alkanoyl group, a substituted alkanoyl group, a benzoyl group, or a substituted benzoyl group; alternatively, an alkanoyl group or a substituted alkanoyl group; alternatively, a benzoyl group, or a substituted benzoyl group; alternatively, an alkanoyl group; alternatively, a substituted alkanoyl group; alternatively, a benzoyl group; or alternatively, a substituted benzoyl group. In any aspect disclosed herein, the $R^2$ alkanoyl group can be a $C_1$ to $C_{20}$, a $C_1$ to $C_{10}$, or a $C_1$ to $C_5$ alkanoyl group. In any aspect disclosed herein, the $R^2$ substituted alkanoyl group can be a $C_1$ to $C_{20}$, a $C_1$ to $C_{10}$, or a $C_1$ to $C_5$ substituted $R^2$ alkanoyl group. In any aspect disclosed herein, the $R^2$ benzoyl group can be a $C_7$ to $C_{20}$, a $C_7$ to $C_{15}$, or a $C_7$ to $C_{10}$ benzoyl group. In any aspect disclosed herein, the $R^2$ substituted benzoyl group can be a $C_7$ to $C_{20}$, a $C_1$ to $C_{15}$, or a $C_1$ to $C_{10}$ substituted $R^2$ benzoyl group. Each substituent of a substituted alkanoyl group (general or specific), and/or substituted benzoyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe substituted alkanoyl groups and/or substituted benzoyl group which can be utilized as $R^2$.

In an aspect, $R^2$ of the $N^2$-phosphinyl amidines and/or the $N^2$-phosphinyl amidine chromium compound complexes can be an alkyl group, a substituted alkyl group, a cycloalkyl group, a substituted cycloalkyl group, an aryl group, a substituted aryl group, an aralkyl group, or a substituted aralkyl group; alternatively, an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other aspects, $R^2$ of the $N^2$-phosphinyl amidine and/or the $N^2$-phosphinyl amidine chromium compound complexes can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group. In any aspect disclosed herein, the $R^2$ alkyl group can be a $C_1$ to $C_{20}$, a $C_1$ to $C_{10}$, or a $C_1$ to $C_5$ alkyl group. In any aspect disclosed herein, the $R^2$ substituted alkyl group can be a $C_1$ to $C_{20}$, a $C_1$ to $C_{10}$, or a $C_1$ to $C_5$ substituted alkyl group. In any aspect disclosed herein, the $R^2$ cycloalkyl group can be a $C_4$ to $C_{20}$, a $C_4$ to $C_{15}$, or a $C_4$ to $C_{10}$ cycloalkyl group. In any aspect disclosed herein, the $R^2$ substituted cycloalkyl group can be a $C_4$ to $C_{20}$, a $C_4$ to $C_{15}$, or a $C_4$ to $C_{10}$ substituted cycloalkyl group. In any aspect disclosed herein, the $R^2$ aryl group can be a $C_6$ to $C_{20}$, a $C_6$ to $C_{15}$, or a $C_6$ to $C_{10}$ aryl group. In any aspect disclosed herein, the $R^2$ substituted aryl group can be a $C_6$ to $C_{20}$, a $C_6$ to $C_{15}$, or a $C_6$ to $C_{10}$ substituted aryl group. In any aspect disclosed herein, the $R^2$ aralkyl group can be a $C_7$ to $C_{20}$, a $C_7$ to $C_{15}$, or a $C_7$ to $C_{10}$ aralkyl group. In any aspect disclosed herein, the $R^2$ substituted aryl group can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^2$.

In an aspect, $R^2$ can be a methyl group, an ethyl group, a propyl group, a butyl group, a pentyl group, a hexyl group, a heptyl group, or an octyl group; or alternatively, a methyl group, an ethyl group, an n-propyl (1-propyl) group, an iso-propyl (2-propyl) group, a tert-butyl (2-methyl-2-propyl) group, or a neopentyl (2,2-dimethyl-1-propyl) group. In some aspects, the alkyl groups which can be utilized as $R^2$ can be substituted. Each substituent of a substituted alkyl group independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group (general or specific) which can be utilized as $R^2$.

In an aspect, $R^2$ can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group. In an aspect, the substituted cycloalkyl group, which can be utilized as $R^2$, can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; or alternatively, a 2,6-disubstituted cyclohexyl group or a 2,5-disubstituted cyclopentyl group. In an aspect, one or more substituents of a multi-substituted cycloalkyl group utilized as $R^2$ can be the same or different; alternatively, all the substituents of a multi-substituted cycloalkyl group can be the same; or alternatively, all the substituents of a multi-substituted cycloalkyl group can be different. Each substituent of a cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^2$.

In a non-limiting aspect, $R^2$ can be a cyclohexyl group, a 2-alkylcyclohexyl group, or a 2,6-dialkylcyclohexyl group; or alternatively, a cyclopentyl group, a 2-alkylcyclopentyl group, or a 2,5-dialkylcyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^2$. Generally, the alkyl substituents of a disubstituted cyclohexyl or cyclopentyl group can be the same; or alternatively, the alkyl substituents of a dialkyl cyclohexyl or cyclopentyl group can be different. In some non-limiting aspects, $R^2$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting aspects, $R^2$ can be, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an aspect, $R^2$ can be a phenyl group, a substituted phenyl group; alternatively, a phenyl group; or alternatively, a substituted phenyl group. In an aspect, the substituted phenyl group, which can be utilized as $R^2$ can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; or alternatively, a 2,4,6-trisubstituted phenyl group. In an aspect, one or more substituents of a multi-substituted phenyl group utilized as $R^2$ can be the same or different; alternatively, all the substituents of a multi-substituted cycloalkyl group can be the same; or alternatively, all the substituents of a multi-substituted cycloalkyl group can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^2$.

In a non-limiting aspect, $R^2$ can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^2$. Generally, the alkyl substituents of a dialkylphenyl group (general or specific) or trialkylphenyl group (general or specific) can be the same; or alternatively, the alkyl substituents of a dialkylphenyl group or trialkylphenyl group can be different. In some non-limiting aspects, $R^2$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting aspect, $R^2$ can be a phenyl group, a 2-alkoxyphenyl group, or a 4-alkoxyphenyl group. In some non-limiting aspects, $R^2$ can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group. In another non-limiting aspect, $R^2$ can be a phenyl group, a 2-halophenyl group, a 4-halophenyl group, or a 2,6-dihalophenyl group. Generally, the halides of a dihalophenyl group can be the same; or alternatively, the halides of a dihalophenyl group can be different. In some aspects, $R^2$ can be a phenyl group, a 2-fluorophenyl group, a 4-fluorophenyl group, or a 2,6-difluorophenyl group.

In an aspect, $R^2$ can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group which can be utilized as $R^2$.

In further aspects, $R^1$ and $R^2$ can be joined to form a ring or a ring system containing the carbon-nitrogen double bond of the $N^2$-phosphinyl amidines and/or the $N^2$-phosphinyl amidine chromium compound complexes. The joining of $R^1$ and $R^2$ can be designated as $L^{12r}$ and can be an organylene group; alternatively, an organylene group consisting of inert functional groups; alternatively, a hydrocarbylene group; or alternatively, an alkylene group. In an aspect, the $L^{12r}$ organylene group, when present, can be a $C_3$ to $C_{30}$, a $C_3$ to $C_{20}$, a $C_3$ to $C_{15}$, or a $C_3$ to $C_{10}$ organylene group. In some aspects, the $L^{12r}$ organylene group consisting of inert functional groups, when present, can be a $C_3$ to $C_{30}$, a $C_3$ to $C_{20}$, a $C_3$ to $C_{15}$, or a $C_3$ to $C_{10}$ organylene group consisting of inert functional groups. In other aspects, the $L^{12r}$ hydrocarbyl group, when present, independently can be a $C_3$ to $C_{30}$, a $C_3$ to $C_{20}$, a $C_3$ to $C_{15}$, or a $C_3$ to $C_{10}$ hydrocarbylene group. In a further aspect, the $L^{12r}$ alkylene group, when present, independently can be a $C_3$ to $C_{30}$, a $C_3$ to $C_{20}$, a $C_3$ to $C_{15}$, or a $C_3$ to $C_{10}$ alkylene group. In an aspect, $L^{12r}$ can be prop-1,3-ylene group, a but-1,3-ylene group, a 3-methylbut-1,3-ylene group ($—CH_2CH_2C(CH_3)_2—$), a but-1,4-ylene group, a 1,4-pent-1,4-ylene group.

Generally, T of the heterocyclic 2-[(phosphinyl)aminyl] imines and/or the heterocyclic 2-[(phosphinyl)aminyl]imine chromium compound complexes can be oxygen or sulfur. In and aspect, T of the heterocyclic 2-[(phosphinyl)aminyl] imines and/or the heterocyclic 2-[(phosphinyl)aminyl]imine chromium compound complexes can be oxygen; or alternatively, sulfur.

Generally, $R^{2a}$ and/or $R^{2b}$, of the $N^2$-phosphinyl guanidines and/or the $N^2$-phosphinyl guanidine chromium compound complexes which have an $R^{2a}$ and/or $R^{2b}$ group, independently can be hydrogen or an organyl group; alternatively, hydrogen or an organyl group consisting of inert functional groups; alternatively, hydrogen or a hydrocarbyl group; alternatively, hydrogen; alternatively, an organyl group; alternatively, an organyl group consisting of inert functional groups; or alternatively, a hydrocarbyl group. In an aspect, the $R^{2a}$ and/or $R^{2b}$ organyl groups independently can be a $C_1$ to $C_{20}$, a $C_1$ to $C_{15}$, a $C_1$ to $C_{10}$, or a $C_1$ to $C_5$ organyl group. In some aspects, the $R^{2a}$ and/or $R^{2b}$ organyl groups consisting of inert functional groups independently can be a $C_1$ to $C_{20}$, a $C_1$ to $C_{15}$, a $C_1$ to $C_{10}$, or a $C_1$ to $C_5$ organyl group consisting of inert functional groups. In other aspects, the $R^{2a}$ and/or $R^{2b}$ hydrocarbyl groups independently can be a $C_1$ to $C_{20}$, a $C_1$ to $C_{15}$, a $C_1$ to $C_{10}$, or a $C_1$ to $C_5$ hydrocarbyl group.

In an aspect, $R^{2a}$ and $R^{2b}$, of the $N^2$-phosphinyl guanidines and/or the $N^2$-phosphinyl guanidine chromium compound complexes which have an $R^{2a}$ and/or $R^{2b}$ organyl group, independently can be an alkyl group, a substituted alkyl group, a cycloalkyl group, a substituted cycloalkyl group, an aryl group, a substituted aryl group, an aralkyl group, or a substituted aralkyl group; alternatively, an alkyl group or a substituted alkyl group; alternatively, a cycloalkyl group or a substituted cycloalkyl group; alternatively, an aryl group or a substituted aryl group; alternatively, an aralkyl group or a substituted aralkyl group; alternatively, an alkyl group, a cycloalkyl group, an aryl group, or an aralkyl group; alternatively, an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group. In any aspect disclosed herein, the $R^{2a}$ and/or $R^{2b}$ alkyl group independently can be $C_1$ to $C_{20}$, a $C_1$ to $C_{10}$, or a $C_1$ to $C_5$ alkyl group. In any aspect disclosed herein, the $R^{2a}$ and/or $R^{2b}$ cycloalkyl group independently can be a $C_4$ to $C_{20}$, a $C_4$ to $C_{15}$, or a $C_4$ to $C_{10}$ cycloalkyl group. In any aspect disclosed herein, the $R^{2a}$ and/or $R^{2b}$ substituted cycloalkyl group independently can be a $C_4$ to $C_{20}$, a $C_4$ to $C_{15}$, or a $C_4$ to $C_{10}$ substituted cycloalkyl group. In any aspect disclosed herein, the $R^{2a}$ and/or $R^{2b}$ aryl group independently can be a $C_6$ to $C_{20}$, a $C_6$ to $C_{15}$, or a $C_6$ to $C_{10}$ aryl group. In any aspect disclosed herein, the $R^{2a}$ and/or $R^{2b}$ substituted aryl group independently can be a $C_6$ to $C_{20}$, a $C_6$ to $C_{15}$, or a $C_6$ to $C_{10}$ substituted aryl group. Each substituent of a substituted cycloalkyl group (general or specific) and/or a substituted aryl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^{2a}$ and/or $R^{2b}$.

In an aspect, $R^1$ and $R^{2a}$ of the $N^2$-phosphinyl guanidines and/or the $N^2$-phosphinyl guanidine chromium compound complexes can be joined to form a group, $L^{12}$, wherein $L^{12}$, the $N^1$ nitrogen atom, and the $N^3$ nitrogen atom form a ring or a ring system. In another aspect, $R^3$ and $R^{2b}$ of the $N^2$-phosphinyl guanidines and/or the $N^2$-phosphinyl guanidine chromium compound complexes can be joined to form a group, $L^{23}$, wherein $L^{23}$, the $N^2$ nitrogen atom, and the $N^3$ nitrogen atom form a ring or a ring system. In an aspect, $L^{12}$ and/or $L^{23}$, of the $N^2$-phosphinyl guanidines and/or the $N^2$-phosphinyl guanidine chromium compound complexes which have an $L^{12}$ group and/or an $L^{23}$ group, independently can be an organylene group; alternatively, an organylene group consisting of inert functional groups; or alternatively, a hydrocarbylene group. The $L^{12}$ and/or $L^{23}$ organylene groups independently can be a $C_2$ to $C_{20}$, a $C_2$ to $C_{15}$, a $C_2$ to $C_{10}$, or a $C_2$ to $C_5$ organylene group. The $L^{12}$ and/or $L^{23}$ organylene groups consisting of inert functional groups independently can be a $C_2$ to $C_{20}$, a $C_2$ to $C_{15}$, a $C_2$ to $C_{10}$, or a $C_2$ to $C_5$ organylene group consisting of inert functional groups. The $L^{12}$ and/or $L^{23}$ hydrocarbylene groups independently can be a $C_2$ to $C_{20}$, a $C_2$ to $C_{15}$, a $C_2$ to $C_{10}$, or a $C_2$ to $C_5$ hydrocarbylene group.

In an aspect, $L^{12}$ of the $N^2$-phosphinyl guanidines, the $N^2$-phosphinyl guanidine chromium compound complexes, the heterocyclic 2-[(phosphinyl)aminyl]imines and/or the heterocyclic 2-[(phosphinyl)aminyl]imine chromium compound complexes which have an $L^{12}$ and $L^{23}$ of the $N^2$-phosphinyl guanidines and/or the $N^2$-phosphinyl guanidine chromium compound complexes which have an $L^{23}$, can have any structure provided in Table 1. In some aspects, $L^{12}$ and/or $L^{23}$ can have Structure 1L, Structure 2L, Structure 3L, Structure 4L or Structure 5L. In some aspects, $L^{12}$ and/or $L^{23}$ can have Structure 2L or Structure 3L; alternatively, Structure 4L or Structure 5L. In other aspects, $L^{12}$ and/or $L^{23}$ can have Structure 1L; alternatively, Structure 2L; alternatively, Structure 3L; alternatively, Structure 4L; or alternatively, Structure 5L. In some $N^2$-phosphinyl guanidine and $N^2$-phosphinyl guanidine chromium compound complex aspects, $L^{12}$ and/or $L^{23}$ can have Structure 6L. It should be noted that when $L^{12}$ or $L^{23}$ has Structure 6L the corresponding $R^{2b}$ or $R^{2a}$ is null because of the double bond link with the $N^3$ nitrogen atom of the $N^2$-phosphinyl guanidine and/or the $N^2$-phosphinyl guanidine chromium compound complex.

TABLE 1

Structures for Linking Groups $L^{12}$ and/or $L^{23}$.

| | |
|---|---|
| —$(CR^{L1}R^{L2})_m$— | Structure 1L |
| —$CR^{L3}R^{L4}$—$CR^{L5}R^{L6}$— | Structure 2L |
| —$CR^{L3}R^{L4}$—$CR^{L7}R^{L8}$—$CR^{L5}R^{L6}$— | Structure 3L |
| —$CR^{L11}$=$CR^{L12}$— | Structure 4L |
| $R^{L23}$—⌬—$R^{L26}$ (with $R^{L24}$, $R^{L25}$ on ring) | Structure 5L |
| =$CR^{L27}$—$CR^{L28}$=$CR^{L29}$— | Structure 6L |

Within the structures of Table 1, the undesignated valences of $L^{12}$ and/or $L^{23}$ represent the points at which $L^{12}$ and/or $L^{23}$, when present, attach to the respective nitrogen atoms of the $N^2$-phosphinyl guanidine and the $N^2$-phosphinyl guanidine chromium compound complex. Additionally, with the structures of Table 1, the undesignated valences of $L^{12}$ represent the points at which $L^{12}$ attach to T and the respective nitrogen atom of the heterocyclic 2-[(phosphinyl) aminyl]imine and/or the heterocyclic 2-[(phosphinyl)aminyl]imine chromium compound complex. Generally, m can be an integer ranging from 2 to 5. In further aspects, m can be 2 or 3; alternatively, m can be 2; or alternatively, m can be 3. $R^{L1}$ and $R^{L2}$ of the linking group having Structure 1L, $R^{L3}$, $R^{L4}$, $R^{L5}$, and $R^{L6}$ of the linking group having Structure 2L, $R^{L3}$, $R^{L4}$, $R^{L5}$, $R^{L6}$, $R^{L7}$, and $R^{L8}$, of the linking group having Structure 3L, $R^{L11}$ and $R^{L12}$ of the linking group having Structure 4L, $R^{L23}$, $R^{L24}$, $R^{L25}$, and $R^{L26}$ of the linking group having Structure 5L, $R^{L27}$, $R^{L28}$, and $R^{L29}$ of the linking group having Structure 6L independently can be a hydrogen or a non-hydrogen substituent group; or alternatively, hydrogen. Non-hydrogen substituent groups (general and specific) are independently disclosed herein and can be utilized without limitation to further describe the linking group having Structure 1L, Structure 2L, Structure 3L, Structure 4L, Structure 5L, and/or Structure 6L. In an aspect, $L^{12}$ and/or $L^{23}$ independently can be an eth-1,2-ylene group (—$CH_2CH_2$—), an ethen-1,2-ylene group (—CH=CH—), a prop-1,3-ylene group (—$CH_2CH_2CH_2$—), a 1-methylethen-1,2-ylene group (—C($CH_3$)=CH—), a but-1,3-ylene group (—$CH_2CH_2CH(CH_3)$—), a 3-methylbut-1,3-ylene group (—$CH_2CH_2C(CH_3)_2$—), or a phen-1,2-ylene group. In some non-limiting aspects, $L^{12}$ and/or $L^{23}$ be an eth-1,2-ylene group (—$CH_2CH_2$—), a prop-1,3-ylene group (—$CH_2CH_2CH_2$—), a 1-methylethen-1,2-ylene group (—C($CH_3$)=CH—), a but-1,3-ylene group (—$CH_2CH_2CH(CH_3)$—), or a 3-methylbut-1,3-ylene group (—$CH_2CH_2C(CH_3)_2$—); alternatively, an eth-1,2-ylene group (—$CH_2CH_2$—), an ethen-1,2-ylene group (—CH=CH—), a prop-1,3-ylene group (—$CH_2CH_2CH_2$—), or a phen-1,2-ylene group; alternatively, an eth-1,2-ylene group (—$CH_2CH_2$—) or a prop-1,3-ylene group (—$CH_2CH_2CH_2$—); alternatively, an ethen-1,2-ylene group (—CH=CH—) or a phen-1,2-ylene group.

In an aspect, $L^{12}$ can have a structure that can comprise at least one substituent located on the carbon atom attached to the $N^1$ nitrogen atom of the $N^2$-phosphinyl guanidine and/or the $N^2$-phosphinyl guanidine chromium compound complex; alternatively, can comprise only one substituent located on the carbon atom attached to the $N^1$ nitrogen atom of the $N^2$-phosphinyl guanidine and/or the $N^2$-phosphinyl guanidine chromium compound complex; or alternatively, can comprise two substituents located on the carbon atom attached to the $N^1$ nitrogen atom of the $N^2$-phosphinyl guanidine and/or the $N^2$-phosphinyl guanidine chromium compound complex. In another aspect, $L^{12}$ can have a structure that can consist of one substituent located on the carbon atom attached to the $N^1$ nitrogen atom the $N^2$-phosphinyl guanidine and/or the $N^2$-phosphinyl guanidine chromium compound complex; or alternatively, can consist of two substituents located on the carbon atom attached to the $N^1$ nitrogen atom of the $N^2$-phosphinyl guanidine and/or the $N^2$-phosphinyl guanidine chromium compound complex.

In an aspect, $R^{2a}$ and $R^{2b}$ of the $N^2$-phosphinyl guanidines and/or the $N^2$-phosphinyl guanidine chromium compound complexes can be joined to form a group, $L^{22}$, wherein $R^2a$ $R^{2b}$, and the $N^3$ nitrogen (or $L^{22}$ and the $N^3$ nitrogen) form a ring or ring system. In an aspect, $L^{22}$ of the $N^2$-phosphinyl guanidines and/or the $N^2$-phosphinyl guanidine chromium compound complexes having an $L^{22}$ group can be an organylene group; alternatively, an organylene group consisting of inert functional groups; or alternatively, a hydrocarbylene group. The $L^{22}$ organylene group can be a $C_3$ to $C_{20}$, a $C_3$ to $C_{15}$, or a $C_3$ to $C_{10}$ organylene group. The $L^{22}$ organylene group consisting of inert functional groups can be a $C_3$ to $C_{20}$, a $C_3$ to $C_{15}$, or a $C_3$ to $C_{10}$ organylene group consisting of inert functional groups. The $L^{22}$ hydrocarbylene group can be a $C_4$ to $C_{20}$, a $C_4$ to $C_{15}$, or a $C_4$ to $C_{10}$ hydrocarbylene group.

In an aspect, $L^{22}$ can have any structure provided in Table 2. In some aspects, $L^{22}$ can have Structure 11L, Structure 12L, Structure 13L, Structure 14L, Structure 15L, or Structure 16L. In other aspects, $L^{22}$ can have Structure 11L; alternatively, Structure 12L; alternatively, Structure 13L; alternatively, Structure 14L; or alternatively, Structure 15L.

TABLE 2

Structures for Linking Groups $L^{22}$.

| | |
|---|---|
| —$(CR^{L31}R^{L32})_n$— | Structure 11L |
| —$CR^{L41}R^{L42}$—$CR^{L45}R^{L46}CR^{L47}R^{L48}CR^{L43}R^{L44}$— | Structure 12L |
| —$CR^{L41}R^{L42}$—$CR^{L45}R^{L46}$—$CR^{L49}R^{L50}$—$CR^{L47}R^{L48}$—$CR^{L43}R^{L44}$— | Structure 13L |
| —$CR^{L41}R^{L42}$—$CR^{L45}R^{L46}$—O—$CR^{L47}R^{L48}$—$CR^{L43}R^{L44}$— | Structure 14L |
| —$CR^{L51}$=$CR^{L53}$—$CR^{L54}$=$CR^{L52}$— | Structure 15L |

Within the structures of Table 2, the undesignated valences represent the points at which $L^{22}$ of the $N^2$-phosphinyl guanidine and/or the $N^2$-phosphinyl guanidine chromium compound complex, when present, attach to the $N^3$ nitrogen atom of the $N^2$-phosphinyl guanidine and/or the $N^2$-phosphinyl guanidine chromium compound complex. Generally, n can be an integer ranging from 4 to 7. In further aspects, n can be 4 or 5; alternatively, n can be 4; or alternatively, n can be 5. $R^{L31}$ and $R^{L32}$ of the linking group having Structure 11 L, $R^{L41}$, $R^{L42}$, $R^{L43}$, $R^{L44}$, $R^{L45}$, $R^{L46}$, $R^{L47}$, and $R^{L48}$ of the linking group having Structure 12L, $R^{L41}$, $R^{L42}$, $R^{L43}$, $R^{L44}$, $R^{L45}$, $R^{L46}$, $R^{L47}$, $R^{L48}$, $R^{L49}$, and $R^{L50}$ of the linking group having Structure 13L, $R^{L41}$, $R^{L42}$, $R^{L43}$, $R^{L44}$, $R^{L45}$, $R^{L46}$, $R^{L47}$, and $R^{L48}$ of the linking group having Structure 14L, and $R^{L41}$, $R^{L42}$, $R^{L43}$, $R^{L44}$, $R^{L45}$, $R^{L46}$, $R^{L47}$, and $R^{L48}$ of the linking group having Structure 15L independently can be a hydrogen or a non-hydrogen substituent group; alternatively, hydrogen. Non-hydrogen substituent groups are independently disclosed herein and can be utilized without limitation to further describe the linking group having Structure 11L, Structure 12L, Structure 13L, Structure 14L, and/or Structure 15L. In an aspect, $L^{22}$ can be a but-1,4-ylene group, a pent-1,4-ylene group, a pent-1,5-ylene group, a hex-2,5-ylene group, a hex-1,5-ylene group, a hept-2,5-ylene group, a buta-1,3-dien-1,4-ylene group, or a bis(eth-2-yl)ether group; or alternatively, a but-1,4-ylene group, a pent-1,5-ylene group, or a bis(eth-2-yl)ether group.

Generally, $R^3$ of the $N^2$-phosphinyl formamidines, the $N^2$-phosphinyl formamidine chromium compound complexes, the $N^2$-phosphinyl amidines, the $N^2$-phosphinyl amidine chromium compound complexes, the $N^2$-phosphinyl guanidines, the $N^2$-phosphinyl guanidine chromium compound complexes, the heterocyclic 2-[(phosphinyl)aminyl] imines, and/or the heterocyclic 2-[(phosphinyl)aminyl] imine chromium compound complexes which have an $R^3$ group can be hydrogen or an organyl group; hydrogen or an organyl group consisting of inert functional group; alternatively, hydrogen or a hydrocarbyl group; alternatively, hydrogen; alternatively, an organyl group; alternatively, an organyl group consisting of inert functional group; or alternatively, a hydrocarbyl group. In an aspect, the $R^3$ organyl group can be a $C_1$ to $C_{20}$, a $C_1$ to $C_{15}$, a $C_1$ to $C_{10}$, or a $C_1$ to $C_5$ organyl group. In an aspect, the $R^3$ organyl group consisting of inert functional groups can be a $C_1$ to $C_{20}$, a $C_1$ to $C_{15}$, a $C_1$ to $C_{10}$, or a $C_1$ to $C_5$ organyl group consisting of inert functional groups. In an aspect, the $R^3$ hydrocarbyl group can be a, a $C_1$ to $C_{20}$, a $C_1$ to $C_{15}$, a $C_1$ to $C_{10}$, or a $C_1$ to $C_5$ hydrocarbyl group. In other aspects, $R^3$ of the $N^2$-phosphinyl formamidine, the $N^2$-phosphinyl formamidine chromium compound complexes, the $N^2$-phosphinyl amidines, the $N^2$-phosphinyl amidine chromium compound complexes, the $N^2$-phosphinyl guanidines, the $N^2$-phosphinyl guanidine chromium compound complexes, the heterocyclic 2-[(phosphinyl)aminyl]imines, and/or the heterocyclic 2-[(phosphinyl)aminyl]imine chromium compound complexes which have an $R^3$ group can be a $C_1$ to $C_{30}$, a $C_1$ to $C_{20}$, a $C_1$ to $C_{15}$, a $C_1$ to $C_{10}$, or a $C_1$ to $C_5$ alkyl group. In yet other aspects, $R^3$ of the $N^2$-phosphinyl formamidine, the $N^2$-phosphinyl formamidine chromium compound complexes, the $N^2$-phosphinyl amidines, the $N^2$-phosphinyl amidine chromium compound complexes, the $N^2$-phosphinyl guanidines, the $N^2$-phosphinyl guanidine chromium compound complexes, the heterocyclic 2-[(phosphinyl)aminyl] imines, and/or the heterocyclic 2-[(phosphinyl)aminyl] imine chromium compound complexes can be a phenyl group or a $C_6$ to $C_{20}$ substituted phenyl group; alternatively, a phenyl group or a $C_6$ to $C_{15}$ substituted phenyl group; or alternatively, a phenyl group or a $C_6$ to $C_{10}$ substituted phenyl group. Substituent groups (general and specific) are provided herein and these substituent groups can be utilized to further describe the substituted phenyl groups which can be utilized as $R^3$ the $N^2$-phosphinyl formamidine, the $N^2$-phosphinyl formamidine chromium compound complexes, the $N^2$-phosphinyl amidines, the $N^2$-phosphinyl amidine chromium compound complexes, the $N^2$-phosphinyl guanidines, and/or the $N^2$-phosphinyl guanidine chromium compound complexes having a non-hydrogen $R^3$ group.

Generally, $R^4$ and/or $R^5$ of the $N^2$-phosphinyl formamidines, the $N^2$-phosphinyl formamidine chromium compound complexes, the $N^2$-phosphinyl amidines, the $N^2$-phosphinyl amidine chromium compound complexes, the $N^2$-phosphinyl guanidines, the $N^2$-phosphinyl guanidine chromium compound complexes, the heterocyclic 2-[(phosphinyl)aminyl]imines, and/or the heterocyclic 2-[(phosphinyl)aminyl]imine chromium compound complexes independently can be an organyl group; alternatively, an organyl group consisting of inert functional groups; or alternatively, a hydrocarbyl group. In an aspect, the $R^4$ and/or $R^5$ organyl groups can be a $C_1$ to $C_{20}$, a $C_1$ to $C_{15}$, a $C_1$ to $C_{10}$, or a $C_1$ to $C_5$ organyl group. In an aspect, the $R^4$ and/or $R^5$ organyl groups consisting of inert functional groups can be a $C_1$ to $C_{20}$, a $C_1$ to $C_{15}$, a $C_1$ to $C_{10}$, or a $C_1$ to $C_5$ organyl group consisting of inert functional groups. In an aspect, the $R^4$ and/or $R^5$ hydrocarbyl groups can be a, a $C_1$ to $C_{20}$, a $C_1$ to $C_{15}$, a $C_1$ to $C_{10}$, or a $C_1$ to $C_5$ hydrocarbyl group. In an aspect, $R^4$ and/or $R^5$ of the $N^2$-phosphinyl formamidine, the $N^2$-phosphinyl formamidine chromium compound complexes, the $N^2$-phosphinyl amidines, the $N^2$-phosphinyl amidine chromium compound complexes, the $N^2$-phosphinyl guanidines, the $N^2$-phosphinyl guanidine chromium compound complexes, the heterocyclic 2-[(phosphinyl)aminyl]imines, and/or the heterocyclic 2-[(phosphinyl)aminyl]imine chromium compound complexes independently can be an alkyl group, a substituted alkyl group, a cycloalkyl group, a substituted cycloalkyl group, an aryl group, a substituted aryl group, an aralkyl group, or a substituted aralkyl group; alternatively, an alkyl group or a substituted alkyl group; alternatively, a cycloalkyl group or a substituted cycloalkyl group; alternatively, an aryl group or a substituted aryl group; alternatively, an aralkyl group or a substituted aralkyl group; alternatively, an alkyl group, a cycloalkyl group, an aryl group, or an aralkyl group; alternatively, an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect disclosed herein, the $R^4$ and/or $R^5$ alkyl groups independently can be a $C_1$ to $C_{20}$, a $C_1$ to $C_{10}$, or a $C_1$ to $C_5$ alkyl group. In any aspect disclosed herein, the $R^4$ and/or $R^5$ substituted alkyl groups independently can be a $C_1$ to $C_{20}$, a $C_1$ to $C_{10}$, or a $C_1$ to $C_5$ substituted alkyl group. In any aspect disclosed herein, the $R^4$ and/or $R^5$ cycloalkyl groups independently can be a $C_4$ to $C_{20}$, a $C_4$ to $C_{15}$, or a $C_4$ to $C_{10}$ cycloalkyl group. In any aspect disclosed herein, the $R^4$ and/or $R^5$ substituted cycloalkyl groups independently can be a $C_4$ to $C_{20}$, a $C_4$ to $C_{15}$, or a $C_4$ to $C_{10}$ substituted cycloalkyl group. In any aspect disclosed herein, the $R^4$ and/or $R^5$ aryl groups independently can be a $C_6$ to $C_{20}$, a $C_6$ to $C_{15}$, or a $C_6$ to $C_{10}$ aryl group. In any aspect disclosed herein, the $R^4$ and/or $R^5$ substituted aryl group independently can be a $C_6$ to $C_{20}$, a $C_6$ to $C_{15}$, or a $C_6$ to $C_{10}$ substituted aryl group. In any aspect disclosed herein, the $R^4$ and/or $R^5$ aralkyl groups independently can be a $C_7$ to $C_{20}$, a $C_7$ to $C_{15}$, or a $C_7$ to $C_{10}$ aralkyl group. In any aspect disclosed herein, the $R^4$ and/or $R^5$ substituted aryl groups independently can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^4$ and/or $R^5$.

In an aspect, $R^4$ and $R^5$ independently can be a methyl group, an ethyl group, a propyl group, a butyl group, a pentyl group, a hexyl group, a heptyl group, or an octyl group; or alternatively, a methyl group, an ethyl group, an n-propyl (1-propyl) group, an iso-propyl (2-propyl) group, a 2-methyl-1-propyl group, a tert-butyl (2-methyl-2-propyl) group, or a neopentyl (2,2-dimethyl-1-propyl) group. In some aspects, the alkyl groups which can be utilized as $R^4$ and/or $R^5$ can be substituted. Each substituent of a substituted alkyl group independently can be a halogen or a hydrocarboxy group; alternatively, a halogen; or alternatively, a hydrocarboxy group. Substituent halogens and substituent hydrocarboxy (general and specific) groups are independently disclosed herein. These substituent halogens and substituent hydrocarboxy groups can be utilized without limitation to further describe a substituted alkyl group which can be utilized as $R^4$ and/or $R^5$.

In an aspect, $R^4$ and $R^5$ independently can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group. In an aspect, the substituted cycloalkyl group, which can be utilized for $R^4$ and/or $R^5$, can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; or alternatively, a 2,6-disubstituted cyclohexyl group or a 2,5-disubstituted cyclopentyl group. In an aspect where the substituted cycloalkyl group (general or specific) has more the one substituent, the substituents can be the same or different; alternatively, the same; or alternatively, different. Each substituent of a cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein.

These substituent halogens, substituent hydrocarbyl groups, and substituent hydrocarboxy groups can be utilized without limitation to further describe a substituted cycloalkyl group (general or specific) which can be utilized as $R^4$ and/or $R^5$.

In a non-limiting aspect, $R^4$ and $R^5$ independently can be a cyclohexyl group, a 2-alkylcyclohexyl group, or a 2,6-dialkylcyclohexyl group; or alternatively, a cyclopentyl group, a 2-alkylcyclopentyl group, or a 2,5-dialkylcyclopentyl group. Alkyl substituent groups (general and specific) are independently described herein and these alkyl substituent groups can be utilized, without limitation, to further described alkylcyclohexyl groups (general or specific), dialkylcyclohexyl groups (general or specific), alkylcyclopentyl groups (general or specific), and/or dialkylcyclopentyl groups (general or specific) which can be utilized as $R^4$ and/or $R^5$. Generally, the alkyl substituents of a disubstituted cyclohexyl or cyclopentyl group can be the same; or alternatively, the alkyl substituents of a dialkyl cyclohexyl or cyclopentyl group can be different. In some non-limiting aspects, $R^4$ and $R^5$ independently can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting aspects, $R^4$ and $R^5$ independently can be, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an aspect, $R^4$ and $R^5$ independently can be a phenyl group, a substituted phenyl group; alternatively, a phenyl group; or alternatively, a substituted phenyl group. In an aspect, the substituted phenyl group, which can be utilized for $R^4$ and/or $R^5$, can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; or alternatively, a 2,4,6-trisubstituted phenyl group. In an aspect, one or more substituents of a multi-substituted phenyl group utilized as $R^4$ and/or $R^5$ can be the same or different; alternatively, all the substituents of a multi-substituted cycloalkyl group can be the same; or alternatively, all the substituents of a multi-substituted cycloalkyl group different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^4$ and/or $R^5$.

In a non-limiting aspect, $R^4$ and $R^5$ independently can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^4$ and/or $R^5$. Generally, the alkyl substituents of a dialkylphenyl group (general or specific) or a trialkylphenyl group (general or specific) can be the same; or alternatively, the alkyl substituents of a dialkylphenyl group (general or specific) or a trialkyl phenyl group (general or specific) can be different. In some non-limiting aspects, $R^4$ and $R^5$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting aspect, $R^4$ and $R^5$ can be a phenyl group, a 2-alkoxyphenyl group, or a 4-alkoxyphenyl group. In some non-limiting aspects, $R^4$ and/or $R^5$ can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group. In a non-limiting aspect, $R^4$ and $R^5$ independently can be a phenyl group, a 2-halophenyl group, a 4-halophenyl group, or a 2,6-dihalophenylgroup. Generally, the halides of a dihalophenyl group can be the same; or alternatively, the halides of a dihalophenyl group can be different. In some aspects, $R^4$ and $R^5$ independently can be a phenyl group, a 2-fluorophenyl group, a 4-fluorophenyl group, or a 2,6-difluorophenyl group.

In an aspect, $R^4$ and $R^5$ independently can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl which can be utilized as $R^4$ and/or $R^5$.

In further aspects, $R^4$ and $R^5$ can be joined to form a ring or a ring system containing the phosphorus atom. The joining of $R^4$ and $R^5$ can be designated as $L^{45}$ and can be an organylene group; alternatively, an organylene group consisting of inert functional groups; alternatively, a hydrocarbylene group; or alternatively, an alkylene group. In an aspect, the $L^{45}$ organylene group, when present, can be a $C_4$ to $C_{30}$, a $C_4$ to $C_{20}$, a $C_4$ to $C_{15}$, or a $C_4$ to $C_{10}$ organylene group. In an aspect, the $L^{45}$ organylene group consisting of inert functional groups, when present, can be a $C_4$ to $C_{30}$, a $C_4$ to $C_{20}$, a $C_4$ to $C_{15}$, or a $C_4$ to $C_{10}$ organylene group consisting of inert functional groups. In an aspect, the $L^{45}$ hydrocarbyl group, when present, independently can be a $C_4$ to $C_{30}$, a $C_4$ to $C_{20}$, a $C_4$ to $C_{15}$, or a $C_4$ to $C_{10}$ hydrocarbylene group. In a further aspect, the $L^{45}$ alkylene group, when present, independently can be a $C_4$ to $C_{30}$, a $C_4$ to $C_{20}$, a $C_4$ to $C_{15}$, or a $C_4$ to $C_{10}$ alkylene group. In an aspect, $L^{45}$ can be a but-1,4-ylene group, a 1,4-diphenylbut-1,4-ylene group, a 1,4-di(2-methylphenyl)but-1,4-ylene group, 1,4-di(4-methylphenyl)but-1,4-ylene group, 1,4-di(4-t-butylphenyl)but-1,4-ylene group, a 1,4-di(3,5-dimethylphenyl)but-1,4-ylene group, a pent-1,4-ylene group, a 1-phenylpenta-1,4-ylene group, a 4-phenylpenta-1,4-ylene group, a hex-2,5-ylene group, a 2,2'-biphenylene group, a 2,2'-(methandiyl)dipheylene group, or a 2,2'-(1,2-ethandiyl)diphenylene group.

In an aspect, the heteroatomic ligand or the heteroatomic ligand of the heteroatomic ligand chromium compound complex can have the formula $(R^{1s})_mX^{1s}(L^{1s})X^{2s}(R^{2s})_n$ while the heteroatomic ligand chromium compound complex can have the formula:

In some aspects, the heteroatomic ligand or the heteroatomic ligand of the heteroatomic ligand chromium compound complex can have two groups capable of being described by the formula $(R^{1s})_mX^{1s}(L^{1s})X^{2s}(R^{2s})_n$. In instances wherein the heteroatomic ligand can have two groups capable of being described by the formula $(R^{1s})_mX^{1s}(L^{1s})X^{2s}(R^{2s})_n$, the two $L^{1s}$ groups are linked and the heteroatomic ligand and the heteroatomic ligand chromium compound complex can have the formulas:

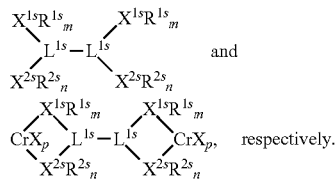

respectively.

In the heteroatomic ligand or the heteroatomic ligand of the heteroatomic ligand chromium compound complex having formula $(R^{1s})_mX^{1s}(L^{1s})X^{2s}(R^{2s})_n$ or having two linked $(R^{1s})_mX^{1s}(L^{1s})X^{2s}(R^{2s})_n$ groups, each $X^{1s}$ and each $X^{2s}$ independently can be selected from the group consisting of N, P, O, and S; each $L^{1s}$ can be an independent linking group between the respective $X^{1s}$s and $X^{2s}$s; each m and each n independently can be 1 or 2; and each $R^{1s}$ and each $R^{2s}$ independently can be a hydrogen, an organyl group (or alternatively, an organyl group consisting of inert functional group; or alternatively, a hydrocarbyl group), or a heterohydrocarbyl group, where when there are two or more $R^{1s}$s and/or two $R^{2s}$s, each $R^{1s}$ can be the same or different (alternatively, the same; or alternatively, different) and/or each $R^{2s}$ can be the same or different (alternatively, the same; or alternatively, different). $L^{1s}$, $X^{1s}$, $X^{2s}$, $R^{1s}$, $R^{2s}$, m, and n are independent elements of any heteroatomic ligand or any heteroatomic ligand of the heteroatomic ligand chromium compound complex which have an $L^{1s}$, $X^{1s}$, $X^{2s}$, $R^{1s}$, $R^{2s}$ m, and/or n and are independently described herein. These independent descriptions of $L^{1s}$, $X^{1s}$, $X^{2s}$, $R^{1s}$, $R^{2s}$, m, and n can be utilized without limitation, and in any combination, to further describe any heteroatomic ligand or any heteroatomic ligand of the heteroatomic ligand chromium compound complex which have an $L^{1s}$, $X^{1s}$, $X^{2s}$, $R^{1s}$, $R^{2s}$, m, and/or n. Additionally, $CrX_p$ is an independent element of the heteroatomic ligand chromium compound complex, and is independently described herein, and can be utilized without limitation, and in any combination with $L^{1s}$, $X^{1s}$, $X^{2s}$, $R^{1s}$, $R^{2s}$, m, and n of the heteroatomic ligand to further describe the heteroatomic ligand chromium compound complexes contemplated herein.

In an aspect, each $X^{1s}$ and each $X^{2s}$ of any heteroatomic ligand or any heteroatomic ligand of any heteroatomic ligand chromium compound complex described herein having an $X^{1s}$ and/or $X^{2s}$ can be independently selected from N, P, O, and S; alternatively, independently selected from N and P; or alternatively, independently selected from O and S. In some aspects, each $X^{1s}$ and each $X^{2s}$ can be N; alternatively, P; alternatively, O; or alternatively, S. Each m and each n of any heteroatomic ligand or any heteroatomic ligand of any heteroatomic ligand chromium compound complex described herein having an m and/or n can be independently selected from 1 or 2; alternatively, 1; or alternatively, 2. Is some particular aspects, each m and/or each n can be 1 when $X^{1s}$ and/or $X^{2s}$, respectively, is O or S; alternatively, O; or alternatively, S. In some other particular aspects, each m and/or each n can be 2 when $X^{1s}$ and/or $X^{2s}$, respectively, is N or P; alternatively, N; or alternatively, P.

In a non-limiting aspect, the heteroatomic ligand can have the formula $R^{1s}S(L^{1s})SR^{2s}$, $(R^{1s})_2P(L^{1s})P(R^{2s})_2$, or $(R^{1s})_2N(L^{1s})N(R^{2s})_2$; alternatively, $R^{1s}S(L^{1s})SR^{2s}$; alternatively, $(R^{1s})_2P(L^{1s})P(R^{2s})_2$; or alternatively, $(R^{1s})_2N(L^{1s})N(R^{2s})_2$ while the heteroatomic ligand chromium compound complex can have any one of the formulas

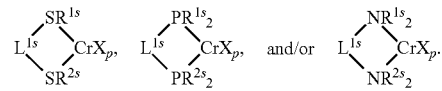

In non-limiting aspects where the heteroatomic ligand or the heteroatomic ligand of the heteroatomic ligand chromium compound complex has two linked heteroatomic groups, the heteroatomic ligand can have the formula selected from one or more of

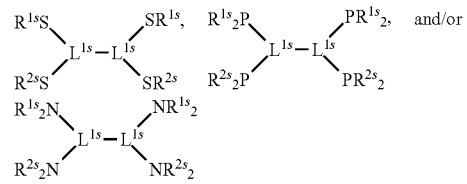

while the heteroatomic ligand chromium compound complex can have any one of the formulas

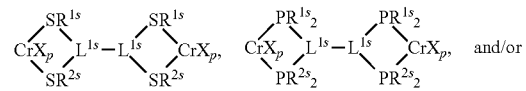

-continued

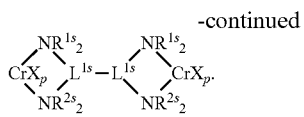

In an aspect, each $L^{1s}$ of any heteroatomic ligand or any heteroatomic ligand of the heteroatomic ligand chromium compound complex described herein independently can be any group capable of linking group $X^{1s}$ and $X^{2s}$ (and other $L^{1s}$ group when the heteroatomic ligand or heteroatomic ligand of the heteroatomic ligand chromium compound complex when there are more than one $L^{1s}$ group). In some aspects, each $L^{1s}$ independently can be an organylene group, an amin-di-yl group, or a phosphin-di-yl group; alternatively, an organylene group consisting of inert functional groups, an amin-di-yl group, or a phosphin-di-yl group; alternatively, a hydrocarbylene group, an amin-di-yl group, or a phosphin-di-yl group; alternatively an amin-di-yl group or a phosphin-di-yl group; alternatively, an organylene group; alternatively, an organylene group consisting of inert functional groups; alternatively, a hydrocarbylene group; alternatively, an amin-di-yl group; or alternatively, a phosphin-di-yl group. When there is more than one $L^{1s}$ group in the heteroatomic ligand or heteroatomic ligand of the heteroatomic ligand chromium compound complex each $L^{1s}$ independently can be an organic, an amine group, or a phosphine group; alternatively, an organic group consisting of inert functional groups, an amine group, or a phosphine group; alternatively, a hydrocarbon group, an amine group, or a phosphine group; alternatively an amine group or a phosphine group; alternatively, an organic group; alternatively, an organic group consisting of inert functional groups; alternatively, a hydrocarbon group; alternatively, an amine group; or alternatively, a phosphine group. In an aspect, the $L^{1s}$ organylene group or organic group can be a $C_1$ to $C_{20}$, a $C_1$ to $C_{15}$, a $C_1$ to $C_{10}$, or, a $C_1$ to $C_5$ organylene or organic group. In an aspect, the $L^{1s}$ organylene group consisting of inert functional groups can be a $C_1$ to $C_{20}$, a $C_1$ to $C_{15}$, a $C_1$ to $C_{10}$, or, a $C_1$ to $C_5$ organylene or organic group consisting of inert functional groups. In an aspect, the $L^{1s}$ hydrocarbylene group can be a $C_1$ to $C_{20}$, a $C_1$ to $C_{15}$, a $C_1$ to $C_{10}$, or a $C_1$ to $C_5$ hydrocarbylene or hydrocarbon group. In an aspect, the amin-di-yl or amine group can be a $C_1$ to $C_{30}$, a $C_1$ to $C_{20}$, a $C_1$ to $C_{15}$, or a $C_1$ to $C_{10}$ amin-di-yl or amine group. In an aspect, the phosphin-di-yl or phosphine group can be a $C_1$ to $C_{30}$, a $C_1$ to $C_{20}$, a $C_1$ to $C_{15}$, or a $C_1$ to $C_{10}$ phosphin-di-yl or phosphine group.

In an aspect, each $L^{1s}$ organylene or organic group can have the formula $-(L^{3s})NR^{5s}(L^{4s})-$ or $-(L^{3s})PR^{5s}(L^{4s})-$; alternatively, $-(L^{3s})NR^{5s}(L^{4s})-$; or alternatively, $-(L^{3s})PR^{5s}(L^{4s})-$. In an aspect, the each amin-di-yl group can have the formula $-N(R^{5s})-$. In an aspect, each phosphin-di-yl group can have the formula $-P(R^{5s})-$. In these $L^{1s}$ group formulas, the dashes represent the undesignated valance to which the $X^{1s}$ and $X^{2s}$ of the heteroatomic ligand or the heteroatomic ligand of the heteroatomic ligand of the heteroatomic ligand chromium compound complex described herein attach. When there is more than one $L^{1s}$ group in the heteroatomic ligand or heteroatomic ligand of the heteroatomic ligand chromium compound complex, the $R^5$, of each $L^{1s}$ group can be combined into a linking group designated as $L^{2s}$. In some non-limiting aspects, the heteroatomic ligand can have Structure PNP1, Structure PNP2, Structure NRNRN, Structure PRPRP, Structure SRNRS, Structure PRNRP, and Structure NRPRN; alternatively, Structure PNP1 or Structure PNP2; alternatively, Structure PRPRP, Structure SRNRS, or Structure PRNRP; alternatively, Structure PNP1; alternatively, Structure PNP2; alternatively, Structure NRNRN; alternatively, Structure PRPRP; alternatively, Structure SRNRS; alternatively, Structure PRNRP; or alternatively, Structure NRPRN. In some non-limiting aspects, the heteroatomic ligand chromium compound complex having a heteroatomic ligand $(R^{1s})_mX^{1s}(L^{1s})X^{2s}(R^{2s})_n$ which can be utilized in catalyst systems described herein can have Structure PNPCr-1, Structure PNPCr-2, Structure NRNRNCr-1, Structure PRPRPC-1r, Structure SRNRSCr-1, Structure PRNRPC-1r, and Structure NRPRNCr-1; alternatively, Structure PNPCr-1 or Structure PNPCr-2; alternatively, Structure PRPRPCr-1, Structure SRNRSCr-1, or Structure PRNRPC-1r; alternatively, Structure PNPCr-1; alternatively, Structure PNPCr-2; alternatively, Structure NRNRNC-1r; alternatively, Structure PRPRPCr-1; alternatively, Structure SRNRSCr-1; alternatively, Structure PRNRPCr-1; or alternatively, Structure NRPRNC-1r.

Structure PNP-1

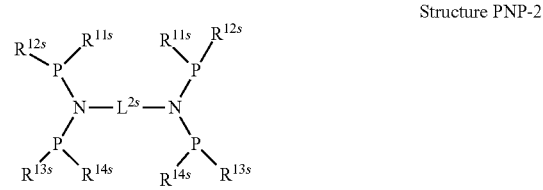

Structure PNP-2

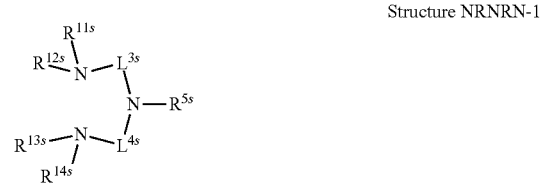

Structure NRNRN-1

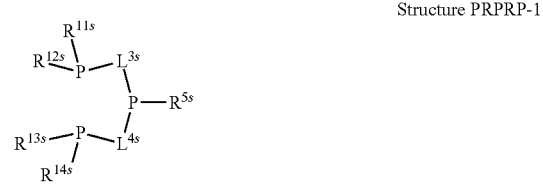

Structure PRPRP-1

Structure SRNRS-1

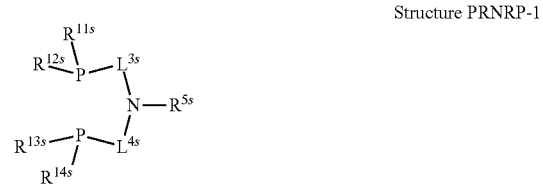

Structure PRNRP-1

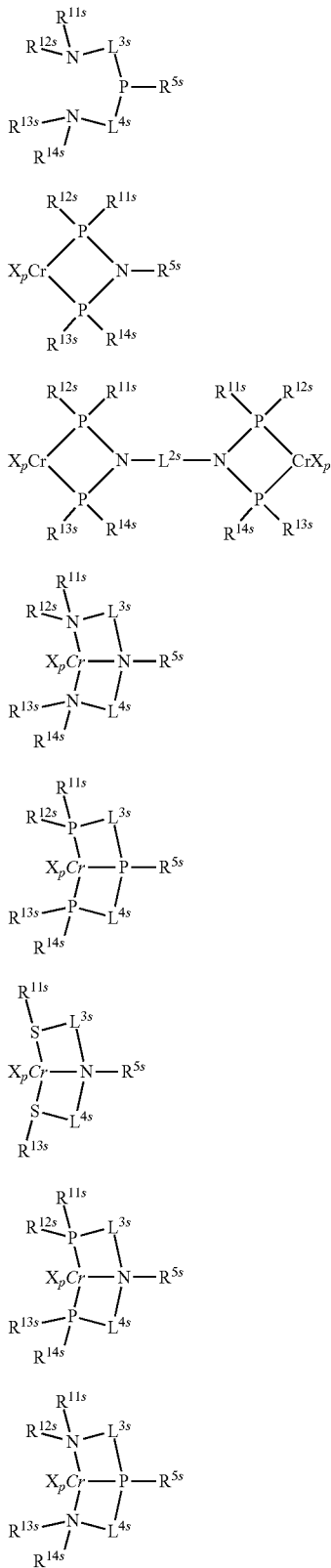

Structure NRPRN-1
Structure PNPCr-1
Structure PNPCr-2
Structure NRNRNCr-1
Structure PRPRPCr-1
Structure SRNRSCr-1
Structure PRNRPCr-1
Structure NRPRNCr-1

The $R^{5s}$, $L^{2s}$, $L^{3s}$, $L^{4s}$, $R^{11s}$, $R^{12s}$, $R^{13s}$, and $R^{14s}$ are each independent elements of the heteroatomic ligands having Structure PNP-1, Structure PNP-2, Structure NRNRN-1, Structure PRPRP-1, Structure SRNRS-1, Structure PRNRP-1, or Structure NRPRN-1, and/or the heteroatomic ligand of the heteroatomic ligand chromium compound complexes having Structure PNPCr-1, Structure PNPCr-2, Structure NRNRNCr-1, Structure PRPRPCr-1, Structure SRNRSCr-1, Structure PRNRPCr-1, and Structure NRPRNCr-1 in which they occur and are independently described herein. The independent descriptions of $R^{5s}$, $L^{2s}$, $L^{3s}$, $L^{4s}$, $R^{11s}$, $R^{12s}$, $R^{13s}$, and $R^{14s}$ can be utilized without limitation, and in any combination, to further describe the heteroatomic ligand structures and/or the heteroatomic ligand chromium compound complex structure in which they occur. Similarly, X and p are independent elements of the heteroatomic ligand chromium compound complexes having Structure PNPCr-1, Structure PNPCr-2, Structure NRNRNCr-1, Structure PRPRPCr-1, Structure SRNRSCr-1, Structure PRNRPCr-1, and Structure NRPRNCr-1 and are independently described herein. The independent description of X and p can be utilized without limitation, and in any combination, with the independently described $R^{5s}$, $L^{2s}$, $L^{3s}$, $L^{4s}$, $R^{11s}$, $R^{12s}$, $R^{13s}$, and $R^{14s}$ provided herein to further describe any heteroatomic ligand chromium compound complex having Structure PNPCr-1, Structure PNPCr-2, Structure NRNRNCr-1, Structure PRPRPCr-1, Structure SRNRSCr-1, Structure PRNRPCr-1, and/or Structure NRPRNCr-1.

Generally, $R^{1s}$, $R^{2s}$, $R^{11s}$, $R^{12s}$, $R^{13s}$, and/or $R^{14s}$, of any heteroatomic ligand structure depicted herein and/or any heteroatomic ligand chromium compound complex depicted herein having an $R^{1s}$, $R^{2s}$, $R^{11s}$, $R^{12s}$, $R^{13s}$, and/or $R^{14s}$ group, independently can be an organyl group; alternatively, an organyl group consisting of inert functional groups; or alternatively, a hydrocarbyl group. In an aspect, the organyl group which can be utilized as $R^{1s}$, $R^{2s}$, $R^{11s}$, $R^{12s}$, $R^{13s}$, and/or $R^{14s}$ independently can be a $C_1$ to $C_{20}$, a $C_1$ to $C_{15}$, a $C_1$ to $C_{10}$, or a $C_1$ to $C_5$ organyl group. In an aspect, the organyl group consisting of inert functional groups which can be utilized as $R^{1s}$, $R^{2s}$, $R^{11s}$, $R^{12s}$, $R^{13s}$, and/or $R^{14s}$ independently can be a $C_1$ to $C_{20}$, a $C_1$ to $C_{15}$, a $C_1$ to $C_{10}$, or a $C_1$ to $C_5$ organyl group consisting of inert functional groups. In an aspect, the hydrocarbyl group which can be utilized as $R^{1s}$, $R^{2s}$, $R^{11s}$, $R^{12s}$, $R^{13s}$, and/or $R^{14s}$ independently can be a $C_1$ to $C_{20}$, a $C_1$ to $C_{15}$, a $C_1$ to $C_{10}$, or a $C_1$ to $C_5$ hydrocarbyl group.

In an aspect, each $R^{1s}$, $R^{2s}$, $R^{11s}$, $R^{12s}$, $R^{13s}$, and/or $R^{14s}$ of any heteroatomic ligand structure depicted herein and/or any heteroatomic ligand chromium compound complex depicted herein having an $R^{1s}$, $R^{2s}$, $R^{11s}$, $R^{12s}$, $R^{13s}$, and/or $R^{14s}$ group independently can an alkyl group, a substituted alkyl group, a cycloalkyl group, a substituted cycloalkyl group, an aryl group, a substituted aryl group, an aralkyl group, or a substituted aralkyl group; alternatively, an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other aspects, each $R^{1s}$, $R^{2s}$, $R^{11s}$, $R^{12s}$, $R^{13s}$, and/or $R^{14s}$ of any heteroatomic ligand structure depicted herein and/or any heteroatomic ligand chromium compound complex depicted herein having an $R^{1s}$, $R^{2s}$, $R^{11s}$, $R^{12s}$, $R^{13s}$, and/or $R^{14s}$ group independently can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect disclosed herein, each $R^{1s}$, $R^{2s}$, $R^{11s}$, $R^{12s}$, $R^{13s}$, and/or $R^{14s}$ alkyl group independently can be a $C_1$ to $C_{20}$, a $C_1$ to $C_{10}$, or a $C_1$ to $C_5$ alkyl group. In any aspect disclosed herein, each $R^{1s}$, $R^{2s}$, $R^{11s}$, $R^{12s}$, $R^{13s}$, and/or $R^{14s}$ substituted alkyl group independently can be a $C_1$ to $C_{20}$, a $C_1$ to $C_{10}$, or a $C_1$ to $C_5$ substituted alkyl group. In any aspect disclosed herein, each $R^{1s}$, $R^{2s}$, $R^{11s}$, $R^{12s}$, $R^{13s}$, and/or $R^{14s}$ cycloalkyl group independently can be a $C_4$ to $C_{20}$, a $C_4$ to $C_{15}$, or a $C_4$ to $C_{10}$ cycloalkyl group. In any aspect disclosed herein, each $R^{1s}$, $R^{2s}$, $R^{11s}$, $R^{12s}$, $R^{13s}$, and/or $R^{14s}$ substituted cycloalkyl group independently can be a $C_4$ to $C_{20}$, a $C_4$ to $C_{15}$, or a $C_4$ to $C_{10}$ substituted cycloalkyl group. In any aspect disclosed herein, each $R^{1s}$, $R^{2s}$, $R^{11s}$, $R^{12s}$, $R^{13s}$, and/or $R^{14s}$ aryl group independently can be a $C_6$ to $C_{20}$, a $C_6$ to $C_{15}$, or a $C_6$ to $C_{10}$ aryl group. In any aspect disclosed herein, each $R^{1s}$, $R^{2s}$, $R^{11s}$, $R^{12s}$, $R^{13s}$, and/or $R^{14s}$ substituted aryl group independently can be a $C_6$ to $C_{20}$, a $C_6$ to $C_{15}$, or a $C_6$ to $C_{10}$ substituted aryl group. In any aspect disclosed herein, each $R^{1s}$, $R^{2s}$, $R^{11s}$, $R^{12s}$, $R^{13s}$, and/or $R^{14s}$ aralkyl group independently can be a $C_7$ to $C_{20}$, a $C_7$ to $C_{15}$, or a $C_7$ to $C_{10}$ aralkyl group. In any aspect disclosed herein, each $R^{1s}$, $R^{2s}$, $R^{11s}$, $R^{12s}$, $R^{13s}$, and/or $R^{14s}$ substituted aralkyl group independently can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarboxy groups, and substituent hydrocarboxy groups can be utilized without limitation to further describe a substituted group (general or specific) which can be utilized $R^{1s}$, $R^{2s}$, $R^{11s}$, $R^{12s}$, $R^{13s}$, and/or $R^{14s}$.

In an aspect, each $R^{1s}$, $R^{2s}$, $R^{11s}$, $R^{12s}$, $R^{13s}$, and/or $R^{14s}$ independently can be a methyl group, an ethyl group, a propyl group, a butyl group, a pentyl group, a hexyl group, a heptyl group, or an octyl group; or alternatively, a methyl group, an ethyl group, an iso-propyl (2-propyl) group, a tert-butyl (2-methyl-2-propyl) group, or a neopentyl (2,2-dimethyl-1-propyl) group. In some aspects, the alkyl groups which can be utilized as each $R^{1s}$, $R^{2s}$, $R^{11s}$, $R^{12s}$, $R^{13s}$, and/or $R^{14s}$ independently can be substituted. Each substituent of a substituted alkyl group independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group (general or specific) which can be utilized as $R^{1s}$, $R^{2s}$, $R^{11s}$, $R^{12s}$, $R^{13s}$, and/or $R^{14s}$.

In an aspect, each $R^{1s}$, $R^{2s}$, $R^{11s}$, $R^{12s}$, $R^{13s}$, and/or $R^{14s}$ independently can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an aspect, the substituted cycloalkyl group, which can be utilized for any of $R^{1s}$, $R^{2s}$, $R^{11s}$, $R^{12s}$, $R^{13s}$, and/or $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; or alternatively, a 2,6-disubstituted cyclohexyl group or a 2,5-disubstituted cyclopentyl group. In an aspect, one or more substituents of a multi-substituted cycloalkyl group utilized as $R^{1s}$, $R^{2s}$, $R^{11s}$, $R^{12s}$, $R^{13s}$, and/or $R^{14s}$ can be the same or different; alternatively, all the substituents of a multi-substituted cycloalkyl group can be the same; or alternatively, all the substituents of a multi-substituted cycloalkyl group can be different. Each substituent of a substituted cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^{1s}$, $R^{2s}$, $R^{11s}$, $R^{12s}$, $R^{13s}$, and/or $R^{14s}$.

In a non-limiting aspect, each $R^{1s}$, $R^{2s}$, $R^{11s}$, $R^{12s}$, $R^{13s}$, and/or $R^{14s}$ independently can be a cyclohexyl group, a 2-alkylcyclohexyl group, or a 2,6-dialkylcyclohexyl group; or alternatively, a cyclopentyl group, a 2-alkylcyclopentyl group, or a 2,5-dialkylcyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^{1s}$, $R^{2s}$, $R^{11s}$, $R^{12s}$, $R^{13s}$, and/or $R^{14}$. Generally, the alkyl substituents of a disubstituted cyclohexyl or cyclopentyl group can be the same, or alternatively, the alkyl substituents can be different. In some non-limiting aspects, each $R^{1s}$, $R^{2s}$, $R^{11s}$, $R^{12s}$, $R^{13s}$, and $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group; alternatively, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an aspect, each $R^{1s}$, $R^{2s}$, $R^{11s}$, $R^{12s}$, $R^{13s}$, and/or $R^{14s}$ independently can be a phenyl group or a substituted phenyl group; alternatively, a phenyl group; or alternatively, a substituted phenyl group. In an aspect, the substituted phenyl group which can be utilized for each $R^{1s}$, $R^{2s}$, $R^{11s}$, $R^{12s}$, $R^{13s}$, and/or $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an aspect, one or more substituents of a multi-substituted phenyl group utilized as $R^{1s}$, $R^{2s}$, $R^{11s}$, $R^{12s}$, $R^{13s}$, and/or $R^{14s}$ can be the same or different; alternatively, all the substituents can be the same; or alternatively, all the substituents can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy group can be utilized without limitation to further describe a substituted phenyl group (general or specific) which can be utilized as $R^{1s}$, $R^{2s}$, $R^{11s}$, $R^{12s}$, $R^{13s}$, and/or $R^{14s}$.

In a non-limiting aspect, each $R^{1s}$, $R^{2s}$, $R^{11s}$, $R^{12s}$, $R^{13s}$, and/or $R^{14s}$ independently can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^{1s}$, $R^{2s}$, $R^{11s}$, $R^{12s}$, $R^{13s}$, and/or $R^{14s}$. Generally, the alkyl substituents of dialkylphenyl groups (general or specific) or trialkylphenyl groups (general or specific) can be the same, or alternatively, the alkyl substituents can be different. In some non-limiting aspects, each $R^{1s}$, $R^{2s}$, $R^{11s}$, $R^{12s}$, $R^{13s}$, and/or $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2-ethylphenyl group, a 2-n-propylphenyl group, a 2-isopropylphenyl group, or a 2-tert-butylphenyl group; or alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting aspect, each $R^{1s}$, $R^{2s}$, $R^{11s}$, $R^{12s}$, $R^{13s}$, and/or $R^{14s}$ independently can be a phenyl group, a 2-alkoxyphenyl group, or a 4-alkoxyphenyl group. In some non-limiting aspects, each $R^{1s}$, $R^{2s}$, $R^{11s}$, $R^{12s}$, $R^{13s}$, and/or $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group. In a non-limiting aspect, each $R^{1s}$, $R^{2s}$, $R^{11s}$, $R^{12s}$, $R^{13s}$, and/or $R^{14s}$ independently can be a phenyl group, a 2-halophenyl group, a 4-halophenyl group, or a 2,6-dihalophenylgroup. Generally, the halides of a dihalophenyl group can be the same, or alternatively, the halides can be different. In some aspects, each $R^{1s}$, $R^{2s}$, $R^{11s}$, $R^{12s}$, $R^{13s}$, and/or $R^{14s}$ independently can be a phenyl group, a 2-fluorophenyl group, a 4-fluorophenyl group, or a 2,6-difluorophenyl group.

In an aspect, each $R^{1s}$, $R^{2s}$, $R^{11s}$, $R^{12s}$, $R^{1s}$, and/or $R^{14s}$ independently can be a benzyl group or a substituted benzyl group; alternatively, a benzyl group; or alternatively, a substituted benzyl group. Each substituent of a substituted benzyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group (general or specific) which can be utilized as $R^{1s}$, $R^{2s}$, $R^{11s}$, $R^{12s}$, $R^{13s}$, and/or $R^{14s}$.

In further aspects, two geminal $R^{1s}$s, two geminal $R^{2s}$s, geminal $R^{11s}$ and $R^{12s}$, and/or geminal $R^{13s}$ and $R^{14s}$ independently can be joined to form a ring or a ring system containing the heteroatom to which they are attached. The joining of two geminal $R^{1s}$s can be designated $L^{11s}$. The joining of two geminal $R^{2s}$s can be designated $L^{22s}$. The joining of geminal $R^{11s}$ and $R^{12s}$ can be designated $L^{12s}$. The joining of geminal $R^{13s}$ and $R^{14s}$ can be designated $L^{34s}$. In an aspect, $L^{11s}$, $L^{22s}$, $L^{12s}$, and/or $L^{34s}$ independently can be an organylene group; alternatively, an organylene group consisting of inert functional groups; alternatively, a hydrocarbylene group; or alternatively, an alkylene group. In an aspect, the $L^{11s}$, $L^{22s}$, $L^{12s}$, and/or $L^{34s}$ organylene group, when present, independently can be a $C_4$ to $C_{30}$, a $C_4$ to $C_{20}$, a $C_4$ to $C_{15}$, or a $C_4$ to $C_{10}$ organylene group. In some aspects, the $L^{11s}$, $L^{22s}$, $L^{12s}$, and/or $L^{34s}$ organylene group consisting of inert functional groups, when present, independently can be a $C_4$ to $C_{30}$, a $C_4$ to $C_{20}$, a $C_4$ to $C_{15}$, or a $C_4$ to $C_{10}$ organylene group consisting of inert functional groups. In other aspects, the $L^{11s}$, $L^{22s}$, $L^{12s}$, and/or $L^{34s}$ hydrocarbyl group, when present, independently can be a $C_4$ to $C_{30}$, a $C_4$ to $C_{20}$, a $C_4$ to $C_{15}$, or a $C_4$ to $C_{10}$ hydrocarbylene group. In a further aspect, the $L^{11s}$, $L^{22s}$ $L^{12s}$, and/or $L^{34s}$ alkylene group, when present, independently can be a $C_4$ to $C_{30}$, a $C_4$ to $C_{20}$, a $C_4$ to $C_{15}$, or a $C_4$ to $C_{10}$ alkylene group. In an aspect, $L^{12s}$ and/or $L^{34s}$, when present, independently can be a can be but-1,4-ylene group, a 1,4-diphenylbut-1,4-ylene group, a 1,4-di(2-methylphenyl)but-1,4-ylene group, 1,4-di(4-methylphenyl)but-1,4-ylene group, 1,4-di(4-t-butylphenyl)but-1,4-ylene group, a 1,4-di(3,5-dimethylphenyl)but-1,4-ylene group, a pent-1,4-ylene group, a 1-phenylpenta-1,4-ylene group, a 4-phenylpenta-1,4-ylene group, a hex-2,5-ylene group, a 2,2'-biphenylene group, a 2,2'-(methandiyl)dipheylene group, or a 2,2'-(1,2-ethandiyl)diphenylene group.

Generally, $R^{5s}$, of any heteroatomic ligand structure depicted herein and any heteroatomic ligand chromium compound complex depicted herein having an $R^{5s}$ group, can be an organyl group; alternatively, an organyl group consisting of inert functional groups; or alternatively, a hydrocarbyl group. In an aspect, the $R^{5s}$ organyl group can be a $C_1$ to $C_{20}$, a $C_1$ to $C_{15}$, a $C_1$ to $C_{10}$, or a $C_1$ to $C_5$ organyl group. In an aspect, the $R^{5s}$ organyl group consisting of inert functional groups can be a $C_1$ to $C_{20}$, a $C_1$ to $C_{15}$, a $C_1$ to $C_{10}$, or a $C_1$ to $C_5$ organyl group consisting of inert functional groups. In an aspect, the $R^{5s}$ hydrocarbyl group can be a $C_1$ to $C_{20}$, a $C_1$ to $C_{15}$, a $C_1$ to $C_{10}$, or a $C_1$ to $C_5$ hydrocarbyl group.

In an aspect, $R^{5s}$, of any heteroatomic ligand structure depicted herein and any heteroatomic ligand chromium compound complex depicted herein having an $R^{5s}$ group, can be an alkyl group, a substituted alkyl group, a cycloalkyl group, a substituted cycloalkyl group, an aryl group, a substituted aryl group, an aralkyl group, or a substituted aralkyl group; can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other aspects, $R^{5s}$ of any heteroatomic ligand structure depicted herein and any heteroatomic ligand chromium compound complex depicted herein having an $R^{5s}$ group, can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group. In any aspect disclosed herein, the $R^{5s}$ alkyl group can be a $C_1$ to $C_{20}$, a $C_1$ to $C_{15}$, or a $C_1$ to $C_{10}$ alkyl group. In any aspect disclosed herein, the $R^{5s}$ substituted alkyl group can be a $C_1$ to $C_{20}$, a $C_1$ to $C_{15}$, or a $C_1$ to $C_{10}$ substituted alkyl group. In any aspect disclosed herein, the $R^{5s}$ cycloalkyl group can be a $C_4$ to $C_{20}$, a $C_4$ to $C_{15}$, or a $C_4$ to $C_{10}$ cycloalkyl group. In any aspect disclosed herein, the $R^{5s}$ substituted cycloalkyl group can be a $C_4$ to $C_{20}$, a $C_4$ to, or a $C_4$ to $C_{10}$ substituted cycloalkyl group. In any aspect disclosed herein, the $R^{5s}$ aryl group can be a $C_6$ to $C_{20}$, a $C_6$ to $C_{15}$, or a $C_6$ to $C_{10}$ aryl group. In any aspect disclosed herein, the $R^{5s}$ substituted aryl group can be a $C_6$ to $C_{20}$, a $C_6$ to $C_{15}$, or a $C_6$ to $C_{10}$ substituted aryl group. In any aspect disclosed herein, the $R^{5s}$ aralkyl group can be a $C_7$ to $C_{20}$, a $C_7$ to $C_{15}$, or a $C_7$ to $C_{10}$ aralkyl group. In any aspect disclosed herein, the $R^{5s}$ substituted aralkyl group can be a $C_7$ to $C_{20}$, a $C_7$ to $C_{15}$, or a $C_7$ to $C_{10}$ substituted aralkyl group. Each substituent of a substituted alkyl group (general or specific), substituted cycloalkyl group (general or specific), substituted aryl group (general or specific), and/or substituted aralkyl group (general or specific) can be a halogen, hydrocarbyl group, or a hydrocarboxy group; alternatively, a halogen or a hydrocarbyl group; alternatively, a halogen or a hydrocarboxyl group; alternatively, a hydrocarbyl group or a hydrocarboxy group; alternatively, a halogen; alternatively, a hydrocarbyl group; or alternatively, a hydrocarboxy group. Substituent halogens, hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted group (general or specific) which can be utilized $R^{5s}$.

In an aspect, $R^{5s}$ can be a methyl group, an ethyl group, a propyl group, a butyl group, a pentyl group, a hexyl group, a heptyl group, or an octyl group; alternatively, a methyl group, an ethyl group, an n-propyl (1-propyl) group, an isopropyl (2-propyl) group, an n-butyl (1-butyl) group, a sec-butyl (2-butyl) group, an isobutyl (2-methyl-1-propyl) group, a tert-butyl (2-methyl-2-propyl) group, an n-pentyl (1-pentyl) group, a 2-pentyl group, a 3-pentyl group, a 2-methyl-1-butyl group, a tert-pentyl (2-methyl-2-butyl) group, a 3-methyl-1-butyl group, a 3-methyl-2-butyl group, or a neo-pentyl (2,2-dimethyl-1-propyl) group; or alternatively, a methyl group, an ethyl group, an iso-propyl (2-propyl) group, a tert-butyl (2-methyl-2-propyl) group, or a neopentyl (2,2-dimethyl-1-propyl) group. In some aspects, the $R^{5s}$ alkyl groups can be substituted. Each substituent of a RSs substituted alkyl group independently can be a halogen or a hydrocarboxy group; alternatively, a halogen; or alternatively, a hydrocarboxy group. Substituent halogens and substituent hydrocarboxy groups (general and specific) are independently described herein and these substituent groups can be utilized without limitation to further describe a substituted alkyl group (general or specific) which can be utilized as $R^{5s}$.

In an aspect, RSs can be a cyclopentyl group, a substituted cyclopentyl group, a cyclohexyl group, a substituted cyclohexyl group; alternatively, a cyclopentyl group or a substituted cyclopentyl group; or alternatively, a cyclohexyl group or a substituted cyclohexyl group. In further aspects, RSs can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; or alternatively, a 2,6-disubstituted cyclohexyl group or a 2,5-disubstituted cyclopentyl group. In an aspect, one or more substituents of a multi-substituted cycloalkyl group utilized as $R^{5s}$ can be the same or different; alternatively, all the substituents of a multi-substituted cycloalkyl group can be the same; or alternatively, all the substituents of a multi-substituted cycloalkyl group can be different. Each substituent of a cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently described herein and these substituent groups can be utilized without limitation to further describe a substituted cycloalkyl group (general or specific) which can be utilized as $R^{5s}$.

In a non-limiting aspect, $R^{5s}$ can be a cyclohexyl group, a 2-alkylcyclohexyl group, or a 2,6-dialkylcyclohexyl group; or alternatively, a cyclopentyl group, a 2-alkylcyclopentyl group, or a 2,5-dialkylcyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^{5s}$. Generally, the alkyl substituents of a disubstituted cyclohexyl or cyclopentyl group can be the same, or alternatively, the alkyl substituents can be different. In some non-limiting aspects, $R^{5s}$ heteroatomic ligand structure provided herein, and/or any heteroatomic ligand chromium compound complex structure provided herein can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting aspects, $R^{5s}$ can be a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group. In an aspect, $R^{5s}$ heteroatomic ligand structure provided herein, and/or any heteroatomic ligand chromium compound complex structure provided herein can be a cyclopentyl group, a 2-methylcyclopentyl group, a cyclohexyl group, or a 2-methylcyclohexyl group; alternatively, a cyclopentyl group or a cyclohexyl group; or alternatively, a 2-methylcyclopentyl group or a 2-methylcyclohexyl group.

In an aspect, $R^{5s}$ can be a phenyl group or a substituted phenyl group; alternatively, a phenyl group; or alternatively, a substituted phenyl group. In some aspects, $R^{5s}$ can be a 2-substituted phenyl group, a 4-substituted phenyl group, a 2,4-disubstituted phenyl group, a 2,6-disubstituted phenyl group, or a 2,4,6-trisubstituted phenyl group; alternatively, a 2-substituted phenyl group or a 4-substituted phenyl group; alternatively, a 2,4-disubstituted phenyl group, a 2,6-disubstituted phenyl group, or a 2,4,6-trisubstituted phenyl group; alternatively, a 2,4-disubstituted phenyl group or a 2,6-disubstituted phenyl group; alternatively, a 2-substituted phenyl group; alternatively, a 4-substituted phenyl group; alternatively, a 2,4-disubstituted phenyl group; alternatively, a 2,6-disubstituted phenyl group; or alternatively, a 2,4,6-trisubstituted phenyl group. In an aspect, one or more substituents of a multi-substituted phenyl group utilized as $R^{5s}$ can be the same or different; alternatively, all the substituents can be the same, or alternatively, all the substituents can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently described herein and these substituent groups can be utilized without limitation to further describe a substituted phenyl group (general or specific) which can be utilized as $R^{5s}$.

In a non-limiting aspect, $R^{5s}$ can be a phenyl group, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group, a 2,4-dialkylphenyl group, a 2,6-dialkylphenyl group, or a 2,4,6-trialkylphenyl group. Alkyl substituent groups (general and specific) are independently described herein and these alkyl substituent groups can be utilized, without limitation, to further describe any alkyl substituted phenyl group which can be utilized as $R^{5s}$. Generally, the alkyl substituents of dialkylphenyl groups (general of specific) or trialkylphenyl groups (general or specific) can be the same, or alternatively, the alkyl substituents can be different. In some non-limiting aspects, $R^{5s}$ can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2,6-dimethylphenyl group, or a 2,4,6-trimethylphenyl group.

Generally, $L^{2s}$, of any heteroatomic ligand and/or any heteroatomic ligand chromium compound complex having an $L^{2s}$ group, can be an organylene group; alternatively, an organylene group consisting of inert functional groups; alternatively, a hydrocarbylene group; or alternatively, an alkylene group. In an aspect, the $L^{2s}$ organylene group can be a $C_1$ to $C_{20}$, a $C_1$ to $C_{15}$, or a $C_1$ to $C_{10}$ organylene group. In an aspect, the $L^{2s}$ organylene group consisting of inert functional groups can be a $C_1$ to $C_{20}$, a $C_1$ to $C_{15}$, or a $C_1$ to $C_{10}$ organylene group consisting of inert functional groups. In an aspect, the $L^{2s}$ alkylene group can be a $C_1$ to $C_{20}$, $C_1$ to $C_{15}$, or a $C_1$ to $C_{10}$ alkylene group.

In an aspect, $L^{2s}$ of any heteroatomic ligand and/or any heteroatomic ligand chromium compound complex having an $L^{2s}$ group can be —$(CR^P R^{P'})_m$— where each $R^P$ and $R^{P'}$ can independently be hydrogen, methyl, ethyl, propyl, isopropyl, or butyl groups and m can be an integer from 1 to 12. In some aspects, $L^{2s}$ of any heteroatomic ligand and/or any heteroatomic ligand chromium compound complex having an $L^{2s}$ group can be a methylene group (—CH$_2$—), an eth-1,2-ylene group (—CH$_2$CH$_2$—), a prop-1,3-ylene group (—CH$_2$CH$_2$CH$_2$—), a prop-1,2-ylene group (—CH(CH$_3$)CH$_2$—), a prop-2,2-ylene group (—C(CH$_3$)$_2$—) group, a but-1,4-ylene group (—CH$_2$CH$_2$CH$_2$CH$_2$—), or a 2-methylprop-1,3-ylene group (—CH$_2$CH(CH$_3$)CH$_2$—); or alternatively a methylene group (—CH$_2$—), an eth-1,2-ylene group (—CH$_2$CH$_2$—), or a prop-1,2-ylene group (—CH(CH$_3$)CH$_2$—).

In an aspect, $L^{2s}$ of any heteroatomic ligand and/or any heteroatomic ligand chromium compound complex having an $L^{2s}$ group, can be 1,2-cyclohexylene, a substituted 1,2-cyclohexylene, 1,3-cyclohexylene, a substituted 1,3-cyclohexylene, 1,4-cyclohexylene, a substituted 1,4-cyclohexylene, 3,3'-bicyclohexylene, a substituted 3,3'-bicyclohexylene, 4,4'-bicyclohexylene, a substituted 4,4'-bicyclohexylene, bis(3-cyclohexylene)methane, a substituted bis(3-cyclohexylene)methane, bis(4-cyclohexylene)methane, a substituted bis(4-cyclohexylene)methane, 1,2-bis(3-cyclohexylene)ethane, a substituted 1,2-bis(3-cyclohexylene)ethane, 1,2-bis(4-cyclohexylene)ethane, a substituted 1,2-bis(4-cyclohexylene)ethane, 1,2-bis(3-cyclohexylene)propane, a substituted 1,2-bis(3-cyclohexylene)propane, 1,2-bis(4-cyclohexylene)propane, a substituted 1,2-bis(4-cyclohexylene)propane, 2,2-bis(3-cyclohexylene)propane, a substituted 2,2-bis(3-cyclohexylene)propane, 2,2-bis(4-cyclohexylene)propane, or a substituted 2,2-bis(4-cyclohexylene)propane. In some aspects, $L^{2s}$ of any heteroatomic ligand and/or any heteroatomic ligand chromium compound complex having an $L^{2s}$ group can be a substituted 1,2-cyclohexylene, a substituted 1,3-cyclohexylene, a substituted 1,4-cyclohexylene, a substituted 3,3'-bicyclohexylene, a substituted 4,4'-bicyclohexylene, a substituted bis(3-cyclohexylene)methane, a substituted bis(4-cyclohexylene)methane, a substituted 1,2-bis(3-cyclohexylene)ethane, a substituted 1,2-bis(4-cyclohexylene)ethane, a substituted 1,2-bis(3-cyclohexylene)propane, a substituted 1,2-bis(4-cyclohexylene)propane, a substituted 2,2-bis(3-cyclohexylene)propane, or a substituted 2,2-bis(4-cyclohexylene)propane. In an aspect, each substituent of a substituted cyclohexylene, a substituted bis(cyclohexylene)methane, a substituted bis(cyclohexylene)ethane, or a substituted 1,2-bis(3-cyclohexylene)propane which can be utilized as $L^{2s}$ can be a hydrocarbyl group. Substituent groups (general and specific) are independently disclosed herein and can be utilized without limitation to further describe a substituted cyclohexylene (general or specific), a substituted bis(cyclohexylene)methane (general or specific), a substituted bis(cyclohexylene)ethane (general or specific), or a substituted 1,2-bis(3-cyclohexylene)propane (general or specific) which can be utilized as $L^{2s}$.

In an aspect, $L^{2s}$ of any heteroatomic ligand and/or any heteroatomic ligand chromium compound complex having an $L^{2s}$ group can be 1,2-phenylene, a substituted 1,2-phenylene, 1,3-phenylene, a substituted 1,3-phenylene, 1,4-phenylene, a substituted 1,4-phenylene, 3,3'-biphenylene, a substituted 3,3'-biphenylene, 4,4'-biphenylene, a substituted 4,4'-biphenylene, bis(3-phenylene)methane, a substituted bis(3-phenylene)methane, bis(4-phenylene)methane, a substituted bis(4-phenylene)methane, 1,2-bis(3-phenylene)ethane, a substituted 1,2-bis(3-phenylene)ethane, 1,2-bis(4-phenylene)ethane, a substituted 1,2-bis(4-phenylene)ethane, 1,2-bis(3-phenylene)propane, a substituted 1,2-bis(3-phenylene)propane, 1,2-bis(4-phenylene)propane, a substituted 1,2-bis(4-phenylene)propane, 2,2-bis(3-phenylene)propane, a substituted 2,2-bis(3-phenylene)propane, 2,2-bis(4-phenylene)propane, or a substituted 2,2-bis(4-phenylene)propane. In some aspects, $L^{2s}$ of any heteroatomic ligand and/or any heteroatomic ligand chromium compound complex having an $L^{2s}$ group can be a substituted 1,2-phenylene, a substituted 1,3-phenylene, a substituted 1,4-phenylene, a substituted 3,3'-biphenylene, a substituted 4,4'-biphenylene, a substituted bis(3-phenylene)methane, a substituted bis(4-phenylene)methane, a substituted 1,2-bis(3-phenylene)ethane, a substituted 1,2-bis(4-phenylene)ethane, a substituted 1,2-bis(3-phenylene)propane, a substituted 1,2-bis(4-phenylene)propane, a substituted 2,2-bis(3-phenylene)propane, or a substituted 2,2-bis(4-phenylene)propane. In an aspect, each substituent of a substituted phenylene (general or specific), a substituted biphenylene (general or specific), a substituted bis(phenylene)methane (general or specific), a substituted bis(phenylene)ethane (general or specific), and/or a substituted bis(phenylene)propane (general or specific) which can be utilized as $L^{2s}$ can be a hydrocarbyl group. Substituent hydrocarbyl groups (general and specific) are independently disclosed herein and can be utilized without limitation to further describe a substituted phenylene (general or specific), a substituted biphenylene (general or specific), a substituted bis(phenylene)methane (general or specific), a substituted bis(phenylene)ethane(general or specific), and/or a substituted bis(phenylene)propane (general or specific) which can be utilized as $L^{2s}$.

Generally, $L^{3s}$ and/or $L^{4s}$, of any heteroatomic ligand and/or any heteroatomic ligand chromium compound complex having an $L^{3s}$ and/or $L^{4s}$ group, independently can be an organylene group; alternatively, an organylene group consisting of inert functional groups; alternatively, a hydrocarbylene group; alternatively, an alkylene group. In an aspect, the $L^{3s}$ and/or $L^{4s}$ organylene group independently can be a $C_1$ to $C_{20}$, a $C_1$ to $C_{15}$, or a $C_1$ to $C_{10}$ organylene group. In an aspect, the $L^{3s}$ and/or $L^{4s}$ organylene group consisting of inert functional groups independently can be a $C_1$ to $C_{20}$, a $C_1$ to $C_{15}$, or a $C_1$ to $C_{10}$ organylene group consisting of inert functional groups. In an aspect, the $L^{3s}$ and/or $L^{4s}$ hydrocarbylene group independently can be a $C_1$ to $C_{20}$, a $C_1$ to $C_{15}$, or a $C_1$ to $C_{10}$ hydrocarbylene group. In an aspect, the $L^{3s}$ and/or $L^{4s}$ alkylene group independently can be a $C_1$ to $C_{20}$, $C_1$ to $C_{15}$, or a $C_1$ to $C_{10}$ alkylene group.

In an aspect, $L^{3s}$ and/or $L^{4s}$ of any heteroatomic ligand structure and/or any heteroatomic ligand chromium compound complex having an $L^{3s}$ and/or $L^{4s}$ group independently can be —(CR$^P$R$^{P'}$)$_m$— where each R$^P$ and R$^{P'}$ can independently be hydrogen, methyl, ethyl, propyl, isopropyl, or butyl groups and m can be an integer from 1 to 12. In some aspects, $L^{3s}$ and/or $L^{4s}$ of any heteroatomic ligand structure and/or any heteroatomic ligand chromium compound complex having an $L^{3s}$ and/or $L^{4s}$ group independently can be a methylene group (—CH$_2$—), an eth-1,2-ylene group (—CH$_2$CH$_2$—), an ethen-1,2-ylene group (—CH=CH—), a prop-1,3-ylene group (—CH$_2$CH$_2$CH$_2$—), a prop-1,2-ylene group (—CH(CH$_3$)CH$_2$—), a prop-2,2-ylene group (—C(CH$_3$)$_2$—), a 1-methylethen-1,2-ylene group (—C(CH$_3$)=CH—), a but-1,4-ylene group (—CH$_2$CH$_2$CH$_2$—CH$_2$—), a but-1,3-ylene group (—CH$_2$CH$_2$CH(CH$_3$)—), a but-2,3-ylene group (—CH(CH$_3$)CH(CH$_3$)—), a but-2-en-2,3-ylene group (—C(CH$_3$)C(CH$_3$)—), a 3-methylbut-1,3-ylene group (—CH$_2$CH$_2$C(CH$_3$)$_2$—), a 1,2-cyclopentylene group, a 1,2-cyclohexylene group, or a phen-1,2-ylene group; alternatively, a methylene group (—CH$_2$—), an eth-1,2-ylene group (—CH$_2$CH$_2$—), a prop-1,3-ylene group (—CH$_2$CH$_2$CH$_2$—), a prop-1,2-ylene group (—CH(CH$_3$)CH$_2$—), a prop-2,2-ylene group (—C(CH$_3$)$_2$—), a but-1,4-ylene group (—CH$_2$CH$_2$CH$_2$—

CH$_2$—), a but-1,3-ylene group (—CH$_2$CH$_2$CH(CH$_3$)—), a but-2,3-ylene group (—CH(CH$_3$)CH(CH$_3$)—), a 1,2-cyclopentylene group, a 1,2-cyclohexylene group, or a phen-1,2-ylene group; or alternatively, an eth-1,2-ylene group (—CH$_2$CH$_2$—), a prop-1,3-ylene group (—CH$_2$CH$_2$CH$_2$—), a prop-1,2-ylene group (—CH(CH$_3$)CH$_2$—), a but-1,3-ylene group (—CH$_2$CH$_2$CH(CH$_3$)—), a but-2,3-ylene group (—CH(CH$_3$)CH(CH$_3$)—), a 1,2-cyclopentylene group, a 1,2-cyclohexylene group, or a phen-1,2-ylene group.

Various aspects described herein refer to non-hydrogen substituents such as halogen (or halo, halide), hydrocarbyl, hydrocarboxy, alkyl, and/or alkoxy substituents. In an embodiment, each non-hydrogen substituent of any aspect calling for a substituent can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Each hydrocarbyl substituent independently can be a $C_1$ to $C_{10}$ hydrocarbyl group; or alternatively, a $C_1$ to $C_5$ hydrocarbyl group. Each hydrocarboxy substituent independently can be a $C_1$ to $C_{10}$ hydrocarboxy group; or alternatively, a $C_1$ to $C_5$ hydrocarboxy group. Each halide substituent independently can be a fluoride, chloride, bromide, or iodide; alternatively, a fluoride or chloride; alternatively, a fluoride; alternatively, a chloride; alternatively, a bromide; or alternatively, an iodide.

In an aspect, any hydrocarbyl substituent independently can be an alkyl group, an aryl group, or an aralkyl group; alternatively, an alkyl group; alternatively, an aryl group; or alternatively, an aralkyl group. In an aspect, any alkyl substituent independently can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an aspect, any aryl substituent independently can be phenyl group, a tolyl group, a xylyl group, or a 2,4,6-trimethylphenyl group; alternatively, a phenyl group; alternatively, a tolyl group, alternatively, a xylyl group; or alternatively, a 2,4,6-trimethylphenyl group. In an aspect, any aralkyl substituent independently can be benzyl group or an ethylphenyl group (2-phenyleth-1-yl or 1-phenyleth-1-yl); alternatively, a benzyl group; alternatively, an ethylphenyl group; alternatively, a 2-phenyleth-1-yl group; or alternatively, a 1-phenyleth-1-yl group.

In an aspect, any hydrocarboxy substituent independently can be an alkoxy group, an aryloxy group, or an aralkoxy group; alternatively, an alkoxy group; alternatively, an aryloxy group, or an aralkoxy group. In an aspect, any alkoxy substituent independently can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an aspect, any aryloxy substituent independently can be phenoxy group, a toloxy group, a xyloxy group, or a 2,4,6-trimethylphenoxy group; alternatively, a phenoxy group; alternatively, a toloxy group, alternatively, a xyloxy group; or alternatively, a 2,4,6-trimethylphenoxy group. In an aspect, any aralkoxy substituent independently can be benzoxy group.

Generally, the transition metal of the heteroatomic ligand transition metal compound complex or the transition metal compound, MX$_p$, can be any transition metal atom. In an embodiment, the transition metal atom of the transition metal compound can comprise, or consist essentially of, a Group 3-12, a Group 4-10, a Group 6-9, or a Group 7-8 transition metal. In some embodiments, the transition metal atom of the transition metal compound can comprise, or consist essentially of, a Group 4 transition metal; alternatively, a Group 5 transition metal; alternatively, a Group 6 transition metal; alternatively, a Group 7 transition metal; alternatively, a Group 8 transition metal; alternatively, a Group 9 transition metal; or alternatively, a Group 10 transition metal. In an embodiment, the transition metal atom of the transition metal compound can comprise, or consist essentially of, titanium, zirconium, hafnium, vanadium, niobium, tantalum, chromium, molybdenum, tungsten, manganese, iron, cobalt, nickel, palladium, platinum, copper, or zinc; alternatively, titanium, zirconium, vanadium, chromium, molybdenum, tungsten, iron, cobalt, nickel, palladium, or platinum; alternatively, chromium, iron, cobalt, or nickel; alternatively, titanium, zirconium, or hafnium; alternatively, vanadium or niobium; alternatively, chromium, molybdenum, or tungsten; alternatively, iron or cobalt; or alternatively, nickel, palladium, platinum, copper, or zinc. In other embodiments, the metal salt can comprise titanium; alternatively, zirconium; alternatively, hafnium; alternatively, vanadium; alternatively, niobium; alternatively, tantalum; alternatively, chromium; alternatively, molybdenum; alternatively, tungsten; alternatively, manganese; alternatively, iron; alternatively, cobalt; alternatively, nickel; alternatively, palladium; alternatively, platinum; alternatively, copper; or alternatively, zinc. Generally, the transition metal atom of the heteroatomic ligand transition metal compound complex or the transition metal compound, MX$_p$, can have any positive oxidation state available to the transition metal atom. In an embodiment, the transition metal atom can have an oxidation state of from +2 to +6; alternatively, from +2 to +4; or alternatively, from +2 to +3. In some embodiments, the transition metal atom of the transition metal compound, MX$_p$, can have an oxidation state of +1; alternatively, +2; alternatively, +3; or alternatively, +4.

Generally, the chromium compound or the chromium compound of the heteroatomic ligand chromium compound complexes described herein can have formula CrX$_p$ where X represents a monoanionic ligand, and p (q of the general heteroatomic ligand formula [(HetLig)CrX$_q$L$_r$]$^{3-q}$ (A)) represents the number of monoanionic ligands (and the oxidation state of the chromium in the chromium compound. The monoanionic ligand (X), and p are independent elements of the chromium compound or the chromium compound of the heteroatomic ligand chromium compound complexes described herein and are independently described herein. The independent descriptions of the monoanionic ligand (X), and p can be utilized without limitation, and in any combination, to further describe the chromium compound or the chromium compound of the heteroatomic ligand chromium compound complexes described herein.

Generally, the chromium atom of the chromium compound ($CrX_p$) can have any positive oxidation state available to a chromium atom. In an aspect, the chromium atom can have an oxidation state of from +2 to +6; alternatively, from +2 to +4; or alternatively, from +2 to +3. In some aspects, the chromium atom of the chromium compound ($CrX_p$) can have an oxidation state of +1; alternatively, +2; alternatively, +3; or alternatively, +4.

The monoanion (X) of the chromium compound can be any monoanion. In an aspect, the monoanion (X) can be a halide, a carboxylate, a β-diketonate, a hydrocarboxide, a nitrate, or a chlorate. In some aspects, the monoanion (X) can be a halide, a carboxylate, a β-diketonate, or a hydrocarboxide. In any aspect, the hydrocarboxide can be an alkoxide, an aryloxide, or an aralkoxide. Generally, hydrocarboxide (and subdivisions of hydrocarboxide) are the anion analogues of the hydrocarboxy group. In other aspects, the monoanion (X) can be a halide, a carboxylate, a β-diketonate, or an alkoxide; or alternatively, a halide or a β-diketonate. In other aspects, the monoanion (X) can be a halide; alternatively, a carboxylate; alternatively, a β-diketonate; alternatively, a hydrocarboxide; alternatively, an alkoxide; or alternatively, an aryloxide. Generally, when the heteroatomic ligand of the heteroatomic ligand chromium compound complex is a neutral heteroatomic ligand the number of monoanions (p) can equal the oxidation state of the chromium atom. When the heteroatomic ligand of the heteroatomic ligand chromium compound complex is an anionic heteroatomic ligand the number of monoanions (p) can equal one less than the oxidation state of the chromium atom. In an aspect, the number of monoanions can be from 2 to 6; alternatively, from 2 to 4; alternatively, from 2 to 3; alternatively, 1; alternatively, 2; alternatively, 3; or alternatively, 4.

Generally, each halide of the chromium compound independently can be fluorine, chlorine, bromine, or iodine; or alternatively, chlorine, bromine, or iodine. In an aspect, each halide monoanion of the chromium compound can be chlorine; alternatively, bromine; or alternatively, iodine.

Generally, each carboxylate of the chromium compound independently can be a $C_1$ to $C_{20}$ carboxylate; or alternatively, a $C_1$ to $C_{10}$ carboxylate. In an aspect, each carboxylate of the chromium compound independently can be acetate, a propionate, a butyrate, a pentanoate, a hexanoate, a heptanoate, an octanoate, a nonanoate, a decanoate, an undecanoate, or a dodecanoate; or alternatively, a pentanoate, a hexanoate, a heptanoate, an octanoate, a nonanoate, a decanoate, an undecanoate, or a dodecanoate. In some aspects, each carboxylate of the chromium compound independently can be acetate, propionate, n-butyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, capronate (n-hexanoate); alternatively, n-heptanoate; alternatively, caprylate (n-octanoate); or alternatively, 2-ethylhexanoate. In some aspects, the carboxylate of the chromium compound can be triflate (trifluoroacetate).

Generally, each β-diketonate of the chromium compound independently can be any $C_1$ to $C_{20}$ a β-diketonate; or alternatively, any $C_1$ to $C_{10}$ β-diketonate. In an aspect, each β-diketonate of the chromium compound independently can be acetylacetonate (i.e., 2,4-pentanedionate), hexafluoroacetylacetonate (i.e., 1,1,1,5,5,5-hexafluoro-2,4-pentanedionate), or benzoylacetonate); alternatively, acetylacetonate; alternatively, hexafluoroacetylacetonate; or alternatively, benzoylacetonate.

Generally, each hydrocarboxide of the chromium compound independently can be any $C_1$ to $C_{20}$ hydrocarboxide; or alternatively, any $C_1$ to $C_{10}$ hydrocarboxide. In an aspect, each hydrocarboxide of the chromium compound independently can be a $C_1$ to $C_{20}$ alkoxide; alternatively, a $C_1$ to $C_{10}$ alkoxide; alternatively, a $C_6$ to $C_{20}$ aryloxide; or alternatively, a $C_6$ to $C_{10}$ aryloxide. In an aspect, each alkoxide of the chromium compound independently can be methoxide, ethoxide, a propoxide, or a butoxide; alternatively, methoxide, ethoxide, isopropoxide, or tert-butoxide; alternatively, methoxide; alternatively, an ethoxide; alternatively, an isopropoxide; or alternatively, a tert-butoxide. In an aspect, the aryloxide can be phenoxide.

In some non-limiting aspects, the chromium compound and/or the chromium compound of the heteroatomic ligand chromium compound complex can comprise, can consist essentially of, or consist of, a chromium(II) halide, a chromium(II) carboxylate, or a chromium(II) β-diketonate; or alternatively, a chromium(III) halide, a chromium(III) carboxylate, or a chromium(III) β-diketonate. In other non-limiting aspects, the chromium compound and/or the chromium compound of the heteroatomic ligand chromium compound complex can comprise, can consist essentially of, or consist of, a chromium(II) halide; alternatively, a chromium(III) halide; alternatively, a chromium (II) carboxylate; alternatively, a chromium(III) carboxylate; alternatively, a chromium(II) β-diketonate; or alternatively, a chromium(III) β-diketonate. Halides, carboxylates, β-diketonates are independently described herein and these halides, carboxylates, β-diketonate and these independently described halides, carboxylates, β-diketonates can be utilized without limitation and in any combination to further described the chromium compound and/or the chromium compound of the heteroatomic ligand chromium compound complex. In further non-limiting aspects, the chromium compound and/or the chromium compound of the heteroatomic ligand chromium compound complex can comprise, can consist essentially of, or consist of, chromium(II) chloride, chromium(III) chloride, chromium(II) fluoride, chromium(III) fluoride, chromium(II) bromide, chromium(III) bromide, chromium (II) iodide, chromium(III) iodide, chromium(II) acetate, chromium(III) acetate, chromium(II) 2-ethylhexanoate, chromium(III) 2-ethylhexanoate, chromium(II) triflate, chromium(III) triflate, chromium(II) nitrate, chromium(III) nitrate, chromium(II) acetylacetonate, chromium(III) acetylacetonate, chromium(II) hexafluoracetylacetonate, chromium(III) hexafluoracetylacetonate, chromium(III) benzoylacetonate, or chromium(III) benzoylacetonate; alternatively, chromium(III) chloride, chromium(III) fluoride, chromium(III) bromide, chromium(III) iodide, chromium(III) chloride (THF) complex, chromium(III) acetate, chromium(III) 2-ethylhexanoate, chromium(III) triflate, chromium(III) nitrate, chromium(III) acetylacetonate, chromium(III) hexafluoracetylacetonate, or chromium(III) benzoylacetonate; alternatively, chromium(III) chloride, or chromium(III) acetylacetonate; alternatively, chromium(III) chloride; or alternatively, chromium(III) acetylacetonate.

In a non-limiting aspect, the one or more first training heteroatomic ligand-metal compound complexes, each comprising a first training heteroatomic ligand, can be selected from, among others, any one or more of a heteroatomic ligand chromium compound complex having i) Structure NPFCr1 where R¹ is 2,6-dimethylphenyl, R³ is H, R⁴ and R⁵ are isopropyl, and X is chlorine; R¹ is 2,6-dimethylphenyl, R³ is H, R⁴ and R⁵ are phenyl, and X is chlorine; R¹ is 2,6-dimethylphenyl, R³ is H, R⁴ and R⁵ are 4-methoxyphenyl, and X is chlorine; R¹ is 2,4,6-trimethylphenyl, R³ is H, R⁴ and R⁵ are isopropyl, and X is chlorine; R¹ is 2,4,6-trimethylphenyl, R³ is H, R⁴ and R⁵ are phenyl, and X is chlorine; and R¹ is 2,4,6-trimethylphenyl, R³ is H, R⁴ and R⁵ are 4-methoxyphenyl, and X is chlorine: ii) Structure NPACr1 where R¹ is 2,6-dimethylphenyl, R² is phenyl, R³ is H, R⁴ and R⁵ are isopropyl, and X is chlorine; R¹ is 2,4,6-trimethylphenyl, R² is phenyl, R³ is H, R⁴ and R⁵ are isopropyl, and X is chlorine; R¹ is 2,6-dimethylphenyl, R² is phenyl, R³ is H, R⁴ and R⁵ are phenyl, and X is chlorine; R¹ is 2,4,6-trimethylphenyl, R² is phenyl, R³ is H, R⁴ and R⁵ are phenyl, and X is chlorine; R¹ is 2,6-dimethylphenyl, R² is 4-methylbenzyl, R³ is H, R⁴ and R⁵ are phenyl, and X is chlorine; R¹ is 2,6-dimethylphenyl, R² is phenyl, R³ is H, R⁴ and R⁵ are 4-methoxyphenyl, and X is chlorine; R¹ is 2,6-dimethylphenyl, R² is 4-t-butylphenyl, R³ is H, R⁴ and R⁵ are methyl, and X is chlorine; R¹ is 2,4,6-trimethylphenyl, R² is 4-t-butylphenyl, R³ is H, R⁴ and R⁵ are methyl, and X is chlorine; R¹ is 2,4,6-trimethylphenyl, R² is 4-methylbenzyl, R³ is H, R⁴ and R⁵ are isopropyl, and X is chlorine; R¹ is 2,4,6-trimethylphenyl, R² is 4-methylbenzyl, R³ is H, R⁴ and R⁵ are phenyl, and X is chlorine; R¹ is 3,5-dimethylphenyl, R² is phenyl, R³ is H, R⁴ and R⁵ are isopropyl, and X is chlorine; R¹ is 2,4,6-trimethylphenyl, R² is 4-methylbenzyl, R³ is H, R⁴ and R⁵ are 4-methoxyphenyl, and X is chlorine; R¹ is 2,4,6-trimethylphenyl, R² is 4-methylbenzyl, R³ is H, R⁴ is t-butyl, R⁵ is phenyl, and X is chlorine; R¹ is 2,4,6-trimethylphenyl, R² is 4-methylbenzyl, R³ is H, R⁴ is methyl, R⁵ is phenyl, and X is chlorine; R¹ and R² are joined to form a prop-1,3-ylene group, R³ is H, R⁴ and R⁵ are isopropyl, and X is chlorine; R¹ and R² are joined to form a but-1,4-ylene group, R³ is H, R⁴ and R⁵ are isopropyl, and X is chlorine; R¹ is 2,4,6-trimethylphenyl, R² is 4-methylbenzyl, R³ is H, R⁴ and R⁵ are joined to form a but-1,4,-ylene group, and X is chlorine; R¹ is 2,4,6-trimethylphenyl, R² is 4-methylbenzyl, R³ is H, R⁴ and R⁵ are joined to form a 2,2'-dimethylbiphenylene group, and X is chlorine: iii) Structure GUCr1 where R¹ is 2-methylphenyl, R²ᵃ is 2-methylphenyl, R²ᵇ is H, R³ is H, R⁴ and R⁵ are isopropyl, and X is chlorine; R¹ is 2,6-dimethylphenyl, R²ᵃ is phenyl, R²ᵇ is H, R³ is H, R⁴ and R⁵ are isopropyl, and X is chlorine; R¹ is 2,6-dimethylphenyl, R²ᵃ is phenyl, R²ᵇ is H, R³ is H, R⁴ and R⁵ are phenyl, and X is chlorine; R¹ is 2,6-dimethylphenyl, R²ᵃ and R²ᵇ are phenyl, R³ is H, R⁴ and R⁵ are isopropyl, and X is chlorine: iv) Structure GUCr4 where L¹² is prop-1,3-ylene, L²³ is prop-1,3-ylene, R⁴ and R⁵ are isopropyl, and X is chlorine; L¹² is prop-1,3-ylene, L²³ is prop-1,3-ylene, R⁴ and R⁵ are cyclopentyl, and X is chlorine; L¹² is prop-1,3-ylene, L²³ is prop-1,3-ylene, R⁴ and R⁵ are cyclohexyl, and X is chlorine; L¹² is prop-1,3-ylene, L²³ is prop-1,3-ylene, R⁴ and R⁵ are phenyl, and X is chlorine; L¹² is but-1,3-ylene, L²³ is prop-1,3-ylene, R⁴ and R⁵ are isopropyl, and X is chlorine; L¹² is but-1,3-ylene, L²³ is prop-1,3-ylene, R⁴ and R⁵ are cyclopentyl, and X is chlorine; L¹² is but-1,3-ylene, L²³ is but-1,3-ylene, R⁴ and R⁵ are isopropyl, and X is chlorine; L¹² is but-1,3-ylene, L²³ is but-1,3-ylene, R⁴ and R⁵ are phenyl, and X is chlorine; L¹² is ethen-1,2-ylene, L²³ is prop-1,3-ylene, R⁴ and R⁵ are isopropyl, and X is chlorine; L¹² is ethen-1,2-ylene, L²³ is prop-1,3-ylene, R⁴ and R⁵ are cyclopentyl, and X is chlorine; L¹² is ethen-1,2-ylene, L²³ is prop-1,3-ylene, R⁴ and R⁵ are cyclohexyl, and X is chlorine; L¹² is phen-1,2-ylene, L²³ is eth-1,2-ylene, R⁴ and R⁵ are isopropyl, and X is chlorine: and v) Structure HCPACr2 where T is sulfur, L¹² is ethen-1,2-ylene, R³ is H, R⁴ and R⁵ are isopropyl, and X is chlorine; and T is sulfur, L¹² is phen-1,2-ylene, R³ is H, R⁴ and R⁵ are isopropyl, and X is chlorine.

In a non-limiting aspect, the one or more first training heteroatomic ligands associated with the one or more first training heteroatomic ligand-metal compound complexes can be selected from, among others, any one or more of HL 1, HL 2, HL 3, HL 4. HL 5, HL 6, HL 7, HL 7, and HL 9. In some non-limiting aspects, the one or more first training heteroatomic ligand-metal compound complexes can be selected from, among others, a diphosphino amine chromium compound complex which can be a chromium compound complex of any one or more of HLCr 1, HLCr 2, HLCr 3, HLCr 4, HLCr 5, HLCr 6, HLCr 7, HLCr 8, and HLCr 9. In other non-limiting aspects, the one or more first training heteroatomic ligand-metal compound complexes can be selected from, among others, the diphosphino amine chromium compound complex can be a chromium(III) chloride or chromium(III) acetylacetonate complex of any one or more of HLCr 1, HLCr 2, HLCr 3, HLCr 4, HLCr 5, HLCr 6, HLCr 7, HLCr 8, and HLCr 9.

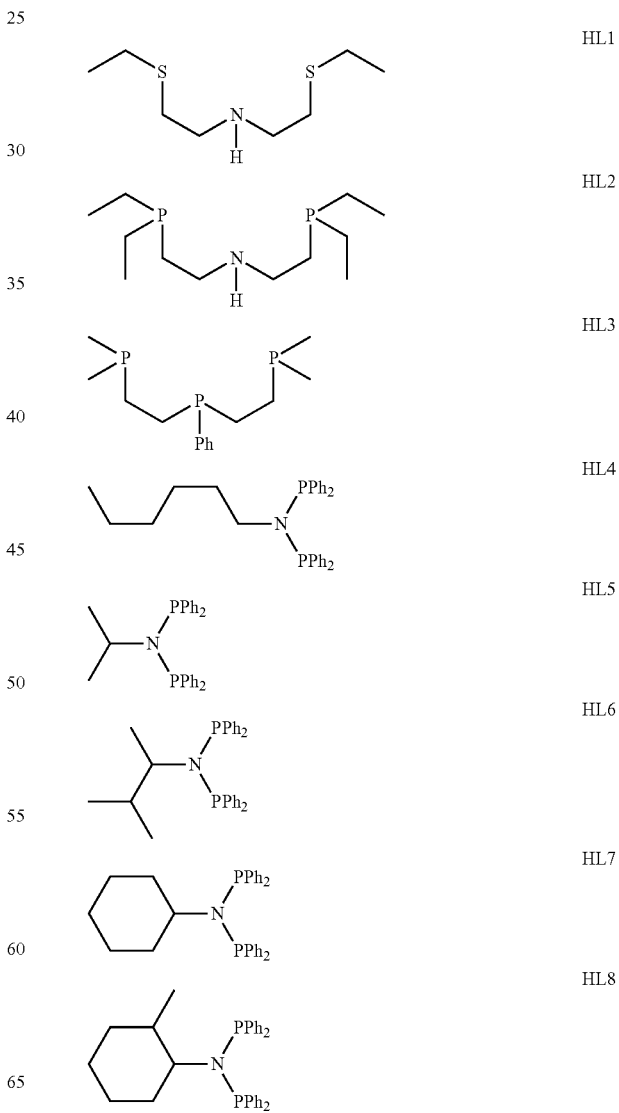

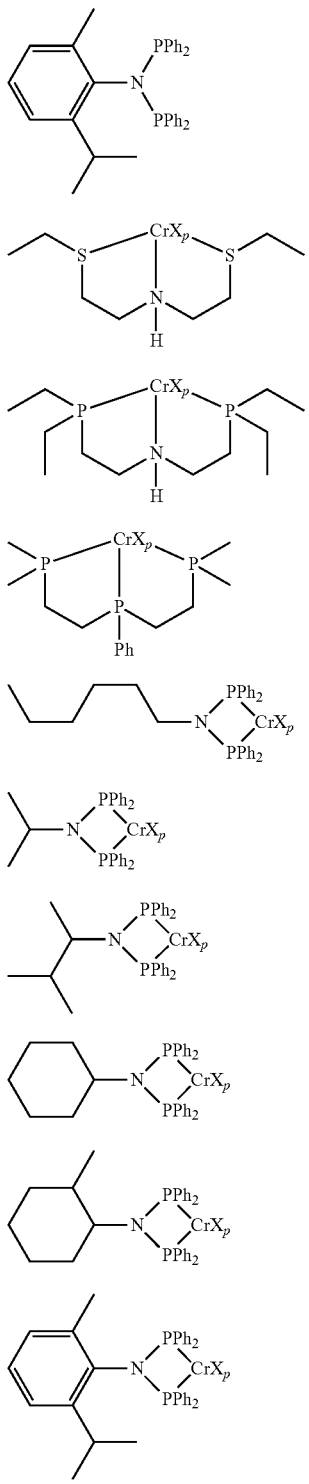

While not shown in all of the chromium compound names and formulas and/or heteroatomic ligand chromium compound complex formulas and structures provided herein, one of ordinary skill in the art will recognize that a neutral ligand, Q (L of the general heteroatomic ligand formula [(HetLig)CrX$_q$L$_r$]$^{3-q}$ (A)), can be associated with the chromium compounds and/or the heteroatomic ligand chromium compound complexes described/depicted herein which do not explicitly disclose/depict a neutral ligand. Additionally it should be understood that while some of the chromium compounds and/or heteroatomic ligand chromium compound complexes described/depicted/provided herein do not formally show the presence of a neutral ligand, the chromium compounds and/or heteroatomic ligand chromium compound complexes having neural ligands (e.g., nitriles and ethers, among others) are implicitly and fully contemplated as potential the chromium compounds and/or heteroatomic ligand chromium compound complexes that can be utilized in the catalyst system used in aspects of the herein described inventions.

Generally, the neutral ligand of any chromium compound and/or heteroatomic ligand chromium compound complex, when present, independently can be any neutral ligand that forms an isolatable compound with the chromium compound and/or heteroatomic ligand chromium compound complex. In an aspect, each neutral ligand independently can be a nitrile or an ether; alternatively, a nitrile; or alternatively, an ether. The number of neutral ligands, q (r of the general formula [(HetLig)CrX$_q$L$_r$]$^{3-q}$ (A)), can be any number that forms an isolatable compound with the chromium compound and/or heteroatomic ligand chromium compound complex. In an aspect, the number of neutral ligands can be from 0 to 6; alternatively, 0 to 3; alternatively, 0; alternatively, 1; alternatively, 2; alternatively, 3; or alternatively, 4.

Generally, each nitrile ligand independently can be a $C_2$ to $C_{20}$ nitrile; or alternatively, a $C_2$ to $C_{10}$ nitrile. In an aspect, each nitrile ligand independently can be a $C_2$ to $C_{20}$ aliphatic nitrile, a $C_7$ to $C_{20}$ aromatic nitrile, a $C_8$ to $C_{20}$ aralkane nitrile, or any combination thereof; alternatively, a $C_2$ to $C_{20}$ aliphatic nitrile; alternatively, a $C_7$ to $C_{20}$ aromatic nitrile; or alternatively, a $C_8$ to $C_{20}$ aralkane nitrile. In some aspects, each nitrile ligand independently can be a $C_2$ to $C_{10}$ aliphatic nitrile, a $C_7$ to $C_{10}$ aromatic nitrile, a $C_8$ to $C_{10}$ aralkane nitrile, or any combination thereof; alternatively, a $C_1$ to $C_{10}$ aliphatic nitrile; alternatively, a $C_7$ to $C_{10}$ aromatic nitrile; or alternatively, a $C_8$ to $C_{10}$ aralkane nitrile. In an aspect, each aliphatic nitrile independently can be acetonitrile, propionitrile, a butyronitrile, benzonitrile, or any combination thereof; alternatively, acetonitrile; alternatively, propionitrile; alternatively, a butyronitrile; or alternatively, benzonitrile.

Generally, each ether ligand independently can be a $C_2$ to $C_{40}$ ether; alternatively, a $C_2$ to $C_{30}$ ether; or alternatively, a $C_2$ to $C_{20}$ ether. In an aspect, each ether ligand independently can be a $C_2$ to $C_{40}$ aliphatic ether, a $C_3$ to $C_{40}$ aliphatic cyclic ether, a $C_4$ to $C_{40}$ aromatic cyclic ether; alternatively, a $C_2$ to $C_{40}$ aliphatic acyclic ether or a $C_3$ to $C_{40}$ aliphatic cyclic ether; alternatively, a $C_2$ to $C_{40}$ aliphatic acyclic ether; alternatively, a $C_3$ to $C_{40}$ aliphatic cyclic ether; or alternatively, a $C_4$ to $C_{40}$ aromatic cyclic ether. In some aspects, each ether ligand independently can be a $C_2$ to $C_{30}$ aliphatic ether, a $C_3$ to $C_{30}$ aliphatic cyclic ether, a $C_4$ to $C_{30}$ aromatic cyclic ether; alternatively, a $C_2$ to $C_{30}$ aliphatic acyclic ether or a $C_3$ to $C_{30}$ aliphatic cyclic ether; alternatively, a $C_2$ to $C_{30}$ aliphatic acyclic ether; alternatively, a $C_3$ to $C_{30}$ aliphatic cyclic ether; or alternatively, a $C_4$ to $C_{30}$ aromatic cyclic ether. In other aspects, each ether ligand independently can be a $C_2$ to $C_{20}$ aliphatic ether, a $C_3$ to $C_{20}$ aliphatic cyclic ether, a $C_4$ to $C_{20}$ aromatic cyclic ether; alternatively, a $C_2$ to $C_{20}$ aliphatic acyclic ether or a $C_3$ to $C_{20}$ aliphatic cyclic ether; alternatively, a $C_2$ to $C_{20}$ aliphatic acyclic ether; alternatively, a $C_3$ to $C_{20}$ aliphatic cyclic ether; or alternatively, a $C_4$ to $C_{20}$ aromatic cyclic ether. In some aspects, each ether ligand independently can be dimethyl ether, diethyl ether, a dipropyl ether, a dibutyl ether, methyl ethyl ether, a methyl propyl ether, a methyl butyl ether, tetrahydrofuran, a dihydrofuran, 1,3-dioxolane, tetrahydropyran, a dihydropyran, a pyran, a dioxane, furan, benzofuran, isobenzofuran, dibenzofuran, diphenyl ether, a ditolyl ether, or any combination thereof; alternatively, dimethyl ether, diethyl ether, a dipropyl ether, a dibutyl ether, methyl ethyl ether, a methyl propyl ether, a methyl butyl ether, or any combination thereof; tetrahydrofuran, a dihydrofuran, 1,3-dioxolane, tetrahydropyran, a dihydropyran, a pyran, a dioxane, or any combination thereof; furan, benzofuran, isobenzofuran, dibenzofuran, or any combination thereof; diphenyl ether, a ditolyl ether, or any combination thereof; alternatively, dimethyl ether; alternatively, diethyl ether; alternatively, a dipropyl ether; alternatively, a dibutyl ether; alternatively, methyl ethyl ether; alternatively, a methyl propyl ether; alternatively, a methyl butyl ether; alternatively, tetrahydrofuran; alternatively, a dihydrofuran; alternatively, 1,3-dioxolane; alternatively, tetrahydropyran; alternatively, a dihydropyran; alternatively, a pyran; alternatively, a dioxane; alternatively, furan; alternatively, benzofuran; alternatively, isobenzofuran; alternatively, dibenzofuran; alternatively, diphenyl ether; or alternatively, a ditolyl ether.

Accordingly, in any of the one or more ground state model structures and any of the plurality of transition state model structures, the model structures comprise a heteroatomic ligand which can be independently selected from:

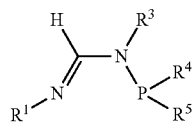

NPF-1

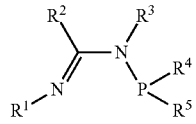

NPA-1

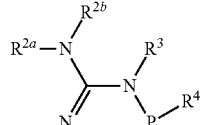

Gu-1

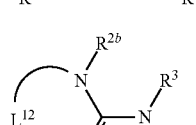

Gu-2

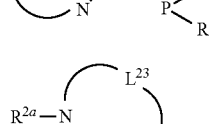

Gu-3

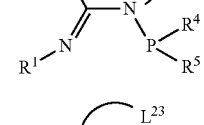

Gu-4

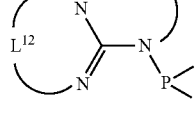

-continued

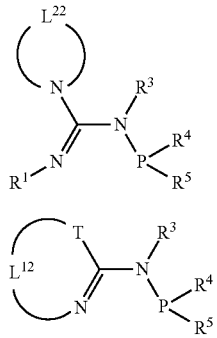

Gu-5

HCPA-1 wherein:
$R^1$ can be a hydrogen or a $C_1$ to $C_{20}$ organyl group;
$R^2$ can be a $C_1$ to $C_{20}$ organyl group;
T can be oxygen or sulfur;
$R^{2a}$ and $R^{2b}$ independently can be $C_1$ to $C_{20}$ organyl groups;
$L^{12}$ and $L^{23}$ independently can be $C_2$ to $C_{20}$ organylene groups;
$L^{22}$ can be a $C_3$ to $C_{20}$ organylene groups;
$R^3$ can be hydrogen or a $C_1$ to $C_{20}$ organyl group; and
$R^4$ and $R^5$ independently can be hydrogen or a $C_1$ to $C_{20}$ organyl groups;
where $R^1$ and $R^2$ optionally can be joined to form $L^{12r}$, and $L^{12r}$ is a $C_3$ to $C_{30}$ organylene group; and
where $R^4$ and $R^5$ optionally can be joined to form $L^{45}$, and $L^{45}$ is a $C_4$ to $C_{30}$ organylene group.

In a further aspect, the model structures can comprise a heteroatomic ligand which can be independently selected from NPF-1, NPA-1, Gu-1, Gu-2, Gu-3, Gu-4, Gu-5, or HCPA-1 as set out herein, wherein:
$R^1$ can be hydrogen, a $C_1$ to $C_{20}$ hydrocarbyl group, or a $C_1$ to $C_{20}$ heterohydrocarbyl group;
$R^2$ can be a $C_1$ to $C_{20}$ hydrocarbyl group or a $C_1$ to $C_{20}$ heterohydrocarbyl group;
$R^{2a}$ and $R^{2b}$ independently can be selected from a $C_1$ to $C_{20}$ hydrocarbyl group or a $C_1$ to $C_{20}$ heterohydrocarbyl group;
$L^{12}$ and $L^{23}$ independently can be selected from a $C_2$ to $C_{20}$ hydrocarbylene group or a $C_2$ to $C_{20}$ heterohydrocarbylene group;
$L^{22}$ can be a $C_3$ to $C_{20}$ hydrocarbylene group or a $C_3$ to $C_{20}$ heterohydrocarbylene group;
$R^3$ can be hydrogen, a $C_1$ to $C_{20}$ hydrocarbyl group, or a $C_1$ to $C_{20}$ heterohydrocarbyl group; and
$R^4$ and $R^5$ independently can be selected from a $C_1$ to $C_{20}$ hydrocarbyl group or a $C_1$ to $C_{20}$ heterohydrocarbyl group;
where $R^1$ and $R^2$ optionally can be joined to form $L^{12r}$, and $L^{12r}$ can be a $C_3$ to $C_{20}$ hydrocarbylene group or a $C_3$ to $C_{20}$ heterohydrocarbylene group; and
where $R^4$ and $R^5$ optionally can be joined to form $L^{45}$, and $L^{45}$ can be a $C_4$ to $C_{20}$ hydrocarbylene group or a $C_4$ to $C_{20}$ heterohydrocarbylene group.

Additional aspects of the model structures can easily be envisioned by those having ordinary skill in the art using the herein independently described $R^1$, $R^2$, T, $R^{2a}$, $R^{2b}$, $R^3$, $R^4$, $R^5$, $L^{12}$, $L^{22}$, $L^{23}$ groups for NPF-1, NPA-1, Gu-1, Gu-2, Gu-3, Gu-4, Gu-5, or HCPA-1 as set out herein. Encompassed in these various selections for the specific "R" and "L" moieties in NPF-1, NPA-1, Gu-1, Gu-2, Gu-3, Gu-4, Gu-5, or HCPA-1, in which "hydrocarbyl", "hydrocarbylene", "heterohydrocarbyl", or "heterohydrocarbylene" moieties are recited, reference is made to the definitions section in which these terms are defined. For example, encompassed in the designations "hydrocarbyl" or a "hydrocarbylene" are included, respectively: aryl and arylene; alkyl and alkanediyl (or "alkylene"); cycloalkyl and cycloalkanediyl (or "cycloalkylene"); aralkyl and aralkanediyl (or "aralkylene"); and so forth; wherein the specified number of carbon atoms is appropriate for the selected group. Similarly, the definitions section describes moieties that can be encompassed by the designations "hydrocarbyl" or a "hydrocarbylene".

In a further aspect, in any of the one or more ground state model structures and any of the plurality of transition state model structures, the model structures comprise a heteroatomic ligand which also may be independently selected from:

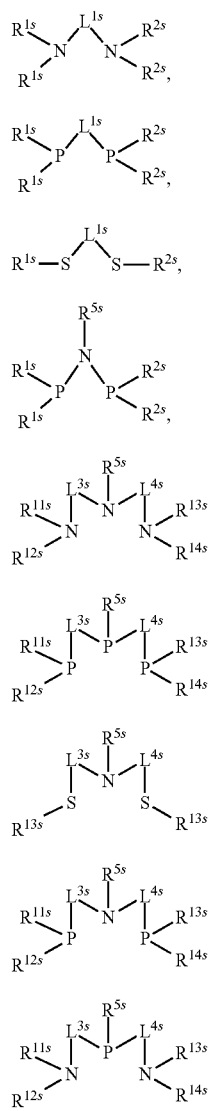

wherein:
each $R^{1s}$, $R^{2s}$, $R^{5s}$, $R^{11s}$, $R^{12s}$, $R^{13s}$, and $R^{14s}$, independently, can be selected from a hydrogen or a $C_1$ to $C_{20}$ organyl group;

each $L^{1s}$, $L^{3s}$, and $L^{4s}$, independently, can be selected from a $C_2$ to $C_{20}$ organylene group; and any two geminal $R^{1s}$ optionally can be joined to form $L^{11s}$, and $L^{11s}$ is a $C_3$ to $C_{30}$ organylene group;

any two geminal $R^{2s}$ optionally can be joined to form $L^{22s}$, and $L^{22s}$ is a $C_3$ to $C_{30}$ organylene group;

any germinal $R^{11s}$ and $R^{12s}$ optionally can be joined to form $L^{12s}$, and $L^{12s}$ is a $C_3$ to $C_{30}$ organylene group; and any germinal $R^{13s}$ and $R^{14s}$ optionally can be joined to form $L^{34s}$, and $L^{34s}$ is a $C_3$ to $C_{30}$ organylene group.

In a further aspect, the model structures can comprise a heteroatomic ligand which can be independently selected from NRN-1, PRP-1, SRS-1, PNP-1, NRNRN-1, PRPRP-1, SRSRS-1, PRNRP-1, or NRPRN-1 as set out above, wherein:
each $R^{1s}$, $R^{2s}$, $R^{5s}$, $R^{11s}$, $R^{12s}$, $R^{13s}$, and $R^{14s}$, independently, can be selected from hydrogen, a $C_1$ to $C_{20}$ hydrocarbyl group, or a $C_1$ to $C_{20}$ heterohydrocarbyl group;

each $L^{1s}$, $L^{3s}$, and $L^{4s}$, independently, can be selected from a $C_2$ to $C_{20}$ hydrocarbylene group or a $C_2$ to $C_{20}$ heterohydrocarbylene group;

any two geminal $R^{1s}$ optionally can be joined to form $L^{11s}$, and $L^{11s}$ is a $C_2$ to $C_{20}$ hydrocarbylene group or a $C_2$ to $C_{20}$ heterohydrocarbylene group;

any two geminal $R^{2s}$ optionally can be joined to form $L^{22s}$, and $L^{22s}$ is a $C_2$ to $C_{20}$ hydrocarbylene group or a $C_2$ to $C_{20}$ heterohydrocarbylene group;

any germinal $R^{11s}$ and $R^{12s}$ optionally can be joined to form $L^{12s}$, and $L^{12s}$ is a $C_2$ to $C_{20}$ hydrocarbylene group or a $C_2$ to $C_{20}$ heterohydrocarbylene group; and any germinal $R^{13s}$ and $R^{14s}$ optionally can be joined to form $L^{34s}$, and $L^{34s}$ is a $C_2$ to $C_{20}$ hydrocarbylene group or a $C_2$ to $C_{20}$ heterohydrocarbylene group.

Additional aspects of the model structures can easily be envisioned by those having ordinary skill in the art using the herein independently described $R^{1s}$, $R^{2s}$, $R^{5s}$, $R^{11s}$, $R^{12s}$, $R^{13s}$, $R^{14s}$, $L^{1s}$, $L^{3s}$, $L^{4s}$, $L^{11s}$, $L^{12s}$, $L^{22s}$, and $L^{34s}$ groups for NRN-1, PRP-1, SRS-1, PNP-1, NRNRN-1, PRPRP-1, SRSRS-1, PRNRP-1, and/or NRPRN-1 as set out herein. Encompassed in these selections for these various "R" and "L" moieties in NRN-1, PRP-1, SRS-1, PNP-1, NRNRN-1, PRPRP-1, SRSRS-1, PRNRP-1, or NRPRN-1, in which "hydrocarbyl", "hydrocarbylene", "heterohydrocarbyl", or "heterohydrocarbylene" moieties are recited, reference is also made to the definitions section in which these terms are defined.

Generally, the organoaluminum compound utilized in the catalyst systems disclosed herein can be any organoaluminum compound which in conjunction with the heteroatomic ligand chromium compound complex (or the chromium compound and heteroatomic ligand) can catalyze the formation of an oligomer product. In an aspect, the organoaluminum compound can be an aluminoxane, an alkylaluminum compound, or any combination thereof, alternatively, an aluminoxane; or alternatively, an alkylaluminum compound. In an aspect, the alkylaluminum compound can be a trialkylaluminum, an alkylaluminum halide, an alkylaluminum alkoxide, or any combination thereof. In some aspects, the alkylaluminum compound can be a trialkylaluminum, an alkylaluminum halide, or any combination thereof, alternatively, a trialkylaluminum, an alkylaluminum alkoxide, or any combination thereof; or alternatively, a trialkylaluminum. In other aspects, the alkylaluminum compound can be a trialkylaluminum; alternatively, an alkylaluminum halide; or alternatively, an alkylaluminum alkoxide. In an aspect, the aluminoxane utilized in the catalyst systems which are utilized in the processes and systems can be any aluminoxane which in conjunction with the heteroatomic ligand chromium compound complex (or the chromium compound and heteroatomic ligand), can catalyze the formation of an oligomer product. In a non-limiting aspect, the aluminoxane can have a repeating unit characterized by the Formula I.

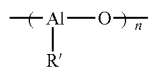

Formula I wherein R' is a linear or branched alkyl group. Alkyl groups of the aluminoxanes and alkylaluminum compounds are independently described herein and can be utilized without limitation to further describe the aluminoxanes having Formula I and/or the alkylaluminum compounds. Generally, n of Formula I can be greater than 1; or alternatively, greater than 2. In an aspect, n can range from 2 to 15; or alternatively, range from 3 to 10.

In an aspect, each halide of any alkylaluminum halide disclosed herein can independently be fluoride, chloride, bromide, or iodide; or alternatively, chloride, bromide, or iodide. In an embodiment, each halide of any alkylaluminum halide disclosed herein can be fluoride; alternatively, chloride; alternatively, bromide; or alternatively, iodide.

In an aspect, each alkyl group of an aluminoxane and/or alkylaluminum compound independently can be a $C_1$ to $C_{20}$ alkyl group; alternatively, a $C_1$ to $C_{10}$ alkyl group; or alternatively, a $C_1$ to $C_6$ alkyl group. In an aspect, each alkyl group of an aluminoxane and/or alkylaluminum compound a methyl group, an ethyl group, a propyl group, a butyl group, a pentyl group, a hexyl group, a heptyl group, or an octyl group; alternatively, a methyl group, a ethyl group, a butyl group, a hexyl group, or an octyl group. In some aspects, each alkyl group of an aluminoxane and/or alkylaluminum compound can be a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In an aspect, each alkoxide group of any alkylaluminum alkoxide disclosed herein independently can be a $C_1$ to $C_{20}$ alkoxy group, a $C_1$ to $C_{10}$ alkoxy group, or a $C_1$ to $C_6$ alkoxy group. In an embodiment, each alkoxide group of any alkylaluminum alkoxide disclosed herein independently can be a methoxy group, an ethoxy group, a propoxy group, a butoxy group, a pentoxy group, a hexoxy group, a heptoxy group, or an octoxy group; alternatively, a methoxy group, an ethoxy group, a butoxy group, a hexoxy group, or an octoxy group. In some embodiments, each alkoxide group of any alkylaluminum alkoxide disclosed herein independently can be a methoxy group, an ethoxy group, an n-propoxy group, an n-butoxy group, an iso-butoxy group, an n-hexoxy group, or an n-octoxy group; alternatively, a methoxy group, an ethoxy group, an n-butoxy group, or an iso-butoxy group; alternatively, a methoxy group; alternatively, an ethoxy group; alternatively, an n-propoxy group; alternatively, an n-butoxy group; alternatively, an iso-butoxy group; alternatively, an n-hexoxy group; or alternatively, an n-octoxy group.

In a non-limiting aspect, useful trialkylaluminum compounds can include trimethylaluminum, triethylaluminum, tripropylaluminum, tributylaluminum, trihexylaluminum, trioctylaluminum, or mixtures thereof. In some non-limiting embodiments, useful trialkylaluminum compounds can include trimethylaluminum, triethylaluminum, tripropylaluminum, tri-n-butylaluminum, tri-isobutylaluminum, tri-hexylaluminum, tri-n-octylaluminum, or mixtures thereof; alternatively, triethylaluminum, tri-n-butylaluminum, tri-isobutylaluminum, trihexylaluminum, tri-n-octylaluminum, or mixtures thereof; alternatively, triethylaluminum, tri-n-butylaluminum, trihexylaluminum, tri-n-octylaluminum, or mixtures thereof. In other non-limiting embodiments, useful trialkylaluminum compounds can include trimethylaluminum; alternatively, triethylaluminum; alternatively, tripropylaluminum; alternatively, tri-n-butylaluminum; alternatively, tri-isobutylaluminum; alternatively, trihexylaluminum; or alternatively, tri-n-octylaluminum.

In a non-limiting embodiment, useful alkylaluminum halides can include diethylaluminum chloride, diethylaluminum bromide, ethylaluminum dichloride, ethylaluminum sesquichloride, and mixtures thereof. In some non-limiting embodiments, useful alkylaluminum halides can include diethylaluminum chloride, ethylaluminum dichloride, ethylaluminum sesquichloride, and mixtures thereof. In other non-limiting embodiments, useful alkylaluminum halides can include diethylaluminum chloride; alternatively, diethylaluminum bromide; alternatively, ethylaluminum dichloride; or alternatively, ethylaluminum sesquichloride In a non-limiting aspect, the aluminoxane can be, comprise, or consist essentially of, methylaluminoxane (MAO), ethylaluminoxane, modified methylaluminoxane (MMAO), n-propylaluminoxane, iso-propyl-aluminoxane, n-butylaluminoxane, sec-butylaluminoxane, iso-butylaluminoxane, t-butylaluminoxane, 1-pentylaluminoxane, 2-entylaluminoxane, 3-pentyl-aluminoxane, iso-pentyl-aluminoxane, neopentylaluminoxane, or mixtures thereof. In some non-limiting aspects, the aluminoxane can be, comprise, or consist essentially of, methylaluminoxane (MAO), modified methylaluminoxane (MMAO), isobutyl aluminoxane, t-butyl aluminoxane, or mixtures thereof. In other non-limiting aspects, the aluminoxane can be, comprise, or consist essentially of, methylaluminoxane (MAO); alternatively, ethylaluminoxane; alternatively, modified methylaluminoxane (MMAO); alternatively, n-propyl-aluminoxane; alternatively, iso-propyl-aluminoxane; alternatively, n-butylaluminoxane; alternatively, sec-butylaluminoxane; alternatively, iso-butylaluminoxane; alternatively, t-butyl aluminoxane; alternatively, 1-pentyl-aluminoxane; alternatively, 2-pentylaluminoxane; alternatively, 3-pentyl-aluminoxane; alternatively, iso-pentyl-aluminoxane; or alternatively, neopentylaluminoxane.

Input Variables for the Model Ground State Structures and Model Transition State Structures In an aspect, in the disclosed method any of the one or more training heteroatomic ligand-metal compound complexes, and any of the one or more target heteroatomic ligand-metal compound complexes can have a formula independently selected from:

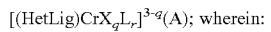

HetLig represents the one or more first training heteroatomic ligands;
X is an anionic ligand, and q is an integer;
L is a neutral ligand, and r is an integer,
wherein any two or more of the X and L ligands may be linked to form a multidentate ligand; and wherein each selected n input variable $I^1, I^2, \ldots I^n$, corresponds to a structural property or an electronic property of any of the one or more ground state model structures $GS^{41}, \ldots GS^{4p}$ or any of the plurality of transition state model structures $TS^{41}, TS^{42}, \ldots TS^{Am}$ associated with the one or more ground state model structures of formula (A).

Based upon the type of heteroatomic ligand and the specific heteroatomic ligand coordinated to the chromium in a ground state model structure and transition state model structure in a training heteroatomic ligand-metal compound complex, the input variables will differ. In one aspect, when the model structures comprise a heteroatomic ligand selected from the general structures NPF-1, NPA-1, Gu-1, Gu-2, Gu-3, Gu-4, Gu-5, or HCPA-1 as set out herein, the chromium heteroatomic ligand moiety can independently be selected from the following structures:

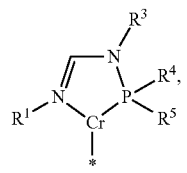

NPFCrM-1

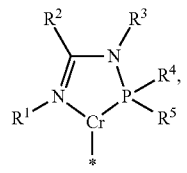

NPACrM-1

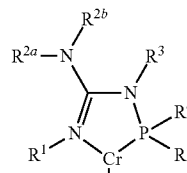

GuCrM-1

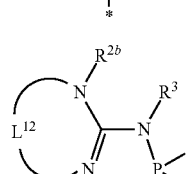

GuCrM-2

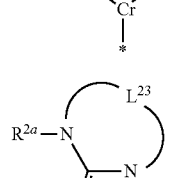

GuCrM-3

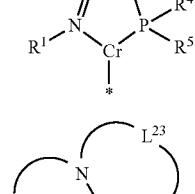

GuCrM-4

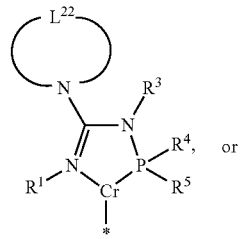

GuCrM-5

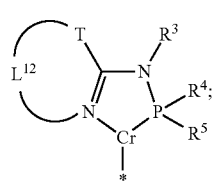

HCPACrM-1 wherein $R^1, R^2, T, R^{2a}, R^{2b}, L^{12}, L^{23}, L^{22}, R^3, R^4, R^5, L^{12}$, and $L^{45}$ are defined as set out herein, and wherein "*" in the structures represents any additional bonding required in [1] any of the one or more ground state model structures or any of the plurality of transition state model structures derived from the one or more first training heteroatomic ligand-metal compound complexes, [2] any of the one or more ground state model structures or any of the plurality of transition state model structures derived from the one or more first target heteroatomic ligand-metal compound complexes, or [3] any of the heteroatomic ligand-metal complexes, first training heteroatomic ligand-metal compound complexes, and/or first target heteroatomic ligand-metal compound complexes.

In an aspect and in view of the model structures comprising the chromium heteroatomic ligand moieties NPFCrM-1, NPACrM-1, GuCrM-1, GuCrM-2, GuCrM-3, GuCrM-4, GuCrM-5, or HCPACrM-1, the n input variables $I^1, I^2, \ldots I^n$ can comprise or can be selected from any one of more of the following variables:

(a) the Cr—P distance (Å);
(b) the Cr—N distance (Å);
(c) the Cr - - - R on α-C distance (Å);
(d) the P—Cr—N angle (deg);
(e) the C—Cr—N angle (deg), wherein C is a non-heteroatomic ligand carbon atom bonded to or within bonding distance of the Cr atom;
(f) the Cr—N—C angle (deg);
(g) the distance out of pocket (Å);
(h) the Cr - - - α-C distance (Å);
(i) the Cr CHELPG (atomic charge);
(j) the P CHELPG (atomic charge);
(k) the N CHELPG (atomic charge);
(l) the Cr—N—C—N Dihedral angle (deg);
(m) the Cr—P—N—C Dihedral angle (deg);
(n) the P—Cr—N—C Dihedral angle (deg);
(o) the P—N—C—N Dihedral angle (deg);
(p) the C—C—N—C Dihedral angle (deg); or
(q) the percent volume buried.

FIG. 1, FIG. 2A, FIG. 2B, and FIG. 2C illustrate some of the input variables recited above using an exemplary heteroatomic ligand-chromium compound complex transition state. Referring to these figures, the Cr—$R^1$ is the distance from the Cr to the group on the carbon alpha to the nitrogen that is bound to the Cr in the FIG. 1 structure. The Cr - - - α-C distance is the direct distance to the carbon itself that is alpha to the nitrogen in the FIG. 1 structure, to which the R group is attached. Referring to FIG. 1, the C—Cr—N angle is an angle formed by the carbon atom attached to the chromium atom an the substrate (i.e., the carbon atom coming from ethylene growth in the ground and/or transition states), the Cr atom, and the nitrogen atom of the heteroatomic ligand complexed to chromium atom of the applicable ground states and transition states. One having ordinary skill in the art will be able to use FIG. 1, FIG. 2A, FIG. 2B, and FIG. 2C to determine the corresponding n input variables $I^1, I^2, \ldots I^n$ for the heteroatomic ligand-chromium compound complexes, heteroatomic ligand-chromium compound complex ground states, heteroatomic ligand-chromium compound complex transition states, and chromium heteroatomic ligand moieties NPFCrM-1, NPACrM-1, GuCrM-1, GuCrM-2, GuCrM-3, GuCrM-4, GuCrM-5, or HCPACrM-1 described herein.

Figures 2A, 2B, 2C:
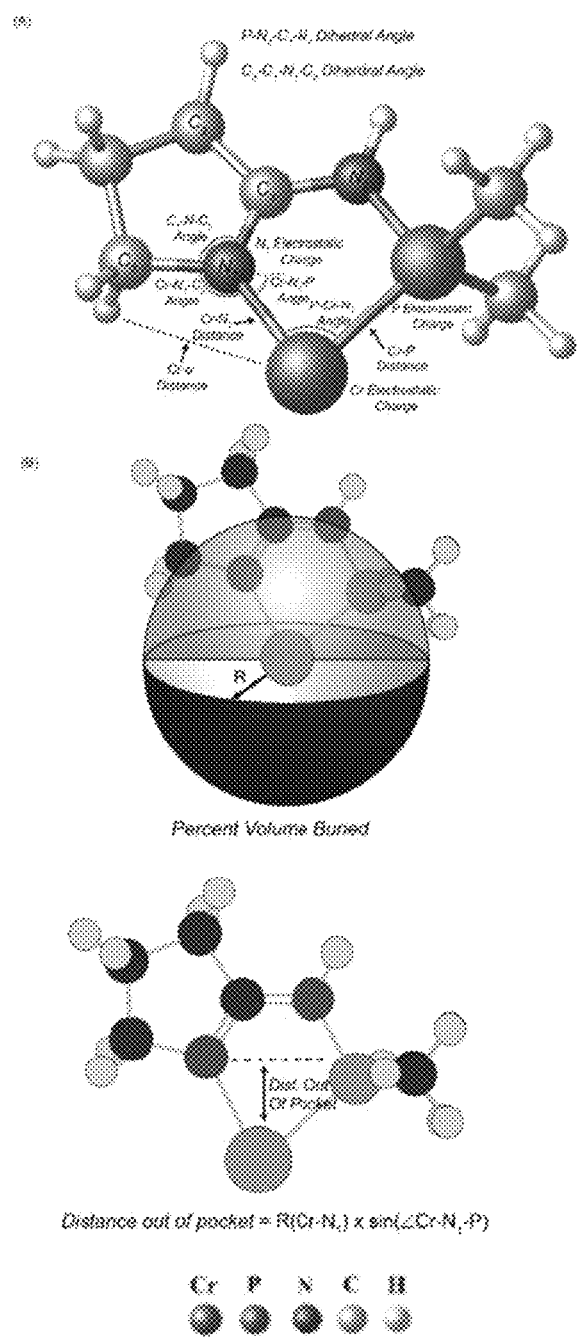
FIG. 2A, FIG. 2B, and FIG. 2C illustrate descriptors extracted for machine learning analysis aspects as follows.

FIGS. 2A-2C provide further explanations and definitions for some of these input variables. For example, these figures illustrate descriptors which can be extracted for machine learning analysis, which include: FIG. 2A, geometric descriptors and description of the electrostatic charges input variables; FIG. 2B, definition of percent volume buried; and FIG. 2C, definition of distance out of pocket. As illustrated, the "distance out of pocket" is defined as follows: Distance out of pocket (d)=R(Cr—N$_1$)·sin(<Cr—N$_1$—P). That is, the distance out of pocket is the Cr—N$_1$ distance times the sine of the Cr—N$_1$—P angle, which describes how far the Cr metal is situated from the (P,N) ligand. The percent volume buried is defined as the extent to which the first coordination sphere of the Cr metal center is occupied by a (P,N) ligand, as used in Falivene, L.; Cao, Z.; Petta, A.; Serra, L.; Poater, A.; Oliva, R.; Scarano, V.; Cavallo, L. Towards the Online Computer-Aided Design of Catalytic Pockets. *Nat. Chem.* 2019, 11 (10), 872-879. https://doi.org/10.1038/s41557-019-0319-5.

In a further aspect, when the model structures comprise a heteroatomic ligand selected from the general structures NRN-1, PRP-1, SRS-1, PNP-1, NRNRN-1, PRPRP-1, SRSRS-1, PRNRP-1, or NRPRN-1 as set out herein, the chromium heteroatomic ligand moiety can independently be selected from the following structures:

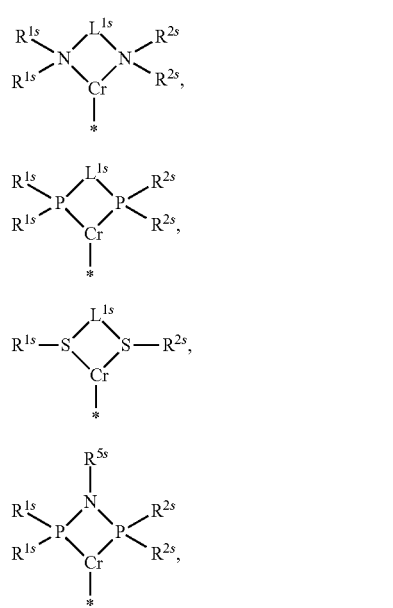

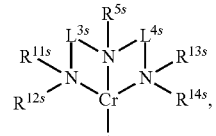

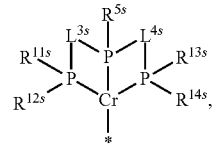

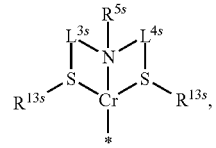

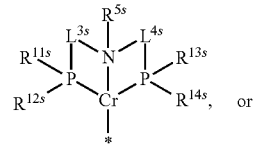

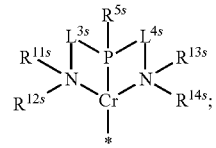

wherein $R^{1s}, R^{2s}, R^{5s}, R^{11s}, R^{12s}, R^{13s}, R^{14s}, L^{1s}, L^{3s}, L^{4s}, L^{11s}, L^{22s}, L^{12s\,r}$, and $L^{34s}$ are defined as set out herein, and wherein "*" in the structures represents any additional bonding required in [1] any of the one or more ground state model structures or any of the plurality of transition state model structures derived from the one or more first training heteroatomic ligand-metal compound complexes, [2] any of the one or more ground state model structures or any of the plurality of transition state model structures derived from the one or more first target heteroatomic ligand-metal compound complexes, or [3] any of the heteroatomic ligand-metal complexes, first training heteroatomic ligand-metal compound complexes, and/or first target heteroatomic ligand-metal compound complexes.

In an aspect and in view of the model structures comprising the chromium heteroatomic ligand moieties NRNCrM-1, PRPCrM-1, SRSCrM-1, PNPCrM-1, NRNRNCrM-1, PRPRPCrM-1, SRNRSCrM-1, PRNRPCrM-1, or NRPRNCrM-1, the n input variables $I^1, I^2, \ldots I^n$ can comprise or can be selected from any one of more of the following variables:

(a) the first, second, or third Cr—N distance (Å);
(b) the first, second, or third Cr—P distance (Å);
(c) the first or second Cr—S distance (Å);
(d) any one or more N—Cr—N angle (deg);
(e) any one or more P—Cr—P angle (deg);
(f) any one or more S—Cr—S angle (deg);
(g) any one or more S—Cr—N angle (deg);
(h) any one or more N—Cr—P angle (deg);
(i) the C—Cr—N angle (deg), wherein C is a non-heteroatomic ligand carbon atom bonded to or within bonding distance of the Cr atom;

(j) the C—Cr—P angle (deg);
(k) the C—Cr—S angle (deg);
(l) the Cr—N—C angle (deg);
(m) the Cr—P—C angle (deg);
(n) the Cr—S—C angle (deg);
(o) the Cr—P—C angle (deg);
(p) the Cr - - - R on α-C distance (Å);
(q) the distance out of pocket (Å);
(r) the Cr - - - α-C;
(s) the Cr CHELPG (atomic charge);
(t) any P CHELPG (atomic charge);
(u) any N CHELPG (atomic charge);
(v) any chelate Cr—N—C—C Dihedral angle (deg);
(w) any chelate Cr—P—C—C Dihedral angle (deg);
(x) any chelate Cr—S—C—C Dihedral angle (deg); or
(y) the percent volume buried.

FIG. 2B illustrates the definition of percent volume buried, and FIG. 2C illustrates the definition of the distance out of pocket.

Performance Parameters and Adjusting Input Variables to Approach the Corresponding Output Variables In the methods of this disclosure, a first target heteroatomic ligand-metal compound complex for olefin oligomerization is generated, based upon the one or more n input variables $I^1, I^2, \ldots I^n$ identified from the machine learning model. The first target heteroatomic ligand-metal compound complex is characterized by n output variables $O^1, O^2, \ldots O^n$, each having a quantitative value corresponding to a structural property or an electronic property of one or more ground state model structures $GS^{B1}, \ldots GS^{Bx}$ (x is an integer) or any of a plurality of transition state model structures $TS^{B1}, TS^{B2}, \ldots TS^{By}$ (y is an integer) associated with the one or more ground state model structures. The first target heteroatomic ligand-metal compound complex comprises a first target heteroatomic ligand which have been generated by computationally evaluating the first training model against the machine learning model to discover the desired adjustments which will generate the first target heteroatomic ligand.

In an aspect, one or more performance parameters associated with an olefin oligomerization reaction are identified, and the value of the performance parameters for the one or more first training heteroatomic ligand-metal compound complexes and the first target heteroatomic ligand-metal compound complex are computationally evaluated, experimentally verified against the training compounds, and subjected to further testing and re-design. In this manner, catalyst performance can be predicted and improved.

As disclosed herein, the quantitative value assigned to each n input variable $I^1, I^2, I^n$, for each of the one or more ground state model structures $GS^{A1}, \ldots GS^{Ap}$ and each of the plurality of transition state model structures $TS^{A1}, TS^{A2}, \ldots TS^{Am}$ derived from the one or more first training heteroatomic ligand-metal compound complexes can be assigned on the basis of calculated, measured, or estimated values, or any combination thereof. Moreover, these quantitative values assigned to each n input variable $I^1, I^2, \ldots I^n$, for each of the one or more ground state model structures $GS^{A1}, \ldots GS^{Ap}$ and each of the plurality of transition state model structures $TS^{A1}, TS^{A2}, \ldots TS^{Am}$ can be independently a raw value or a normalized value. Additionally, determining the relative energies of each of the ground state model structures $GS^{A1}, \ldots GS^{Ap}$ and each of the transition state model structures $TS^{A1}, TS^{A2}, \ldots TS^{Am}$, these determined relative energies can be independently the relative energies of a possible ensemble of conformations or one specific conformation of the ground state model structures and the transition state model structures. Also, the one or more of the n input variables $I^1, I^2, \ldots I^n$ associated with [1] ΔG(TS-GS) or ΔΔG(TS-GS) or [2] ΔG(TS-TS) or ΔΔG(TS-TS), these ΔG or ΔΔG energy differences can be based upon a Boltzmann ensemble ΔG or ΔΔG values. For example, as explained in detail in this disclosure, in one aspect, any of the ground state model structures $GS^{A1}, \ldots GS^{Ap}$ or any of the plurality of transition state model structures $TS^{A1}, TS^{A2}, \ldots TS^{Am}$ derived from the one or more first training heteroatomic ligand-metal compound complexes can be calculated using a density functional theory (DFT) calculations. Further, generating the machine learning model of the disclosed method can comprises a Gaussian Process Algorithm or a Random Forest Algorithm.

According to one aspect of the disclosure, the one or more performance parameters associated with the olefin oligomerization reaction can be selected from: (a) an olefin oligomer purity (also referred to herein as purity or product purity); (b) an olefin oligomer selectivity (also referred to herein as selectivity or product selectivity); (c) a heteroatomic ligand-metal compound complex productivity (also referred to herein as activity/productivity or oligomer productivity); or (d) any combination thereof. More specifically, in an aspect, the one or more performance parameters associated with the olefin oligomerization reaction can be selected from: (a) 1-hexene purity; (b) 1-octene purity; (c) 1-hexene:1-octene ratio ($C_6/C_8$ ratio); (d) 1-hexene productivity; (e) 1-octene productivity; (f) the total 1-hexene plus 1-octene productivity; (g) trimerization selectivity to 1-hexene; (h) tetramerization selectivity to 1-octene; (i) 1-octene efficiency of fourth ethylene addition; or any combination thereof. Based upon these performance parameters, the relevant ground state model structures and the relevant transition state model structures can include or can be selected as follows.

Regarding olefin productivity, the performance parameter associated with the olefin oligomerization reaction can be a heteroatomic ligand-metal compound complex 1-hexene productivity, 1-octene productivity, or a total 1-hexene and 1-octene productivity. Accordingly, when the performance parameter is one of these productivity parameters: [1] the one or more ground state model structures $GS^{A1}, \ldots GS^{Ap}$ derived from one or more first training heteroatomic ligand-metal compound complexes can comprise or can be selected independently from $GS^I$-I, $GS^I$-II, $GS^I$-III, $GS^I$-IV, $GS^I$-V, $GS^I$-VI, $GS^I$-VII, or any combination thereof; [2] the plurality of transition state model structures $TS^{A1}, TS^{A2}, \ldots TS^{Am}$ derived from one or more first training heteroatomic ligand-metal compound complexes can comprise or can be selected independently from $TS^I$-I, $TS^I$-II, $TS^I$-III, $TS^I$-IV, $TS^I$-V, or any combination thereof; [3] the one or more ground state model structures $GS^{B1}, \ldots GS^{Bp}$ derived from the first target heteroatomic ligand-metal compound complex can comprise or can be selected independently from $GS^T$-I, $GS^T$-II, $GS^T$-III, $GS^T$-IV, $GS^T$-V, $GS^T$-VI, $GS^T$-VII, or any combination thereof; and/or [4] the plurality of transition state model structures $TS^{B1}, TS^{B2}, \ldots TS^{Bm}$ derived from the first target heteroatomic ligand-metal compound complex can comprise or can be selected independently from $TS^T$-I, $TS^T$-II, $TS^T$-III, $TS^T$-IV, $TS^T$-V, or any combination thereof. When the one or more performance parameters associated with the olefin oligomerization comprises or is selected from heteroatomic ligand-metal compound complex productivity, it can be determined based upon the grams of olefin oligomer(s) (grams 1-hexene, grams 1-octene, or the total grams of 1-hexene and 1-octene) per grams of the heteroatomic ligand-metal compound complex per hour.

Figure 3:
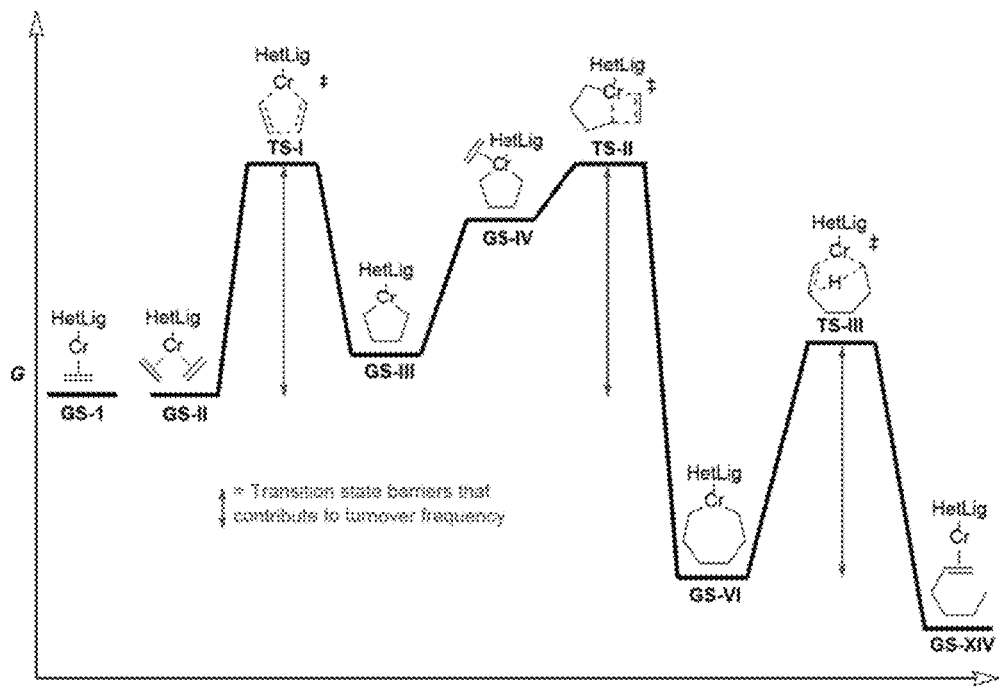
FIG. 3 illustrates the 1-hexene turnover frequency reaction scheme showing various ground states and transition states, and illustrating transition state energy barriers that can contribute to 1-hexene turnover frequency and hence productivity.
Figure 4:
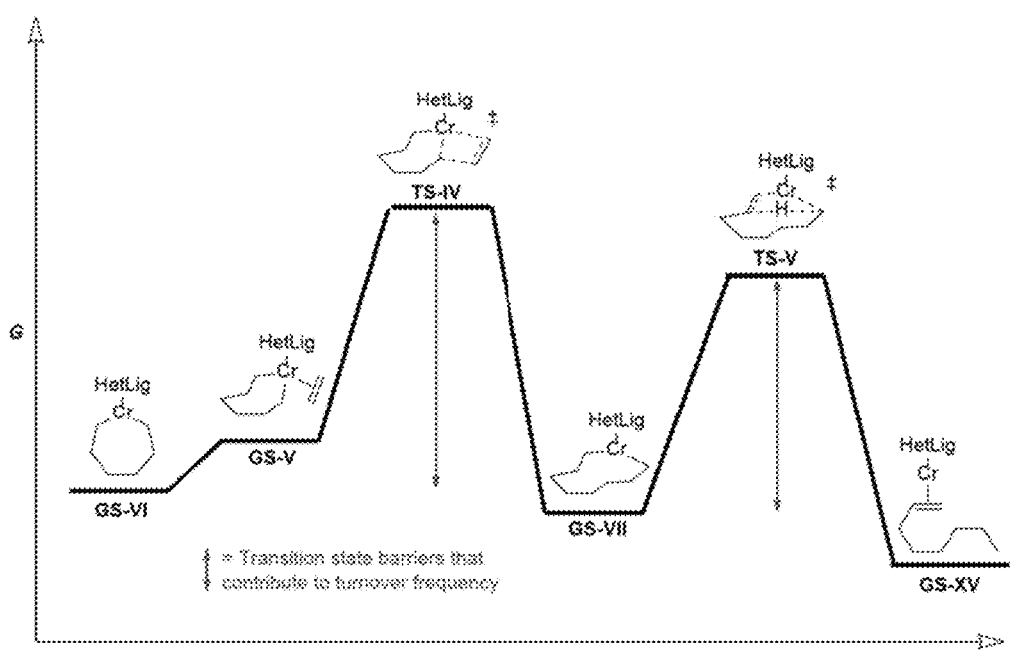
FIG. 4 illustrates the ground states and transition states, and transition state energy barriers, in addition to the ground states and transition states, and transition state energy barriers depicted in FIG. 3, which may be needed for the 1-octene turnover frequency reaction scheme starting with GS-VI that can contribute to 1-octene turnover frequency, hence activity/productivity.

In an aspect, for example, FIG. 3 illustrates the 1-hexene turnover frequency reaction scheme which can be utilized to calculate/determine/estimate 1-hexene productivity showing various ground states and transition states, and illustrating transition state energy barriers that can contribute to the 1-hexene turnover frequency. The 1-hexene turnover frequency is then converted to a 1-hexene productivity. In a further aspect the 1-octene turnover frequency can calculated/determined/estimated using the ground states transition states FIG. 3 plus the ground states and transition states depicted in FIG. 4. FIG. 4 illustrates the 1-octene turnover frequency reaction scheme with its ground states and transition states which must be included with the ground states and transition states of FIG. 3 starting with GS-VI. Thus FIG. 3 plus FIG. 4, illustrates all the transition state energy barriers that contribute to 1-octene turnover frequency which can them be converted to a 1-octene productivity.

When determining the 1-hexene turnover frequency plus 1-octene turnover frequency (hence combined turnover frequency) one can separately determine the 1-hexene turnover frequency and 1-octene turnover frequency using the procedure exemplified for determining 1-hexene turnover frequency herein and then add the separately determined turnover frequency to obtain the combined turnover frequency (total 1-hexene plus 1-octene turnover frequency) which can then be converted to a 1-hexene plus 1-octene productivity.

Figure 5A:
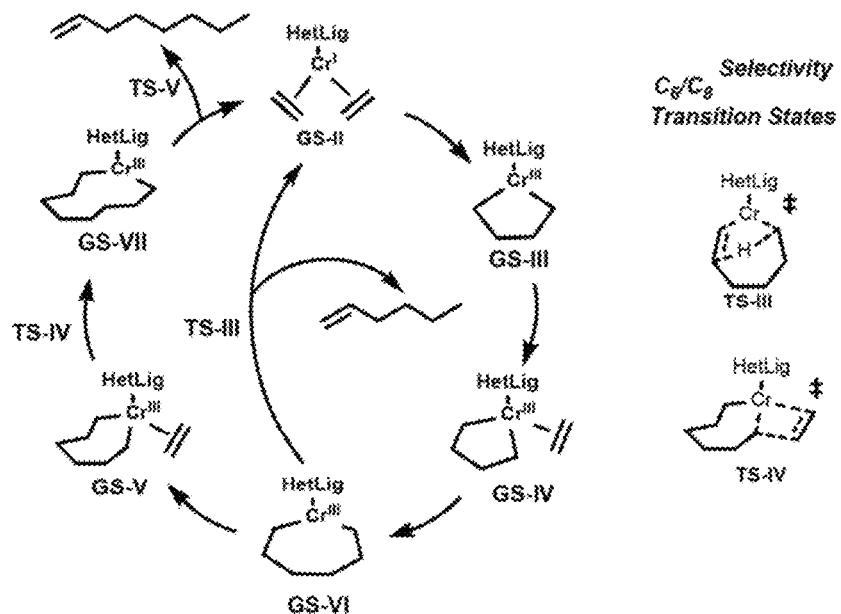
FIG. 5A illustrates one aspect of the disclosure, showing the catalytic cycle pathways by which 1-hexene and/or 1-octene are accessible from a common ground state and can be utilized to calculate $C_6/C_8$ selectivity.

Regarding olefin selectivity, when the performance parameter associated with the olefin oligomerization reaction is product selectivity, which may be referred to simply as the $C_6/C_8$ ratio or the $C_8/C_6$ ratio, FIG. 5A illustrates pathways by which 1-hexene and 1-octene can be formed. The ground state and transition state designations correspond to the ground state and transition state structures disclosed herein. As illustrated, both 1-hexene and 1-octene formation can proceed via common ground state GS-VI. The olefin selectivity, is then determined by whether GS-VI undergoes a β-hydride elimination and reductive elimination through TS-III to generate 1-hexene, versus an ethylene insertion into GS-VI to provide grounds state GS-V and pass through TS-IV to generate the metallacyclanonane GS-VII, which itself then undergoes a β-hydride elimination and reductive elimination to generate 1-octene. The product selectivity can then be determined using the relative amount of ground state GS-VI which undergoes β-hydride elimination to give 1-hexene versus the amount of ground state GS-VI which insets ethylene to give the metallacyclanonane GS-VII using the rate determining transition state (usually TS-III and TS-IV).

Accordingly, regarding selectivity, when the performance parameter associated with the olefin oligomerization reaction is 1-hexene selectivity or 1-octene selectivity, which may be referred to simply as the a $C_6/C_8$ ratio: [1] the one or more ground state model structures $GS^{A1}, \ldots GS^{Ap}$ derived from one or more first training heteroatomic ligand-metal compound complexes can comprise $GS^I$-VI; [2] the plurality of transition state model structures $TS^{A1}, TS^{A2}, \ldots TS^{Am}$ derived from one or more first training heteroatomic ligand-metal compound complexes can comprise $TS^I$-III and $TS^I$-IV; [3] the one or more ground state model structures $GS^{B1}, \ldots GS^{Bp}$ derived from the first target heteroatomic ligand-metal compound complex can comprise $GS^T$-VI; and/or [4] the plurality of transition state model structures $TS^{B1}, TS^{B2}, TS^{Bm}$ derived from the first target heteroatomic ligand-metal compound complex can comprise $TS^T$-III and $TS^T$-IV. Thus, when the one or more performance parameters comprises or is selected from olefin oligomer selectivity, the product selectivity can be determined by determining Gibbs free energy difference between the transition state leading from a common ground state (typically GS-VI) and the transition states 1) leading to 1-hexene production (typically TS-III) and 2) the transition state leading to 1-octene production (typically TS-IV). The Gibbs free energy difference can then be utilized to determine the amounts of 1-hexene and 1-octene from a plot of calculated Gibbs free energy difference, $\Delta\Delta G[TS(1\text{-hexene})\text{-}TS(1\text{-octene})]$ versus the natural logarithm of a set of heteroatomic ligand-metal compound complexes for which experimentally determined Gibbs free energy difference and experimentally determined masses of 1-hexene and 1-octene are known. Alternatively, the experimentally determined masses of 1-hexene and 1-octene can be replace by calculated activities/productivities as calculated/determined/estimated by the methods described herein (via determining the turnover frequencies for 1-hexene production and 1-octene production).

Selective ethylene oligomerization to 1-hexene and 1-octene can produce by-products. Consequently, the selectivity of the trimerization catalytic cycle to 1-hexene (also referred to as the trimerization cycle selectivity to 1-hexene) and/or the selectivity of the tetramerization catalytic cycle to 1-octene (also referred to as the tetramerization cycle selectivity to 1-octene) can be performance parameters associated with olefin oligomerization which impacted by the heteroatomic ligand-metal compound complexes. The trimerization cycle selectivity to 1-hexene is the number of moles 1-hexene produced divided by the number of moles of 1-hexene produced plus the number of moles of non-1-hexene by-products produced by the trimerization catalytic cycle. The tetramerization cycle selectivity to 1-octene is the number of moles of 1-octene produced divided by the number of moles of 1-octene produced plus the number of moles of non-1-octene by-products produced by the tetramerization catalytic cycle.

The trimerization cycle selectivity to 1-hexene and the tetramerization cycle selectivity to 1-octene can also be utilized to focus on particular/specific non-1-hexene by-products produced by the trimerization catalytic cycle and/or particular/specific non-1-octene by by-products produced by the tetramerization catalytic cycle. In these instances, the trimerization cycle selectivity would be the number of moles of 1-hexene produced divided by the number of moles of 1-hexene produced plus the number of moles of the particular non-1-hexene by-products produced in the trimerization catalytic cycle while the tetramerization cycle selectivity to 1-octene would be the number of moles 1-octene produced as compared to the total number of moles of 1-octene produced plus the number of moles of the particular non-1-octene by-products produced in the tetramerization catalytic cycle.

Figure 5B:
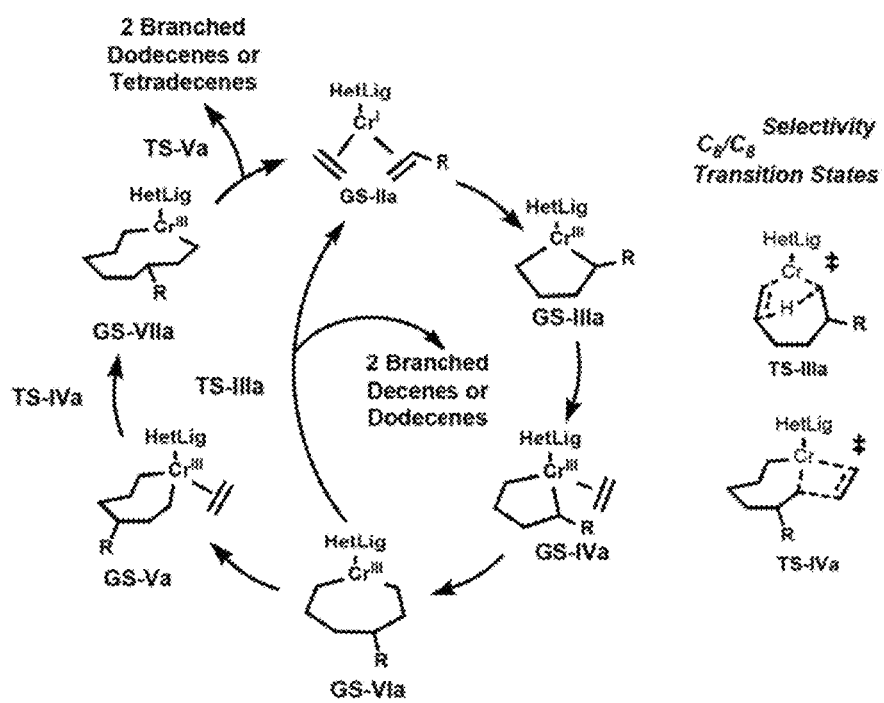
FIG. 5B illustrates another aspect of the disclosure, showing the catalytic cycle pathways by which 1-hexene and/or 1-octene can propagate through the trimerization and/or tetramerization catalytic cycles to produce branched decenes, branched dodecenes, and/or branched tetradecenes.
Figure 5C:
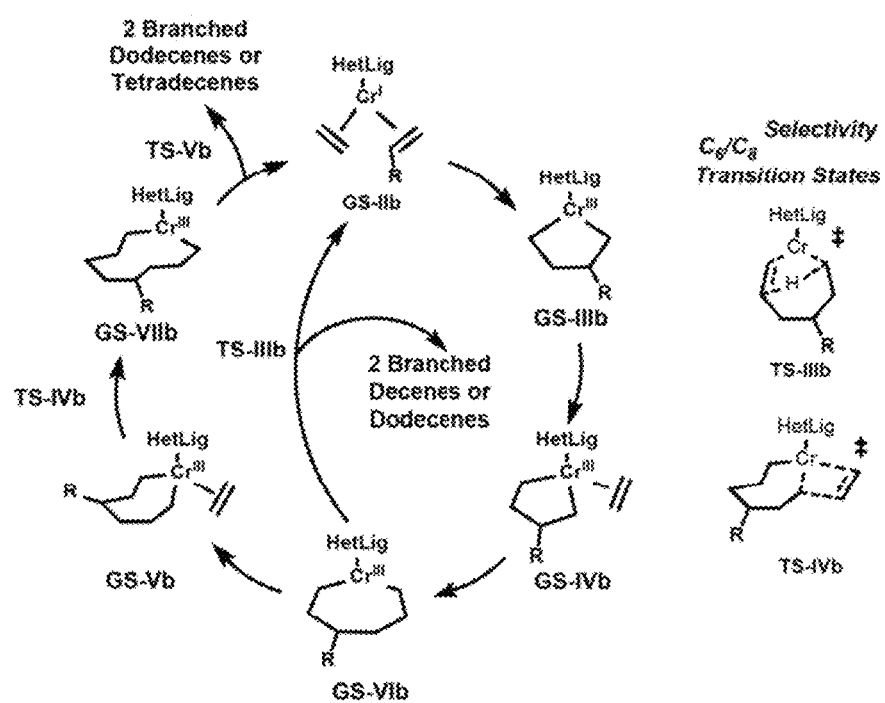
FIG. 5C illustrates a further aspect of the disclosure, showing the catalytic cycle pathways by which 1-hexene and/or 1-octene can propagate through the trimerization and/or tetramerization catalytic cycles to produce branched decenes, branched dodecenes, and/or branched tetradecenes.

A particular set of non-1-hexene by-products produced by the trimerization catalytic cycle and/or non-1-octene by-products produced by the tetramerization catalytic cycle can occur when 1-hexene or 1-octene produced in the trimerization and/or tetramerization replaces one of the ethylenes in the trimerization and/or tetramerization catalytic cycle. A particular relevant case is where the produced 1-hexene or 1-octene complexes with the chromium species to form a ground state structure analogous to GS-II of the trimerization and tetramerization catalytic cycle depicted in FIG. 5A. The 1-hexene or 1-octene participating in the trimerization and/or tetramerization cycle can take two different orientations leading to two structurally different chromatocyclopentanes. FIG. 5B and FIG. 5C shows how the 1-hexene or 1-octene can propagate through the trimerization and/or tetramerization catalytic cycles to produce branched decenes, branched dodecenes, and/or branched tetradecenes.

Additionally, each different 1-hexene or 1-octene orientation leading to the two structurally different substituted chromatocyclopentanes in turn leads to two different branched decenes (for 1-hexene insertion) and two different branched dodecenes (for 1-octene insertion) in the trimerization catalytic cycle and/or two different branched dodecenes (for 1-hexene insertion) and two different branched tetradecenes (for 1-octene insertion) in the tetramerization catalytic cycle.

The methods disclosed herein can be utilized to design/identify heteroatomic ligand-metal compound complexes for olefin oligomerization which have desirable trimerization cycle selectivity to 1-hexene (based on all non-1-hexene catalytic trimerization by-products or based upon particular/specific non-1-hexene catalytic trimerization by-products) and/or desirable tetramerization cycle selectivity to 1-octene (based on all non-1-octene hexene catalytic trimerization by-products or based upon particular/specific non-1-hexene catalytic trimerization by-products).

The trimerization cycle selectivity to 1-hexene (based upon either all non-1-hexene catalytic trimerization by-products or based upon particular/specific non-1-hexene catalytic trimerization by-products) can be determined using different methods described herein.

In a non-limiting first method, the amounts of 1-hexene and the non-1-hexene catalytic trimerization by-products can be determined from non-1-hexene catalytic trimerization by-product to 1-hexene ratios. In this method the non-1-hexene catalytic trimerization by-product to 1-hexene ratio for each non-1-hexene catalytic trimerization by-product upon which the trimerization cycle selectivity to 1-hexene is based is determined by determining the Gibbs free energy difference, $\Delta\Delta G$, between 1) the rate determining transition state/reaction step leading to 1-hexene production and 2) the rate determining transition state/reaction step leading to non-1-hexene catalytic trimerization by-product. The Gibbs free energy difference can then be utilized to determine the amounts of 1-hexene and non-1-hexene catalytic trimerization by-products from a plot of calculated Gibbs free energy difference, $\Delta\Delta G[TS(1\text{-hexene})\text{-}TS(\text{non-1-hexene catalytic trimerization by-product})]$ versus the natural logarithm of a set of heteroatomic ligand-metal compound complexes for which experimentally determined Gibbs free energy difference and experimentally determined amounts of 1-hexene and non-1-hexene catalytic trimerization by-product are known. It should be noted that the selectivity determining transition state/reaction step of the trimerization catalytic cycle is not predetermined and can only be determined by doing the necessary calculations for the trimerization catalytic cycle; the specific selectivity determining transition state/reaction step can be ligand dependent.

As an example, the trimerization cycle selectivity to 1-hexene based upon the branched decenes and/or dodecenes can be calculated using the proposed trimerization reaction pathways depicted in FIG. 5A (via the GS-II/GS-III/GS-IV/GV-VI/TS-III ethylene trimerization pathway), FIG. 5B (via the GS-IIa/GS-IIIa/GS-IVa/GV-VIa/TS-IIIa branched decene or dodecene pathway), and FIG. 5C (via the GS-IIb/GS-IIIb/GS-IVb/GV-VIb/TS-IIIb branched decene or dodecene pathway). In this example, one would calculate 1) the Gibbs free energy of rate determining transition state/reaction step for 1-hexene production depicted in FIG. 5A, 2) the Gibbs free energy of the rate determining step/reaction step for each branched decene and/or branched dodecene produced in the trimerization cycle depicted in FIG. 5B, and 3) the Gibbs free energy of the rate determining step/reaction step for each branched decene and/or branched dodecene produced in the trimerization cycle depicted in FIG. 5C. These Gibbs free energies would then be utilized to calculate the Gibbs free energy difference, $\Delta\Delta G[TS(1\text{-hexene})\text{-}TS(\text{non-1-hexene catalytic trimerization by-product})]$ for each branched decene and/or dodecene utilized in the trimerization cycle selectivity to 1-hexene calculation.

Mathematical relationships between the calculated Gibbs free energy difference, $\Delta\Delta G[TS(1\text{-hexene})\text{-}TS(\text{branched decene or branched dodecene})]$ and the natural logarithm of a set of heteroatomic ligand-metal compound complexes for which experimentally determined 1-hexene to branched decene or dodecenes ratio are then determined for each branched decene and/or dodecene utilized in the trimerization cycle selectivity to 1-hexene calculation. The mathematical relationship can then utilized to determine the amounts of non-experimentally determined amounts 1-hexene and each branched decene and/or dodecene utilized in the trimerization cycle selectivity to 1-hexene calculation via interpolation and extrapolation for calculated Gibbs free energy difference, $\Delta\Delta G[TS(1\text{-hexene})\text{-}TS(\text{branched decene or branched dodecene})]$ for which experimentally amounts of 1-hexene and each branched decene and/or dodecene are not known.

The second non-limiting method for determining the trimerization cycle selectivity to 1-hexene (based upon either all non-1-hexene catalytic trimerization by-products or based upon particular/specific non-1-hexene catalytic trimerization by-products) would replace the number of moles of 1-hexene and number of moles of each non-1-hexene catalytic trimerization by-product with their respective calculated activities/productivities determined by the turnover frequency calculation) for 1-hexene and each non-1-hexene catalytic trimerization by-product utilized in the trimerization cycle selectivity to 1-hexene calculation. For example, if one were determining the trimerization cycle selectivity to 1-hexene based upon the number of moles of 1-hexene produced and the number of moles of branched decenes and/or branched dodecenes produced when 1-hexene and/or 1-octene participates the trimerization catalytic cycle, one would replace 1) the number of moles of 1-hexene produced with the calculated activity/productivity determined by the turnover frequency calculation using all the ground states and transition states in the GS-II/GS-III/GS-IV/GS-VI/TS-III pathway, and 2) the number of moles for each branched decenes and/or branched dodecenes produced with the appropriate calculated activities/productivities determined by the turnover frequency calculation for each branched decene and/or branched dodecene produced using all the ground states and transition states in the GS-IIa/GS-IIIa/GS-IVa/GS-VIa/TS-IIIa pathway and/or in the GS-IIb/GS-IIIb/GS-IVb/GS-VIb/TS-IIIb pathway. If other non-1-hexene catalytic trimerization by-product(s) are included in determining the trimerization cycle selectivity to 1-hexene, the number of moles of these other non-1-hexene catalytic trimerization by-product(s) would be replaced by the calculated activities/productivities determined using the turnover frequency calculation using all the ground state and transition states in the pathway appropriate for the non-1-hexene catalytic trimerization by-product(s).

The tetramerization cycle selectivity to 1-octene (based upon either all non-1-octene catalytic tetramerization by-products or based upon particular/specific non-1-octene catalytic trimerization by-products) can be determined using different methods described herein.

In a non-limiting first method, the amounts of 1-octene and the non-1-octene catalytic tetramerization by-products can be determined from non-1-octene catalytic tetramerization by-product to 1-octene ratios. In this method the non-1-octene catalytic tetramerization by-product to 1-hexene ratio for each non-1-octene catalytic tetramerization by-product upon which the tetramerization cycle selectivity to 1-octene is based is determined by determining the Gibbs free energy difference, $\Delta\Delta G$, between 1) the rate determining transition state/reaction step leading to 1-ocene production and 2) the rate determining transition state/reaction step leading to non-1-octene catalytic tetramerization by-product. The Gibbs free energy difference can then be utilized to determine the amounts of 1-octene and non-1-octene catalytic trimerization by-products from a plot of calculated Gibbs free energy difference, $\Delta\Delta G$[TS(1-octene)-TS(non-1-octene catalytic tetramerization by-product)] versus the natural logarithm of a set of heteroatomic ligand-metal compound complexes for which experimentally determined Gibbs free energy difference and experimentally determined amounts of 1-octene and non-1-octene catalytic trimerization by-product are known. It should be noted that the selectivity determining transition state/reaction step of the tetramerization catalytic cycle is not predetermined and can only be determined by doing the necessary calculations for the tetramerization catalytic cycle: the specific selectivity determining transition state/reaction step can be ligand dependent.

As an example, the tetramerization cycle selectivity to 1-octene based upon the branched dodecenes and/or tetradecenes can be calculated using the proposed tetramerization reaction pathways depicted in FIG. 5A (via the GS-II/GS-III/GS-IV/GS-VI/GS-V/TS-IV/GS-VII/TS-V octene pathway), FIG. 5B (via the GS-IIa/GS-IIIa/GS-IVa/GS-VIa/GS-Va/TS-IVa/GS-VIIa/TS-Va branched dodecene or tetradecene pathway), and FIG. 5C (via the GS-IIb/GS-IIIb/GS-IVb/GS-VIb/GS-Vb/TS-IVb/GS-VIIb/TS-Vb branched dodecene or tetradecene pathway). In this example, one would calculate 1) the Gibbs free energy of rate determining transition state/reaction step for 1-octene production depicted in FIG. 5A, 2) the Gibbs free energy of the rate determining step/reaction step for each branched dodecene and/or branched tetradecene produced in the tetramerization cycle depicted in FIG. 5B, and 3) the Gibbs free energy of the rate determining step/reaction step for each branched dodecene and/or branched tetradecene produced in the trimerization cycle depicted in FIG. 5C. These Gibbs free energies would then be utilized to calculate the Gibbs free energy difference, $\Delta\Delta G$[TS(1-octene)-TS(non-1-octene catalytic trimerization by-product)] for each branched dodecene and/or tetradecene utilized in the trimerization cycle selectivity to 1-hexene calculation. Mathematical relationships between the calculated Gibbs free energy difference, $\Delta\Delta G$[TS(1-octene)-TS(branched dodecene or branched tetradecene)] and the natural logarithm of a set of heteroatomic ligand-metal compound complexes for which experimentally determined 1-octene to branched dodecene or tetradecene ratios are then determined for each branched dodecene and/or tetradecene utilized in the tetramerization cycle selectivity to 1-octene calculation. The mathematical relationship is then utilized to determine the amounts of non-experimentally determined amounts 1-octene and each branched dodecene and/or tetradecene utilized in the tetramerization cycle selectivity to 1-octene calculation via interpolation and extrapolation for calculated Gibbs free energy difference, $\Delta\Delta G$[TS(1-octene)-TS(branched dodecene or branched tetradecene)] for which experimentally amounts of 1-octene and each branched dodecene and/or tetradecene are not known.

The second non-limiting method for determining the tetramerization cycle selectivity to 1-octene (based upon either all non-1-octene catalytic tetramerization by-products or based upon particular/specific non-1-octene catalytic tetramerization by-products) would replace the number of moles of 1-octene and number of moles of each non-1-octene catalytic tetramerization by-product with their respective calculated activities/productivities determine using the turnover frequency calculation for 1-octene and each non-1-octene catalytic tetramerization by-product utilized in the tetramerization cycle selectivity to 1-octene calculation. For example, if one were determining the tetramerization cycle selectivity to 1-octene based upon the number of moles of 1-octene produced and the number of moles of branched dodecenes and/or branched tetradecenes produced when 1-hexene and/or 1-octene participates the tetramerization catalytic cycle, one would replaces 1) the number of moles of 1-octene produced with the calculated activity/productivity determined by the turnover frequency calculation using all the ground states and transition states in the GS-II/GS-III/GS-IV/GS-VI/GS-V/TS-IV/GS-VII/TS-V pathway, and 2) the number of moles for each branched dodecenes and/or branched tetradecenes produced would be replaced with the appropriate calculated activities/productivities determined by the turnover frequency calculation using all the ground states and transition states in the GS-IIa/GS-IIIa/GS-IVa/GS-VIa/GS-Va/TS-IVa/GS-VIIa/TS-Va pathway and/or in the GS-IIb/GS-IIIb/GS-IVb/GS-VIb/GS-Vb/TS-IVb/GS-VIIb/TS-Vb pathway. If other non-1-octene catalytic tetramerization by-product(s) are included in determining the tetramerization cycle selectivity to 1-octene, the number of moles of these other non-1-octene catalytic tetramerization by-product(s) would be would be replaced by the calculated activities/productivities determined using the turnover frequency calculation using all the ground state and transition states in the pathway appropriate for the non-1-octene catalytic tetramerization by-product(s).

Figure 6:
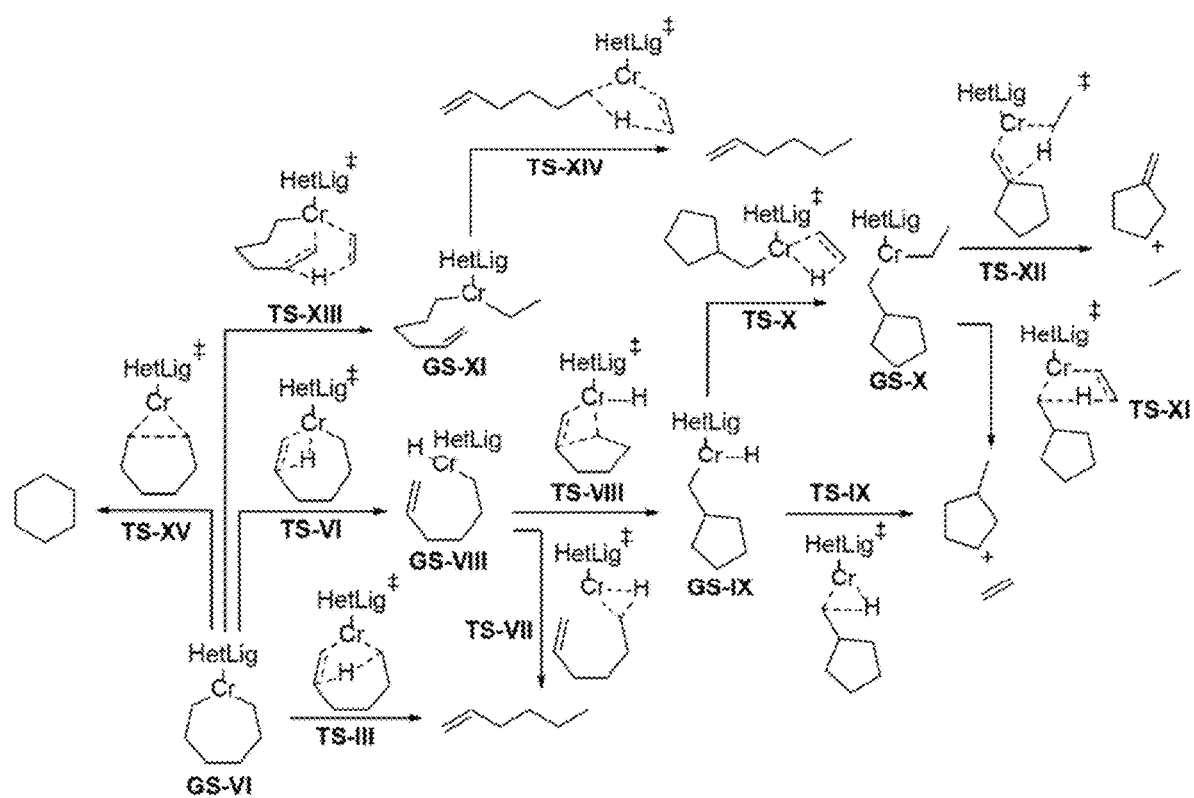
FIG. 6 illustrates pathways by which 1-hexene may be formed and pathways in which six-carbon impurities may arise in the production of 1-hexene.

Regarding olefin purity, when the performance parameter associated with the olefin oligomerization reaction is 1-hexene purity, FIG. 6 illustrates pathways by which 1-hexene may be formed and pathways in which six-carbon impurities may arise in the production of 1-hexene. The ground state and transition state designations correspond to those ground state and transition state structures disclosed herein. Referring to this figure, 1-hexene ($C_6$) may arise for example by way of the following pathways: [1] GS-VI→TS-III; [2] GS-VI→TS-VI→GS-VIII→TS-VII; and [3] GS-VI→TS-XIII→GS-XI→TS-XIV. In a further aspect, in FIG. 6, 1-hexene ($C_6$) impurities may arise for example by way of the following pathways: [1] GS-VI→TS-VI→GS-VIII→TS-VIII→GS-IX→TS-IX; [2] GS-VI→TS-VI→GS-VIII→TS-VIII→GS-IX→TS-X→GS-X→TS-XI; [3] GS-VI→TS-VI→GS-VIII→TS-VIII→GS-IX→TS-X→GS-X→TS-XII; and [4] GS-VI→TS-XV.

Figure 7:
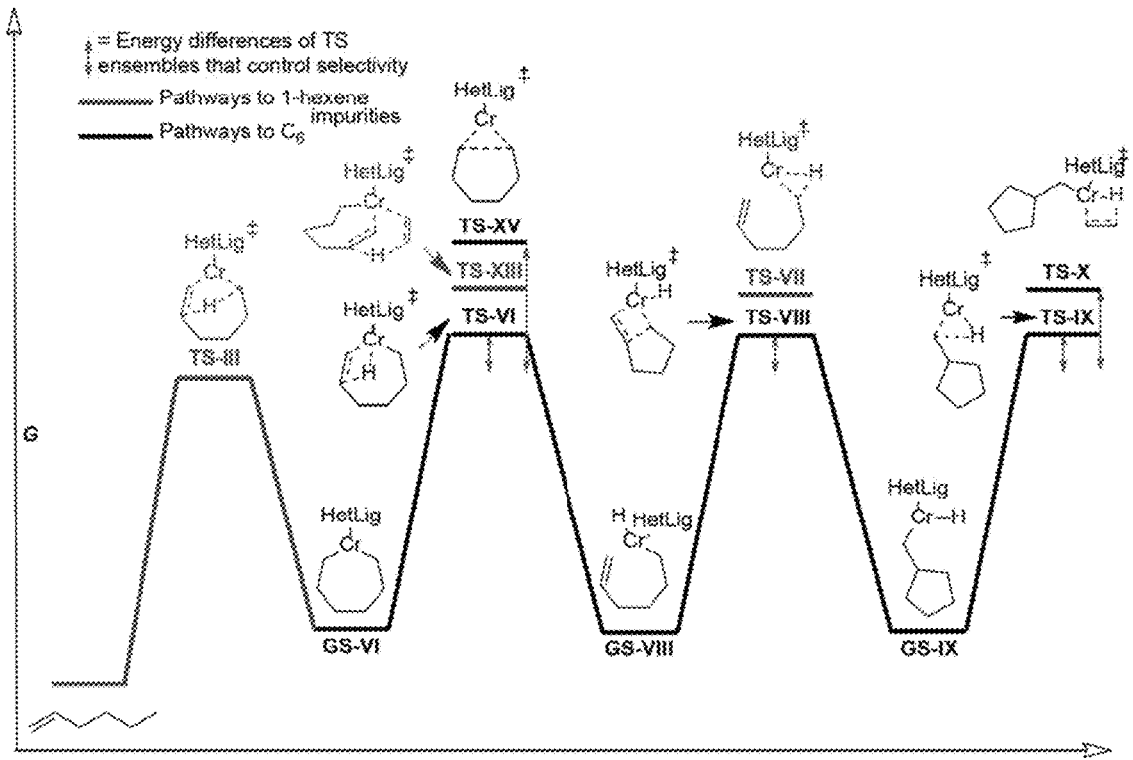
FIG. 7 illustrates the energy differences of transition state (TS) ensembles that can control the pathways to 1-hexene and the pathways to other $C_6$ compound which can be impurities in an isolated 1-hexene product.

In this aspect, FIG. 6 illustrates that various collections of ground states and transition states which can control selectivity to produce 1-hexene versus six-carbon impurities or (1-hexene impurities). This concept is illustrated in FIG. 7, where the energy differences of transition states (TS) that control the pathways to 1-hexene and the pathways to $C_6$ impurities (1-hexene impurities).

Therefore, regarding olefin purity, specifically "1-hexene purity", when the performance parameter associated with the olefin oligomerization reaction is 1-hexene purity: [1] the one or more ground state model structures $GS^{A1}, \ldots GS^{Ap}$ derived from one or more first training heteroatomic ligand-metal compound complexes can comprise or can be selected independently from $GS^I$-VI, $GS^I$-VIII, $GS^I$-IX, $GS^I$-X, $GS^I$-XI, or any combination thereof; [2] the plurality of transition state model structures $TS^{A1}, TS^{A2}, \ldots TS^{Am}$ derived from one or more first training heteroatomic ligand-metal compound complexes can comprise or can be selected independently from $TS^I$-III, $TS^I$-VI, $TS^I$-VII, $TS^I$-VIII, $TS^I$-IX, $TS^I$-X, $TS^I$-XI, $TS^I$-XII, $TS^I$-XIII, $TS^I$-XIV, $TS^I$-XV, or any combination thereof; [3] the one or more ground state model structures $GS^{B1}, \ldots GS^{Bp}$ derived from the first target heteroatomic ligand-metal compound complex can comprise or can be selected independently from $GS^I$-VI, $GS^I$-VIII, $GS^I$-IX, $GS^I$-X, $GS^I$-XI, or any combination thereof; and/or [4] the plurality of transition state model structures $TS^{B1}, TS^{B2}, \ldots TS^{Bm}$ derived from the first target heteroatomic ligand-metal compound complex can comprise or can be selected from $TS^I$-III, $TS^I$-VI, $TS^I$-VII, $TS^I$-VIII, $TS^I$-IX, $TS^I$-X, $TS^I$-XI, $TS^I$-XII, $TS^I$-XIII, $TS^I$-XIV, $TS^I$-XV, or any combination thereof. One method for determining the 1-hexene purity can be upon the mass ratio of 1-hexene to the total of other (non-1-hexene) $C_6$ products calculated as ln[(mass 1-hexene)/(mass non-1-hexene $C_6$)] versus $\Delta\Delta G[TS(1\text{-hexene})\text{-}TS(\text{non-1-hexene } C_6)]$.

Another method for determining the 1-hexene purity can entail separately determining the 1-hexene activity/productivity for each 1-hexene route in FIG. 6, separately determining the activity/productivity for each $C_6$ impurity produced by the routes in FIG. 6, and the percentage that the sum of all the 1-hexene activities/productivities determining is of the sum of all the 1-hexene activities/productivities plus the sum of the activities/productivities of all the $C_6$ impurities. The activities/productivities for each 1-hexene producing route in FIG. 6 and each $C_6$ impurity producing route can be calculated/activities/productivities as calculated/determined/estimated by the methods described herein (e.g., via determining the turnover frequencies for all the 1-hexene producing routes and all the $C_6$ producing routes in FIG. 6.)

Regarding "1-octene purity", when the performance parameter associated with the olefin oligomerization reaction is 1-octene purity: [1] the one or more ground state model structures $GS^{A1}, \ldots GS^{Ap}$ derived from one or more first training heteroatomic ligand-metal compound complexes can comprise or can be selected independently from $GS^I$-VII, $GS^I$-XII, $GS^I$-XIII, or any combination thereof; and/or [2] the one or more ground state model structures $GS^{B1}, GS^{Bp}$ derived from the first target heteroatomic ligand-metal compound complex can comprise or can be selected independently from $GS^T$-VII, $GS^T$-XII, $GS^T$-XIII, or any combination thereof. When the one or more performance parameters comprises or is selected from 1-octene purity, it can be determined based upon the mass ratio of 1-octene to the total of other (non-1-octene) $C_8$ products and calculated as ln[(mass 1-octene)/(mass non-1-octene $C_8$)] versus $\Delta G[TS(1\text{-octene})\text{-}TS(\text{non-1-octene } C_8)]$.

Reviewing FIG. 5C and FIG. 6 one can see that every addition of a fourth ethylene does not lead to the production of 1-octene. For example, in FIG. 6 it can be seen that ethylene can complex to a) GS-IX and form 1) methylenecyclopentane through the GS-IX/TS-X/GS-X/TS-XII pathway and/or 2) methylcyclopentane and ethylene through the GS-IX/TS-X/GS-X/TS-XI pathway, and/or b) GS-VI to form 1-hexene and ethane through the GS-VI/TS-XIII/GS-XI/TS-XIV pathway. Thus, these pathways lead to an inefficiency of the fourth ethylene addition in an olefin tetramerization. Thus, a particular parameter associated with olefin oligomerization reactions can be a 1-octene efficiency of the fourth ethylene addition.

The 1-octene efficiency of the fourth ethylene addition can be stated as the number of moles of 1-octene produced divided by the number of moles 1-octene produced plus one or more of the number of moles of methylenecyclopentane, methylcyclopentane, and/or 1-hexene produce via the addition of a fourth ethylene. Any one or more of the number of moles of methylenecyclopentane, methylcyclopentane, and 1-hexene can be utilized in the calculation of the 1-octene efficiency of the fourth ethylene addition and can be decided based upon the relative number of moles of methylenecyclopentane, methylcyclopentane, or 1-hexene produced by the fourth ethylene addition.

The methods described herein can be utilized to determine the 1-octene efficiency of the fourth ethylene addition. One particular non-limiting method would replace the number of moles 1-octene and methylenecyclopentane, methylcyclopentane, and/or 1-hexene with their activity/productivity determined by the turnover frequency calculation described herein. In this method, one would replace 1) the number of moles of 1-octene with the calculated activity/productivity determined by the turnover frequency calculation using all the ground states and transition states in the GS-II/GS-III/GS-IV/GS-VI/TS-IV/GS-V/TS-IV/GS-VII/TS-V pathway, 2) the number of moles of methylenecyclopentane with the calculated activity/productivity determined by the turnover frequency calculation using all the ground states and transition states in the GS-II/GS-III/GS-IV/GS-VI/TS-VI/GS-VIII/TS-VIII/GS-IX/TS-X/GS-X/TS-XII pathway, 3) the number of moles of methylcyclopentane with the calculated activity/productivity determined by the turnover frequency calculation using all the ground states and transition states in the GS-II/GS-III/GS-IV/GS-VI/TS-VI/GS-VIII/TS-VIII/GS-IX/TS-X/GS-X/TS-XI, and 4) the number of moles of methylcyclopentane with the calculated activity/productivity determined by the turnover frequency calculation using all the ground states and transition states in the GS-II/GS-III/GS-IV/GS-VI/TS-XIII/GS-XI/TS-XIV pathway. If other significant fourth ethylene additions to produce products instead of 1-octene are discovered, they can be added to the determination of the 1-octene efficiency of the fourth ethylene addition and the amount of additional fourth ethylene addition can be determined by the calculated activity/productivity determined by the turnover frequency calculation using all the ground states and transition states in the appropriate reaction pathway.

In one aspect, understanding the detailed parameters affecting the selectivity of olefin oligomerization is a goal which can lead to heteroatomic ligand-metal compound complexes producing a higher proportion of 1-octene when desired and heteroatomic ligand-metal compound complexes producing a higher proportion of 1-hexene when desired. In this aspect, the ground states leading to 1-hexene (ethylene trimerization), and the evolution of these ground states to form transition states that either eliminate 1-hexene or add another molecule of ethylene to form transition states and ground states leading to 1-octene (ethylene tetramerization) are of great interest. In this aspect of selectivity ($C_6/C_8$ ratio): [1] the plurality of transition state model structures $TS^{A1}, TS^{A2}, \ldots TS^{Am}$ derived from one or more first training heteroatomic ligand-metal compound complexes can comprise a transition state for the addition of the olefin to ground state model structure $GS^I$-VI to form ground state model structure $GS^I$-VII; and/or [2] the plurality of transition state model structures $TS^{B1}, TS^{B2}, \ldots TS^{Bm}$ derived from one or more first target heteroatomic ligand-metal compound complexes can comprise a transition state for the addition of the olefin (e.g., ethylene) to ground state model structure $GS^T$-VI to form ground state model structure $GS^T$-VII. Also in this aspect of selectivity ($C_6/C_8$ ratio): [1] the plurality of transition state model structures $TS^{A1}, TS^{A2}, \ldots TS^{Am}$ derived from the first training heteroatomic ligand-metal compound complex can comprise the transition state $TS^I$-IV; and/or [2] the plurality of transition state model structures $TS^{B1}, TS^{B2}, \ldots TS^{Bm}$ derived from the first target heteroatomic ligand-metal compound complex can comprise the transition state $TS^T$-IV.

Further to this aspect of selectivity ($C_6/C_8$ ratio): [1] the plurality of transition state model structures $TS^{A1}, TS^{A2}, \ldots TS^{Am}$ derived from one or more first training heteroatomic ligand-metal compound complexes can comprise a transition state for β-H extraction from ground state model structure $GS^I$-VI leading to 1-hexene production and/or a transition state for β-H extraction from ground state model structure $GS^I$-VII leading to 1-octene production; and/or [2] the plurality of transition state model structures $TS^{B1}, TS^{B2}, \ldots TS^B m$ derived from one or more first target heteroatomic ligand-metal compound complexes can comprise a transition state for β-H extraction from ground state model structure $GS^T$-VI leading to 1-hexene production and/or a transition state for β-H extraction from ground state model structure $GS^T$-VII leading to 1-octene production. Regarding β-H extraction from these ground state model structures recited above: [1] the plurality of transition state model structures $TS^{A1}, TS^{A2}, \ldots TS^{Am}$ derived from the first training heteroatomic ligand-metal compound complex can comprise $TS^I$-III; [2] the plurality of transition state model structures $TS^{B1}, TS^{B2}, \ldots TS^{Bm}$ derived from the first target heteroatomic ligand-metal compound complex can comprise $TS^T$-III; [3] the plurality of transition state model structures $TS^{A1}, TS^{A2}, \ldots TS^{Am}$ derived from the first training heteroatomic ligand-metal compound complex can comprise $TS^I$-V; and/or [4] the plurality of transition state model structures $TS^{B1}, TS^{B2}, \ldots TS^B m$ derived from the first target heteroatomic ligand-metal compound complex can comprise $TS^T$-V. Moreover, for the β-H extraction from ground state model structures the transition state model for β-H extraction from ground state model structure $GS^I$-VI and/or $GS^T$-VI leading to 1-hexene production can be $TS^I$-III and/or $TS^I$-III, respectively; and/or the transition state model for β-H extraction from ground state model structure $GS^I$-VII and/or $GS^T$-VII leading to 1-octene production is $TS^I$-V and/or $TS^I$-V, respectively.

The disclosed method includes an iterative process that repeats the steps (a)-(f) of the method described above one or more times using the quantitative values of the n output variables $O^1, O^2, \ldots O^n$ of the first target heteroatomic ligand-metal compound complex as an input dataset of new n input variables $I^{1.1}, I^{2.1}, \ldots I^{n.1}$ derived from one or more second training heteroatomic ligand-metal compound complexes for olefin oligomerization, comprising a second training heteroatomic ligand, which is computationally evaluated against the machine learning model to generate a second target heteroatomic ligand-metal compound complex comprising a second target heteroatomic ligand, wherein the second target heteroatomic ligand-metal compound complex is characterized by quantitative values of an output dataset of new n output variables $O^{1.1}, O^{2.1}, \ldots O^{n.1}$, and having one or more second target heteroatomic ligand-metal compound complex performance parameter values.

In one aspect, when the chromium heteroatomic ligand moiety is independently selected from NPFCrM-1, NPACrM-1, GuCrM-1, GuCrM-2, GuCrM-3, GuCrM-4, GuCrM-5, or HCPACrM-1, this step of generating the second target heteroatomic ligand-metal compound complex can comprise:

(a) adjusting the quantitative value of one or more n input variables $I^1, I^2, \ldots I^n$ or $I^{1.1}, I^{2.1}, \ldots I^{n.1}$ to approach the value of the corresponding n output variables $O^1, O^2, \ldots O^n$ or $O^{1.1}, O^{2.1}, \ldots O^{n.1}$ in any first training heteroatomic ligand-metal compound complex comprising a chromium heteroatomic ligand moiety independently selected from NPFCrM-1, NPACrM-1, GuCrM-1, GuCrM-2, GuCrM-3, GuCrM-4, GuCrM-5, or HCPACrM-1, by:
  [1] independently increasing or decreasing the steric bulk of one or more of the groups $R^1, R^2, L^{12r}, R^{2a}, R^{2b}, L^{12}, L^{23}, L^{22}, R^3, R^4, R^5$, and $L^{45}$;
  [2] independently changing the inductive electronic effects of one or more of the groups $R^1, R^2, L^{12r}, R^{2a}, R^{2b}, L^{12}, L^{23}, L^{22}, R^3, R^4, R^5$, and $L^{45}$ with one or more +I substituent or one or more −I substituent;
  [3] independently increasing or decreasing the saturation in one or more of the organyl groups or organylene groups;
  [4] increasing or decreasing the polarity of a solvent used for olefin oligomerization; or
  [5] any combination thereof;
and
(b) generating, based upon the at least one adjusted n input variable from step (a) a second target heteroatomic ligand-metal compound complex for olefin oligomerization and comprising a second target heteroatomic ligand.

In a further aspect, when the chromium heteroatomic ligand moiety is independently selected from NRNCrM-1, PRPCrM-1, SRSCrM-1, PNPCrM-1, NRNRNCrM-1, PRPRPCrM-1, SRNRSCrM-1, PRNRPCrM-1, or NRPRNCrM-1, this step of generating the second target heteroatomic ligand-metal compound complex can comprise:

(a) adjusting the quantitative value of one or more n input variables $I^1, I^2, \ldots I^n$ or $I^{1.1}, I^{2.1}, \ldots I^{n.1}$ to approach the value of the corresponding n output variables $O^1, O^2, \ldots O^n$ or $O^{1.1}, O^{2.1}, \ldots O^{n.1}$ in any first training heteroatomic ligand-metal compound complex comprising a chromium heteroatomic ligand moiety independently selected from NRNCrM-1, PRPCrM-1, SRSCrM-1, PNPCrM-1, NRNRNCrM-1, PRPRPCrM-1, SRNRSCrM-1, PRNRPCrM-1, or NRPRNCrM-1, by:
  [1] independently increasing or decreasing the steric bulk of one or more of the groups $R^{1s}, R^{2s}, R^{5s}, R^{11s}, R^{12s}, R^{13s}, R^{14s}, L^{1s}, L^{3s}, L^{4s}, L^{1sr}, L^{1sr}, L^{12sr}$, and $L^{34sr}$.
  [2] independently changing the inductive electronic effects of one or more of the groups $R^{1s}, R^{2s}, R^{5s}, R^{11s}, R^{12s}, R^{13s}, R^{14s}, L^{1s}, L^{3s}, L^{4s}, L^{1sr}, L^{1sr}, L^{12sr}$, and $L^{34sr}$ with one or more +I substituent or one or more −I substituent;
  [3] independently increasing or decreasing the saturation in one or more of the organyl groups or organylene groups;
  [4] increasing or decreasing the polarity of a solvent used for olefin oligomerization; or
  [5] any combination thereof;
and
(b) generating, based upon the at least one adjusted n input variable from step (a) a second target heteroatomic ligand-metal compound complex for olefin oligomerization and comprising a second target heteroatomic ligand.

The person of ordinary skill in the relevant art will understand how independently increasing or decreasing the steric bulk of these groups, and independently changing the inductive electronic effects of these groups and the like will adjust the various input variables. In this aspect, for example, when a first training heteroatomic ligand-metal compound complex comprising a chromium heteroatomic ligand moiety selected from NPFCrM-1, NPACrM-1, GuCrM-1, GuCrM-2, GuCrM-3, GuCrM-4, GuCrM-5, or HCPACrM-1, independently increasing or decreasing the steric bulk of one or more of the groups can be used to adjust the N—Cr—P bond angle, the Cr—N and Cr—P bond distances, the Cr - - - α-C distance, the Cr - - - R on α-C distance, the distance out of pocket, the percent volume buried, various dihedral angles, and the like. Independently increasing or decreasing the saturation in one or more of the organyl groups or organylene groups can be used, for example, to adjust various input variables such as the Cr—N—C—N Dihedral angle, the Cr—P—N—C Dihedral angle, the P—Cr—N—C Dihedral angle, P—N—C—N Dihedral angle, the C—C—N—C Dihedral angle, the Cr—N—C angle, among others described herein. Independently changing the inductive electronic effects of one or more of the "R" or "L" groups with one or more +I substituents or one or more –I substituents can be used, for example, to adjust the atomic charge on the Cr, P, and/or N atoms, and these substituents can also have a steric effect which will influence bond distances and angles.

Determining and Modifying Reactivity (Productivity) in Heteroatomic Ligand-Metal Compound Complexes Among other things, this disclosure demonstrates how the olefin oligomerization activity/productivity, selectivity, and/or product purity of heteroatomic ligand-chromium compound complex can be determined and modified using density functional theory calculations. In an aspect, this disclosure also demonstrates that combining machine learning computational methods in combination with quantum mechanical transition state models can identify specific catalyst design features for selective olefin oligomerization using heteroatomic ligand-chromium compound complexes. In an aspect, similar procedures can be utilized by combining machine learning computational methods with quantum mechanical transition state models using density functional theory (DFT) calculations to identify specific catalyst design features for improved activity/productivity and/or improved product purity using heteroatomic ligand-chromium compound complexes.

Density functional theory calculations can be used in accordance with the methods of this disclosure to address turnover frequency, reactivity, or activity/productivity for ethylene oligomerizations using a heteroatomic ligand-metal compound complex (e.g., a heteroatomic ligand-chromium compound complex). This aspect of the disclosure allows the discovery of empirical parameters or design principles that provide prediction of high heteroatomic ligand-metal compound complex (e.g., a heteroatomic ligand-chromium compound complex) activity. Specifically, this section demonstrates the use of ground states, transition states and the energetic span model, can be utilized to determine turnover frequency of a reaction to a particular product which can give a activity/productivity for the reaction. Thus, density function theory calculation can be used to develop ethylene oligomerization heteroatomic ligand-metal compound complexes (e.g., a heteroatomic ligand chromium compound complexes). This section demonstrates the method using ground states, transition states and the energetic span model for determining turnover frequency (hences activity/productivity for a trimerization reaction using the bidentate (P,N)Cr heteroatomic ligand-chromium compound complex 1a, illustrated in Scheme 1.

Scheme 1 a) SELECTIVE OLIGOMERIZATION

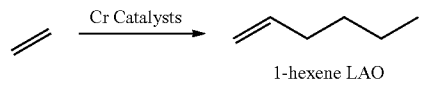

1-hexene LAO b) Active Catalyst

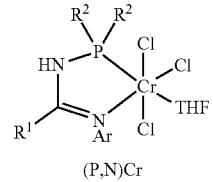

(P,N)Cr

1a Ar = 2,6-Me$_2$C$_6$H$_3$;
R$^1$ = 4-tBuC$_6$H$_4$; R$^2$ = iPr

Inactive Catalyst

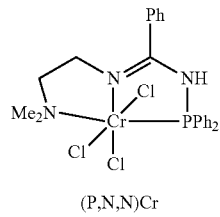

(P,N,N)Cr

Scheme 1a illustrates an overview of the selective ethylene oligomerization process to form 1-hexene. Scheme 1b illustrates the bidentate (P,N)Cr selective ethylene trimerization heteroatomic ligand-chromium compound complex. This section also uses the ground states, transition states and the energetic span model to show why the tridentate (P,N,N)Cr heteroatomic ligand-chromium compound complex also shown in Scheme 1b, is inactive toward ethylene oligomerization/trimerization.

The bidentate N$^2$-phosphinylamidine ligand of heteroatomic ligand-chromium compound complex 1a having the indicated aryl and benzyl groups provides a useful platform for illustrating the discovery and iterative heteroatomic ligand-chromium compound complex improvement as provided in the present disclosure. The N$^2$-phosphinylamidine ligand 1a can be synthesized in a flexible and modular route, and metalation to form the heteroatomic ligand-chromium compound complex and characterization is straightforward using methods described in US patent application publication 2012/0309965. Ethylene oligomerization reactions with this class of compound are generally reproducible and lead to high purity linear alpha-olefins (LAOs) with only trace co-polymer production. For example, heteroatomic ligand-chromium compound complex 1a (Scheme 1b) can result in 94% mass selectivity for C$_6$ products with 1-hexene purity of >99%. This disclosure demonstrates how the N$^2$-phosphinylamidine-chromium compound complex can be modified to discover new heteroatomic ligan-chromium compound complexes which produce a substantial amount of 1-octene; for example, providing a method to determine how to modify $N^2$-phosphinylamidine-chromium compound complexes to produce a roughly equal mixture of 1-hexene and 1-octene using the methods disclosed here. Using a quantitative density functional theory (DFT) transition-state model, new phosphine monocyclic imine catalysts that resulted in >50% 1-octene production were predicted and then experimentally verified (see Kwon, D.-H. et al., *ACS Catal.* 2018, 8, 1138-1142).

In one aspect, quantitative density functional theory (DFT) calculations can be used as described herein to develop heteroatomic ligand-chromium compound complexes showing high 1-hexene catalyst reactivity. Such calculations may help explain why other seemingly related catalysts exhibit low or no activity. For example, many known ethylene trimerization catalysts contain tridentate ligand coordination, such as Sasol's (S,N,S)Cr (S,N, S=RSCH$_2$CH$_2$)$_2$NH; R=alkyl) ligand falling within the SRNRS-1 heteroatomic ligand-chromium compound complexes described herein and (P,N,P)Cr (P,N, P=R$_2$PCH$_2$CH$_2$)$_2$NH; R=Ar or alkyl) falling in the PRNRP-1 heteroatomic ligand-chromium compound complexes described herein, which can have productivities >10$^3$ g/g Cr·h. The bidentate (P,N)Cr heteroatomic ligand-chromium compound complexes described herein can be highly reactive with activities generally between about 10$^4$ to about 10$^6$ g of oligomerization product per gram of Cr catalyst per hour (g product/g Cr·h). Therefore, it was surprising that modification of the (P,N) ligand core with a third donor group to give a tridentate (P,N,N) ligand (defined in Scheme 1b) resulted in no ethylene oligomerization activity when subjected to similar conditions as the (P,N) catalysts. The methods of this disclosure can shed light on these observations, which can result in the design and development of new heteroatomic ligand-chromium compound complexes with tailored activities, product purities, and/or selectivities.

In an aspect, a density functional theory (DFT) analysis of model 1-hexene producing heteroatomic ligand-chromium compound complexes was carried out, as it was unclear why the bidentate (P,N)Cr heteroatomic ligand-chromium compound complexes are highly active, but the tridentate (P,N, N)Cr heteroatomic ligand-chromium compound complexes is inactive. A high-spin Cr$^{I/III}$ chromacycle mechanism consistent with previous experimental kinetic studies served as the starting point for developing the disclosed methods. It was discovered that for the (P,N)Cr heteroatomic ligand-chromium compound complexes (1a, Scheme 1b), there are multiple Cr$^I$ ethylene coordinated ground states and multiple transition states which control turnover frequency (TOF). In was further discovered, that the contribution of the turnover controlling transition states depends upon the ethylene pressure. In contrast, the (P,N,N)Cr heteroatomic ligand-chromium compound complex was discovered to have a stabilized chromacyclopentane resting state, which provides a rationale for its slower reactivity/activity/productivity. The DFT analysis was also used to calculate and compare the moderate activity of several other 1-hexene tridentate heteroatomic ligand-chromium compound complexes, in which catalytic energy span calculations were able to qualitatively and semi-quantitatively replicate relative catalyst reactivity.

Scheme 2

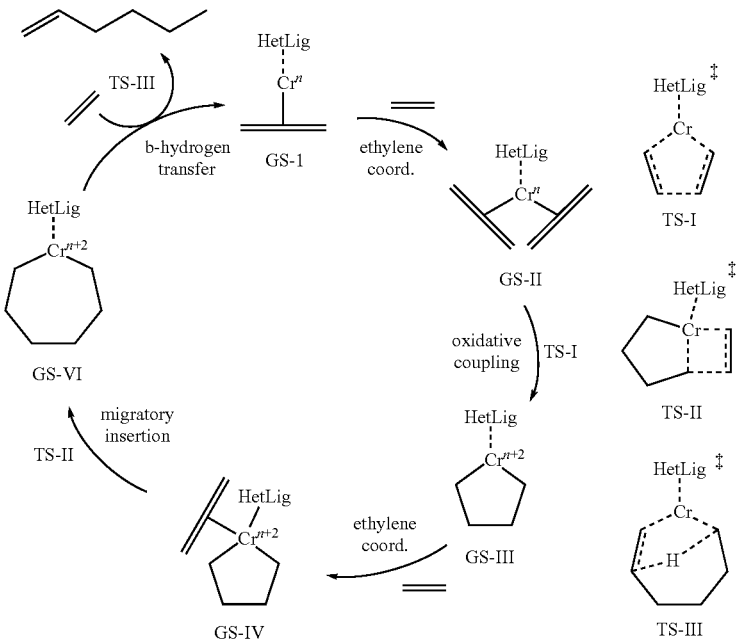

Scheme 2 illustrates a generalized mechanism for the heteroatomic ligand-chromium compound complex catalyzed ethylene trimerization involving chromacycle intermediates. A DFT analysis based on this proposed chromacycle mechanism can help define a quantitative transition-state model to predict selectivity of short-chain LAOs, specifically, 1-hexene and/or 1-octene selectivity. The general chromacycle mechanism for 1-hexene formation outlined in Scheme 2 begins with pre-catalyst activation to give a (mono)ethylene low-valent Cr-species GS-I followed by ethylene coordination to form the (bis)ethylene-coordinated intermediate GS-II. Oxidative C—C bond coupling forms chromacyclopentane GS-III. Ethylene coordination gives intermediate GS-IV and migratory insertion leads to the chromacycloheptane intermediate GS-VI that can produce 1-hexene via β-hydrogen transfer (βHT). An examination of this mechanism using the disclosed methods can shed light on issues such as Cr oxidation state and spin state, the potential involvement of cationic versus neutral Cr heteroatomic ligand complexes in the catalytic cycle, resting states and kinetic features of the catalytic cycle, and the like.

Computational details, model, and experimental reactivity values. The unrestricted M06-L functional (Zhao, Y.; Truhlar, D.; *Theor. Chem. Acc.* 2008, 120, 215-241) was used with a 6-31G**[LANL2DZ for Cr] (Hay, P. J.; Wadt, W. R.; *J. Chem. Phys.* 1985, 82, 270-283) for geometry optimizations in Gaussian 09 (Frisch, M.; Trucks, G.; Schlegel, H.; Scuseria, G.; Robb, M.; Cheeseman, J.; Scalmani, G.; Barone, V.; Mennucci, B.; Petersson, G. Gaussian 09, revision B. 01. Gaussian, Inc., Wallingford, CT 2010.). Stationary points were verified as either minima or transition-state structures by calculation and visualization of vibrational frequencies. Intrinsic reaction coordinate (IRC) calculations were used to verify connection between transition states and intermediates on each spin-state surface. For all ground-state and transition-state structures that were calculated, all reasonable conformations and lowest energy conformations were determined. Free energies at 1 atm and room temperature with an ultrafine integration grid correspond to (U)M06-L/def2-TZVP//(U)M06-L/6-31G**[LANL2DZ for Cr] were determined using the SMD cyclohexane, toluene, or methylcyclohexane solvent models unless otherwise noted for pressure or temperature corrections. That is, unless otherwise specified, calculations provide values at STP (Standard Temperature and Pressure), however temperature and/or pressure corrections may be made to the calculations, if values are desired for different conditions. The use of the M06-L density functional was used as it was thought to give similar spin-state energies and reaction energies compared with the generally accurate G4(MP2,rel) and CCSD(T)/CBS wavefunction methods (McGuinness, D. S.; Chan, B.; Britovsek, G. J. P.; Yates, B. F.; *Aust. J Chem.* 2014, 67, 1481-1490.).

Figure 8:
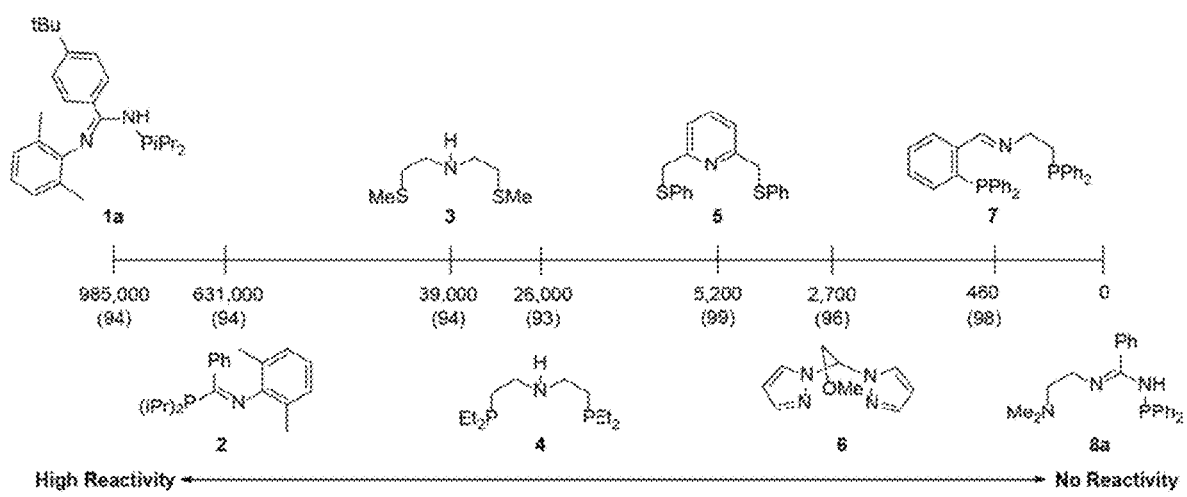
FIG. 8 illustrates a comparison of ligands used in experimentally reported heteroatomic ligand-chromium compound complex ethylene trimerizations and their productivities in g 1-$C_6$/g Cr·h. The mass percentage of 1-hexene out of the total mass of $C_6$ products is given in parentheses.

The complete heteroatomic ligands were used to examine heteroatomic ligand-chromium compound complex reactivity, but an explicit counterion was not used for the monocationic heteroatomic ligand-chromium compound complexes. FIG. 8 illustrates a comparison of experimentally reported ethylene trimerization productivities, in g 1-$C_6$/g Cr·h, for the heteroatomic ligand-chromium compound complexes using the designated ligands. The mass percentage of 1-hexene out of the total mass of $C_6$ products is given in parentheses. These productivity values were scaled to provide an estimate for 1-hexene productivities (labeled as: g 1-$C_6$/g Cr·h), which could then be directly compared with calculated 1-hexene catalytic cycle turnover frequencies (TOFs). The experimental reaction conditions varied slightly among this set of ligands. See the Examples for details. For example, MAO or MMAO are the typical co-catalysts for activating the $CrCl_3$(THF) pre-catalysts and vary between 100-800 molar equivalents relative to Cr. The co-activator can significantly affect heteroatomic ligand-chromium compound complex activity and selectivity. These heteroatomic ligand-chromium compound complex activities were measured in either toluene, cyclohexane, or methylcyclohexane, and typically, the best heteroatomic ligand-chromium compound complex performance was achieved at temperatures between 60-110° C.

(P,N)Cr and (P,N,N)Cr Reactivity Comparison. The major chromacycle mechanistic features of the (P,N)Cr heteroatomic ligand-chromium compound complex 1a were examined. It was observed that the spin crossover from sextet to quartet with a $Cr^{I/III}$ cycle was lower in energy than non-spin crossover or a $Cr^{II/IV}$ cycle (see FIG. 9A and Examples). Ligand 1a is similar to 3, (S,N,S)Cr, and 4, (P,N,P)Cr catalysts where a N—H group can potentially be deprotonated. Therefore, an MMAO induced deprotonation of the N—H proton as well as a N(AlMe$_2$) type heteroatomic ligand-chromium compound complex models were considered. While the N—H protonated ligand catalytic cycles showed the smallest energy difference between the resting states and turnover controlling transition states, the deprotonated and N(AlMe$_2$) heteroatomic ligand-chromium compound complex models did not have a significantly larger energy difference and can also provide a reactivity model. Mechanistic variations were also examined where additional ethylene is coordinated to the Cr center in the oxidative coupling, migratory insertion, and 1-hexene production reaction steps. For example, the β-hydride transfer transition state was calculated with an additional ethylene and found that it was ~2 kcal/mol higher in enthalpy and ~13 kcal/mol higher in Gibbs free energy compared with the non-coordinated transition state. See Examples. The traditional multi-step β-hydride elimination and reductive elimination for formation of 1-hexene was also examined. For (P,N)Cr heteroatomic ligand-chromium compound complex 1a, the calculations showed that β-hydride elimination and reductive elimination are 3.7 kcal/mol and 11.4 higher in free energy than the β-hydride transfer transition state, respectively, which is consistent with this higher energy pathway leading to cyclic impurities and potentially polyethylene impurity.

Figures 9A, 9B:
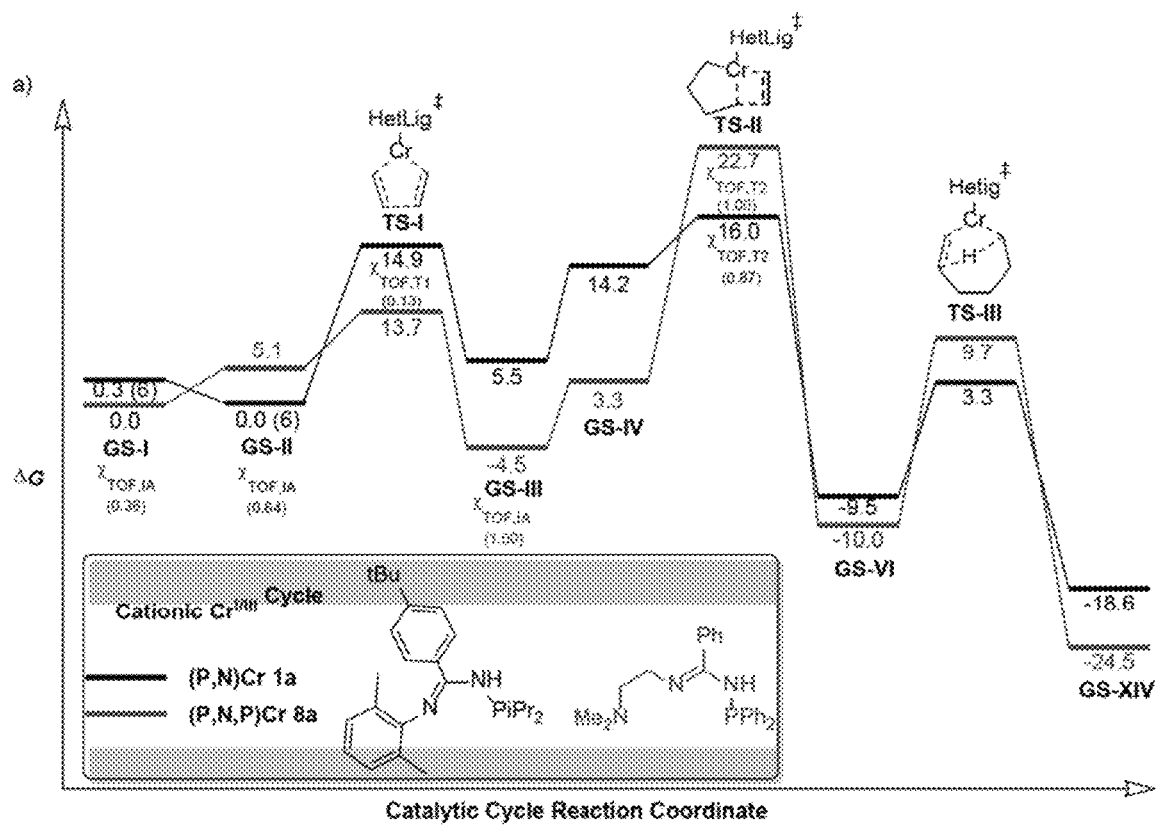
FIG. 9A provides an abbreviated Gibbs free energy landscape for ethylene trimerization using two different heteroatomic ligands for a heteroatomic ligand-chromium compound complex (i.e., (P,N)Cr 1a and (P,N,P)Cr 8a), where the ligands are represented by HetLig. Intermediates GS-I and GS-II for catalyst 1a are sextet spin and all other intermediates and transition states are quartet spin. The numbers denoted in parentheses represent the relative contribution of the structure to the ground state or transition state to the turnover frequency of the heteroatomic ligand-chromium compound complex.
FIG. 9B illustrates the Gibbs free energy values for ground states and transition states of the ethylene trimerization catalytic cycle with the heteroatomic ligand-chromium compound complexes using ligands 2-7 in kcal/mol.

The simplified chromacycle M06-L Gibbs free energy landscape for ethylene trimerization by (P,N)Cr heteroatomic ligand-chromium compound complexes is shown in FIG. 9A. Thus, FIG. 9A provides an abbreviated Gibbs free energy landscape for ethylene trimerization with (P,N)Cr heteroatomic ligand-chromium compound complex 1a and (P,N,P)Cr heteroatomic ligand-chromium compound complex 8a. The ligands are omitted from each structure for clarity. Ground states GS-I and GS-II for heteroatomic ligand-chromium compound complex 1a are sextet spin states denoted in parentheses as they were determined to be lower in energy than their quartet spin state. All other ground states and transition states are quartet spin. The table in FIG. 9B illustrates the Gibbs free energy values of the catalytic cycle with the heteroatomic ligand-chromium compound complexes using ligands 2-7 in kcal/mol.

Figure 10:
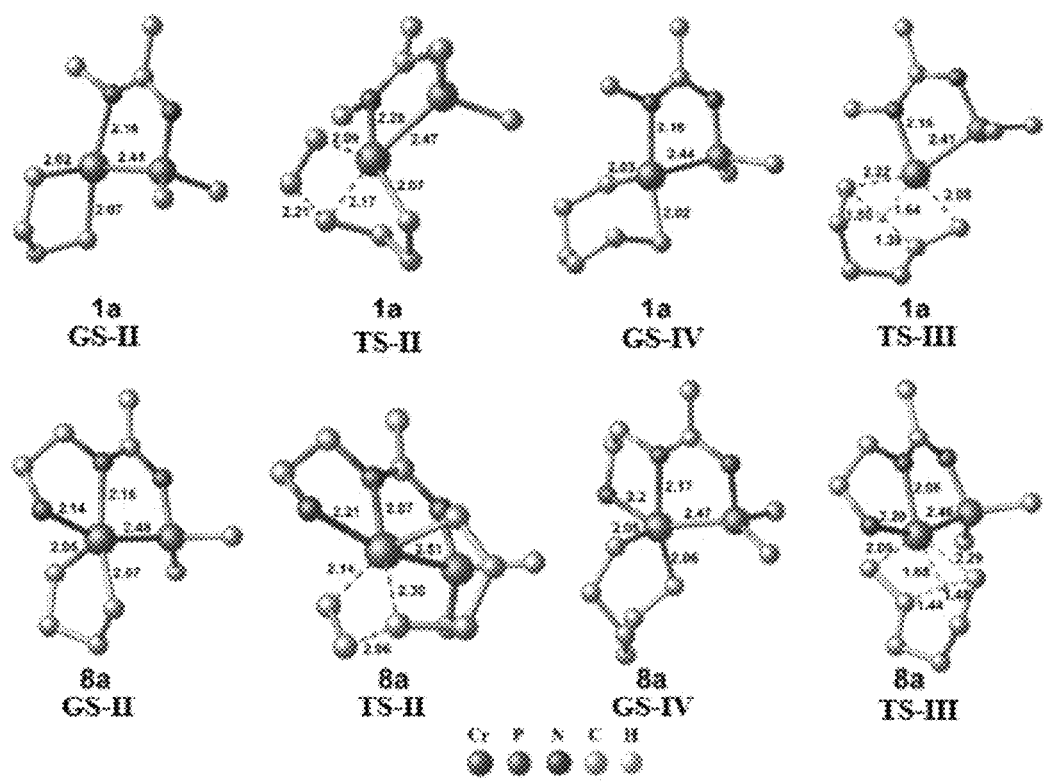
FIG. 10 illustrates 3D representations of key intermediates and transition states for catalysts 1a and 8a. Some atoms are removed for clarity.

In FIG. 9A, starting at the sextet spin (P,N)Cr$^1$($C_2H_4$), GS-I, a second ethylene coordinates to generate the diethylene coordinated (P,N)Cr$^1$($C_2H_4$)$_2$, GS-II. Spin crossover to the quartet surface facilitates oxidative C—C coupling to provide TS-I (see FIG. 10) with a ΔG‡ value of 14.9 kcal/mol. This endergonic ethylene coordination indicates that ethylene-coordinated chromacyclopentane intermediate GS-III is unlikely to be a catalytic resting state. FIG. 10 illustrates 3D representations of key intermediates and transition states for heteroatomic ligand-chromium compound complexes 1a and 8a (some atoms are removed in the FIG. 10 structures for clarity). The barrier for migratory ethylene insertion to provide TS-II and then to give the chromacycloheptane GS-VI is small. It requires only 1.8 kcal/mol relative to the ethylene-coordinated chromacyclopentane and 16.0 kcal/mol relative to the bis(ethylene) complex GS-II. The resulting chromacycloheptane GS-VI is exergonic by 9.5 kcal/mol relative to GS-II. To achieve the β-hydride transfer transition state TS-III, a barrier of 12.8 kcal/mol is required from the chromacycloheptane. The energy of TS-III relative to GS-II is 3.3 kcal/mol, and the formation of 1-hexene is 18.6 kcal/mol exergonic.

Because the energies of GS-I, GS-II, TS-I, and TS-II in FIG. 9A are very close, and the chromacycloheptane, GS-VI, that is after these transition states is exergonic, to identify the ground state(s) and rate-limiting transition state(s) Kozuch and Shaik's definition of energetic span for catalytic reactions was utilized (see Kozuch, S.; Shaik, S.; *Acc. Chem. Res.* 2011, 44, 101-110), which is related to Campbell's definition (see Campbell, C. T.; *Top Catal.* 1994, 1, 353-366; Campbell, C. T.; *ACS Catal.* 2017, 7, 2770-2779). In this energetic-span model, calculated Gibbs free energies for each ground state and transition state are translated to a relative contribution/degree of control to the overall turnover frequency (TOF), which is referred to as $\chi_{TOF}$. The TOF described in eq 1 includes the Boltzmann constant, $k_b$, temperature, T, Planck's constant, h, gas constant, R, number of steps in the catalytic cycle, N, free energy of the overall catalytic reaction, $\Delta G_r$, free energy of the transition state, $T_i$, free energy of the intermediate $I_j$, and $\delta G'_{ij}$, which is described by eq 2. Equations eq 3 and eq 4 provide the degree of rate control of the TOF for each intermediate $I_j$ (eq 3) and each transition state $T_i$ (eq 4). The sum of $\chi_{TOF,I_K}$ values is 1 and the sum of all $\chi_{TOF,T_K}$ values is 1.

$$TOF = \frac{k_b T}{h} \frac{e^{\frac{-\Delta G_r}{RT}} - 1}{\sum_{i=1, j=1}^{N} e^{(T_i - I_j - \delta G'_{ij})/RT}} \quad (\text{eq 1})$$

$$\delta G'_{ij} = \begin{cases} \Delta G_r & \text{if } T_i \text{ follows } I_j \quad (a) \\ 0 & \text{if } T_i \text{ precedes } I_j \quad (b) \end{cases} \quad (\text{eq 2})$$

$$\chi_{TOF,I_K} = \frac{\sum_i e^{(T_i - I_k - \delta G'_{ik})/RT}}{\sum_{ij} e^{(T_i - I_j - \delta G'_{ij})/RT}} \quad (\text{eq 3})$$

$$\chi_{TOF,T_K} = \frac{\sum_j e^{(T_k - I_j - \delta G'_{kj})/RT}}{\sum_{ij} e^{(T_i - I_j - \delta G'_{ij})/RT}} \quad (\text{eq 4})$$

Analysis of the energy span (see Uhe, A.; Kozuch, S.; Shaik, S.; *J. Comput. Chem.* 2011, 32, 978-985) and TOF based on the Gibbs free energy landscape for (P,N)Cr heteroatomic ligand-chromium compound complex 1a shown in FIG. 9A suggests a mixed ground state between $(P,N)Cr^1(C_2H_4)$ GS-I (36%) and $(P,N)Cr^1(C_2H_4)_2$ GS-II (64%). The small energy difference between TS-I and TS-II2 indicates that they both contribute to controlling the overall turnover rate, with $\chi_{TOF}$ values of 0.13 and 0.87, respectively. Because of the mixed resting state and TS-II controlling the majority of the TOF, this would lead to an approximate ethylene rate order of 1.2 (see Examples for details). The estimated TOF for the Boltzmann weighted energy span is 6.5 mol 1-$C_6$·s$^{-1}$, which would result in a calculated ~23,400 turnovers·h$^{-1}$ and a calculated total productivity mass of ~2.0×10$^6$ g·h$^{-1}$.

FIG. 9A also compares the Gibbs free energy landscape of for (P,N)Cr heteroatomic ligand-chromium compound complex 1a with the energy landscape for the tridentate (P,N,N)Cr heteroatomic ligand-chromium compound complex of ligand 8a. Different from (P,N)Cr heteroatomic ligand-chromium compound complex 1a, the lowest energy catalytic cycle does not require spin crossover because the lowest energy ground state mono(ethylene) GS-I and bis(ethylene) GS-II for heteroatomic ligand-chromium compound complex 8a are quartet spin. Also, the mono(ethylene) complex GS-I is slightly more stabilized (~5 kcal/mol) than the bis(ethylene) GS-II. TS-I requires ΔG‡ value of 13.7 kcal/mol, and this slightly lower barrier compared to heteroatomic ligand 1a is consistent with the $Cr^I$ to $Cr^{III}$ oxidation. This $Cr^{III}$ oxidation state stabilization is also manifested in the −4.5 kcal/mol ΔG value for formation of the chromacyclopentane GS-VI relative to GS-I. Continuation to the chromacycloheptane intermediate GS-VI by TS-II requires a Gibbs free energy change of 27.1 kcal/mol relative to GS-III, consistent with the experimental lack of reactivity. The ΔG‡ value relative to GS-I is 22.7 kcal/mol, which is ~7 kcal/mol higher than this TS-II compared to GS-I A for heteroatomic ligand-chromium compound complex 1a. Similar to heteroatomic ligand-chromium compound complex 1a, the chromacycloheptane GS-VI is exergonic and the barrier for conversion to 1-hexene is 24.5 kcal/mol relative to ground state GS-XIV (the species where 1-hexene is coordinated to the chromium heteroatomic ligand moiety). The energy span analysis of the (P,N,N)Cr heteroatomic ligand-chromium compound complex 8a landscape shows that resting state is entirely the chromacyclopentane GS-III and the turnover limiting transition state is exclusively TS-II. This gives a calculated TOF of 8.0×10$^{-8}$ s$^{-1}$, which translates to only ~0.02 g of 1-$C_6$·hr$^{-1}$, consistent with no product observation.

Figure 11:
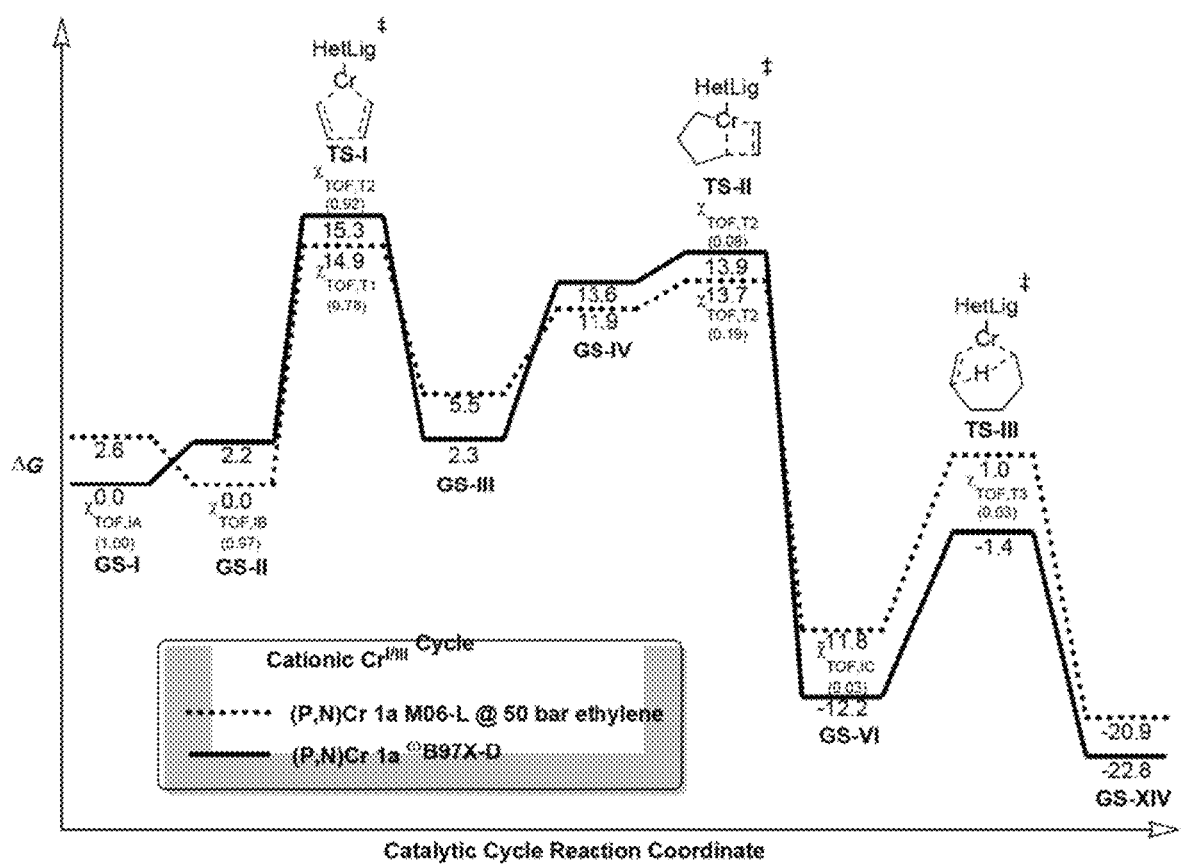
FIG. 11 illustrates a Gibbs free energy surface for ethylene trimerization with catalyst 1a. The solid surface is the abbreviated Gibbs free energy surface for ethylene trimerization with catalyst 1a at an ethylene pressure of 50 bar with M06-L, and the dotted surface is the ωB97X-D Gibbs free energy landscape (kcal/mol).

Kinetic studies with (P,N)Cr heteroatomic ligand-chromium compound complex 1a were performed at high ethylene pressure (Gunasekara, T.; Kim, J.; Preston, A.; Steelman, D. K.; Medvedev, G. A.; Delgass, W. N.; Sydora, O. L.; Caruthers, J. M.; Abu-Omar, M. M.; *ACS Catal.* 2018, 8, 6810-6819; which is incorporated by reference in its entirety, including its Supporting Information), therefore, an ethylene pressure corrected Gibbs free energy surface at 50 bar was constructed, as illustrated in FIG. 11. In FIG. 11, the solid surface is the abbreviated Gibbs free energy surface for ethylene trimerization with (P,N)Cr heteroatomic ligand-chromium compound complex 1a at an ethylene pressure of 50 bar with M06-L, and the dotted surface is the ωB97X-D Gibbs free energy landscape (kcal/mol).

As illustrated in FIG. 11, inclusion of ethylene pressure in the calculations results in a several kcal/mol lowering of the TS-II barrier, and the surrounding landscape. With ωB97X-D/def2-TZVP//M06-L/6-31G**[LANL2DZ for Cr] (FIG. 11) the Gibbs free energy surface showed a similar profile to the M06-L surface without correction for ethylene pressure (see SI for ωB97X-D values with ethylene pressure correction). Except for lowering of the landscape in the vicinity of TS-II, the M06-L pressure corrected surface, and the ωB97X-D surface, in their shape are qualitatively similar to the M06-L Gibbs free energy surface presented in FIG. 9A. However, on the ωB97X-D surface, $(P,N)Cr^1(C_2H_4)$ GS-I is 2.2 kcal/mol lower in energy than $(P,N)Cr^1(C_2H_4)_2$ GS-II, which results in the resting state dominated by GS-I with a little contribution from chromaheptacycle GS-VI. The energy difference between GS-I and GS-I is still consistent with the experimentally observed reversible coordination of an ethylene because TS-I has a relatively large barrier. Because the ethylene pressure correction lowers TS-II relative to TS-II, on this surface TS-II now dominates controlling the TOF, but there remains a small, but significant contribution from TS-II. Because the resting state is dominated by GS-I, and TS-I and TS-II both influence the TOF, the predicted rate order for ethylene remains >1 (see Examples). The calculated TOFs for the pressure-corrected and ωB97X-D energy landscapes are 67 and 33 mol 1-C$_6$·s$^{-1}$, which gives predicted total productivity masses of 2.0×10$^7$ g·h$^{-1}$ and 1.0×10$^7$ g·h$^{-1}$ that overestimates but is consistent with the experimental productivity values. Examination of the pressure corrected surface also provides a possible rationale for experimentally observed irreversible coordination of ethylene to the chromacyclopentane intermediate GS-III. The barrier from GS-IV to TS-II is 1.9 kcal/mol on the M06-L and only 0.3 kcal/mol on the (ωB97X-D surface. These barriers are likely lower than the reverse barrier for ethylene dissociation back to GS-III.

To further understand the greatly decreased TOF for the (P,N,N)Cr heteroatomic ligand-chromium compound complex 8a catalyst, potential steric and electronic effects, as well as ring strain energies were investigated. To determine the influence of steric effects, heteroatomic ligands 1a and 8a were altered to change aryl and isopropyl groups to methyl groups. Scheme 3 a) illustrates model heteroatomic ligands 1b and 8b which are used to examine the impact of steric influence on ethylene trimerization reactivity. Gibbs free energy spans are in kcal/mol. Somewhat surprisingly, for the modified heteroatomic ligands 1b and 8b, the free energy landscapes are very similar to those presented in FIG. 9A, which indicates the ligand size is not responsible for the decreased activity (see Scheme 3 and Examples). The impact of the third amino donor group on the stability of the chromapentacycle ring was then examined. Scheme 3 b) illustrates the dissociation of an amine arm to mimic a bidentate ligand framework. The Cr—C bond homolysis energies were computed to estimate chromapentacycle ring strains for intermediate GS-III (FIG. 9A) with (P,N)Cr heteroatomic ligand-chromium compound complex 1a and (P,N,N)Cr heteroatomic ligand-chromium compound complex 8a. Unexpectedly, the Cr—C bond energies for both these intermediates were similar in energy and calculated to be ~25 kcal/mol, indicating ring strain does not significantly impact reactivity.

Scheme 3 a)

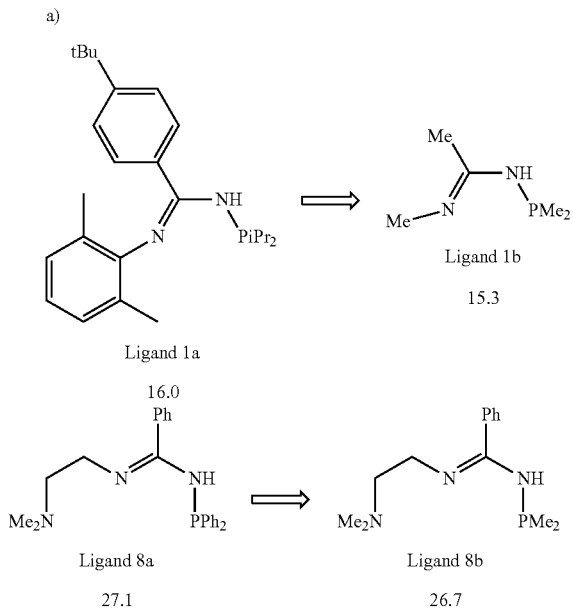

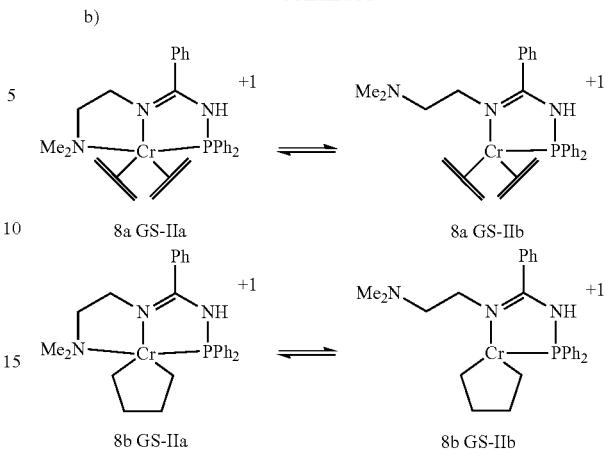

Because the bidentate (P,N)Cr heteroatomic ligand-chromium compound complexes are significantly more reactive than the tridentate heteroatomic ligand-chromium compound complexes shown in Scheme 3, this discovery could signal that for the tridentate catalysts to be reactive, one of the ligand arms may need to dissociate in a hemilabile mechanism (see FIG. 11 and Scheme 3 b)). For the bis (ethylene) (P,N,N)Cr ground state GS-II, —NMe$_2$ arm dissociation requires 14.3 kcal/mol. For the predicted ground state GS-III, —NMe$_2$ arm dissociation requires 29.5 kcal/mol. All other intermediates and transition states were also calculated with —NMe$_2$ arm dissociation. Without —NMe$_2$ coordination, the ground state GS-II and the turnover limiting transition state has an energy span of 15.4 kcal/mol, which is very similar to the (P,N)Cr catalyst 1a. Overall, this appears to indicate that for this type of Cr ligand the third amine coordination overstabilizes the Cr$^{III}$ ground state and prevents further expansion of the chromacycle.

Reactivity Comparison of Heteroatomic Ligand-Chromium Compound Complexes 2-7.

Ligands 2-7 used for the heteroatomic ligand-chromium compound complexes are shown FIG. 8. For ligand 2, similar to ligand 1a, the mono(ethylene) and bis(ethylene) complexes are sextet spin states; however, ground state GS-I is 3.7 kcal/mol lower in energy than ground state GS-II (see Examples for energy surface). The following oxidative C—C coupling barrier is 13.3 kcal/mol relative to ground state GS-I and 1.6 kcal/mol lower in energy than 1a. The formation of the chromacyclopentane ground state GS-III and ethylene coordinated chromacycle ground state GS-IV are endergonic, analogous to 1a. The subsequent migratory insertion barrier is 17.8 kcal/mol, which then forms an exergonic chromacycloheptane ground state GS-VI. The β-hydrogen transfer transition state to form ground state GS-XIV is 14.8 kcal/mol relative to GS-VI. The overall energy span using ligand 2 is 1.8 kcal/mol higher than using ligand 1a and slightly underestimates the productivity as shown in Table 3 but is consistent with the experimentally observed catalytic activities.

Tridentate heteroatomic ligand-chromium compound complexes (S,N,S)Cr and (P,N,P)Cr using heteroatomic ligands 3 and 4 were modeled as the NH protonated monocationic Cr$^{I/III}$ (see Yang, Y.; Liu, Z.; Zhong, L.; Qiu, P.; Dong, Q.; Cheng, R.; Vanderbilt, J.; Liu, B.; *Organometallics* 2011, 30, 5297-5302; Kwon, D.-H.; Fuller, J. T.; Kilgore, U. J.; Sydora, O. L.; Bischof, S. M.; Ess, D. H.; *ACS Catal.* 2018, 8, 1138-1142). The resulting calculations were qualitatively consistent with the previous B3LYP calculations using ligand 3 with one notable exception. While the same sextet to quartet spin crossing during oxidative coupling was predicted, this energy difference is only ~23 kcal/mol compared to the >30 kcal/mol previously reported. Because the model for the inactivity of the tridentate ligand 8a involves the stability of the chromacyclopentane ground state GS-II, FIG. 9B gives the energies of this intermediate for the (S,N,S)Cr and (P,N,P)Cr heteroatomic ligand-chromium compound complexes. For (S,N,S)Cr, the migratory insertion barrier for transition state TS-II is 17.9 and 23.1 kcal/mol relative to ground state GS-II and ground state GS-III, respectively. For this catalytic cycle, the Boltzmann weighted energy span of 23.1 kcal/mol results in a predicted TOF of $4.2 \times 10^{-5}$ mol $1\text{-}C_6/s^{-1}$ and productivity of 12.7 g $1\text{-}C_6/hr^{-1}$. While this predicted productivity underestimates the 1-hexene product compared to experiment, it does capture the moderate reactivity between using ligands 1a and 8a.

Consistent with (S,N,S)Cr, the chromacyclopentane ground state GS-III regarding the (P,N,P)Cr heteroatomic ligand-chromium compound complex is stabilized relative to ground state GS-I ($\Delta G = -5.7$ kcal/mol). The overall Boltzmann weighted energy span that includes the proceeding migratory insertion barrier is 23.8 kcal/mol and translates to a TOF of $1.6 \times 10^{-5}$ mol $1\text{-}C_6/s^{-1}$ and productivity of 4.8 g $1\text{-}C_6/h^{-1}$. The nearly equivalent energy spans of the (S,N,S)Cr and (P,N,P)Cr heteroatomic ligand-chromium compound complexes capture the similar experimental productivity values (FIG. 9A and FIG. 9B). Furthermore, the energy spans demonstrate that the S,N,S and P,N,P type ligands provide similar effects in stabilizing the chromacyclopentane ground state GS-III resulting in a relatively high migratory insertion barrier. Ligand complexes featuring tridentate coordination spheres S,N,S (5; see Temple, C. N.; Gambarotta, S.; Korobkov, I.; Duchateau, R.; *Organometallics* 2007, 26, 4598-4603), N,O,N (6; see Zhang, J.; Braunstein, P.; Hor, T. S. A.; *Organometallics* 2008, 27, 4277-4279), and P,N,P (7; see Bluhm, M. E.; Walter, O.; Döring, M.; *J. Organomet. Chem.* 2005, 690, 713-721), mirror the S,N,S (exemplified by ligand 3) and P,N,P (exemplified by ligand 4) complexes with increasing migratory insertion or enhanced stability of the chromacycloheptane ground state GS-IV leading to larger energy spans (see table in FIG. 9B, Table 3, and Examples). Conversely, the (P,N)Cr heteroatomic ligand-chromium compound complex provides a balance of moderate to low stability of the chromacyclopentane ground state GS-III and stabilizes the migratory insertion barrier with the phosphine ligand arm resulting in a relatively low migratory insertion barrier.

Comparison of Calculated and Experimental Productivity. To build a general reactivity model that could be useful across several ligand types, the TOF energy spans including temperature and pressure corrections were approximated that reasonably model experimental conditions for the ligands shown in FIG. 8 (see Examples for full experimental details and reaction condition corrected Gibbs free energy surfaces). Because there was a switch in ground state and turnover limiting transition states for heteroatomic ligand-chromium compound complex 1a versus heteroatomic ligand-chromium compound complex 8a, this analysis required calculation of all ground states and transition states for each ligand. Generally, it was discovered that for meridional coordination complexes, transition state TS-II dominates rate control and for facial complexes transition state TS-III dominates rate control. Table 3 provides an overview of the calculated Boltzmann weighted energy span $\Delta G\ddagger$, TOF, calculated productivity and reported experimental productivity values. A summary of experimental conditions is provided in the Examples section.

TABLE 3

Comparison of Calculated and Experimental Productivity.

| Complex | Pressure[a] | Temperature[b] | $\Delta G^{\ddagger d}$ | TOF[e] | Productivity[f] | Exp. Productivity[g] |
|---|---|---|---|---|---|---|
| 1a | 60 | 70 | 17.1 | 1.4 | $4.2 \times 10^5$ | $9.9 \times 10^5$ |
| 2 | 40 | 60 | 17.6 | $7.2 \times 10^{-1}$ | $2.2 \times 10^5$ | $6.3 \times 10^5$ |
| 3 | 40 | 80 | 23.9 | $1.2 \times 10^{-5}$ | 3.6 | $3.9 \times 10^4$ |
| 4 | 40 | 80 | 25.0 | $2.4 \times 10^{-6}$ | $7.2 \times 10^{-1}$ | $2.6 \times 10^4$ |
| 5 | 35 | 50 | 23.1 | $3.4 \times 10^{-5}$ | 10.3 | $5.2 \times 10^3$ |
| 6 | 25 | 80 | 27.4 | $4.6 \times 10^{-8}$ | $1.4 \times 10^{-2}$ | $2.7 \times 10^3$ |
| 7 | 30 | 24 | 27.1 | $8.3 \times 10^{-8}$ | $2.5 \times 10^{-2}$ | $4.6 \times 10^2$ |
| 8a | 30 | 55 | 26.7 | $1.7 \times 10^{-7}$ | $5.1 \times 10^{-2}$ | 0 |

[a]Experimental ethylene pressure (bar).
[b]Experimental temperature (° C.).
[c]TOF determining transition state contributions.
[d]Boltzmann weighted Gibbs free energy span in kcal/mol.
[e]Calculated TOF in mol of $1\text{-}C_6 \cdot s^{-1}$.
[f]Calculated productivities of $1\text{-}C_6$ in g · hr$^{-1}$.
[g]Experimental productivities of 1-hexene in g $1\text{-}C_6$/g Cr · h.

Figure 12:
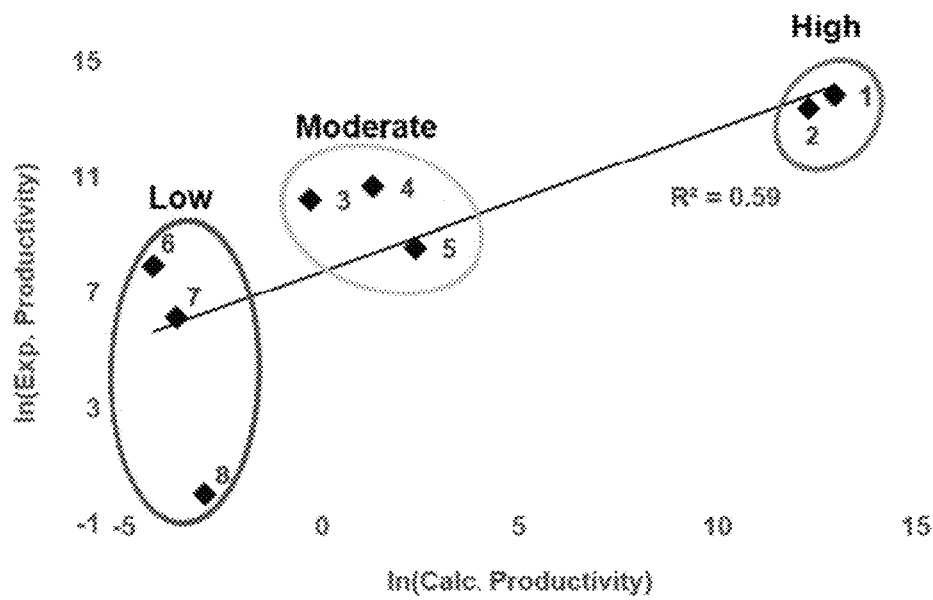
FIG. 12 shows a plot of the natural log of experimental productivity values corrected for 1-hexene only (g 1-$C_6$/g Cr·h) versus the natural log calculated 1-$C_6$ productivity values. The 8a productivity was evaluated as the natural log of 1.

FIG. 12 provides a quantitative assessment of the natural log of experimental productivity values versus the natural log of pressure and temperature corrected calculated productivity values for the Boltzmann averaged energy spans that dominate rate control. The natural log transformations were used to compare the very high activities of heteroatomic ligand-chromium compound complexes using ligands 1a and 2 to slow or inactive heteroatomic ligand-chromium compound complexes using ligands 6, 7, and 8. While there is clearly a linear correlation in FIG. 12, the regression curve is not highly quantitative with an $R^2$ value of 0.59. However, the moderate correlation results from the predicted productivity for the non-reactive heteroatomic ligand-chromium compound complex using ligand 8a, which was overestimated relative to the other complexes. A similar moderate correlation was also found using the ωB97X-D functional (see Examples), which indicates multiple functionals are able to replicate experimental productivity. This graph does showcase high, moderate, and low reactivity groupings of ligands. For example, highly active heteroatomic ligand-chromium compound complexes using ligands 1a and 2 are grouped together in a similar region ("High" in FIG. 12), while the "Moderate" tridentate heteroatomic ligand-chromium compound complexes using ligands 3, 4, 5 which yield moderate productivities are grouped. "Low" or no productivity heteroatomic ligand-chromium compound complexes using ligands 6, 7, and 8a are shown grouped together in FIG. 12.

To summarize, DFT calculations and an energy-span type analysis were successfully used to examine the difference between the highly reactive (P,N)Cr heteroatomic ligand-chromium compound complexes and unreactive (P,N,P)Cr heteroatomic ligand-chromium compound complex for ethylene trimerization. These calculations suggested a low energy $Cr^{I/III}$ chromacycle catalytic mechanism. For (P,N)Cr heteroatomic ligand-chromium compound complex using ligand 1a, this analysis revealed there are multiple $Cr^I$ ethylene coordinated resting states and multiple turnover-controlling transition states, which can account for a partial rate order in ethylene. The calculated productivity mass of $3.0 \times 10^6$ g·h$^{-1}$ is within one order of magnitude of the experimental value. In contrast to this highly reactive heteroatomic ligand-chromium compound complex using ligand 1a, for the (P,N,N)Cr heteroatomic ligand-chromium compound complex using ligand 8a, the calculations also revealed a much larger energy span and is ~$10^7$ slower, which is due to stabilized chromacyclopentane ground state GS-III intermediate along with a higher barrier for the subsequent migratory insertion reaction step. The energy spans of the intermediate activity tridentate catalysts are smaller than (P,N,N)Cr heteroatomic ligand-chromium compound complex using ligand 8a but larger than (P,N)Cr heteroatomic ligand-chromium compound complex using ligand 1a. Heteroatomic ligand-chromium compound complex using ligands 3, 4, 5 were found to have moderate activity for different reasons. For example, heteroatomic ligand-chromium compound complexes thiol ether ligand 3 and alkyl phosphine ligand 4 do not overstabilize the chromacyclopentane ground state GS-III and provide a relatively low barrier for migratory insertion. While there is clearly a linear correlation between experimental productivity values and the calculated energy spans, the correlation is modest, but useful to qualitatively segregate poor versus highly active Cr catalysts.

In another aspect, similar methodology can be utilized to calculate/determine/estimate the octene turnover frequency (hence 1-octene activity/productivity) using the basic reaction pathways illustrated in FIG. 4 where the reaction pathway ground states and transition states from GS-1 to TS-V are utilized. Additionally, similar methodology can be utilized to calculate/determine/estimate total productivity by separating calculating the hexene productivity and octene productivity using the reaction pathways in FIG. 4. In a further aspect, similar methodology can be utilized to determine 1-hexene purity by separately calculating/determining/estimating the turnover frequency (hence activity/productivity) for every 1-hexene producing and $C_6$ impurity producing pathways in FIG. 6. In yet a further aspect, similar methodology can be utilized to determine the $C_6/C_8$ selectivity by separately determining the turnover frequency (hence activity/productivity) for the 1-hexene producing and 1-octene producing pathways in FIG. 4.

Combining Machine Learning with the Quantum Mechanical Transition State Model to Provide Catalyst Design Features for Selective Cr-Olefin Oligomerization Among other things, this disclosure demonstrates how the olefin oligomerization activity/productivity, selectivity, and/or product purity of heteroatomic ligand-chromium compound complex can be determined and modified using density functional theory (DFT) calculations. In an aspect, it is demonstrated here that combining machine learning computational methods in combination with quantum mechanical transition state models can identify specific catalyst design features for selective olefin oligomerization using heteroatomic ligand-chromium compound complexes.

Moreover, in an aspect of this disclosure, a similar procedure can be utilized by combining machine learning computational methods with quantum mechanical transition state models using density functional theory (DFT) calculations of the turn-over frequencies (TOF)/productivities to identify specific catalyst design features for improved activity/productivity using heteroatomic ligand-chromium compound complexes. Similarly, in an aspect, machine learning computational methods can be combined with quantum mechanical transition state models using DFT calculations to identify specific catalyst design features for improved product purity using heteroatomic ligand-chromium compound complexes.

Computational chemistry can be used in molecular heteroatomic ligand and/or heteroatomic ligand-chromium compound complex design and optimization by either testing chemical hypotheses or directly evaluating heteroatomic ligand and/or heteroatomic ligand-chromium compound complex candidates. However, no general strategy for virtual ligand or complex design or improvement has emerged, and specific ligand and/or complex prediction followed by experimental realization is elusive. This disclosure provides for computational heteroatomic ligand-chromium compound complex design using quantum-mechanical methods to model reaction pathways using ground states and transition states. Quantum mechanical analysis of the reaction pathway ground states and transition states may replicate experiment and can be used for heteroatomic ligand-chromium compound complex prediction, however, it remains difficult to identify simple chemical features that control ethylene oligomerization, especially for selectivity, activity/productivity, and/or product purity where small energy quantities can impart significant influence.

In one aspect, this disclosure provides the development of a density functional theory (DFT) transition-state model that can provide quantitative and/or qualitative prediction of molecular heteroatomic ligand-chromium compound complexes for controlling selective ethylene trimerization and/or tetramerization is described. In another aspect, a heteroatomic ligand and/or heteroatomic ligand-chromium compound complex design workflow that combines quantum-mechanical transition state modeling with machine learning can reveal specific heteroatomic ligand-chromium compound complex design features. For example, FIG. 13A outlines the heteroatomic ligand-chromium compound complex catalyzed selective ethylene oligomerization reaction conditions with targets of 1-hexene and 1-octene. The studied heteroatomic ligand-chromium compound complex involves a Cr metal center with phosphine and imine ligand coordination, "Cr(P,N)" (see FIG. 13B). A modified methylaluminoxane (MMAO) such as an isobutyl-modified methylaluminoxane is typically used to activate the heteroatomic ligand-chromium compound complex.

Figures 13A, 13B, 13C:
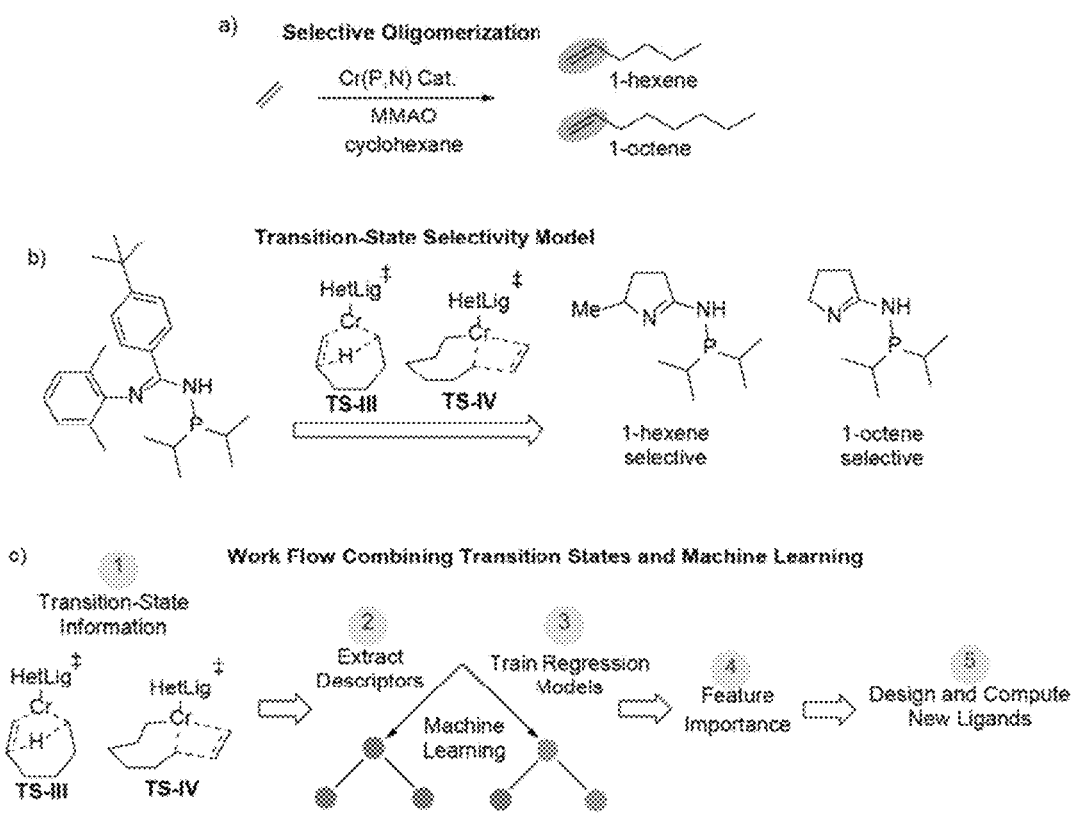
FIG. 13A outlines the heteroatomic ligand-chromium compound complex catalyzed selective ethylene oligomerization reaction conditions with targets of 1-hexene and 1-octene, using a heteroatomic ligand-chromium compound complex having phosphine and imine ligand coordination, "Cr(P,N)", for which a modified methylaluminoxane (MMAO) is typically used to activate the pre-catalyst complex.
FIG. 13B illustrates the transition state selectivity model used in this disclosure, in which the computational examination examined the cationic high-spin transition-states TS-III leading to 1-hexene and TS-IV leading to 1-octene, to develop a linear correlation model between DFT computed values and experimental 1-hexene:1-octene ratios.
FIG. 13C illustrates the workflow of this disclosure which combined transition states and machine leaning, using the 1-hexene/1-octene transition-state selectivity model disclosed herein. By combining the transition states with machine learning models, the selectivity controlling features can be discovered, which are then used for virtual design new catalyst ligands.

The computational examination considered the cationic high-spin transition states TS-III (leading to 1-hexene) and TS-IV (leading to 1-octene) shown in FIG. 13B to develop a linear correlation model between DFT computed values and experimental 1-hexene:1-octene ratios. This design allowed the use of calculations to computationally design a new general class of phosphine monocyclic imine Cr(P,N) catalysts where changes in the ligand structure can control 1-hexene:1-octene selectivity (see FIG. 13B). Experimental ligand and catalyst synthesis, and reaction testing, quantitatively confirmed the transition-state predictions from the computational design effort. FIG. 13C presents an aspect of this disclosure, which involves using the 1-hexene/1-octene transition-state selectivity model disclosed herein, combined with machine learning models to reveal selectivity controlling features, which are then used for virtual design new ligands for heteroatomic ligand-metal compound complexes (e.g., heteroatomic ligand-chromium compound complexes).

The DFT transition-state model disclosed herein is practical, accurate, and successfully identified new ligands that were experimentally validated. The machine learning aspect builds upon the transition state model and provides general heteroatomic ligand-metal compound complex (e.g., heteroatomic ligand-chromium compound complex) design guidance to enhance 1-octene selectivity. The interpretation of singular controlling transition-state features, those that are the major contributes to selectivity, is nonobvious since the energy difference between 1-hexene and 1-octene selectivity controlling species is relatively small. However, this combination of the transition-state model with quantitative data science methods can provide the emergence of chemical features to enhance 1-octene selectivity. There are currently no examples of an experimentally verified quantum-mechanical transition model merged with machine learning methods. The methods described herein can also be utilized to enhance 1-hexene selectivity.

Data science approaches to molecular catalyst design generally emphasize ground-state properties of either heteroatomic ligand-chromium compound complex and/or heteroatomic ligands without metal centers. As shown in FIG. 13C, the approach provided in the present disclosure involves using DFT-computed transition state features and selectivities for machine learning analysis. The analysis of >100 heteroatomic ligand-chromium compound complexes and 14 heteroatomic ligand descriptors through machine learning regression algorithms with multifold cross validation resulted in a low root mean square error (RMSE) and emergence of three primary design elements to enhance 1-octene selectivity. The utility of these machine-learning identified selectivity features was demonstrated by the design and calculation of several new heteroatomic ligands that are predicted to give >90% 1-octene selectivity. That is, this disclosure combines an experimentally verified transition-state model with machine learning analysis as a workflow to design new heteroatomic ligand-chromium compound complexes.

Therefore, it has been discovered that one or more machine learning algorithms could perform well for the heteroatomic ligand-chromium compound complex design workflow which combines quantum-mechanical transition state modeling with machine learning, and such algorithms could narrow down the steric and electronic features of the catalyst to those key features having the greatest influence on the product selectivity, product purity, and/or activity/productivity. The unrestricted M06L density functional (Zhao, Y.; Truhlar, D. G.; *Theor. Chem. Acc.* 2008, 120 (1-3), 215-241.) was used for describing the electronic structure of Cr(P,N) catalysts. The UM06L/Def2-TZVPP//UM06L/6-31G**[LANL2DZ] level of theory was combined with the SMD continuum model (Frisch, M. J.; Trucks, G. W.; Schlegel, H. B.; Scuseria, G. E.; Robb, M. A.; Cheeseman, J. R.; Scalmani, G.; Barone, V.; Mennucci, B.; Petersson, G. A.; Nakatsuji, H.; Caricato, M.; Li, X.; Hratchian, H. P.; Izmaylov, A. F.; Bloino, J.; Zheng, G.; Sonnenb, D. J.; Gaussian 09 Revision D.01. Gaussian Inc.: Wallingford, C T 2009) for cyclohexane to estimate the free energies of transition states TS-III and TS-IV. In this transition state model, the relative free energies of transition state TS-III and TS-IV provide selectivity under the assumption of Curtin-Hammett type conditions. All transition state structures were optimized and vibrational frequencies were computed to verify the stationary points as first-order saddle points. Normal rigid-rotor harmonic oscillator approximations were applied with free energies at 1 atm and 298 K. Because the transition-state model is a linear correlation scheme, no temperature or pressure corrections were applied. All DFT calculations were performed using Gaussian 09 (Frisch, M. J.; Trucks, G. W.; Schlegel, H. B.; Scuseria, G. E.; Robb, M. A.; Cheeseman, J. R.; Scalmani, G.; Barone, V.; Mennucci, B.; Petersson, G. A.; Nakatsuji, H.; Caricato, M.; Li, X.; Hratchian, H. P.; Izmaylov, A. F.; Bloino, J.; Zheng, G.; Sonnenb, D. J.; Gaussian 09 Revision D.01. Gaussian Inc.: Wallingford, C T 2009). Machine learning analyses were performed using scipy (Jones, E.; Oliphant, T.; Peterson, P. SciPy: Open Source Scientific Tools for Python. 2001), numpy (Oliphant, T. *A Guide to NumPy*; Trelgol Publishing: USA, 2006), pandas (McKinney, W. Data Structures for Statistical Computing in Python. *In Proceedings of the 9th Python in Science Conference*; van der Walt, S., Millman, J., Eds.; 2010; pp 51-56), and scikit-learn (Pedregosa, F.; Varoquaux, G.; Gramfort, A.; Michel, V.; Thirion, B.; Grisel, O.; Blondel, M.; Prettenhofer, P.; Weiss, R.; Dubourg, V.; et al. Scikit-Learn: Machine Learning in Python. *J. Mach. Learn. Res.* 2011, 12, 2825-2830) in Python 2.7.

Figure 14:
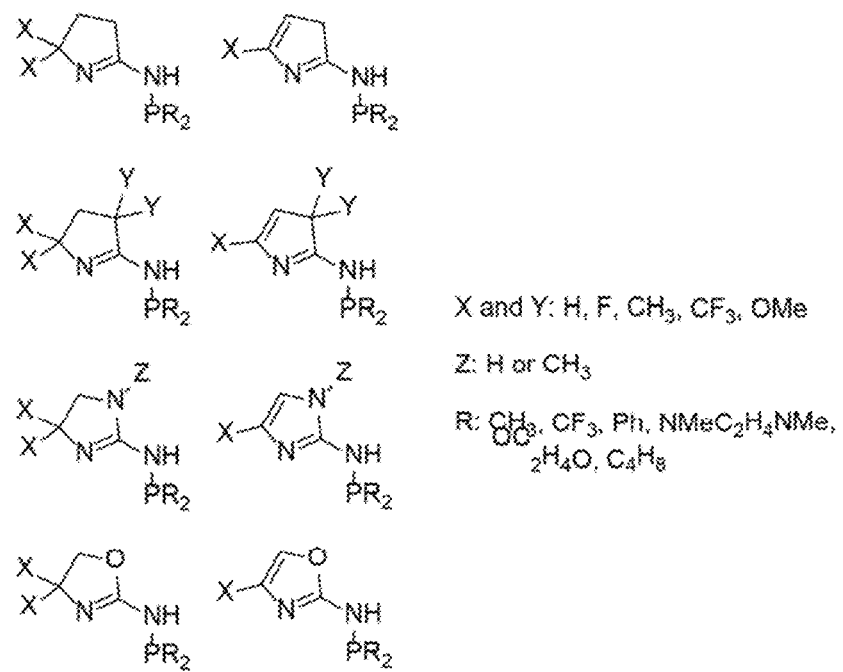
FIG. 14 outlines the 105 unique heteroatomic ligand-chromium compound complexes having phosphine and imine ligand coordination, "Cr(P,N)"ligands" in the transition-state training or instructive data set, which have a variety of different functional groups, but retain the phosphine and imine, or imine-like, ligand coordination for which the DFT transition-state model was developed.

A total of 105 unique (P,N) heteroatomic ligands were used in the transition-state training data set, which included experimentally measured $C_6/C_8$ ratios for 14 heteroatomic ligands. FIG. 14 outlines the 105 unique (P,N) heteroatomic ligands in the transition state training data set, which have a variety of different functional groups, but retain the phosphine and imine, or imine-like, heteroatomic ligand coordination for which the DFT transition state model was developed. These 105 heteroatomic ligands were selected because of the ability to further improve or optimize the five-membered imine ring system and to stay within the bounds of accuracy for the correlation model. As shown in FIG. 14, this set includes a variety of substituted heterocycles such as pyrroles, imidazoles, and oxazoles. In each of these cases, their combinations with alkyl, fluoroalkyl, aryl, and amido phosphines as well as phospholanes were examined. These ligands in FIG. 14 were used to calculate selectivity based on transition states TS-III and TS-IV. Transition state features were then harvested from the electronic structure and geometries of transition states TS-III and TS-IV.

In this process, 14 atomic and molecular descriptors or features were extracted from transition states TS-III and TS-IV for each of the 105 heteroatomic ligands shown in FIG. 14. These atomic and molecular descriptors extracted for machine learning analysis are illustrated in FIG. 2A, FIG. 12B, and FIG. 2C, and include: geometric parameters such as bond lengths, angles, and dihedrals as illustrated in FIG. 2A; the percent volume buried as defined and illustrated in FIG. 2B; and the Cr metal center distance out of pocket as defined and illustrated in FIG. 2C. Several electronic features were also harvested, such as electrostatic-based atomic charges; see FIG. 2A. The percent volume buried describes the extent to which the first coordination sphere of the Cr metal center is occupied by a (P,N) heteroatomic ligand (see Falivene, L.; Cao, Z.; Petta, A.; Serra, L.; Poater, A.; Oliva, R.; Scarano, V.; Cavallo, L. Towards the Online Computer-Aided Design of Catalytic Pockets. *Nat. Chem.* 2019, 11 (10), 872-879. https://doi.org/10.1038/s41557-019-0319-5). The distance out of pocket describes how far the Cr metal is situated from the (P,N) heteroatomic ligand and is calculated as shown in FIG. 2C.

Figure 15:
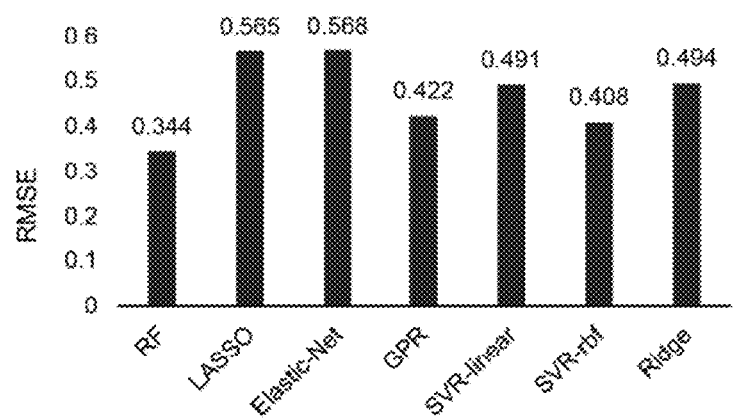
FIG. 15 illustrates the root mean square error (RMSE) for machine learning regression algorithms to quantitatively predict TS-III an TS-IV energy differences using 14 atomic and molecular features. In this figure, RF=random forest, LASSO=least absolute shrinkage and selection operator, GPR=Gaussian process regression, SVR=support vector regression.

The Scikit-Learn python library was used to set up and train regressors on this transition-state data set, which was split into 25% training and 75% testing sets. Seven regression algorithms were tested including: random forest, Gaussian process regression, LASSO, elastic-net, ridge regression and support vector regression with both a linear and radial basis function kernel. Multifold cross validation was performed to protect against model overfitting common in small datasets. This random sampling was performed 10 times and 20-fold cross validation was used at each iteration to determine regression accuracy. The RMSE (root mean square error) of each model determined using cross validation averaged across iterations is shown in FIG. 15.

The machine learning regression algorithms were used to evaluate the use of the 14 atomic and molecular features to quantitatively correlate with the DFT calculated energy differences between transition state TS-III and TS-IV. The RMSE of the regression algorithms ranged from 0.344 to 0.568 (see FIG. 15). The best performing model was random forest (RMSE=0.344) and the poorest performing model was elastic-net (RMSE=0.568). The LASSO and ridge algorithms, which are related to elastic-net, also performed rather poorly with RMSEs of 0.565 and 0.494, respectively. The performance of support vector regression improved by almost 10% when changing from a linear (RMSE=0.491) to a radial basis function (RMSE=0.408) kernel. Gaussian process regression performed comparable to SVR-rbf.

Because the random forest algorithm performed well, this algorithm was chosen for further hyperparameter optimization using the GridSearch CV method from SciKit-Learn. Different permutations of hyperparameters and five-fold cross validation were tested in order to determine the set of hyperparameters that maximized the performance of the model. The number of trees in each forest was varied from 20 to 210 and the trees were split from 5 to 125 times. Both mean signed error and mean absolute error were considered when determining the quality of each split and between three and 14 features were examined when considering the best split. The optimized random forest model was then re-fit to the training data to validate the hyperparameter optimization. The RMSE of the random forest model decreased from 0.344 to 0.272 after optimization. The RMSE of the 1-hexene to 1-octene selectivities are 0.275 and 0.269, respectively.

Figure 16A:
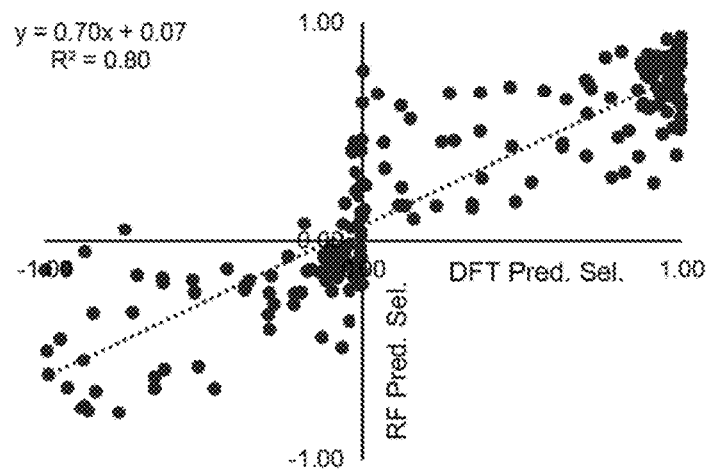
FIG. 16A shows the linear regression of selectivities predicted by DFT selectivity model (x-axis) and optimized random forest (RF) model (y-axis). Negative values correspond to high 1-hexene selectivity, positive values to high 1-octene selectivity.
Figure 17:
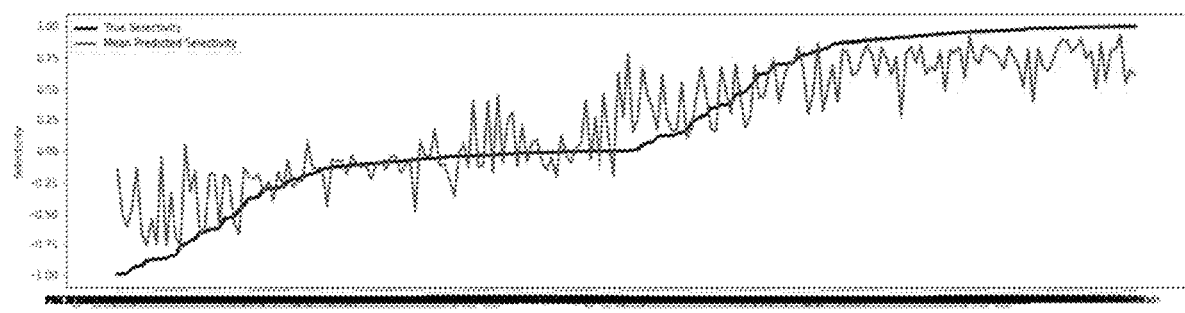
FIG. 17 compares the machine learning mean predicted selectivities (red) to DFT computed selectivities.

FIG. 16A plots the selectivities determined from the optimized random model plotted against those determined from the DFT selectivity model. In this data set, overall 1-hexene selective (i.e. >50% 1-hexene vs. 1-octene) is labeled as a negative value and overall 1-octene selective is labeled as a positive value (i.e. >50% 1-octene vs. 1-hexene). The random forest model correctly predicted the overall 1-hexene versus 1-octene selectivity for 83 heteroatomic ligands and incorrectly predicted the overall selectivity for 22 heteroatomic ligands. This incorrect assignment occurs in cases where the DFT computed 1-hexene selectivity of a heteroatomic ligand is less than 1%. The random forest model tends to perform best for heteroatomic ligands ranging from 20:80 to 50:50 1-hexene:1-octene selectivity, as illustrated in FIG. 17. FIG. 17 shows the machine learning mean predicted selectivities as compared to DFT computed selectivities for all 105 heteroatomic ligands examined. The majority of heteroatomic ligands in the data set are overall 1-octene selective, which demonstrates improving the percentage of 1-octene, but it is likely that the RMSE of the random forest model would be reduced if the data set were more evenly distributed between overall 1-hexene and overall 1-octene selective.

Figure 16B:
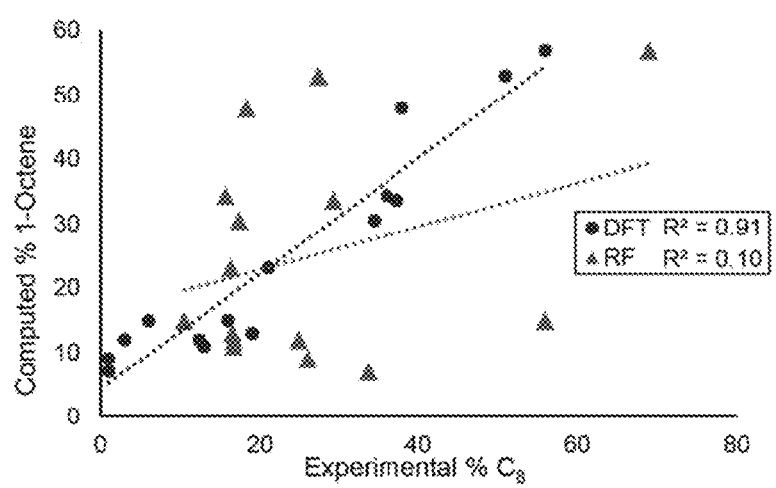
FIG. 16B provides the linear regressions of 1-octene selectivities predicted by the DFT selectivity model (circles) and optimized random forest (RF) model (triangles) models compared to experimental values.
Figure 18:
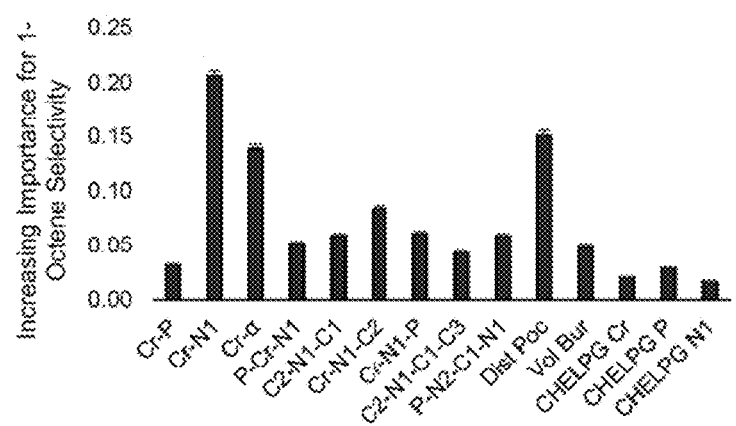
FIG. 18 illustrates the normalized feature importance determined from random forest model with 95% confidence intervals (red bars). Dist Poc is distance out of pocket; Vol Bur is percent volume buried; the other parameters are shown in FIG. 1 and FIG. 2A.

In FIG. 16B, the 1-octene selectivities calculated using the DFT selectivity model and the optimized random forest (RF) model are plotted against the experimentally determined selectivities. The DFT selectivity model agreed with experiment very well ($R^2$=0.91, mean absolute deviation=4.4%). The DFT model underestimates the experimental selectivity, however, this is overall advantageous with the goal to increase 1-octene production. In contrast to the DFT calculated values, the random forest model was unable to quantitatively reproduce the experimental selectivities with a high degree of linear correlation. The lack of very high quantitative correlation between random forest and experiment values is likely due to the relatively small sample size of experimentally studied heteroatomic ligands. Despite this, the random forest can be used effectively to determine key chemical features that are primarily responsible for enhancing 1-octene selectivity. The relative importance of the 14 features included in the dataset can be determined by replacing data with random values and observing the impact on the RMSE value. If replacing data of a feature with random values results in a small change to the RMSE then it has a low degree of importance. Conversely, if there is a large change in the RMSE, the feature has a large importance. FIG. 18 displays this feature importance analysis using the optimized random forest model, specifically, the normalized feature importance determined from random forest model with 95% confidence intervals, shown in FIG. 18.

Inspection of FIG. 18 reveals that the Cr—N distance, Cr-α distance, and distance out of pocket were identified as being most relevant in enhancing 1-octene selectivity. The Cr—N—$C_2$ distance, which is related to the Cr-α distance, was also identified as a key 1-octene enhancing feature. Despite the possible importance of the ligand bite angle, especially for phosphine catalysts, it was found that the P—Cr—$N_1$ ligand bite angle is among several lesser important features.

Figure 19A:
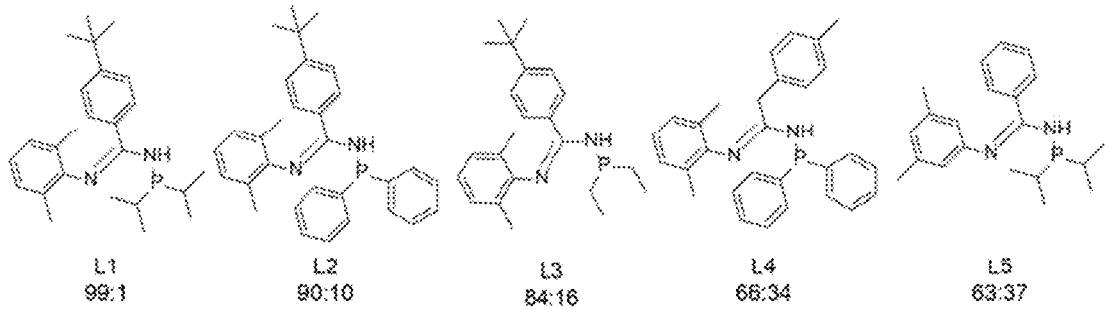
FIG. 19A illustrates the structures for previous (P,N) ligand generations and the new proposed ligands (generation 3) based on machine-learning identified features. The 1-hexene:1-octene selectivity (predicted) is given below each structure.
Figure 19A:
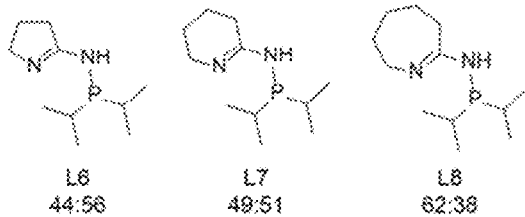
Figure 19A:
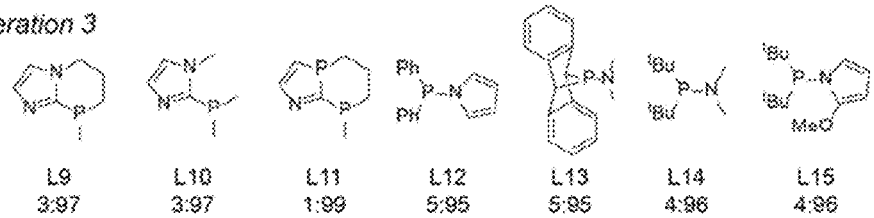
Figure 19B:
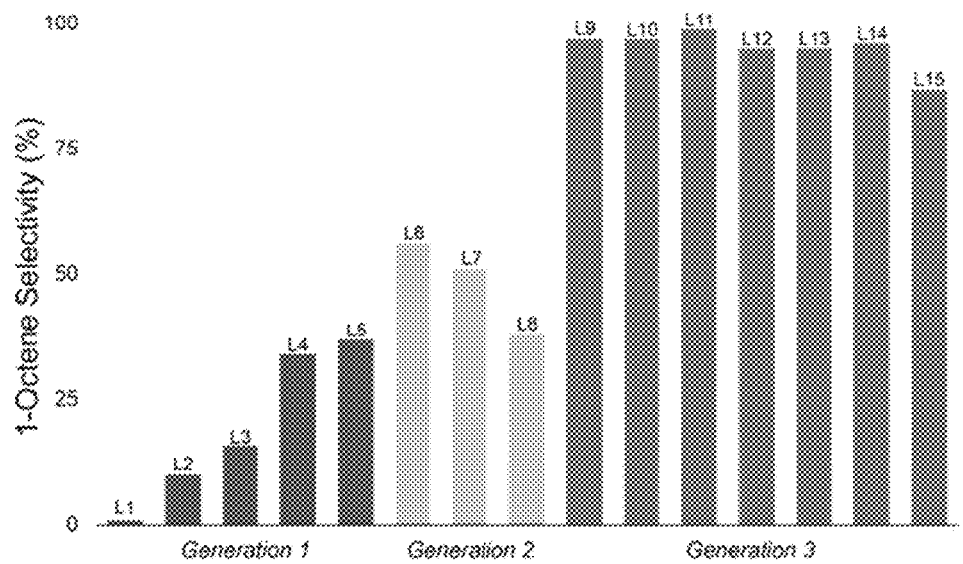
FIG. 19B plots the 1-octene selectivity for previous heteroatomic ligand-chromium compound complexes having phosphine and imine ligand coordination, "Cr(P,N) ligand generations and new generation heteroatomic ligands developed in this disclosure.

With the emergence of chemical features by the random forest machine learning model, the next and final step of the workflow involved using this information to virtually identify new heteroatomic ligands for the heteroatomic ligand-chromium compound complex (FIG. 13C). Based on the important features identified, heteroatomic ligands L9-L15 shown in FIG. 19A were designed. Thus, FIG. 19A illustrates structures for previous (P,N) heteroatomic ligand generations (generation 1 and generation 2) and the newly designed heteroatomic ligands (generation 3) based on machine-learning identified features. The 1-hexene:1-octene selectivity (predicted) is given below each structure. The machine learning features indicated that a change to the 4-membered (P,N) heteroatomic ligand scaffold found in generations 1 (L1-L5) and 2 (L6-L8) to a 3-membered (P,N) heteroatomic ligand scaffold, which the machine learning features indicated could potentially alter the Cr—N distance, Cr-α distance, and Cr distance out of ligand pocket. The description of the scaffold as 4-, 3-, or 2-membered is used for convenience to refer to the number of ligand atoms included in the ring formed with the chromium atom in the complex. This machine-learning driven modification led to the proposal of ligands L9-L11 having a 3-membered (P,N) heteroatomic ligand scaffold and with the described transition-state model they are predicted to be 97-99% 1-octene selective. With the very rapid success of this new generation 3 type of (P,N) heteroatomic ligand scaffold the ligand was further decreased to a 2-membered (P,N) ligand scaffold to have direct phosphine-nitrogen connection, which led to the proposal of ligands L12-L14. Based on using the transition-state model, heteroatomic ligands L12-L14 have predicted selectivities of >95% for 1-octene. As demonstrated at FIG. 19B, the use of the transition-state model combined with translation of machine learning features to new heteroatomic ligands resulted in increasing the prediction of 1-octene from between <35% for generation 1 and ~50% for generation 2 to >95% for generation 3.

With the success of designing ligands L9-L15, there are a number of new candidates available for experimental testing, and several more heteroatomic ligands can now be virtually and rapidly designed. As one experimental confirmation of these results, subsequent to the design of ligands L9-L15, a literature search of all reported Cr-phosphine heteroatomic ligand-chromium compound complexes for ethylene oligomerization revealed that ligand L12 is indeed highly 1-octene selective (see Yang, Y.; Liu, Z.; Liu, B.; Duchateau, R.; ACS Catal. 2013, 3 (10), 2353-2361).

To summarize these aspects of the disclosure for Cr(P,N) heteroatomic ligand-chromium compound complex catalyzed ethylene oligomerization, the combination of the experimentally verified DFT-transition-state model with a random forest machine learning model in a workflow involved the calculation of transition-state 1-hexene:1-octene selectivity for 105 heteroatomic ligands and the harvesting of 14 descriptors, which were then used to build a random forest regression model with a low RMSE. This model revealed that Cr—N distance, Cr-α distance, and Cr distance out of pocket were key features for enhancing 1-octene selectivity, which then allowed the rapid design of several generation third Cr(P,N) heteroatomic ligands that are predicted to give >95% selectivity for 1-octene. Therefore, the utility of combining an accurate quantum-mechanical transition state model with machine learning has been shown to advance molecular catalyst design in a novel and non-obvious manner.

In another aspect, similar machine learning methodology in combination with computational chemistry described herein (e.g., density functional theory calculations) can also be utilized to design heteroatomic ligands of the heteroatomic ligand-metal compound complex (e.g., heteroatomic ligand-chromium compound complex) which lead to improved activity/productivity (1-hexene, 1-octene, or total 1-hexene+1-octene activity/productivity). In yet another aspect, similar machine learning methodology in combination with computational chemistry (e.g., density functional theory calculations) described herein can be also be utilized to design heteroatomic ligands of the heteroatomic ligand-metal compound complex (e.g., heteroatomic ligand-chromium compound complex) which lead to improved product purity (e.g., 1-hexene purity).

The present disclosure is further illustrated by the following examples, which are not to be construed in any way as imposing limitations upon the scope thereof. O" the contrary, it is to be clearly understood that resort can be had to various other aspects, embodiments, modifications, and equivalents thereof which, after reading the description herein, may suggest themselves to one of ordinary skill in the art without departing from the spirit of the present invention or the scope of the appended claims.

In the following examples, unless otherwise specified, the syntheses and preparations described therein were carried out under an inert atmosphere such as nitrogen and/or argon. Solvents were purchased from commercial sources and were typically dried prior to use. Unless otherwise specified, reagents were obtained from commercial sources.

Examples

The following example utilizes Gibbs free energies for many of its calculation. One can appreciate that enthalpies and/or Helmholtz energies can also be utilized as an approximation for the Gibbs free energies.

I. Heteroatomic Ligand-Metal Compound Complex Productivity Determination

Electronic structure calculations are carried out in software, such as Gaussian 09 (Frisch, M. J. et al. Gaussian 09™, Revision B.01, Gaussian, Inc.; Wallingford, Conn., USA 2009). Molecular electronic structure theory calculations within the Born-Oppenheimer approximation are carried out using a density-functional theory (DFT) method combined with a basis set to treat electrons and continuum solvent model to include bulk solvent effects. In a typical case for geometry optimizations, the unrestricted formalism of the Minnesota 06 local functional (UM06L) is used with the 6-31G(d,p) basis set for all non-metal atoms and LANL2DZ pseudopotential and basis set for metal atoms. Functionals that are accurate for spin states, transition metals, and dispersion effects can be used. While any continuum solvent model can in principle be used, a typical calculation uses the SMD implicit solvation model for cyclohexane (as implemented in Marenich, A. V.; Cramer, C. J.; Truhlar, D. G., J Phys. Chem. B. 2009, 113, 6378-6396), which provides an estimate of the Gibbs free energy of solvation for each calculated structure. Therefore, the effect of increasing or decreasing the polarity of the solvent can be readily evaluated, as the software includes parameters for over 100 solvents that can be utilized, other solvents can be utilized by specifying experimental data for the solvent such as dielectric constant.

Generally, for a specific heteroatomic ligand-metal complex (or heteroatomic ligand and metal compound combination), a specific reaction mechanism including the oxidation state and the spin state, for each ground-state structure, which can be a resting-state structure, and each transition-state structure is optimized with the methodology and process described herein, and can be denoted by UM06L/6-31 g(d,p)[LANL2DZ] (small). The optimization provides the electronic energy of each structure at the specified charge and spin state (E) can be compared to any other structure with the same atomic composition. E is often called the self-consistent field electronic energy, which contains the electron kinetic energies, electron-nuclear potential energies, and nuclear repulsion energy. For each ground state and each transition state, a collection of local minima structures is optimized, which comprises a ground-state ensemble or a transition-state ensemble. Typically, each structure in the collection represents a unique conformation or stereoisomer. Each optimized structure is confirmed to be a minimum or a transition-state saddle point on the reaction coordinate by calculation of vibrational frequencies. Ground states have zero negative vibrational frequencies while transition-state structures have one negative vibrational frequency that corresponds to the reaction coordinate.

The vibrational frequency calculation provides estimated thermochemical values, such as, zero point energy ($E_{ZPE(small)}$), vibrational, rotational, and translation energies ($vib_{(small)}$, $U_{rot(small)}$, and $U_{trans(small)}$, respectively), and vibrational, rotational and translation entropies ($Svib_{(small)}$, $S_{rot(small)}$, and $\Delta S_{trans(small)}$, respectively).

In addition to a geometry optimization and vibrational frequency calculation, the geometry optimized with the small basis set is used to perform a large basis set electronic energy evaluation ($E_{(large)}$), and if needed, a solvation Gibbs free energy calculation ($\Delta G_{solv(large)}$) evaluation. In the current formulation, the Def2-TZVP basis set can be used, which can be referred to as UM06L/Def2-TZVP (large).

Typically, the final Gibbs energies for each ground state and transition state used for analysis of catalyst turnover rates or frequencies (TOFs) use UM06L/Def2-TZVP// UM06L/6-31g(d,p)[LANL2DZ]. The final Gibbs energies of each ground state and transition state utilized comprises:

$E_{(large)} + E_{ZPE(small)} + U_{vib(small)} + U_{rot(small)} + U_{trans(small)} + nRT - TS_{vib(small)} - TS_{rot(small)} - T S_{trans(small)} + \Delta G_{solv(large)}$ where R is the ideal gas constant and T is the temperature (e.g. 298 K or any other catalytic temperature).

For a specific heteroatomic ligand-metal compound complex (or heteroatomic ligand and metal compound combination), a specific reaction mechanism including the oxidation state and the spin state, the Gibbs free energies of all ground states and transition structures leading from substrates to products (called an energy surface), are calculated either using the lowest-energy conformation/stereoisomer or a Boltzmann-weighted average energy, and are combined to analyze the energy span that limits the rate of catalysis or TOF. This analysis can be done for a single adiabatic spin-state surface; that is, connection of all reactants to products through intermediates and transition states with the same spin state or can be done by allowing, if necessary, the crossing of spin states through spin crossover or spin intersystem crossing. Spin crossover is treated by optimizing geometries, similar to energy minima and transition-state structures, so-called minimum energy crossing points where there is a seam with a structure that has an identical structure and energy at two spin states. For a Gibbs free energy surface, or an approximate enthalpy surface or Helmholtz energies, energies of all ground states and transition states are input into an energy-span model (e.g. Kozuch, S.; Shaik, S. *Acc. Chem. Res.* 2011, 44, 101-110; AUTOF (Excel version) downloaded from: http://www.bsu.ac.il/~kozuch/software.html). The output of an energy-span model is an estimate of the catalytic TOF as well as an estimate of the contribution of each ground state and transition state to the total TOF. This is often called the degree of rate control ($c_{TOF}$).

In the energy-span model referenced herein, the TOF is estimated by eq 1 and includes the Boltzmann constant, $k_b$, temperature, T, Planck's constant, h, gas constant, R, number of steps in the catalytic cycle, N, Gibbs free energy of the overall catalytic reaction, $\Delta G_r$, Gibbs free energy of the transition state, $T_i$, Gibbs free energy of the intermediate, $I_j$, and $\delta G_{ij}'$, which is described by eq 2. Equations eq 3 and eq 4 provide the degree of rate control of the TOF for each intermediate $I_j$ (eq 3) and each transition state $T_i$ (eq 4). The sum of $\chi_{TOF,I_K}$ values is 1 and the sum of all $\chi_{TOF,T_K}$ values is 1.

$$TOF = \frac{k_b T}{h} \frac{e^{\frac{-\Delta G_r}{RT}} - 1}{\sum_{i=1,j=1}^{N} e^{(T_i - I_j - \delta G_{ij}')/RT}} \quad (1)$$

$$\delta G_{ij}' = \begin{cases} \Delta G_r & \text{if } T_i \text{ follows } I_j \quad (a) \\ 0 & \text{if } T_i \text{ precedes } I_j \quad (b) \end{cases} \quad (2)$$

$$\chi_{TOF,J_K} = \frac{\sum_i e^{(T_i - I_k - \delta G_{ik}')/RT}}{\sum_{ij} e^{(T_i - I_j - \delta G_{ij}')/RT}} \quad (3)$$

$$\chi_{TOF,T_K} = \frac{\sum_j e^{(T_k - I_j - \delta G_{kj}')/RT}}{\sum_{ij} e^{(T_i - I_j - \delta G_{ij}')/RT}} \quad (4)$$

II. Heteroatomic Ligand-Metal Compound $C_6/C_8$ Ratio Determination

Development of accurate density-functional theory (DFT), solvation methods, and quantum mechanical tools have emerged that can enable prediction of products from heteroatomic ligand-metal compound complexes (e.g., heteroatomic ligand-chromium compound complexes). One area of interest is to be able to predict the relative amounts of hexenes and/or octenes produced by an ethylene trimerization and/or tetramerization catalyst system. To be able to use computation methods (e.g., density functional theory calculations) to predict the relative amounts of hexenes and/or octenes produced by a particular ethylene trimerization and/or tetramerization catalyst system, a plausible mechanism capable of demonstrating hexenes and/or octenes selectivity is desired. Using computational and experimental studies of i) Britovsek, G. J. P. and McGuinness, D. S. *Chem. Eur. J.* 2016, 22, 16891-16896, ii) Britovsek, G. J. P.; McGuinness, D. S.; Tomov, A. K. *Catal. Sci. Technol.* 2016, 6, 8234-8241, iii) Hossain, M. A.; Kim, H. S.; Houk, K. N. Cheong, M. *Bull. Korean Chem. Soc.* 2014, 35, 2835-2838, iv) Gong, M.; Liu, Z.; Li, Y.; Ma, Y.; Sun, Q.; Zhang, J.; Liu, B. *Organometallics* 2016, 35, 972-981, v) Yang, Y.; Liu, Z.; Cheng, R.; He, X.; Liu, B. *Organometallics* 2014, 33, 2599-2607, vi) Qi, Y.; Zhong, L.; Liu, Z.; Qiu, P.; Cheng, R.; He, X.; Vanderbilt, J.; Liu, B. *Organometallics* 2010, 29, 1588-1602, vii) Budzelaar, P. H. M. *Can. J. Chem.* 2009, 87, 832-837, viii) Bhaduri, S.; Mukhopadhyay, S.; Kulkarni, S. A. *J. Organomet. Chem.* 2009, 694, 1297-1307, and ix) van Rensburg, W. J.; Grove, C.; Steynberg, J. P.; Stark, K. B.; Huyser, J. J.; Steynberg, P. J. *Organometallics* 2004, 23, 1207-1222, and experimental studies of Bartlett, S. A.; Moulin, J.; Tromp, M.; Reid, G.; Dent, A. J.; Cibin, G.; McGuinness, D. S.; Evans, J. *ACS Catal.* 2014, 4, 4201-4204, and without being limited by theory, FIG. 5A was developed as a plausible catalytic mechanism for ethylene trimerization and/or tetramerization.

In FIG. 5A, heteroatomic ligand-chromium compound complex activation in the presence of ethylene can generate a low-valent Cr ethylene coordination ground GS-II. Oxidative C—C bond coupling of the two ethylene units can form chromacyclopentane ground state GS-III which can then coordinate with another ethylene to form the chromacyclopentane ethylene coordination ground state GS-IV followed by migratory ethylene insertion which can lead to the chromacycloheptane ground state GS-VI. Ground state GS-VI represents the common intermediate in the mechanistic paths where the mechanisms for producing hexenes and octenes can diverge. Hexenes can be produced from the chromacycloheptane ground state GS-VI by β-hydrogen transfer via transition state TS-III to form 1-hexene and a reduced Cr species which can then reform, in the presence of ethylene, the low-valent Cr ethylene coordination ground state GS-II. Octenes can be produced from the chromacycloheptane ground state GS-VI by i) ethylene coordination to form the ethylene coordinated ground state GS-V, ii)

migratory insertion of ethylene through transition state TS-IV to form the chromacyclononane ground state GS-VII, and iii) β-hydrogen transfer within chromacyclononane ground state GS-VII to produce 1-octene and a reduced Cr species which can then reform, in the presence of ethylene, the low-valent Cr ethylene coordination ground state GS-II. This two-transition state model assumes dynamic equilibrium, often known as Curtin-Hammett conditions, where transition states TS-III and TS-IV arise from the common chromacycloheptane ground state GS-VI and a fast equilibrium of possible intermediates leading up to transition states TS-III and TS-IV. Via this mechanism selectivity can result from competitive β-hydrogen transfer of transition state TS-III and the migratory ethylene insertion from ground state GS-VI through transition state TS-IV. See also FIG. 3 and FIG. 4 for ground state and transition state designations.

Without being limited by theory, the mechanism in FIG. 5A was then applied to allow for prediction of the relative amounts of hexenes and/or octenes for previously unknown heteroatomic ligand-chromium compound complexes I. In this predictive method, Density Functional Theory calculations were applied to experimentally evaluated $N^2$-phosphinyl amidine chromium salt complexes to provide a correlation between the Density Functional Theory calculations and the experimentally observed amounts of hexenes and/or octenes. The correlation was then used to predict the amounts of hexenes and/or octenes produced by previously unknown heteroatomic ligand-chromium compound complexes.

Figure 20:
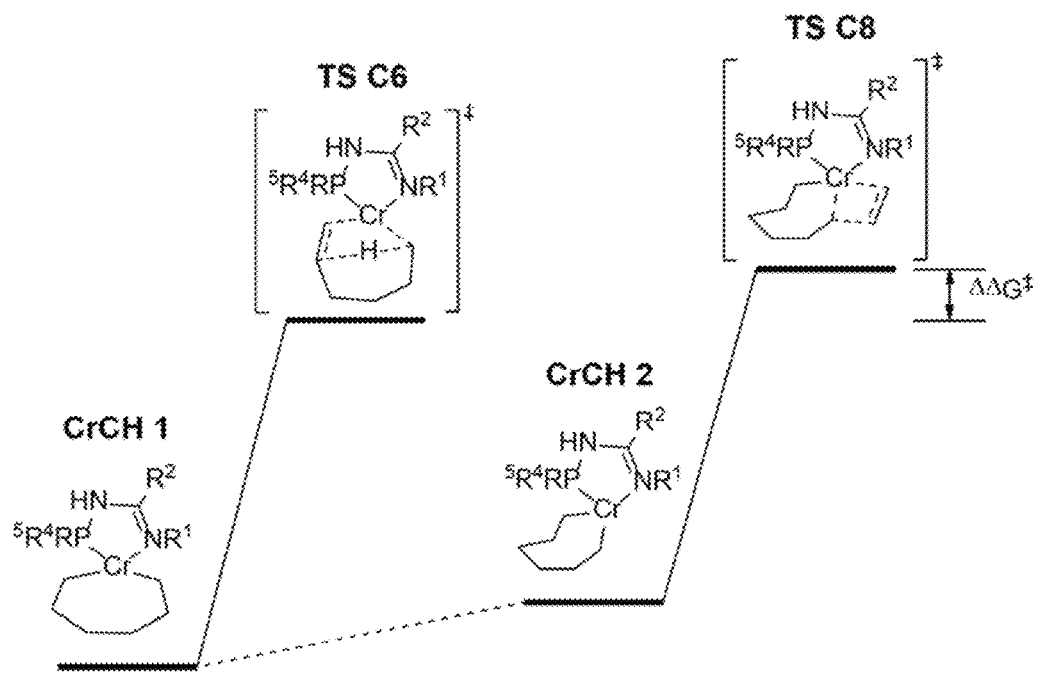
FIG. 20 depicts the competing and selectivity determining reaction coordinate pathways for producing hexenes and octenes including the general $N^2$-phosphinyl amidine chromacycloheptane complexes CrCH 1 and CrCH 2, and the general $N^2$-phosphinyl amidine chromium salt complex hexene transition state TS C6, and the general $N^2$-phosphinyl amidine chromium salt complex octene transition state TS C8.

Without wishing to be limited by theory, FIG. 20 illustrates the competing and selectivity determining reaction coordinate pathways for producing hexenes and octenes including the general $N^2$-phosphinyl amidine chromium chromacycloheptane ground state CrCH 1, the general $N^2$-phosphinyl amidine chromium chromacycloheptane ground state CrCH 2, the general $N^2$-phosphinyl amidine chromium salt complex hexene transition state TS C6, and the general $N^2$-phosphinyl amidine chromium salt complex octene transition state TS C8. Thus, for catalyst systems based upon general $N^2$-phosphinyl amidine chromium salt complexes, the Gibbs free energy difference, $\Delta\Delta G\ddagger$, between: 1) the difference in the Gibbs free energy of the general $N^2$-phosphinyl amidine chromium chromacycloheptane ground state CrCH 1 and the general $N^2$-phosphinyl amidine chromium salt complex hexene transition state TS C6; and 2) the difference in the Gibbs free energy of the general $N^2$-phosphinyl amidine chromium chromacycloheptane ground state CrCH 2 and the general $N^2$-phosphinyl amidine chromium salt complex octene transition state TS C8 can be utilized in a predictive correlative method to predict the relative amounts of hexenes and/or octenes produced by an $N^2$-phosphinyl amidine chromium salt complex, e.g., an $N^2$-phosphinyl amidine chromium salt complex having the structure shown in FIG. 20 wherein $R^1$, $R^2$, $R^4$, and $R^5$ are each independently defined as provided herein. Further, and without being limited by theory, since general $N^2$-phosphinyl amidine chromium chromacycloheptane ground state CrCH 1 and the general $N^2$-phosphinyl amidine chromium chromacycloheptane ground state CrCH 2 are carbon-carbon chromacycloheptane rotational isomers of each other and it is expected that there is a low energy barrier for their interconversion, the calculation of the Gibbs free energy difference, $\Delta\Delta G\ddagger$, can be simplified to the calculation of the Gibbs free energy difference between the general $N^2$-phosphinyl amidine chromium salt complex hexene transition state TS C6 and the general $N^2$-phosphinyl amidine chromium salt complex octene transition state TS C8 ($\Delta\Delta G\ddagger$, in FIG. 20). Thus, the Gibbs free energy difference $\Delta\Delta G\ddagger$ was correlated with the experimentally observed amounts of hexenes and/or octenes produced by the experimentally tested $N^2$-phosphinyl amidine chromium salt complexes.

III. Density Functional Theory Calculations for Heteroatomic Ligand-Metal Compound $C_6/C_8$ Ratio Determination Density Functional Theory calculations (specifically, unrestricted UM06L/Def2-TZVP//UM06/6-31G(d,p) (LANL2DZ) theory) combined with the SMD implicit solvent model for cyclohexane (as implemented in Marenich, A. V.; Cramer, C. J.; Truhlar, D. G., *J. Phys. Chem. B.* 2009, 113, 6378-6396) was used to calculate the Gibbs free energy of the cationic $N^2$-phosphinyl amidine chromium salt complex hexene transition state TS C6 (hereafter $N^2$-phosphinyl amidine chromium salt complex hexene transition state TS C6) and the cationic $N^2$-phosphinyl amidine chromium salt complex octene transition state TS C8 (hereafter $N^2$-phosphinyl amidine chromium salt complex octene transition state TS C8), for each $N^2$-phosphinyl amidine chromium salt complex. The Gibbs free energy difference between the $N^2$-phosphinyl amidine chromium salt complex hexene transition state TS C6 and the $N^2$-phosphinyl amidine chromium salt complex octene transition state TS C8, $\Delta\Delta G\ddagger$, for each $N^2$-phosphinyl amidine chromium salt complex was then calculated. The calculations of the Gibbs free energy of the cationic $N^2$-phosphinyl amidine chromium salt complex hexene transition state TS C6 (and other transition state energies used herein) and the cationic $N^2$-phosphinyl amidine chromium salt complex octene transition state TS C8 (and other transition state energies used herein) were performed without considering the impact of the balancing anion.

The density functional theory calculations were carried out using Gaussian 09 (Frisch, M. J. et al. *Gaussian 09*™, *Revision B*.01, Gaussian, Inc.: Wallingford, CT, USA, 2009). Geometries to account for each degree of freedom and each spin state for the $N^2$-phosphinyl amidine chromium salt complex hexene transition state TS C6 (3 to 40 conformations depending on the exact ligand) and the $N^2$-phosphinyl amidine chromium salt complex octene transition state TS C8 (3 to 40 conformations depending on the exact ligand) for each $N^2$-phosphinyl amidine chromium salt complex were calculated using the pseudopotential LANL2DZ basis set for chromium (integrated into the *Gaussian 09* ™, *Revision B*.01) and the unrestricted approximation of local Minnesota 06 density functional theory 6-31G(d,p) basis set (i.e., UM06/6-31G(d,p) basis set) for all other atoms in the $N^2$-phosphinyl amidine chromium salt transition states. The transition-state structures with a complete set of force constants were calculated to ensure a single negative vibrational frequency that corresponded to the reaction coordinate. Additionally, the ground-state structure vibrational frequencies were calculated to correspond to the second-order energy derivatives (i.e., force constants) and were analyzed to confirm a local minimum energy structure. Additionally, zero point energies ($\Delta E_{ZPE(small)}$), vibrational, rotational, and translational energies ($\Delta U_{vib(small)}$, $\Delta U_{rot(small)}$, $\Delta U_{trans(small)}$, respectively), and vibrational, rotational, and translational entropies ($\Delta S_{vib(small)}$, $\Delta S_{rot(small)}$, $\Delta S_{trans(small)}$, respectively) were obtained to use in the calculation of the Gibbs free energy for the $N^2$-phosphinyl amidine chromium salt complex hexene transition state TS C6 and the $N^2$-phosphinyl amidine chromium salt complex octene transition state TS C8.

The solvated geometries for the $N^2$-phosphinyl amidine chromium salt complex hexene transition state TS C6 conformation having the lowest energy and the $N^2$-phosphinyl amidine chromium salt complex octene transition state TS C8 conformation having the lowest energy, along with any conformations having an energy relatively close to the $N^2$-phosphinyl amidine chromium salt complex hexene transition state TS C6 conformation having the lowest energy and the $N^2$-phosphinyl amidine chromium salt complex octene transition state TS C8 conformation having the lowest energy, were calculated using a continuum model (SMD) that was parametrized and implemented in Gaussian 09 for cyclohexane. The transition-state structures with a complete set of force constants were calculated to ensure a single negative vibrational frequency that corresponded to the reaction coordinate. Additionally, the ground-state structure vibrational frequencies were calculated to correspond to the second-order energy derivatives (i.e., force constants) and were analyzed to confirm a local minimum energy structure.

The total self-consistent field electronic energy containing the electron kinetic and potential energies, and nuclear repulsion energy ($E_{(large)}$) and the standard state solvation free energy change ($\Delta G_{solv(large)}$) for the $N^2$-phosphinyl amidine chromium salt complex hexene transition state TS C6 and the $N^2$-phosphinyl amidine chromium salt complex octene transition state TS C8 were then calculated using the unrestricted approximation of local Minnesota 06 density functional theory Def2-TZVP basis set UM06L/Def2-TZVP (downloaded from https://bse.pnl.gov/bse/portal on Jan. 1, 2016) to provide accurate spin state energies and accurate calculations for weak dispersion forces. Large=M06L/def2-TZVP. Small=M06L/6-31G(d,p)[LANL2DZ for Cr. 3-D structures were generated using CYLview.

The Gibbs free energy of the cationic $N^2$-phosphinyl amidine chromium salt complex hexene transition state TS C6 and the cationic $N^2$-phosphinyl amidine chromium salt complex octene transition state TS C8 were then calculated the $N^2$-phosphinyl amidine chromium salt complex hexene transition state TS C6 and the $N^2$-phosphinyl amidine chromium salt complex octene transition state TS C8 for each $N^2$-phosphinyl amidine chromium salt complex was then calculated as the Gibbs free energy of the $N^2$-phosphinyl amidine chromium salt complex hexene transition state TS C6 minus the Gibbs free energy of the $N^2$-phosphinyl amidine chromium salt complex octene transition state TS C8.

IV. Ethylene Oligomerization Conditions for Heteroatomic Ligand Chromium Compound Complexes 1a-8a Table 4 summarizes some of the experimental ethylene oligomerization conditions for the heteroatomic ligand-chromium compound complexes using ligands 1a-8a. The high pressure NMR kinetic studies reported by Sydora and Abu-Omar and were performed at 50 bar of ethylene, room temperature, 5 µmol of Cr catalyst, cyclohexane solvent, and 600 eq of MMAO-3A (Gunasekara, T.; Kim, J.; Preston, A.; Steelman, D. K.; Medvedev, G. A.; Delgass, W. N.; Sydora, O. L.; Caruthers, J. M.; Abu-Omar, M. M. ACS Catal. 2018, 8, 6810-6819). See Table 4 and these references for more details of 1a (Sydora, O. L.; Jones, T. C.; Small, B. L.; Nett, A. J.; Fischer, A. A.; Carney, M. J. ACS Catal. 2012, 2, 2452-2455), 2 (Radcliffe, J. E.; Batsanov, A. S.; Smith, D. M.; Scott, J. A.; Dyer, P. W.; Hanton, M. J. ACS Catal. 2015, 5, 7095-7098), 3 (McGuinness, D. S.; Wasserscheid, P.; Morgan, D. H.; Dixon, J. T. Organometallics 2005, 24, 552-556), 4 (McGuinness, D. S.; Wasserscheid, P.; Morgan, D. H.; Dixon, J. T. Organometallics 2005, 24, 552-556), 5 (Temple, C. N.; Gambarotta, S.; Korobkov, I.; Duchateau, R. Organometallics 2007, 26, 4598-4603), 6 (Zhang, J.; Braunstein, P.; Hor, T. S. A. Organometallics 2008, 27, 4277-4279), 7 (Bluhm, M. E.; Walter, O.; Döring, M. J. Organomet. Chem. 2005, 690, 713-721),[9] and 8a (Sydora, O. L.; Jones, T. C.; Small, B. L.; Nett, A. J.; Fischer, A. A.; Carney, M. J. ACS Catal. 2012, 2, 2452-2455).

TABLE 4

Summary of experimental reaction conditions for ethylene trimerization Cr catalysts examined in this computational study.

| Complex | Ethylene pressure (bar) | Catalyst (µmol) | Co-catalyst (equivalents) | Solvent | T (° C.) | Productivity (g/g Cr · h) | $C_6$ [1-$C_6$] (% mass) | Polyethylene (mass %) |
|---|---|---|---|---|---|---|---|---|
| 1a | 60 | 10 | MMAO-3A (400-800) | cyclohexane | 70 | 1,054,000 | 94 [>99] | Trace |
| 1a[a] | 50 | 5 | MMAO-3A (600) | cyclohexane | 25 | — | — | — |
| 2 | 40 | 1.3 | MMAO-3A (500) | methyl-cyclohexane | 60 | 672,000 | 94 [>99] | 6.5 |
| 3 | 40 | 11 | MAO (600) | toluene | 80 | 42,000 | 94 [>99] | 0.1 |
| 4 | 40 | 11.3 | MAO (660) | toluene | 120 | 27,000 | 93 [>99] | 0.2 |
| 5 | 35 | 30 | MAO (1000) | toluene | 50 | 5,200 | 99 [—] | 1.8 |
| 6 | 25 | 20 | MAO (200) | toluene | 80 | 2,800 | 96 [99] | <0.1 |
| 7 | 30 | 10 | MAO (100) | toluene | 24 | 470 | 98 [99] | 2 |
| 8a | 60 | 10 | MMAO-3A (400-800) | cyclohexane | 55 | 0 | trace | 100 |

Figure 21A:
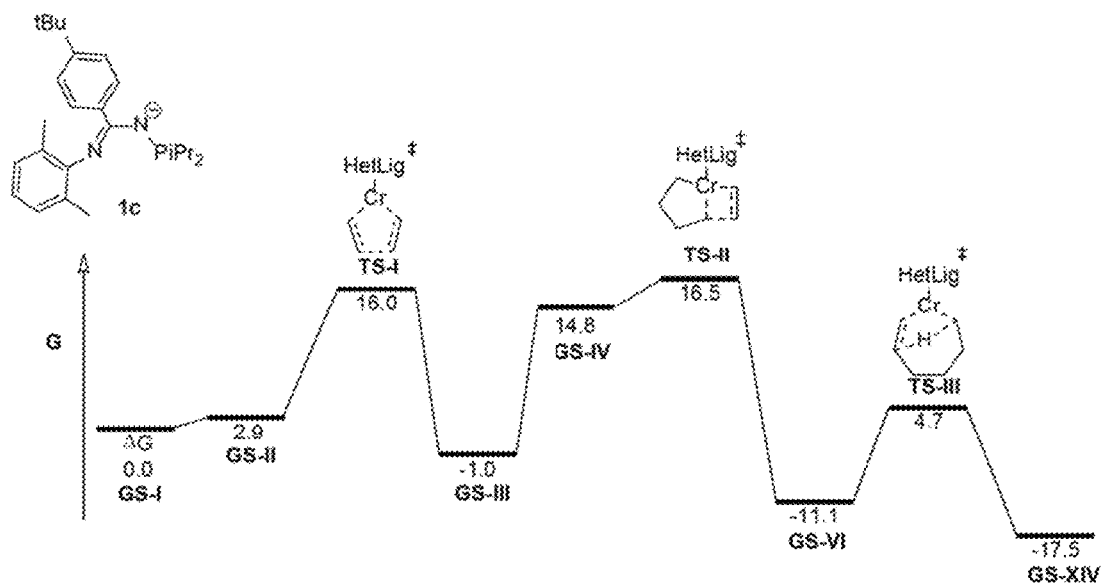
FIG. 21A illustrates the Gibbs free energy landscape of deprotonated N—H $N^2$-phosphinyl amidine ligand and an overall neutral Cr catalyst complex with a $Cr^{I/III}$ cycle, with energies shown in kcal/mol. Ground state GS-I and GS-II have a sextet spin state as the lower energy and all other ground states and transition states have a quartet spin state as the lowest energyGround states GS-I and GS-II have a sextet spin state as the lowest energy and all other ground states and transition state have a quartet spin state as the lowest energy.
Figure 21B:
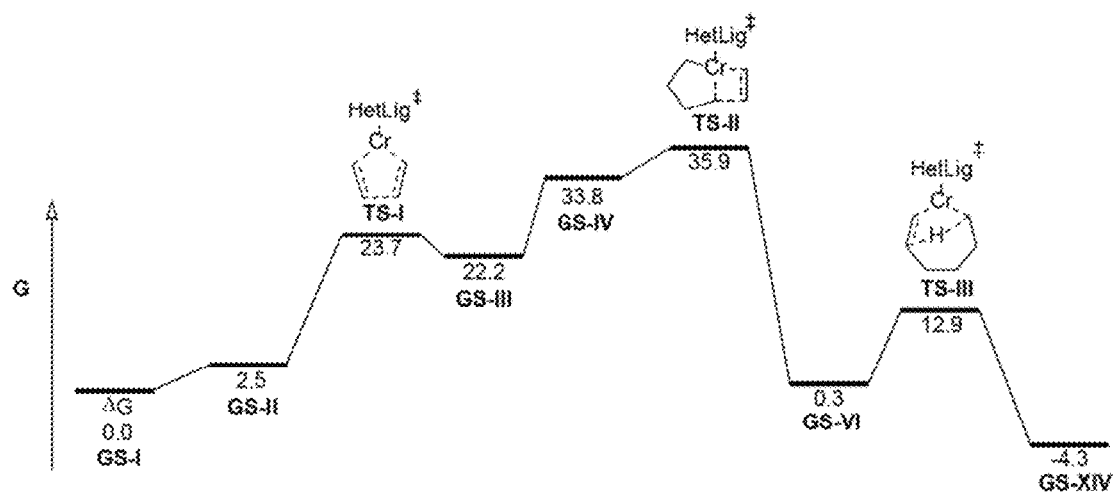
FIG. 21B shows the Gibbs free energy landscape of deprotonated N—H $N^2$-phosphinyl amidine ligand and overall cationic Cr complex with a $Cr^{II/IV}$ cycle, with energies shown in kcal/mol. Ground states GS-I and GS-II have a quintet spin state as the lowest energy and all other ground states have a triplet spin state as the lowest energy.

[a]Reaction conditions for high pressure NMR kinetic experiments with 1a.

using the equation $E_{(large)} + \Delta E_{ZPE(small)} + \Delta U_{vib(small)} + \Delta U_{rot(small)} + \Delta U_{trans(small)} + nRT - T\Delta S_{vib(small)} - T\Delta S_{rot(small)} - T\Delta S_{trans(small)} + \Delta G_{solv(large)}$ where R is the ideal gas constant and T is the temperature (298 K was used for these calculations). The Gibbs free energy difference, $\Delta\Delta G\ddagger$, between V. Reactivity Analysis of Chromium Phosphinamidine Ethylene Trimerization Catalysts Anionic (P,N) Ligand The possibility of $N^2$-phosphinyl amidine ligand N—H deprotonation and the resulting in a heteroatomic ligand-chromium compound complex with ligand 1c was examined. An overall neutral Cr complex would mediate a $Cr^{I/III}$ catalytic cycle while a cationic system would operate by a $Cr^{II/IV}$ cycle. FIG. 21A and FIG. 21B display the Gibbs free energy surfaces for the neutral and cationic heteroatomic ligand-chromium compound complex models. The neutral $Cr^{I/III}$ system energy span is mainly controlled by transition state TS-II with a barrier of 17.5 kcal/mol relative to ground state GS-III. This energy span is <2 kcal/mol higher in energy than the energy span calculated with the protonated ligand 1a. This indicates that the heteroatomic ligand-chromium compound complex with ligand 1c, compared to the heteroatomic ligand-chromium compound complex with ligand 1a, could provide a nearly equivalent computational model to analyze activity/productivity. Additionally, it is possible that heteroatomic ligand-chromium compound complex with both ligand 1a and 1c can contribute to catalysis. With the deprotonated ligand and an overall cationic complex, the transition state TS-II barrier is >30 kcal/mol, and suggest that this would not be a viable catalyst.

FIG. 21A (energies in kcal/mol) illustrates the Gibbs free energy landscape of deprotonated N—H phosphinamidine ligand and an overall neutral heteroatomic ligand-chromium compound complex with a $Cr^{I/III}$ cycle. Ground state GS-I and GS-II have a sextet spin state as the lower energy and all other ground states and transition states have a quartet spin state as the lowest energy. FIG. 21B shows the Gibbs free energy landscape of deprotonated N—H phosphinamidine ligand and overall cationic Cr complex with a $Cr^{II/IV}$ cycle. Ground states GS-I and GS-II have a quintet spin state as the lowest energy and all other ground states have a triplet spin state as the lowest energy. See also FIG. 3 for ground state and transition state designations.

N-Dimethylaluminum Ligand (N—Al)

Figure 22:
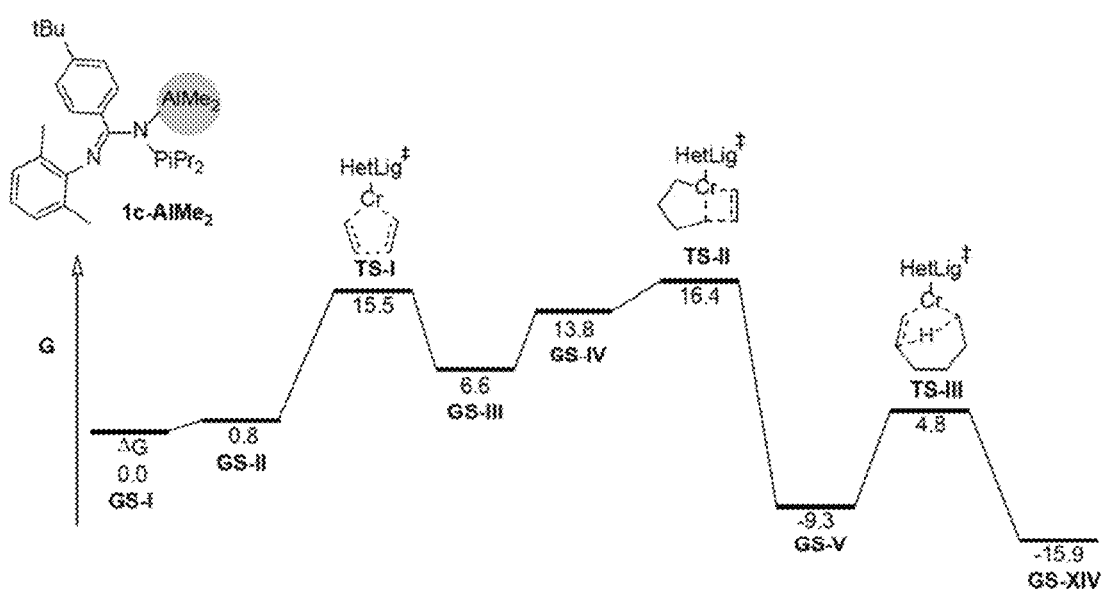
FIG. 22 illustrates the Gibbs free energy landscape of N-dimethylaluminum substituted model (kcal/mol), specifically the Gibbs free energy surface with the 1c-AlMe$_2$ catalyst, the cationic $Cr^{I/III}$ reaction channel. Ground states GS-I and GS-II have a sextet spin state as the lowest energy and all other ground states and transition state have a quartet spin state as the lowest energy.

As a possible alternative to phosphinamidine ligand N—H deprotonation, the N-dimethylaluminum ligand (shown below, 1c-AlMe$_2$) that potentially results from MMAO exchanging an aluminum group for the N—H proton was examined. FIG. 22 illustrates Gibbs free energy landscape of N-dimethylaluminum substituted model (energies in kcal/mol), specifically the Gibbs free energy surface with the heteroatomic ligand-chromium compound complex with ligand 1c-AlMe$_2$, the cationic $Cr^{I/III}$ reaction channel. Ground states GS-I and GS-II have a sextet spin state as the lowest energy and all other ground states and transition state have a quartet spin state as the lowest energy. Based on the results with the anionic ligand, the 1c-AlMe$_2$ catalytic energy surface is qualitatively and quantitatively very similar to the protonated N—H 1a landscape. Again, this indicates that heteroatomic ligand-chromium compound complex with ligand 1c-AlMe$_2$ could also provide a computational model for productivity, and may contribute to catalysis along with heteroatomic ligand-chromium compound complex with ligand 1a and 1c. See also FIG. 3 for ground state and transition state designations.

Ethylene Coordination

Figure 23:
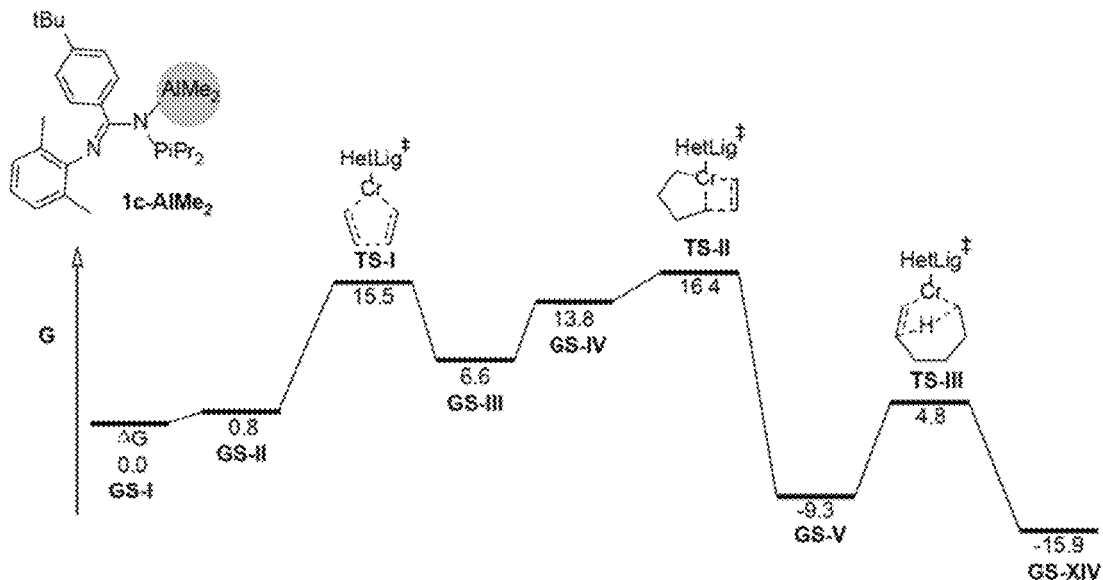
FIG. 23 illustrates the relative energies for all ethylene coordination structures and alternative mechanistic pathways involving coordinated ethylene (energies in kcal/mol).

All ethylene coordination structures were examined, starting with no ethylene coordinated to Cr, shown as 0EC in FIG. 23 (energies in kcal/mol). Thus, FIG. 23 illustrates ethylene coordination to Cr and alternative mechanistic pathways considered. In FIG. 23 the heteroatomic ligand has be omitted to simplify the structures and diagrams. Species 0EC, ground state GS-I, and ground state GS-II have a sextet spin state as the lowest energy, while all other ground states and transition states have a quartet spin state as the lowest energy. All spin states were examined, and the sextet spin (S=5/2) was the lowest in energy for ethylene coordinated complexes preceding oxidative coupling. This result is comparable to the computational data reported by McGuinness, although McGuinness proposed sextet to quartet spin crossing is favorable with 3EC and 4EC coordinated complexes (Britovsek, G. J. P.; McGuinness, D. S.; Wierenga, T. S.; Young, C. T. ACS Catal. 2015, 5, 4152-4166).

The first ethylene coordination is favorable by 20.8 kcal/mol to form ground state GS-I. The second ethylene coordination forms ground state GS-I and is only lower in energy by 0.3 kcal/mol. These calculated coordination energies are consistent with Sydora and Abu-Omar's kinetic study indicating that only one ethylene coordination is reversible (Gunasekara, T.; Kim, J.; Preston, A.; Steelman, D. K.; Medvedev, G. A.; Delgass, W. N.; Sydora, O. L.; Caruthers, J. M.; Abu-Omar, M. M. ACS Catal. 2018, 8, 6810-6819).

Oxidative coupling with additional ethylene coordination was also considered. For 3EC the calculated barrier is 32.3 kcal/mol, which suggests it is unlikely to occur compared to transition state TS-I. Despite significant searching, the transition state 2EC-TS1 could not be located. Ethylene coordinating to intermediate ground state GS-VI is endergonic by 7.2 kcal/mol. β-hydrogen transfer with an additional ethylene coordinated transition state 1EC-TS3 is 13.0 kcal/mol higher in energy than transition state TS-III.

Alternative Pathways to 1-Hexene and Alternative Products

Once the chromacycloheptane ground state GS-IV is generated, two possible pathways were considered for the formation of the 1-hexene product: β-hydrogen transfer via transition state TS-III and stepwise/hydride elimination via transition state TS-VI followed by reductive elimination via transition state TS-VII, which are illustrated in Scheme 4. Thus, Scheme 4 illustrates the alternative mechanistic pathway to 1-hexene and alternative products, with energies in kcal/mol. These calculations indicate that the β-hydrogen transfer pathway is the lower energy pathway to form the 1-hexene product. While transition state TS-VI is 3.7 kcal/mol higher than transition state TS-III, if ground state GS-VIII is reached it is unlikely to produce 1-hexene through transition state TS-VII. Instead, it will likely undergo migratory insertion tor give transition state TS-VIII to form methylenecyclopentane ground state GS-IX as the barrier is 4.4 kcal/mol lower in energy than transition state TS-VII. References of interest to this aspect of the disclosure are provided at Yang, Y.; Liu, Z.; Zhong, L.; Qiu, P.; Dong, Q.; Cheng, R.; Vanderbilt, J.; Liu, B. Organometallics 2011, 30, 5297-5302; Britovsek, G. J. P.; McGuinness, D. S. Chem. Eur. J. 2016, 22, 16891-16896.

Scheme 4

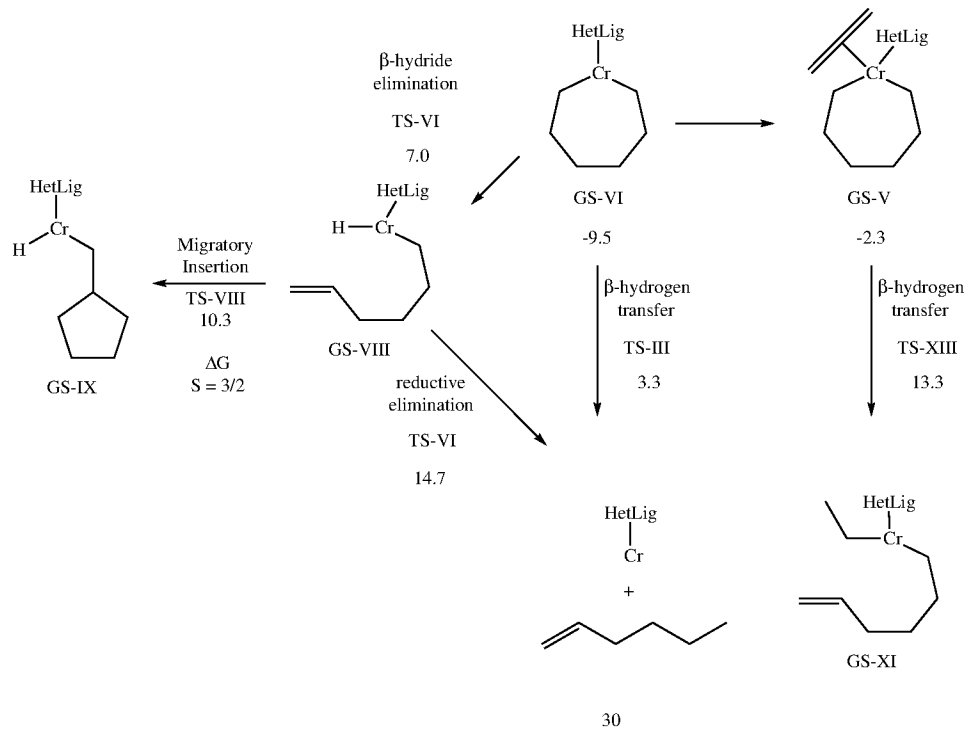

Comparison of (P,N)Cr Energy Landscapes

Figure 24:
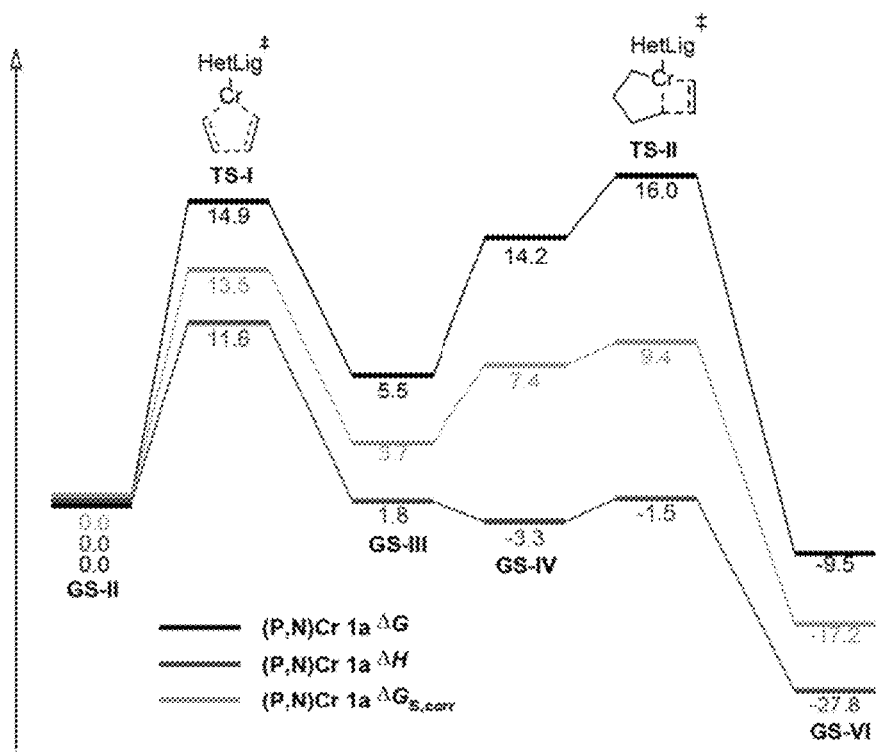
FIG. 24 compares the enthalpy, Gibbs free energy, and entropy-scaled Gibbs free energy surfaces ($\Delta G_{S,corr}$) from ground state GS-II to GX-VI involving transition states TS-I and TS-II.

FIG. 24 illustrates an abbreviated Gibbs free energy, enthalpy, and entropy-corrected Gibbs free energy surface comparisons of the heteroatomic ligand-chromium compound complex with ligand 1a performed at 1 atm and room temperature without pressure corrections (energies in kcal/mol). Ground state GS-II has a sextet spin state as the lowest energy and all other ground states and transition states have a quartet spin state as the lowest energy. Specifically, FIG. 24 compares the enthalpy, Gibbs free energy, and entropy-scaled Gibbs free energy surfaces ($\Delta G_{S,corr}$) from ground state GS-II to GS-VI involving transition states TS-I and TS-II. The major difference between these surfaces is the region surrounding transition states TS-II, which results from the gas-phase $-T\Delta S$ value that is potentially overestimated. Therefore, the use of a 0.67 scaled $\Delta S$ term that Ziegler and co-workers (Tobisch, S.; Ziegler, T. J. Am. Chem. Soc. 2004, 126, 9059-9071) demonstrated captures the entropic penalty for association and dissociation of ethylene under condensed phase catalytic conditions of Zr and Hf ethylene oligomerization reactions was examined. The middle (orange) energy surface ((P,N)Cr, 1a, $\Delta G_{S,corr}$) in FIG. 24 shows that the entropy scaling lowers the transition state TS-II barrier to 9.4 kcal/mol. The predicted turnover frequency of the entropy-scaled Gibbs free energy is 250 mol 1-$C_6 \cdot s^{-1}$ that translates to a predicted total productivity mass of 7.6×10$^7$ g·h$^{-1}$, which overestimates but is close to the experimental productivity value.

Ethylene Pressure Correction

As discussed in this disclosure, ethylene pressure corrections to the calculated Gibbs free energy surfaces of heteroatomic ligand-chromium compound complex with ligand 1a were included because the kinetic experiments were run at high pressures of ethylene (50 bars) (see Gunasekara, T.; Kim, J.; Preston, A.; Steelman, D. K.; Medvedev, G. A.; Delgass, W. N.; Sydora, O. L.; Caruthers, J. M.; Abu-Omar, M. M. ACS Catal. 2018, 8, 6810-6819).

$$\Delta_r G = \Delta_r G^0 + RT \ln \frac{P_f}{P_i}$$

Figure 25:
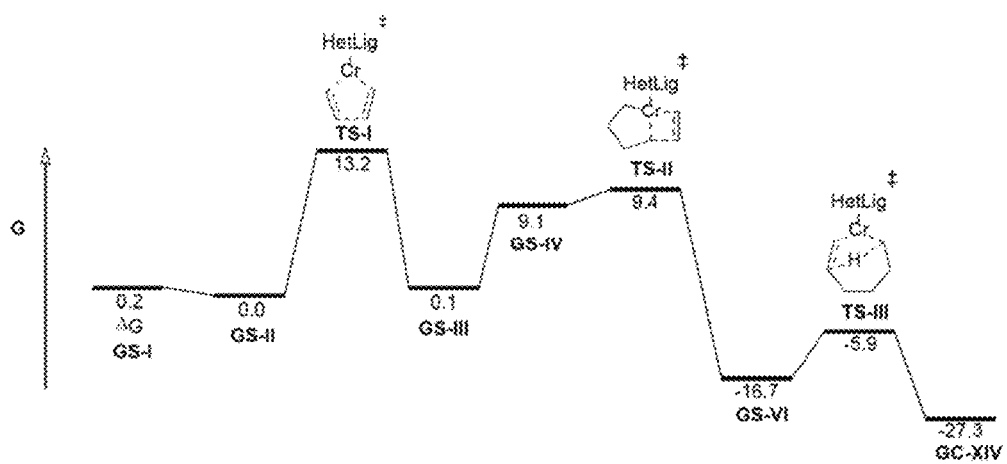
FIG. 25 illustrates the ωB97X-D Gibbs free energy surface with ethylene pressure corrections to the calculated Gibbs free energy surfaces of 1a, where kinetic experiments were run at high ethylene pressures (50 bars).

The ωB97X-D Gibbs free energy surface with ethylene pressure corrections shown in FIG. 25 was examined. In this scheme, ground states GS-I and GS-II have a sextet spin state as the lowest energy and all other ground states and transition states have a quartet spin state as the lowest energy. (See also FIG. 3 and FIG. 4 for ground state and transition state designations.) Qualitatively, the surface is very similar to M06-L ethylene pressure corrected energy span. FIG. 25 displays the ωB97X-D energy surface. The predicted turnover frequency is 1300 mol 1-$C_6 \cdot s^{-1}$ that translates to a predicted total productivity mass of 3.9×10$^8$ g·h$^{-1}$ that slightly overestimates the experimental productivity.

Ethylene Kinetic Order

Utilizing the energy span model, it is possible to express the ethylene rate dependence using ground states GS-I and GS-II as turnover controlling ground states and transition states TS-I and TS-II as turnover controlling transition states. Each ground state-transition state pair can contribute to the total turnover frequency and has a specific ethylene rate dependence. As an example, for the landscape shown in FIG. 9A, the following provides an estimate of 1.2 for the rate order of ethylene.

$K_i$=GS-I×TS-I[$C_2H_4$]

$K_{ii}$=GS-I×TS-II[$C_2H_4$]$^2$ $K_{iii}$=GS-II×TS-I $K_{iv}$=GS-II×TS-II[C$_2$H$_4$]

$k_{total}$=(0.36×0.13)[C$_2$H$_4$]+(0.36×0.87)[C$_2$H$_4$]$^2$+(0.64× 0.13)+(0.64×0.87)[C$_2$H$_4$]

Ethylene dependent term sum: (0.36×0.13)[1]+(0.36× 0.87)[2]+(0.64×0.87)[1]=1.2

Chromacyclopentane Ring Strain

The stability of the chromacyclopentane ground state GS-III was considered as a potential impact on catalytic activity. Scheme 5 illustrates the bond homolysis energies of chromacyclopentane ground states GS-III, with free energies shown in kcal/mol. Initially, it was thought that the tridentate heteroatomic ligand 8 would lead to a more strained metallacycle. However, the Cr—C bond homolysis energy from the chromacyclopentane ground state GS-III of 1a was almost identical to that with heteroatomic ligand 8a with only a 0.9 kcal/mol free energy difference. Therefore, stability of the chromacyclopentane intermediate does not affect catalyst activity.

Scheme 5

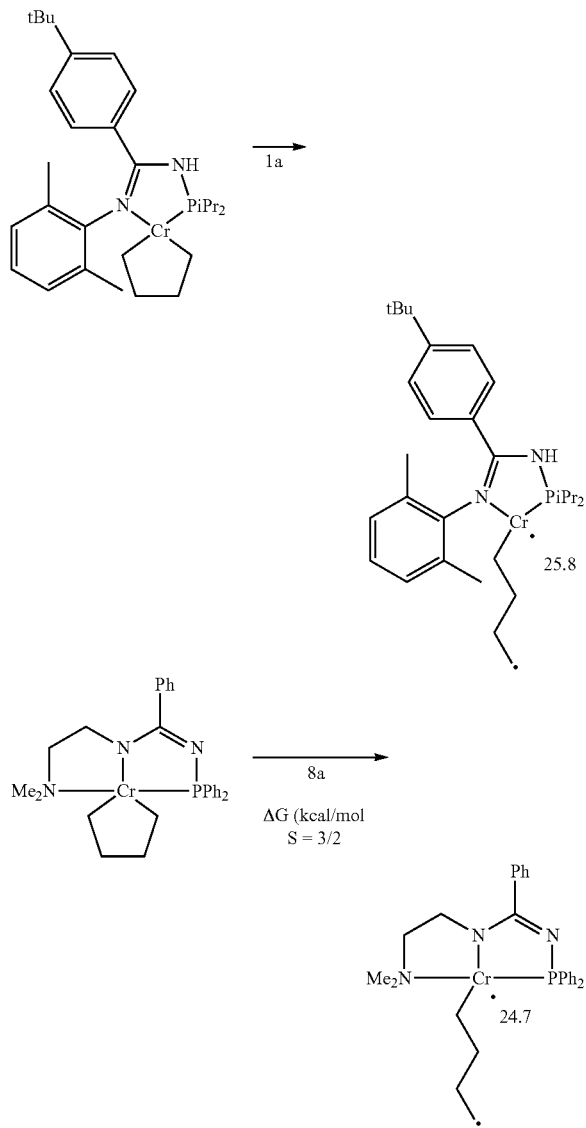

8a Amine Dissociation

To probe electronic and coordination effects that drastically slow down catalysis, heteroatomic ligand-chromium compound complex with ligand 8a with the amine arm dissociated to model a bidentate coordination environment was modeled. Scheme 6 displays the energy of amine dissociation for the mono(ethylene) coordinated ground state 8c GS-I', that is, the energy penalty to dissociate an amine arm at the mono(ethylene) intermediate.

Scheme 6

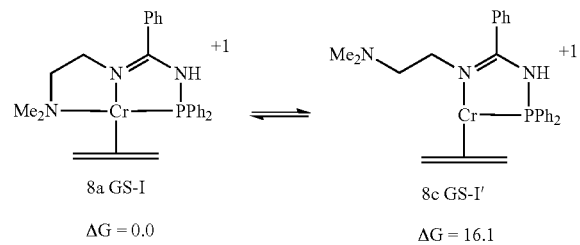

8a GS-I       8c GS-I'
ΔG = 0.0      ΔG = 16.1

Figure 26:
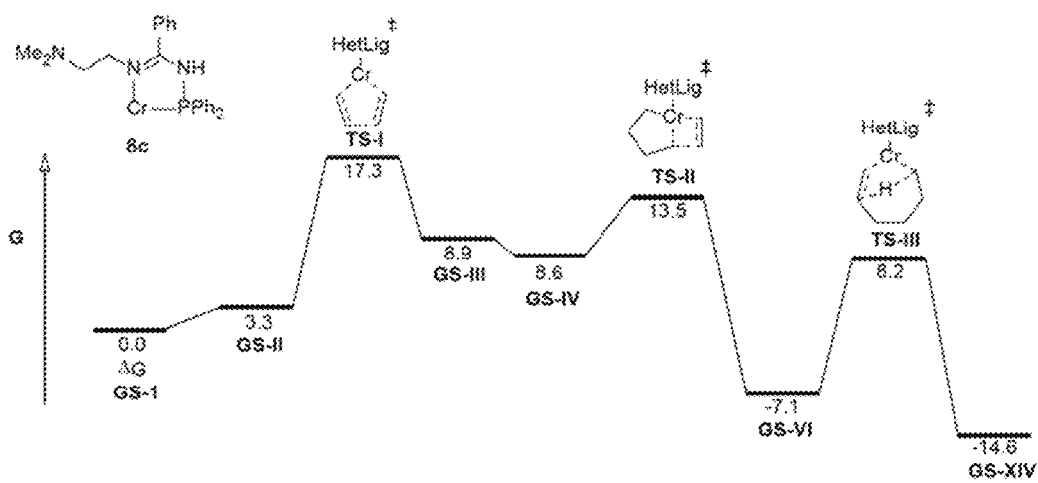
FIG. 26 illustrates the Gibbs free energy surface of dissociated amine ligand 8c (energies in kcal/mol). Ground states GS-I and GS-II have a sextet spin state as the lowest energy and all other ground states and transition states have a quartet spin state as the lowest energy.

Considering the dissociated amine arm ground state 8c GS-I' as the starting point of catalysis, a new Gibbs free energy surface was constructed displayed in FIG. 26. Thus, FIG. 26 illustrates the Gibbs free energy surface of dissociated amine ligand 8c, with energies shown in kcal/mol. (See also FIG. 3 and FIG. 4 for ground state and transition state designations.) Ground states GS-I and GS-II have a sextet spin state as the lowest energy and all other ground states and transition states have a quartet spin state as the lowest energy. This energy span quantitatively mirrors the bidentate nature of heteroatomic ligand 1a and demonstrates the extra coordination at the Cr metal and the augmented electron density through the tridentate framework shuts down catalysis. The predicted TOF is 1.3 mol 1-C$_6$·s$^{-1}$, which translates to a productivity of 3.9×10$^5$ g·h$^{-1}$.

Spin Crossover

Figure 27:
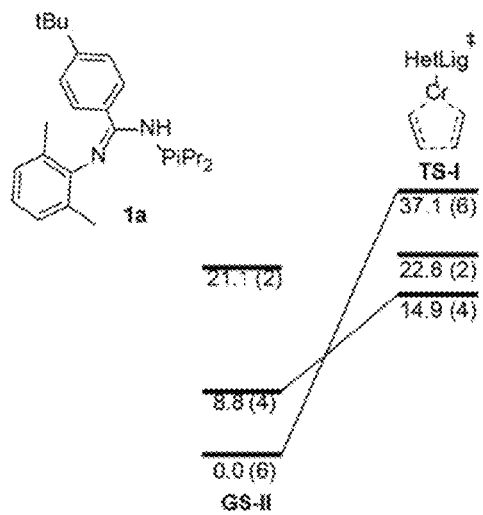
FIG. 27 illustrates spin crossover which is shown to provide lower energy pathways from bis(ethylene) coordinated Cr ground state GS-II (lowest energy sextet spin state) to transition state TS-I, where spin states are shown in parentheses (energies in kcal/mol).

Bis(ethylene) coordinated Cr ground state GS-II is lowest in energy as a sextet spin state. The doublet and quartet spin states are >8 kcal/mol compared to the sextet. Oxidative coupling favors the quartet spin state while the doublet and sextet spin configurations are >8 kcal/mol relative to the quartet spin. Spin crossover facilitates catalysis by accessing lower energy intermediates and transition state barriers. FIG. 27 illustrates that spin crossover provides lower energy pathways, where spin states are shown in parentheses, and energies are reported in kcal/mol.

Modified Heteroatomic Ligands 1a and 8a

Figure 28A:
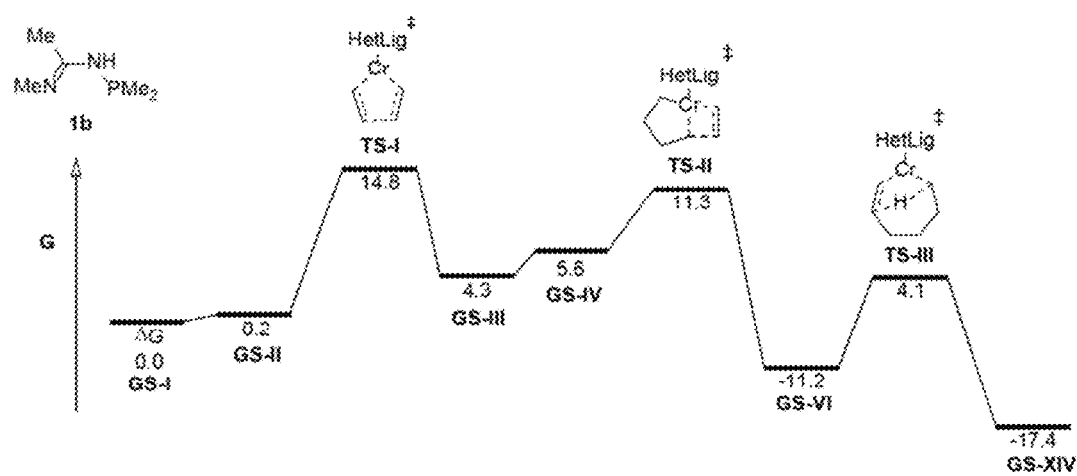
FIG. 28A depicts the computed free energy landscape for the "truncated" models 1b (energies in kcal/mol).
Figure 28B:
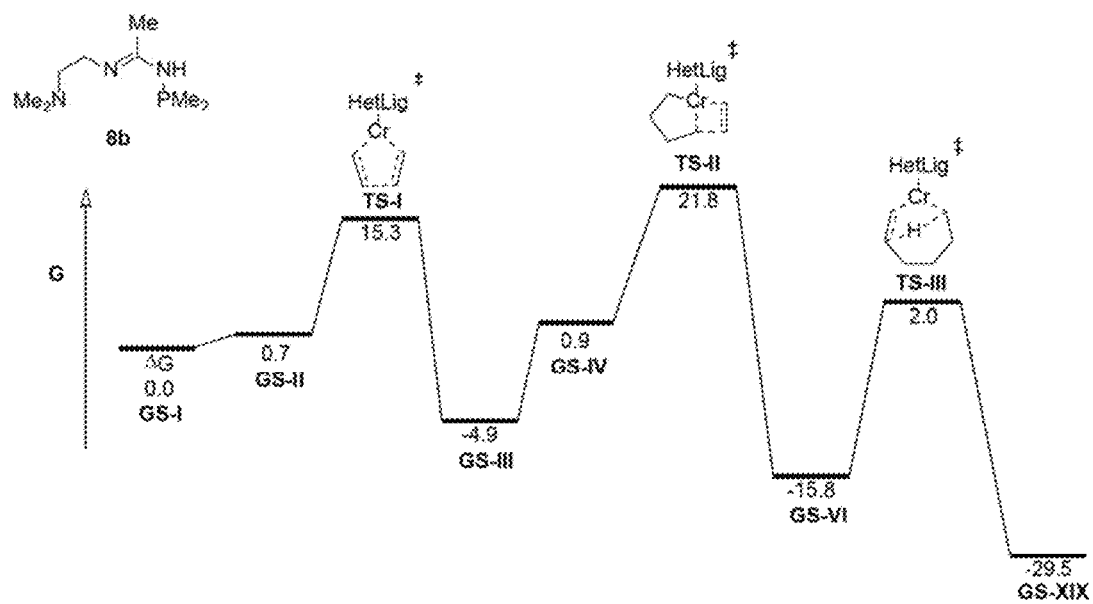
FIG. 28B depicts the computed free energy landscape for the "truncated" models 8b (energies in kcal/mol).
Figure 29A:
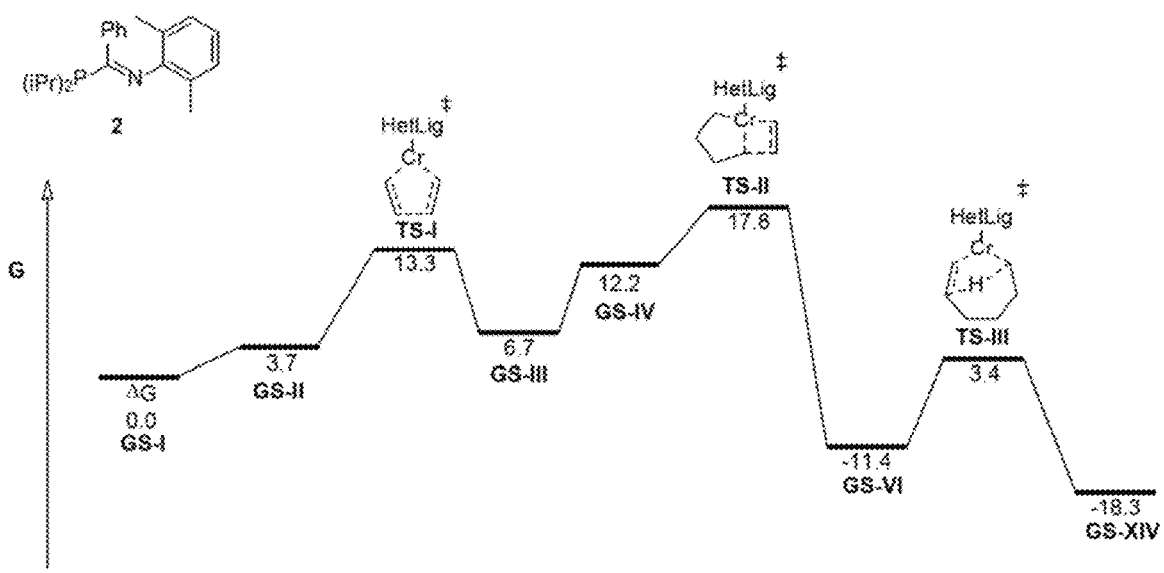
FIG. 29A through FIG. 29F illustrate the Gibbs free energy surfaces for the chromium complexes comprising ligands 2-7, respectively, at 298 K, 1 atm, and with solvents listed in Table S1. Thus, the FIG. 29A surface is for the ligand 2 complex; the FIG. 29B surface is for the ligand 3 complex; the FIG. 29C surface is for the ligand 4 complex; the FIG. 29D surface is for the ligand 5 complex; the FIG. 29E surface is for the ligand 6 complex; and the FIG. 29F surface is for the ligand 7 complex.
Figure 29B:
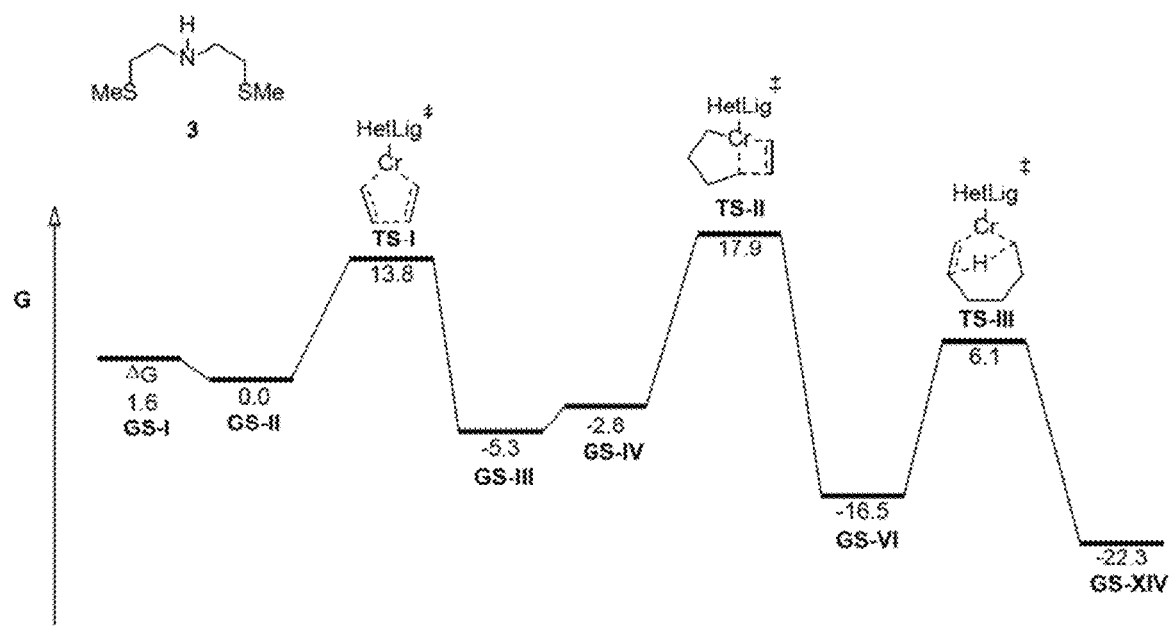
Figure 29C:
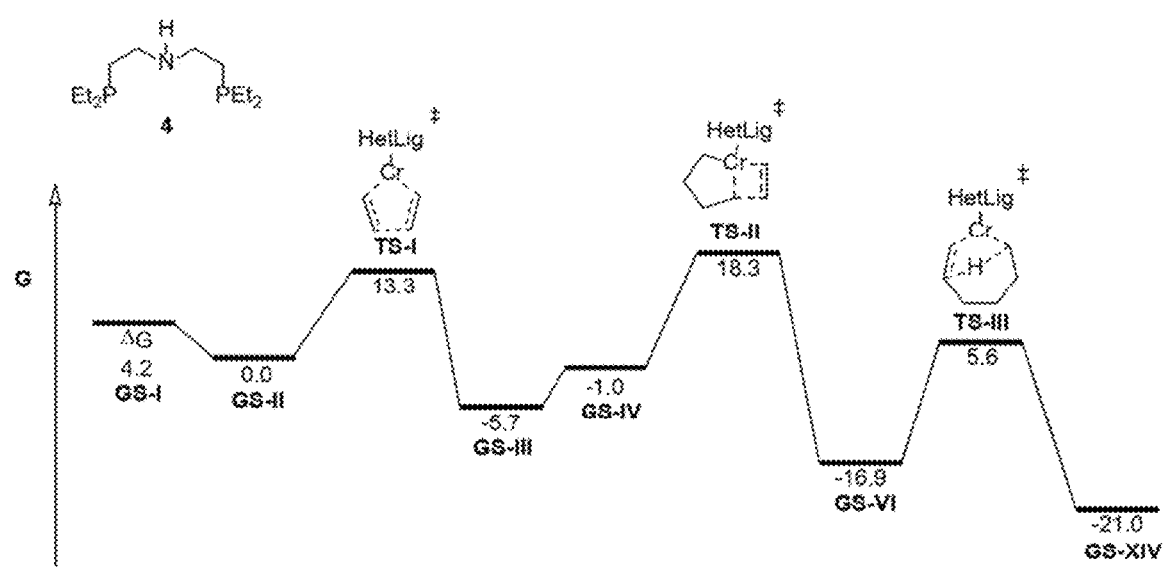
Figure 29D:
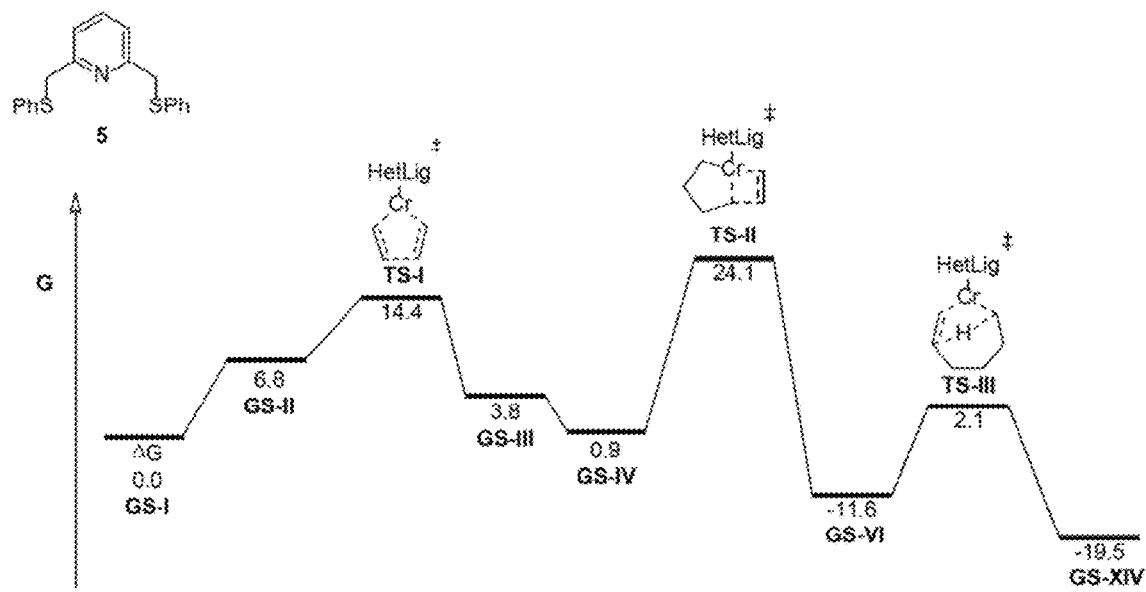
Figure 29E:
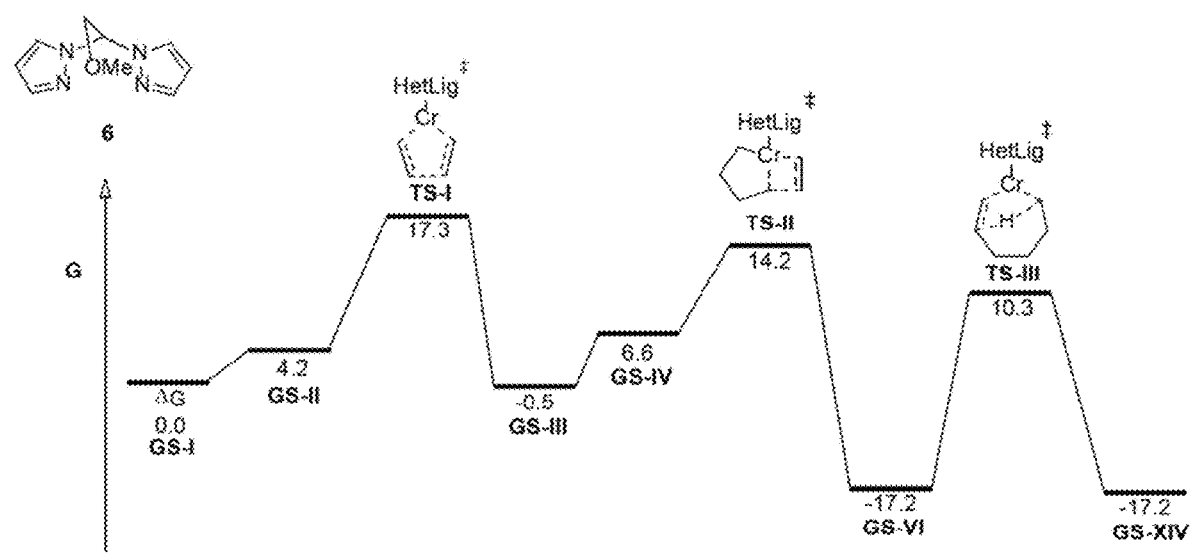
Figure 29F:
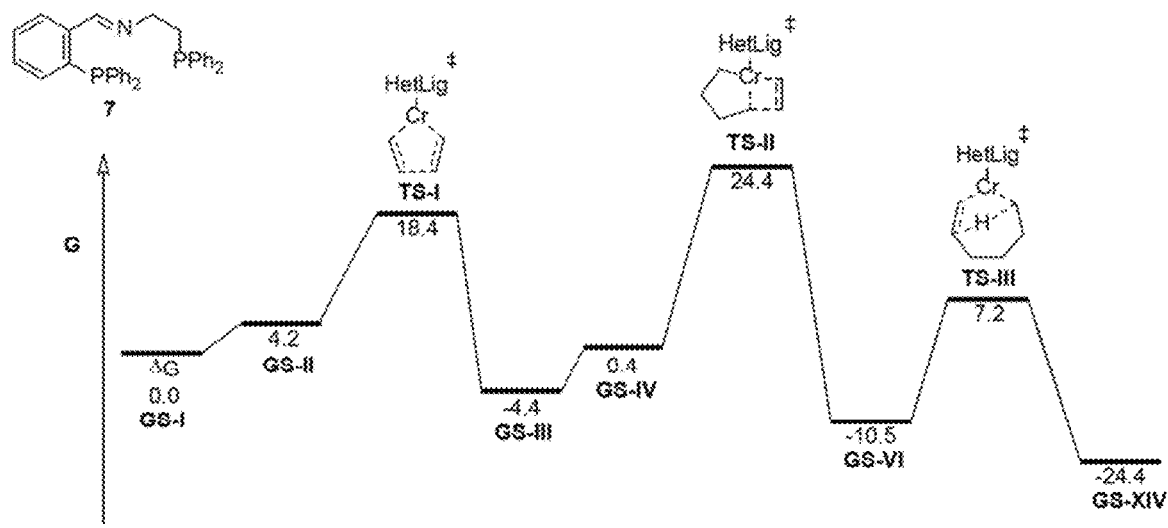

To evaluate steric effects on activity, truncated model versions of heteroatomic ligands 1a and 8a were computed. The energy spans of the modified heteroatomic ligands 1b and 8b very closely reflected the parent heteroatomic ligands 1a and 8a respectively. The computed free energy surfaces for the modified model heteroatomic ligands 1b and 8b are shown in FIG. 28A and FIG. 28B. In FIG. 28A, the free energy landscape for heteroatomic ligand 1b is shown, and in FIG. 28B, the free energy landscape for heteroatomic ligand 8b is shown, with energies reported in kcal/mol. See also FIG. 3 and FIG. 4 for ground state and transition state designations. Ground states GS-I and GS-II have a sextet spin state as the lowest energy and all other ground states and transition states have a quartet spin state as the lowest energy. The energy span of heteroatomic ligand-chromium compound complex with heteroatomic ligand 1b is 33% and 67% controlled by TS-I and TS-III respectively with an overall barrier of ~14.8 kcal/mol, closely reflecting the energy span for heteroatomic ligand 1a which is 16.0 kcal/mol. For heteroatomic ligand 8b, the energy span is completely controlled by transition state TS-II, a barrier of 26.7 kcal/mol which closely resembles the 27.1 kcal/mol energy span for heteroatomic ligand 8a.

Energy Landscapes for Complexes with Heteroatomic Ligands 2-7

The following FIGS. 29A-29F illustrate the energy landscapes for heteroatomic ligand-chromium compound complexes with ligands 2-7. In each of FIGS. 29A-29F, the Gibbs free energy surfaces at 298 K, 1 atm, and with solvents defined in Table 4 are shown with energies in kcal/mol. For heteroatomic ligand-chromium compound complexes with ligands 2, 5, 6, ground states GS-I and GS-II have a sextet spin state as the lowest energy and all other ground states and transition states have a quartet spin state as the lowest energy. For heteroatomic ligand-chromium compound complexes with ligand 3, 4, and 7, ground states and transition state had a quartet spin state as the lowest energy. FIG. 3 and FIG. 4 illustrate all of the ground state and transition state designations.

Figure 30:
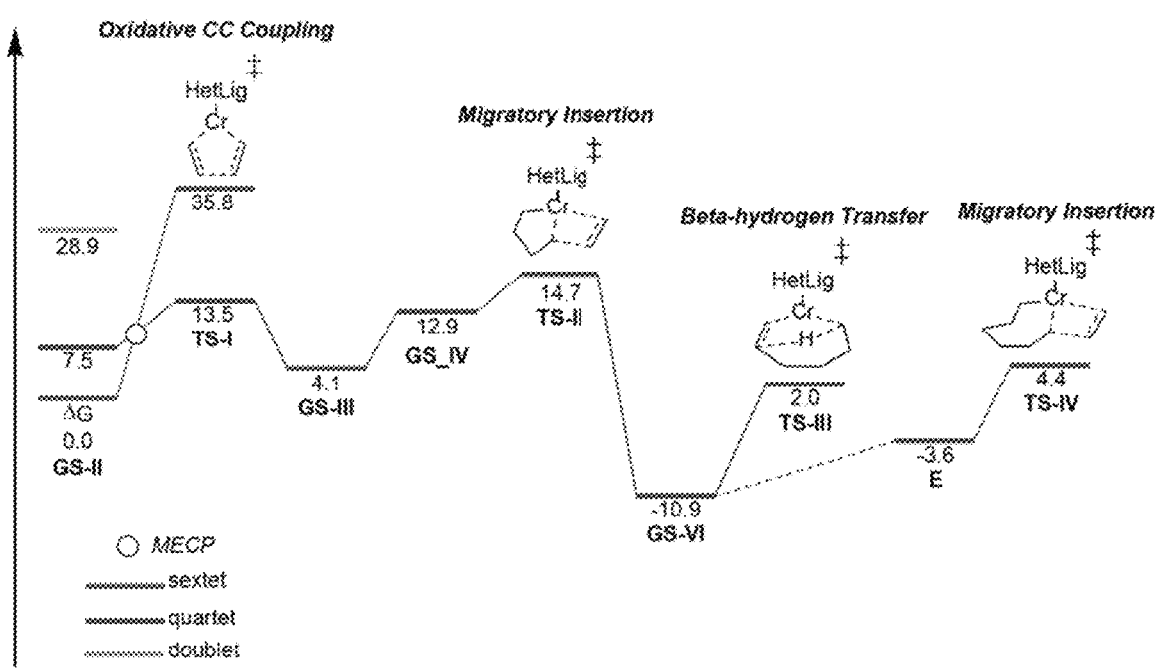
FIG. 30 shows the M06L energy landscape for catalyst 1a. The free energy barriers between 6-15 kcal/mol are consistent with experimental reaction temperatures.

VI. Experimentally Verified Computational Transition-State Design for Cr(P,N) Catalysts for Control of Ethylene Trimerization and Tetramerization Mechanistic Energy Landscape The M06L energy landscape for heteroatomic ligand-chromium compound complex with ligand 1a is illustrated in FIG. 30, with energies in kcal/mol. The free energy barriers between 6-15 kcal/mol are consistent with experimental reaction temperatures.

Transition-State Ensemble

Figure 31:
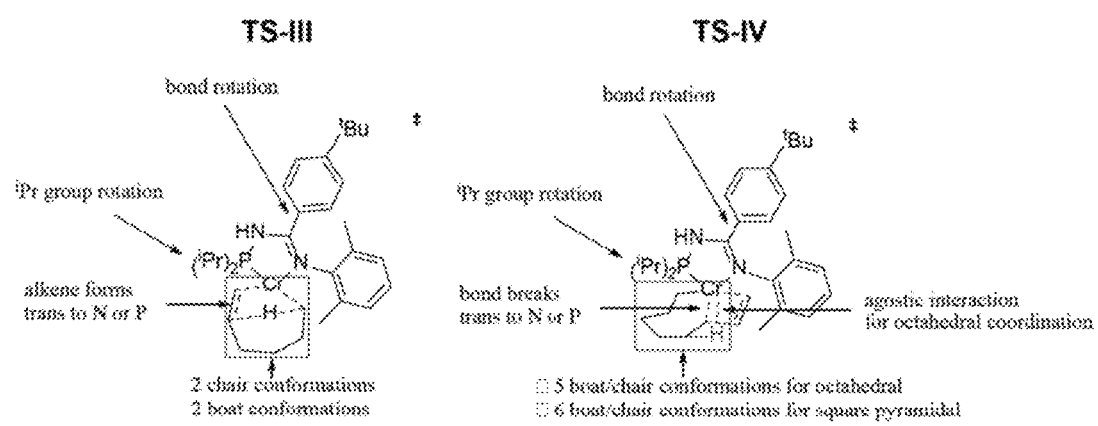
FIG. 31 depicts possible conformations for transition states TS-III and TS-IV, for an exemplary heteroatomic ligand-chromium compound complex, that is, conformational changes that result in unique transition-state geometries.

The large number of conformations in each transition state results from the flexibility of the chromacycloheptane ring and rotation of the aryl and isopropyl groups. FIG. 31 depicts the possible conformations for transition states TS-III and TS-IV, that is, the conformational changes that result in unique transition-state geometries. For transition state TS-III, a staggered conformation of the chromacycle with the alkene forming trans to the nitrogen is the lowest in free energy. For transition state TS-IV, the Cr—C bond-breaking trans to the phosphine and a staggered metallacycle structure is the lowest in free energy. Also forming an agostic interaction with a hydrogen in the chromacycle to the chromium metal center forms an octahedral-like geometry.

Figure 32:
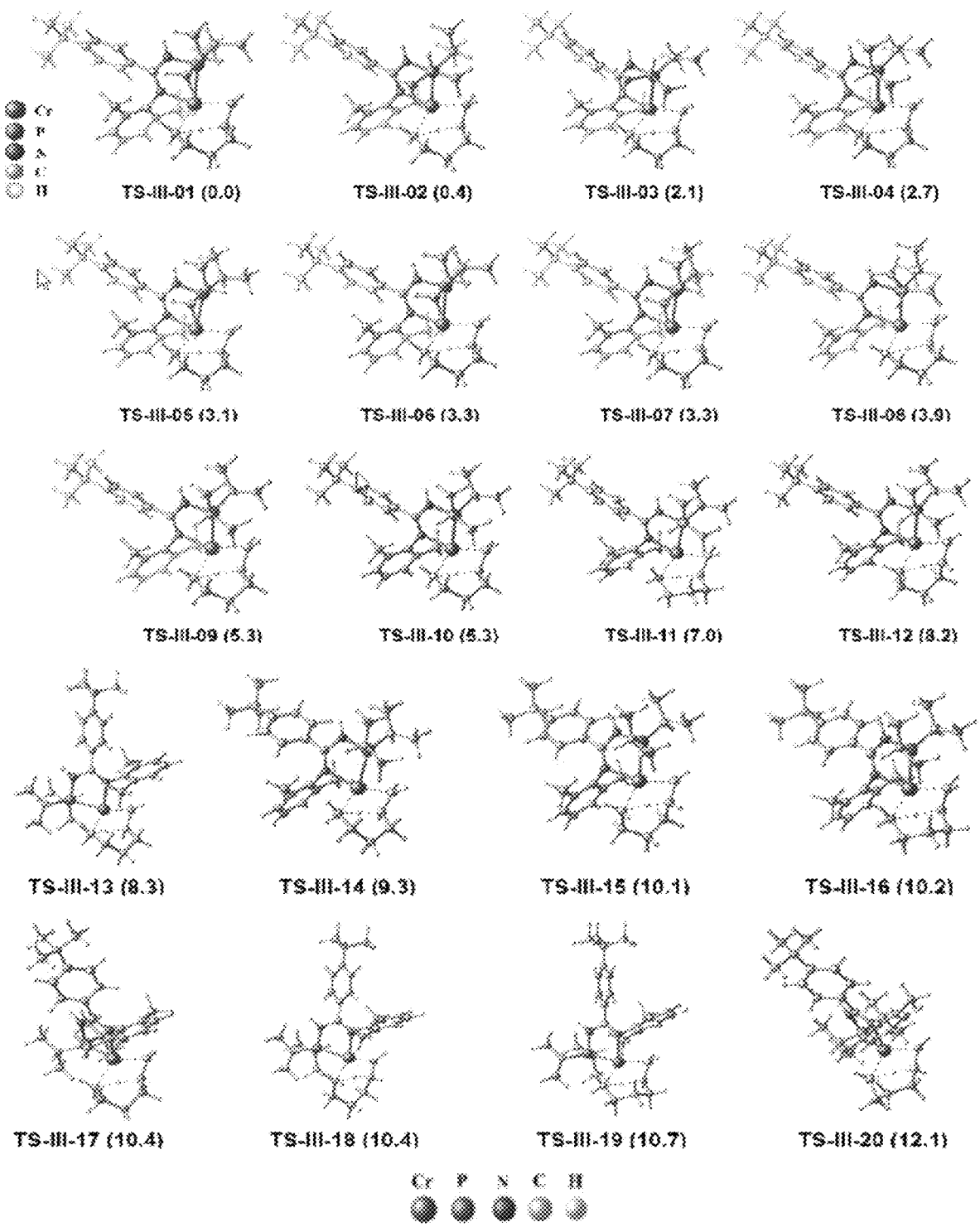
FIG. 32 illustrates the 3-D structures of the 20 lowest transition-state conformations for the TS-III ensemble for an exemplary heteroatomic ligand-chromium compound complex, with relative free energies in kcal/mol.
Figure 33:
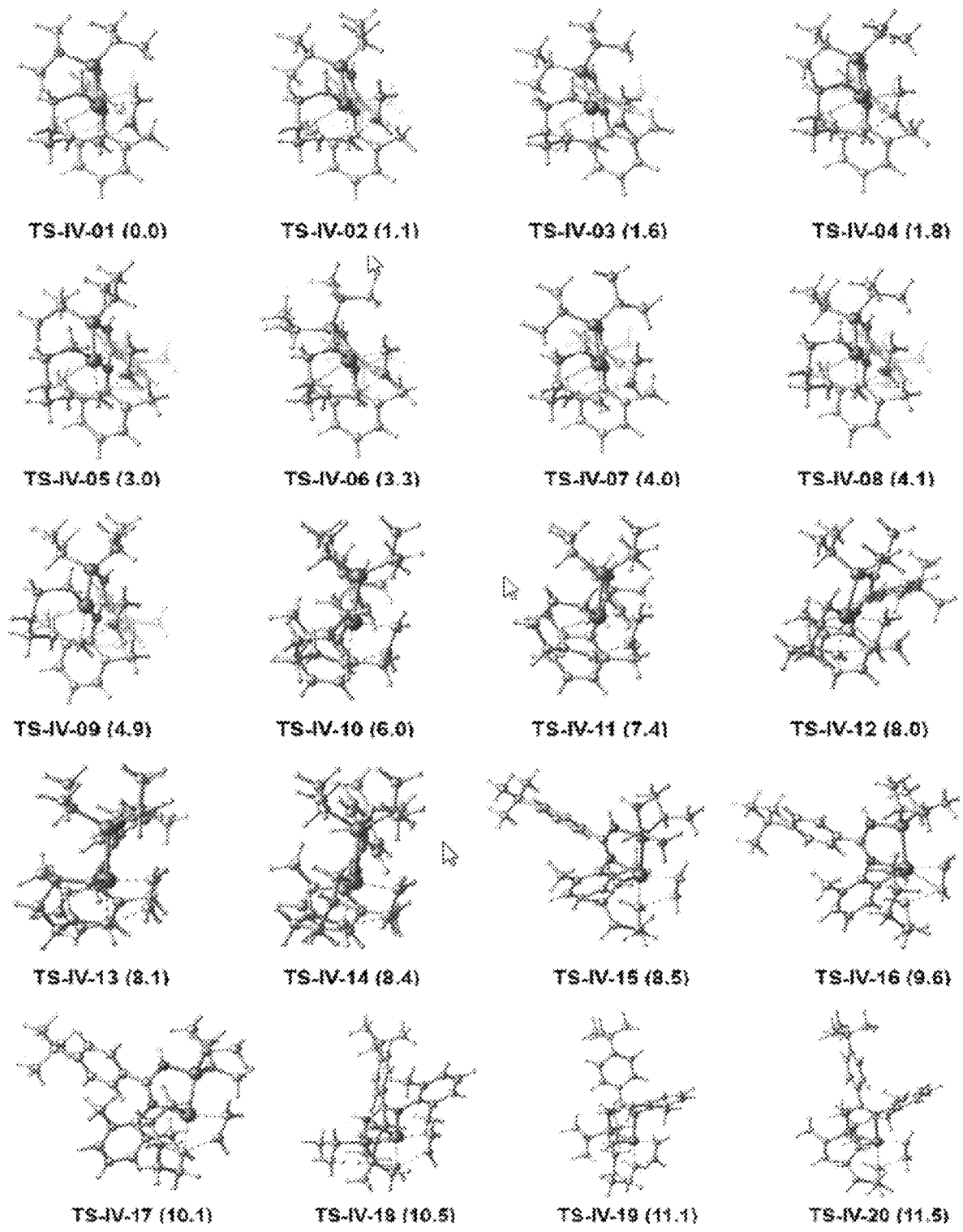
FIG. 33 illustrates the 3-D structures of the 20 lowest transition-state conformations for the TS-IV ensemble for an exemplary heteroatomic ligand-chromium compound complex, with relative free energies in kcal/mol.

FIG. 32 and FIG. 33 show 3-D representations of the 20 lowest free energy conformations of TS-III and TS-IV, respectively.

Details of the Correlation Plot

The calibration for heteroatomic ligands L1-L5 was calculated by taking the lowest energy structures for transition states TS-III and TS-IV ($\Delta\Delta G = \Delta G_{TS2} - \Delta G_{TS1}$) versus the the natural logarithm of the $C_6$ to $C_8$ mass ratio (ln(mass $C_6$/mass $C_8$— or alternatively $\ln(C_6/C_8)$) observed when the chromium compound complexes of L1-L5 were utilized in a catalyst system for oligomerizing ethylene.

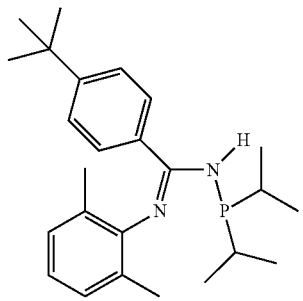

L1

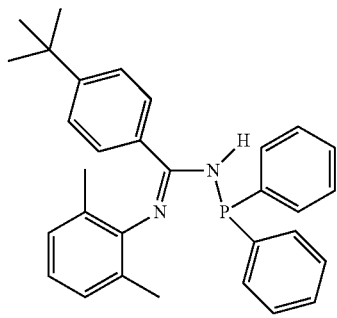

L2

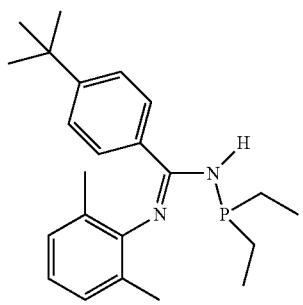

L3

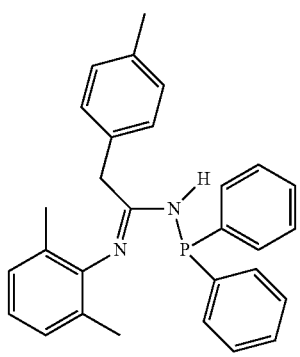

L4

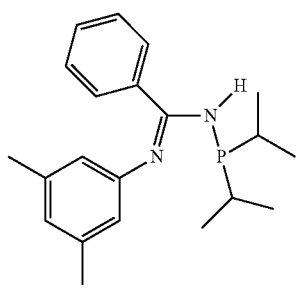

L5

Linear regression models were developing using the LINEST function in Microsoft Excel. This afforded a high degree of linear correlation with a slope of 1.08 (y=1.079x+

2.076) and an $R^2$ value of 0.97. This calibration curve was then used to predict $C_6$ to $C_8$ mass ratio selectivity for new ligands L6, L6a, L7, L7a, L8, and L8a when the chromium compound complexes of L6, L6a, L7, L7a, L8, and L8a are utilized in a catalyst system for oligomerizing ethylene based on calculated $\Delta\Delta G$ for L6, L6a, L7, L7a, L8, and L8a.

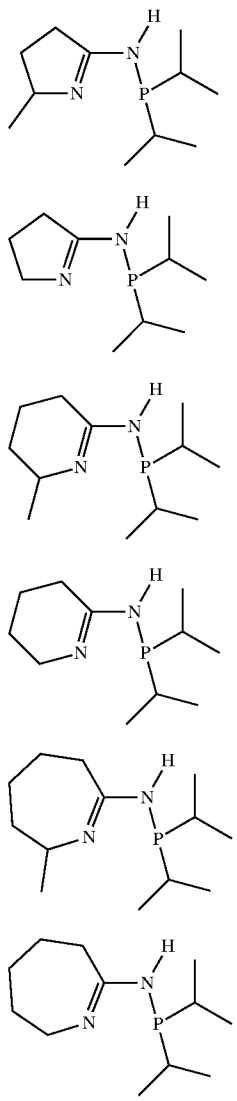

L6a

L6

L7a

L7

L8a

L8

Table 5 presents the calculated calibration curve data, and Table 6 presents the calculated free energy differences for designed ligands L6, L6a, L7, L7a, L8, and L8a. See FIG. 19A.

TABLE 5

Calculated calibration curve data.

| Catalyst | Experiment $C_6$ % | Experiment $C_8$ % | $\ln(C_6/C_8)$ | $\Delta\Delta G = \Delta G_{TS2} - \Delta G_{TS1}$ |
|---|---|---|---|---|
| L1 | 93.6 | 0.9 | 4.6 | 2.4 |
| L2 | 85.4 | 12.0 | 2.0 | −0.5 |
| L3 | 79.3 | 15.0 | 1.7 | −0.2 |
| L4 | 65.2 | 30.5 | 0.8 | −1.3 |
| L5 | 52.2 | 33.7 | 0.4 | −1.3 |

TABLE 6

Calculated free energy differences for designed ligands L1-L6.

| Catalyst | $\Delta\Delta G = \Delta G_{TS2} - \Delta G_{TS1}$ |
|---|---|
| L6a | 0.6 |
| L6 | −2.1 |
| L7a | 4.0 |
| L7 | −2.0 |
| L8a | 2.4 |
| L8 | −1.5 |

Figure 34:
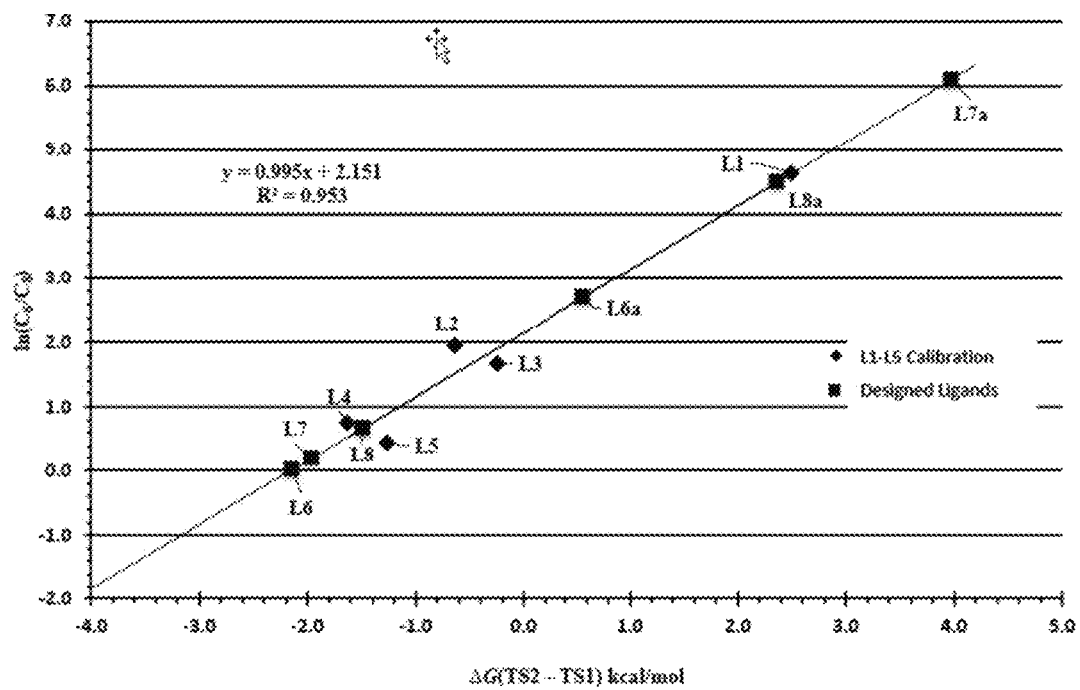
FIG. 34 provides the linear correlation plot using Boltzmann distributions that includes the ensemble of all the calculated transition states for TS-III and TS-IV, using the ligands shown.

The calibration curve was also calculated with a Boltzmann distribution (see Equation S1) that included the ensemble of all the calculated transition states TS-III and TS-IV. Thus, Equation S1 sets out the Boltzmann distribution where pi is the probability of the state i, $\varepsilon_i$ is the energy of the state i, k the Boltzmann constant, and T the temperature of the system, and M is the number of states accessible to the system. See McQuarrie, D. A. *Statistical Mechanics*; Sausalito, California, University Science Books, 2000). As described above, an extensive conformational search for the transition states TS-III and TS-IV using the heteroatomic ligand L1 was performed. For the heteroatomic ligands L2-L5, a slightly smaller number of conformations based on knowledge from the conformational searches with ligand 1a were sampled. The Boltzmann averaged calibration curve produced a regression line very similar to the methodology describe above. See Table 7 which presents the calculated calibration using Boltzmann distributions and FIG. 34 provides a linear correlation plot using Boltzmann distributions.

$$p_i = \frac{e^{-\varepsilon_i/kT}}{\sum_{j=1}^{M} e^{-\varepsilon_i/kT}} \quad \text{(Eq. S1)}$$

Equation S1 Boltzmann distribution where:

$p_i$ is the probability of the state i;

$\varepsilon_i$ is the energy of the state i;

k the Boltzmann constant;

T is the temperature of the system; and

M is the number of states accessible to the system.

TABLE 7

Calculated calibration using Boltzmann distributions.

| Catalyst | TS-III Conformations | TS-VI Conformations | $\Delta\Delta G = \Delta G_{TS2} - \Delta G_{TS1}$ |
|---|---|---|---|
| L1 | 25 | 42 | 2.5 |
| L2 | 12 | 14 | −0.6 |
| L3 | 8 | 10 | −0.2 |
| L4 | 16 | 13 | −1.6 |
| L5 | 5 | 7 | −1.3 |

VII. Ligand and Catalyst Synthesis and Characterization

Experimental Materials and Methods

Deuterated NMR solvents were degassed and stored on 13× molecular sieves. 2-Amino-1-pyrroline hydrochloride, 2-Iminopiperidine hydrochloride, 6-Methyl-3,4,5,6-tetrahydropyridin-2-amine hydrochloride, 2-Methyl-3,4-dihydro-2H-pyrrol-5-amine hydrochloride, and 7-Methoxy-3,4,5,6-tetrahydro-2H-azepine were obtained from commercial vendors and used as received. 3,4,5,6-Tetrahydro-2H-azepin-7-amine hydrochloride was synthesized from 7-Methoxy-3,4,5,6-tetrahydro-2H-azepine using literature procedures. Anhydrous solvents were obtained from Sigma Aldrich, degassed, and stored on molecular sieves. Ligands 1 and 3 were prepared according to previously published procedures: (a) Sydora, O. L.; Jones, T. C.; Small, B. L.; Nett, A. J.; Fischer, A. A.; Carney, M. J. ACS Catal. 2012, 2, 2452-2455; (b) U.S. Pat. No. 8,680,003. (c) U.S. Pat. No. 9,283,555.

Preparation of Phosphine Imine Ligands

Ligand L6: In an inert atmosphere glove box, 2-Amino-1-pyrroline hydrochloride (6.14 g, 50.9 mmol) was suspended in THF with stirring. To the suspension was added n-butyl lithium (41 mL, 102 mmol) dropwise over 60 minutes. The resulting yellow solution was allowed to stir for 5 h followed by addition of chlorodiisopropylphosphine (7.70 g, 50.4 mmol) dropwise. This mixture was allowed to stir overnight resulting in a cloudy solution. The solvent is removed from the filtrate in vacuo. The resulting oily material contains a mixture of both the desired ligand and a diphosphinylated compound. The oily material is dissolved in the minimum amount of diethyl ether and filtered through celite. Slow evaporation of the solvent from the filtrate results in the formation of large block crystals. The crystals are collected and dried in multiple crops. Ligand 2 is collected as a white solid (3.88 g 19.3 mmol) largely free of impurities.

$^1$H NMR (400 MHz, CD$_2$Cl$_2$): 6.90 (broad, 1H, N—H), 3.56 (t, 2H), 2.63 (t, 2H), 1.93 (pent., 2H), 1.81 (m, 2H, (CH$_3$)$_2$C—H), 1.11 (m, 12H, (CH$_3$)$_2$CH). $^{31}$P NMR: (202.5 MHz, CD$_2$Cl$_2$): δ=59.1. EI-MS m/z [M]+: 200.1.

Ligand L7: In an inert atmosphere glove box, 2-Iminopiperidine hydrochloride (1.5 g, 11 mmol) was suspended in THF with stirring. To the suspension was added n-butyl lithium (9 mL, 22 mmol) dropwise over 5 minutes. The resulting yellow solution was allowed to stir for 2 h followed by addition of chlorodiisopropylphosphine (1.7 g, 11 mmol) dropwise. This mixture was allowed to stir overnight resulting in a cloudy solution. The solvent is removed from the filtrate in vacuo. The resulting oily material contains a mixture of both the desired ligand and a diphosphinylated compound which is extracted from the mixture with pentane. The resulting white solids are dissolved in diethyl ether and filtered on a frit. Drying the filtrate in vacuo allows for isolation of Ligand 4 as a white solid (0.90 g, 4.2 mmol) largely free of impurities.

$^1$H NMR (400 MHz, CD$_2$Cl$_2$): 5.43 (broad, 1H, N—H), 3.34 (t, 2H), 2.38 (t, 2H), 1.73 (m, 4H), 1.58 (m, 2H, (CH$_3$)$_2$C—H), 1.06 (m, 12H, (CH$_3$)$_2$CH). $^{31}$P NMR: (202.5 MHz, CD$_2$Cl$_2$): δ=46.8. EI-MS m/z [M]+: 214.1.

Ligand L8: In an inert atmosphere glove box, 3,4,5,6-Tetrahydro-2H-azepin-7-amine hydrochloride (3.00 g, 20.2 mmol) was suspended in THF with stirring. To the suspension was added n-butyl lithium (16.1 mL, 40.2 mmol) dropwise over 5 minutes. The resulting yellow solution was allowed to stir for 2 h followed by addition of chlorodiisopropylphosphine (3.00 g, 19.6 mmol) dropwise. This mixture was allowed to stir overnight resulting in a cloudy solution. The solvent was from the filtrate removed in vacuo. The resulting oily material contains a mixture of both the desired compound (Ligand 6) and a diphosphinylated compound (~7:3 mass ratio by GC-MS). Colorless crystals of Ligand 1 (0.382 g 1.67 mmol) were obtained by dissolving a 1 gram sample of the crude material in a mixture of pentane and hexamethyldisiloxane followed by filtration, and cooling to −20° C.

$^1$H NMR (400 MHz, CD$_2$Cl$_2$): 6.36 (broad, 1H, N—H), 3.26 (m, 2H), 2.61 (m, 2H), 1.78 (m, 4H), 1.64 (m, 2H), 1.60 (m, 2H, (CH$_3$)$_2$C—H), 1.03 (m, 12H, (CH$_3$)$_2$CH). $^{31}$P NMR: (202.5 MHz, CD$_2$Cl$_2$): δ=51.2. EI-MS m/z [M]+: 228.2.

Ligands 6a and 7a were prepared from 2-methyl-3,4-dihydro-2H-pyrrol-5-amine hydrochloride and 6-methyl-3,4,5,6-tetrahydropyridin-2-amine hydrochloride using methods similar to the preparation of Ligands 6, 7, and 8.

Preparation of Cr Complexes

All complexes were prepared by the following procedure: In an inert atmosphere glove box, one equivalent of CrCl$_3$(THF)$_3$ was suspended in THF with stirring. To the suspension was added a solution of the corresponding ligand (1.05 equivalents) in THF dropwise. The resulting blue solution was allowed to stir overnight. The solvent was removed in vacuo. The resulting solids were stirred in pentane for 30 min and the liquids decanted. The resulting solids were stirred in diethyl ether then filtered. The blue solids were collected and dried in vacuo. These were used in the reactor experiments described herein.

Characterization and Instrumentation

NMR spectra were collected on a 400 MHz Bruker Avance II. GC-MS results were obtained using an Agilent 7890A series gas chromatograph coupled to an Agilent 5975C series Inert XL mass spectrometer with Triple-Axis detector.

Standard Reaction Procedure for Complexes L1-L5

In a dry box, a 20 mL glass vial was charged with the desired complex, the desired amount of catalyst system solvent, and MMAO-3A or MMAO-20 (7 wt. % Al solution in heptanes) to provide the desired Al:Cr molar ratio. This solution was then aged for the desired time in the absence of ethylene to provide an aged catalyst system mixture. The catalyst mixture was then added to 0.5 L glass charger containing 200 mL of cyclohexane. The glass charger was removed from the dry box and charged into an evacuated 0.5 L stainless steel reactor having an internal temperature of 60° C. Hydrogen was charged to the reactor to the desired pressure. Ethylene was then charged to the reactor to the desired pressure. The reaction was allowed to proceed at the conditions indicated at 70° C. with ethylene being fed on demand to maintain desired reactor pressure. Upon reaction completion, water cooling was applied to the 0.5 L stainless steel reactor using the internal cooling coils. When the reactor contents reached 35° C., the unreacted ethylene and hydrogen gas were vented from the stainless-steel reactor. A 2 mL sample of the liquid sample was collected, filtered, and analyzed by GC-FID. The reaction solids were collected by filtering the liquid solution and cleaning the reactor walls and internal cooling coils.

These and other features of the invention can further include the various statements, embodiments, and aspects which are presented below.

Figure 35:
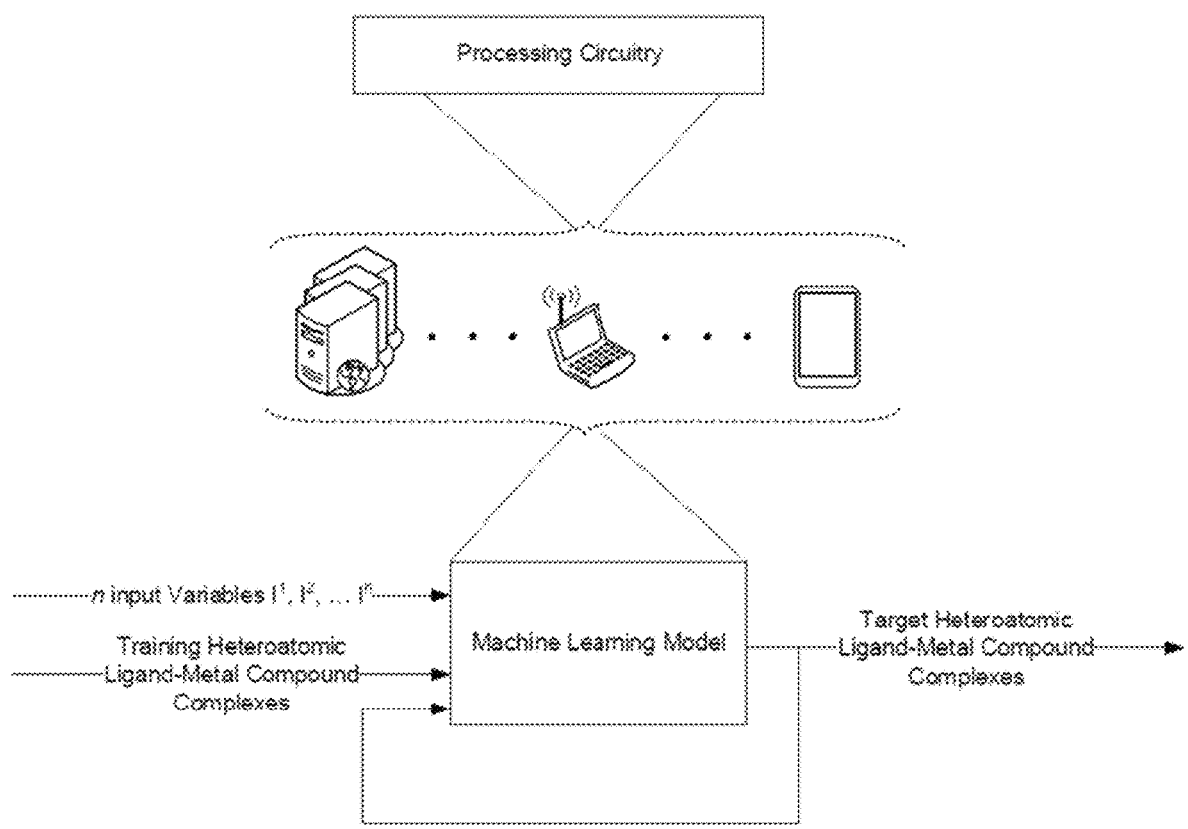
FIG. 35 illustrates a schematic diagram of a machine learning model used to generate target heteroatomic ligan-metal compound complexes.

VIII. Machine Learning for Generating Target Heteroatomic Ligan-Metal Compound Complexes FIG. 35 illustrates a schematic diagram of a machine learning model used to generate target heteroatomic ligan-metal compound complexes.

A machine learning model may receive n input variables $I^1, I^2, \ldots I^n$ (n is an integer), each input variable corresponding to a structural property or an electronic property of one or more ground state model structures $GS^{A1}, \ldots GS^{Ap}$ (p is an integer) and a plurality of transition state model structures $TS^{A1}, TS^{A2}, \ldots TS^{Am}$ (m is an integer) associated with the one or more ground state model structures, wherein each of the one or more ground state model structures $GS^{A1}, \ldots GS^{Ap}$ and each of the plurality of transition state model structures $TS^{A1}, TS^{A2}, \ldots TS^{Am}$ are generated from one or more first training heteroatomic ligand-metal compound complexes, each complex comprising a first training heteroatomic ligand.

The machine learning model may assign a quantitative value to each n input variable $I^1, I^2, \ldots I^n$, for each of the ground state model structures $GS^{A1}, \ldots GS^{Ap}$ and each of the transition state model structures $TS^{A1}, TS^{A2}, \ldots TS^{Am}$.

The machine learning model may determine the relative energies of each of the ground state model structures $GS^{A1}, \ldots GS^{Ap}$ and each of the transition state model structures $TS^{A1}, TS^{A2}, \ldots TS^{Am}$.

The machine learning model may generate to correlate the quantitative value of each n input variable $I^1, I^2, \ldots I^n$ and the relative energies of each of the ground state model structures $GS^{A1}, \ldots GS^{Ap}$ and each of the transition state model structures $TS^{A1}, TS^{A2}, \ldots TS^{Am}$;

The machine learning model may determine a relationship between one or more of the n input variables $I^1, I^2, \ldots I^n$ and [1] the difference in energies between one of the ground state model structures $GS^{A1}, \ldots GS^{Ap}$ and at least one of the plurality of transition state model structures $TS^{A1}, TS^{A2}, \ldots TS^{Am}$ [$\Delta G(TS\text{-}GS)$ or $\Delta\Delta G(TS\text{-}GS)$] or [2] the difference in energies between any two or more of the plurality of transition state model structures $TS^{A1}, TS^{A2}, \ldots TS^{Am}$ [$\Delta G(TS\text{-}TS)$ or $\Delta\Delta G(TS\text{-}TS)$];

The machine learning model may generate, based upon the relationship identified from step (e), an output of the machine learning model comprising a first target heteroatomic ligand-metal compound complex for olefin oligomerization and comprising a first target heteroatomic ligand, wherein the first target heteroatomic ligand-metal compound complex is characterized by n output variables $O^1, O^2, \ldots O^n$, each having a quantitative value corresponding to a structural property or an electronic property of one or more ground state model structures $GS^{B1}, \ldots GS^{Bx}$ (x is an integer) or any of a plurality of transition state model structures $TS^{B1}, TS^{B2}, \ldots TS^{By}$ (y is an integer) associated with the one or more ground state model structures, wherein each of the one or more ground state model structures $GS^{B1}, \ldots GS^{Bx}$ and each of the plurality of transition state model structures $TS^{B1}, TS^{B2}, \ldots TS^{By}$ are generated from the first target heteroatomic ligand-metal compound complex, each complex comprising a first target heteroatomic ligand, and wherein the n output variables $O^1, O^2, \ldots O^n$ are reused as new n input variables $I^{1.1}, I^{2.1}, \ldots I^{n.1}$ to the machine learning model.

The machine learning model may identify one or more performance parameters associated with an olefin oligomerization reaction and the value of the performance parameters for the one or more first training heteroatomic ligand-metal compound complexes and the first target heteroatomic ligand-metal compound complex.

The machine learning model may repeat the above steps one or more times using the quantitative values of the n output variables $O^1, O^2, \ldots O^n$ of the first target heteroatomic ligand-metal compound complex as an input dataset of the new n input variables $I^{1.1}, I^{2.1}, \ldots I^{n.1}$, the new n input variables $I^{1.1}, I^{2.1}, \ldots I^{n.1}$ derived from one or more second training heteroatomic ligand-metal compound complexes for olefin oligomerization and comprising a second training heteroatomic ligand, which is input into the machine learning model to generate a second target heteroatomic ligand-metal compound complex comprising a second target heteroatomic ligand, wherein the second target heteroatomic ligand-metal compound complex is characterized by quantitative values of an output dataset of new n output variables $O^{1.1}, O^{2.1}, \ldots O^{n.1}$, and having one or more second target heteroatomic ligand-metal compound complex performance parameter values.

The machine learning model may be implemented on one or more devices, such as a client device, server device, or the like, having processing circuitry and memory for storing data and computer-executable instructions. For example, the one or more devices may have a central processing unit (CPU), a graphics processing unit (GPU), and/or a tensor processing unit (TPU) having an artificial intelligence accelerator application-specific integrated circuit (ASIC) for performing the steps of any of the statements presented herein, including facilitating the machine learning model.

Statements of the Disclosure

Statement 1. A method for designing a heteroatomic ligand-metal compound complex for olefin oligomerization, the method comprising:
(a) selecting n input variables $I^1, I^2, \ldots I^n$ (n is an integer), each input variable corresponding to a structural property or an electronic property of one or more ground state model structures $GS^{A1}, \ldots GS^{Ap}$ (p is an integer) and a plurality of transition state model structures $TS^{A1}, TS^{A2}, \ldots TS^{Am}$ (m is an integer) associated with the one or more ground state model structures,
wherein each of the one or more ground state model structures $GS^{A1}, \ldots GS^{Ap}$ and each of the plurality of transition state model structures $TS^{A1}, TS^{A2}, \ldots TS^{Am}$ are derived from one or more first training heteroatomic ligand-metal compound complexes, each complex comprising a first training heteroatomic ligand;
(b) assigning a quantitative value to each n input variable $I^1, I^2, \ldots I^n$, for each of the ground state model structures $GS^{A1}, \ldots GS^{Ap}$ and each of the transition state model structures $TSA^1, TS^{A2}, \ldots TS^{Am}$;
(c) determining, by at least one processor of a device, the relative energies of each of the ground state model structures $GS^{A1}, \ldots GS^{Ap}$ and each of the transition state model structures $TS^{A1}, TS^{A2}, \ldots TS^{Am}$;
(d) generating a machine learning model based upon correlating the quantitative value of each n input variable $I^1, I^2, \ldots I^n$ with the relative energies of each of the ground state model structures $GS^{A1}, \ldots GS^{Ap}$ and each of the transition state model structures $TS^{A1}, TS^{A2}, \ldots TS^{Am}$;
(e) identifying, based on the machine learning model, one or more of the n input variables $I^1, I^2, \ldots I^n$ associated with [1] the difference in energies between one of the ground state model structures $GS^{A1}, \ldots GS^{Ap}$ and at least one of the plurality of transition state model structures $TS^{A1}, TS^{A2}, \ldots TS^{Am}$ [$\Delta G(TS\text{-}GS)$ or $\Delta\Delta G(TS\text{-}GS)$] or [2] the difference in energies between any two or more of the plurality of transition state model structures $TS^{A1}, TS^{A2}, \ldots TS^{Am}$ [$\Delta G(TS\text{-}TS)$ or $\Delta\Delta G(TS\text{-}TS)$];
(f) generating, based upon the one or more n input variables $I^1, I^2, \ldots I^n$ identified from step (e), a first target heteroatomic ligand-metal compound complex for olefin oligomerization and comprising a first target heteroatomic ligand, wherein the first target heteroatomic ligand-metal compound complex is characterized by n output variables $O^1, O^2, \ldots O^n$, each having a quantitative value corresponding to a structural property or an electronic property of one or more ground state model structures $GS^{B1}, \ldots GS^{Bx}$ (x is an integer) or any of a plurality of transition state model structures $TS^{B1}, TS^{B2}, \ldots TS^{By}$ (y is an integer) associated with the one or more ground state model structures, wherein each of the one or more ground state model structures $GS^{B1}, \ldots GS^{Bx}$ and each of the plurality of transition state model structures $TS^{B1}, TS^{B2}, \ldots TS^{By}$ are derived from the first target heteroatomic ligand-metal compound complex, each complex comprising a first target heteroatomic ligand;

(g) identifying one or more performance parameters associated with an olefin oligomerization reaction and the value of the performance parameters for the one or more first training heteroatomic ligand-metal compound complexes and the first target heteroatomic ligand-metal compound complex; and (h) repeating steps (a)-(f) one or more times using the quantitative values of the n output variables $O^1, O^2, \ldots O^n$ of the first target heteroatomic ligand-metal compound complex as an input dataset of new n input variables $I^{1.1}, I^{2.1}, \ldots I^{n.1}$ derived from one or more second training heteroatomic ligand-metal compound complexes for olefin oligomerization and comprising a second training heteroatomic ligand, which is computationally evaluated against the machine learning model to generate a second target heteroatomic ligand-metal compound complex comprising a second target heteroatomic ligand, wherein the second target heteroatomic ligand-metal compound complex is characterized by quantitative values of an output dataset of new n output variables $O^{1.1}, O^{2.1}, \ldots O^{n.1}$, and having one or more second target heteroatomic ligand-metal compound complex performance parameter values.

Statement 2. The method of Statement 1, further comprising the step of:
(i) [1] synthesizing the first target heteroatomic ligand and/or the second target heteroatomic ligand; or [2] synthesizing the first target heteroatomic ligand and/or the second target heteroatomic ligand, followed by synthesizing the first target heteroatomic ligand-metal compound complex or the second target heteroatomic ligand-metal compound complex.

Statement 3. The method of Statement 2, further comprising the step of:
(j) performing the olefin oligomerization reaction by: [1] contacting the first target heteroatomic ligand or the second target heteroatomic ligand, a metal compound, an organometal compound, and an olefin; or [2] contacting the first target heteroatomic ligand-metal compound complex or the second target heteroatomic ligand-metal compound complex, an organometal compound, and an olefin.

Statement 4. The method of any of Statements 1-3, wherein at least one input variable $I^1, I^2, \ldots I^n$ corresponds to a structural property or an electronic property of at least one of the one or more ground state model structures $GS^{A1}, \ldots GS^{Ap}$.

Statement 5. The method of any of Statements 1-4, wherein at least one input variable $I^1, I^2, \ldots I^n$ corresponds to a structural property or an electronic property of at least one of the plurality of transition state model structures $TS^{A1}, TS^{A2}, \ldots TS^{Am}$.

Statement 6. The method of any of Statements 1-5, wherein step (e) identifies, based on the machine learning model, one or more of the n input variables $I^1, I^2, \ldots$ $I^n$ associated with the difference in energies between any of the one or more ground state model structures $GS^{A1}, \ldots GS^{Ap}$ and at least one of the plurality of transition state model structures $TS^{A1}, TS^{A2}, \ldots TS^{Am}$ [$\Delta G(TS\text{-}GS)$ or $\Delta\Delta G(TS\text{-}GS)$].

Statement 7. The method of any of Statements 1-6, wherein step (e) identifies, based on the machine learning model, one or more of the n input variables $I^1, I^2, \ldots I^n$ associated with the difference in energies between any two or more of the plurality of transition state model structures $TSA^1, TS^{A2}, \ldots TS^{Am}$ [$\Delta\Delta G(TS\text{-}TS)$].

Statement 8. The method of any of Statements 1-7, wherein the one or more first training heteroatomic ligand-metal compound complexes have a formula independently selected from:

[(HetLig)$CrX_qL_r$]$^{3-q}$(A); wherein:

HetLig represents the one or more first training heteroatomic ligands;
X is an anionic ligand, and q is an integer;
L is a neutral ligand, and r is an integer,
wherein any two or more of the X and L ligands may be linked to form a multidentate ligand; and
wherein each selected n input variable $I^1, I^2, \ldots I^n$, corresponds to a structural property or an electronic property of any of the one or more ground state model structures $GS^{A1}, \ldots GS^{Ap}$ or any of the plurality of transition state model structures $TS^{A1}, TS^{A2}, \ldots TS^{Am}$ associated with the one or more ground state model structures of formula (A).

Statement 9. The method of any of Statements 1-8, wherein the one or more ground state model structures $GS^{A1}, \ldots GS^{Ap}$ derived from the one or more first training heteroatomic ligand-metal compound complexes are selected independently from:

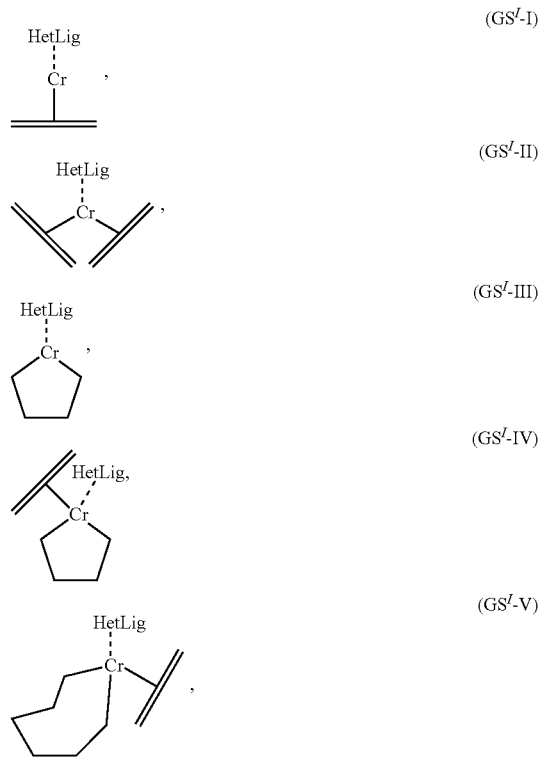

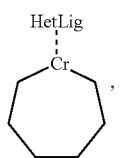 (GS$^I$-VI)

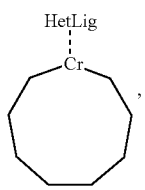 (GS$^I$-VII)

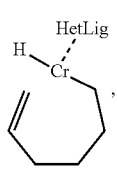 (GS$^I$-VIII)

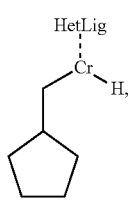 (GS$^I$-IX)

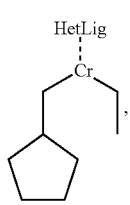 (GS$^I$-X)

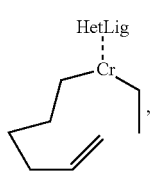 (GS$^I$-XI)

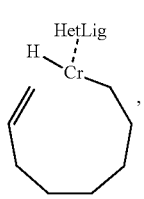 (GS$^I$-XII)

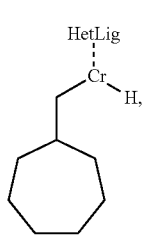 (GS$^I$-XIII)

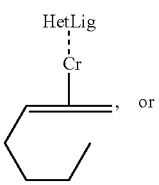 , or (GS$^I$-XIV)

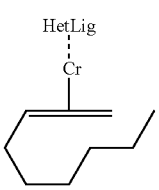 ; (GS$^I$-XV)

wherein HetLig represents the one or more first training heteroatomic ligands.

Statement 10. The method of any of Statements 1-9, wherein the plurality of transition state model structures $TS^{A1}$, $TS^{A2}$, ... $TS^{Am}$ derived from the one or more first training heteroatomic ligand-metal compound complexes are selected independently from:

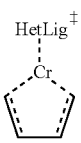 (TS$^I$-I)

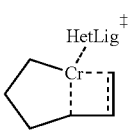 (TS$^I$-II)

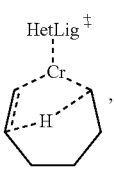 (TS$^I$-III)

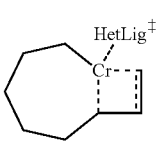 (TS$^I$-IV)

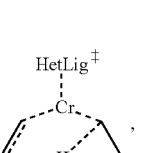 (TS$^I$-V)

-continued (TS$^I$-VI)
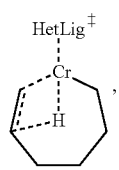

(TS$^I$-VII)
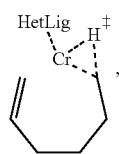

(TS$^I$-VIII)
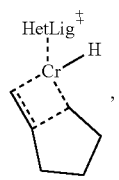

(TS$^I$-IX)
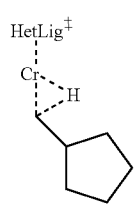

(TS$^I$-X)
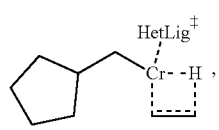

(TS$^I$-XI)
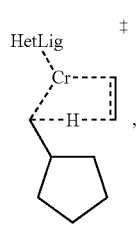

(TS$^I$-XII)
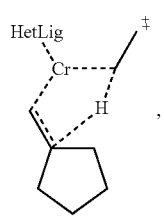

(TS$^I$-XIII)
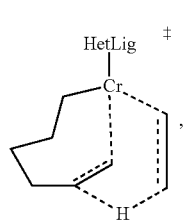

-continued (TS$^I$-XIV)
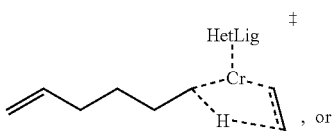, or (TS$^I$-XV)
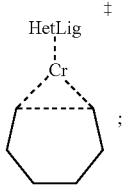;

wherein HetLig represents the one or more first training heteroatomic ligands.

Statement 11. The method of any of Statements 1-10, wherein the one or more ground state model structures $GS^{B1}, \ldots GS^{Bx}$ derived from the one or more first target heteroatomic ligand-metal compound complexes are selected independently from:

(GS$^T$-I)
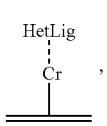

(GS$^T$-II)
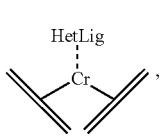

(GS$^T$-III)
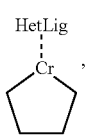

(GS$^T$-IV)
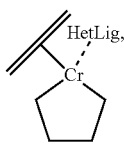

(GS$^T$-V)
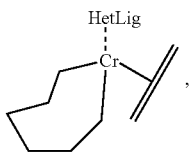

(GS$^T$-VI)
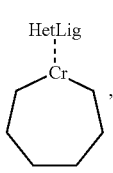

-continued (GS^T-VII) 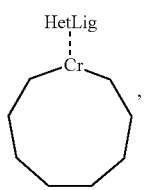

(GS^T-VIII) 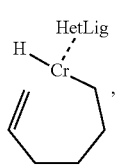

(GS^T-IX) 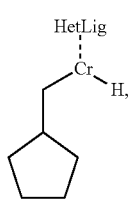

(GS^T-X) 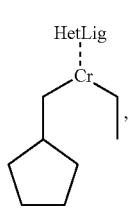

(GS^T-XI) 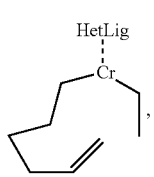

(GS^T-XII) 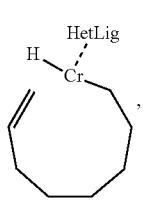

(GS^T-XIII) 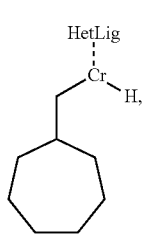

(GS^T-XIV) 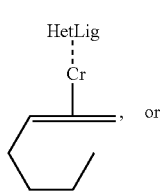, or (GS^T-XV) 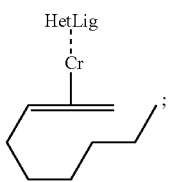;

wherein HetLig represents the one or more first target heteroatomic ligands.

Statement 12. The method of any of Statements 1-11, wherein the plurality of transition state model structures $TS^{A1}, TS^{A2}, \ldots TS^{Am}$ derived from the one or more first target heteroatomic ligand-metal compound complexes are selected independently from:

(TS^T-I) 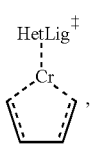, (TS^T-II) 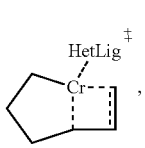, (TS^T-III) 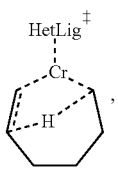, (TS^T-IV) 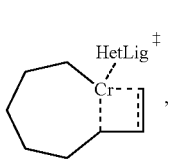, (TS^T-V) 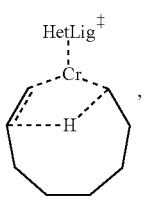, (TS^T-VI) 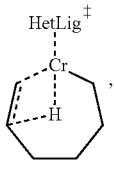,

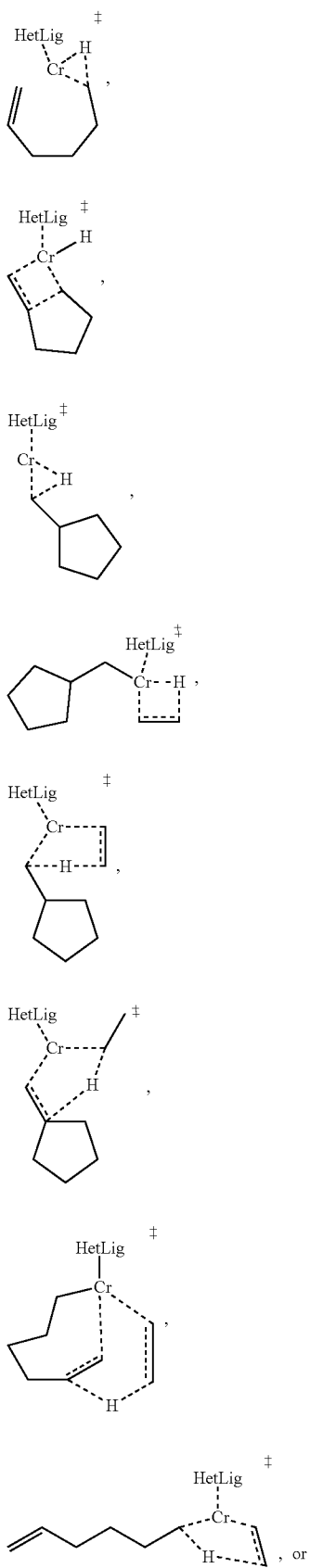
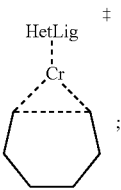
(TS$^T$-XV)
wherein HetLig represents the one or more first target heteroatomic ligands.
Statement 13. The method of any of Statements 1-12, wherein the one or more ground state model structures and any of the plurality of transition state model structures comprise a chromium heteroatomic ligand moiety independently selected from:
NPFCrM-1
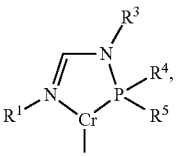
NPACrM-1
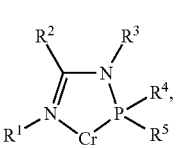
GuCrM-1
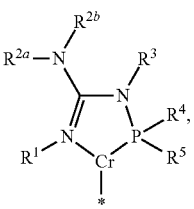
GuCrM-2
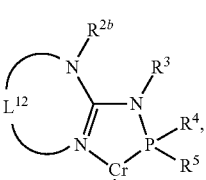
GuCrM-3
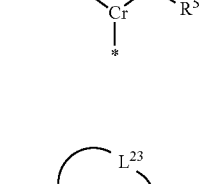

-continued

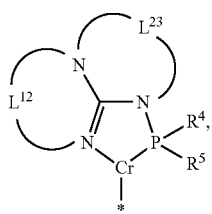

GuCrM-4

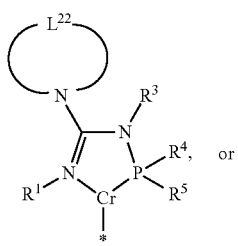

GuCrM-5

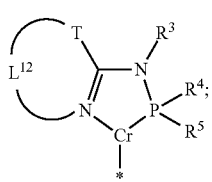

HCPACrM-1 wherein:
$R^1$ is a hydrogen or a $C_1$ to $C_{20}$ organyl group;
$R^2$ is a $C_1$ to $C_{20}$ organyl group;
T is oxygen or sulfur;
$R^{2a}$ and $R^{2b}$ independently are $C_1$ to $C_{20}$ organyl groups;
$L^{12}$ and $L^{23}$ independently are $C_2$ to $C_{20}$ organylene groups;
$L^{22}$ is a $C_3$ to $C_{20}$ organylene groups;
$R^3$ is hydrogen or a $C_1$ to $C_{20}$ organyl group; and
$R^4$ and $R^5$ independently are hydrogen or a $C_1$ to $C_{20}$ organyl groups;
where $R^1$ and $R^2$ are optionally joined to form $L^{12r}$, and $L^{12r}$ is a $C_3$ to $C_{30}$ organylene group;
where $R^4$ and $R^5$ are optionally joined to form $L^{45}$, and $L^{45}$ is a $C_4$ to $C_{30}$ organylene group; and
where "*" represents any additional bonding required in [1] any of the one or more ground state model structures or any of the plurality of transition state model structures derived from the one or more first training heteroatomic ligand-metal compound complexes, or [2] any of the one or more ground state model structures or any of the plurality of transition state model structures derived from the one or more first target heteroatomic ligand-metal compound complexes.

Statement 14. The method of Statement 13, wherein:
$R^1$ is hydrogen, a $C_1$ to $C_{20}$ hydrocarbyl group, or a $C_1$ to $C_{20}$ heterohydrocarbyl group;
$R^2$ is a $C_1$ to $C_{20}$ hydrocarbyl group or a $C_1$ to $C_{20}$ heterohydrocarbyl group;
$R^{2a}$ and $R^{2b}$ are independently selected from a $C_1$ to $C_{20}$ hydrocarbyl group or a $C_1$ to $C_{20}$ heterohydrocarbyl group;
$L^{12}$ and $L^{23}$ are independently selected from a $C_2$ to $C_{20}$ hydrocarbylene group or a $C_2$ to $C_{20}$ heterohydrocarbylene group;
$L^{22}$ is a $C_3$ to $C_{20}$ hydrocarbylene group or a $C_3$ to $C_{20}$ heterohydrocarbylene group;
$R^3$ is hydrogen, a $C_1$ to $C_{20}$ hydrocarbyl group, or a $C_1$ to $C_{20}$ heterohydrocarbyl group; and
$R^4$ and $R^5$ are independently selected from a $C_1$ to $C_{20}$ hydrocarbyl group or a $C_1$ to $C_{20}$ heterohydrocarbyl group;
where $R^1$ and $R^2$ are optionally joined to form $L^{12r}$, and $L^{12r}$ is a $C_3$ to $C_{20}$ hydrocarbylene group or a $C_3$ to $C_{20}$ heterohydrocarbylene group; and
where $R^4$ and $R^5$ are optionally joined to form $L^{45}$, and $L^{45}$ is a $C_4$ to $C_{20}$ hydrocarbylene group or a $C_4$ to $C_{20}$ heterohydrocarbylene group.

Statement 15. The method of any of Statements 13-14, wherein the n input variables $I^1, I^2, \ldots I^n$ comprise or are selected from any one of more of the following variables:
(a) the Cr—P distance (Å);
(b) the Cr—N distance (Å);
(c) the Cr - - - R on α-C distance (Å);
(d) the P—Cr—N angle (deg);
(e) the C—Cr—N angle (deg), wherein C is a non-heteroatomic ligand carbon atom bonded to or within bonding distance of the Cr atom;
(f) the Cr—N—C angle (deg);
(g) the distance out of pocket (Å);
(h) the Cr - - - α-C distance (Å);
(i) the Cr CHELPG (atomic charge);
(j) the P CHELPG (atomic charge);
(k) the N CHELPG (atomic charge);
(l) the Cr—N—C—N Dihedral angle (deg);
(m) the Cr—P—N—C Dihedral angle (deg);
(n) the P—Cr—N—C Dihedral angle (deg);
(o) the P—N—C—N Dihedral angle (deg);
(p) the C—C—N—C Dihedral angle (deg); or
(q) the percent volume buried.

Statement 16. The method of any of Statements 1-12, wherein the one or more ground state model structures and any of the plurality of transition state model structures comprise a chromium heteroatomic ligand moiety independently selected from:

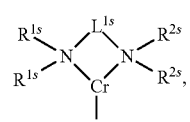

NRNCrM-1

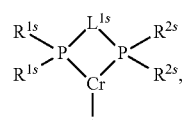

PRPCrM-1

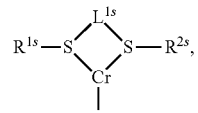

SRSCrM-1

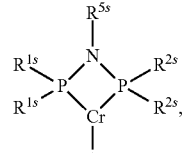

PNPCrM-1

-continued

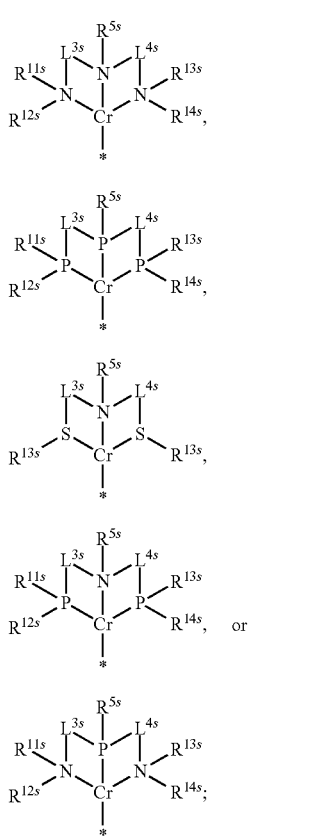

NRNRNCrM-1

PRPRPCrM-1

SRNRSCrM-1

PRNRPCrM-1

NRPRNCrM-1 wherein:
each $R^{1s}$, $R^{2s}$, $R^{5s}$, $R^{11s}$, $R^{12s}$, $R^{13s}$, and $R^{14s}$, independently, is selected from a hydrogen or a $C_1$ to $C_{20}$ organyl group;
each $L^{1s}$, $L^{3s}$, and $L^{4s}$, independently, is selected from a $C_2$ to $C_{20}$ organylene group; and
any two geminal $R^{1s}$ are optionally joined to form $L^{1sr}$, and $L^{1sr}$ is a $C_3$ to $C_{30}$ organylene group;
any two geminal $R^{2s}$ are optionally joined to form $L^{2sr}$, and $L^{2sr}$ is a $C_3$ to $C_{30}$ organylene group;
any germinal $R^{11s}$ and $R^{12s}$ are optionally joined to form $L^{1112sr}$, and $L^{1112sr}$ is a $C_3$ to $C_{30}$ organylene group;
any germinal $R^{13s}$ and $R^{14s}$ are optionally joined to form $L^{1314sr}$, and $L^{1314sr}$ is a $C_3$ to $C_{30}$ organylene group;
where "*" represents any additional bonding required in [1] any of the one or more ground state model structures or any of the plurality of transition state model structures derived from the one or more first training heteroatomic ligand-metal compound complexes, or [2] any of the one or more ground state model structures or any of the plurality of transition state model structures derived from the one or more first target heteroatomic ligand-metal compound complexes.

Statement 17. The method of Statement 16, wherein:
each $R^{1s}$, $R^{2s}$, $R^{5s}$, $R^{11s}$, $R^{12s}$, $R^{13s}$, and $R^{14s}$, independently, is selected from hydrogen, a $C_1$ to $C_{20}$ hydrocarbyl group, or a $C_1$ to $C_{20}$ heterohydrocarbyl group;
each $L^{1s}$, $L^{3s}$, and $L^{4s}$, independently, is selected from a $C_2$ to $C_{20}$ hydrocarbylene group or a $C_2$ to $C_{20}$ heterohydrocarbylene group;

any two geminal $R^{1s}$ are optionally joined to form $L^{1sr}$, and $L^{1sr}$ is a $C_2$ to $C_{20}$ hydrocarbylene group or a $C_2$ to $C_{20}$ heterohydrocarbylene group;
any two geminal $R^{2s}$ are optionally joined to form $L^{2sr}$, and $L^{2sr}$ is a $C_2$ to $C_{20}$ hydrocarbylene group or a $C_2$ to $C_{20}$ heterohydrocarbylene group;
any germinal $R^{11s}$ and $R^{12s}$ are optionally joined to form $L^{12sr}$, and $L^{12sr}$ is a $C_2$ to $C_{20}$ hydrocarbylene group or a $C_2$ to $C_{20}$ heterohydrocarbylene group; and
any germinal $R^{13s}$ and $R^{14s}$ are optionally joined to form $L^{34sr}$, and $L^{34sr}$ is a $C_2$ to $C_{20}$ hydrocarbylene group or a $C_2$ to $C_{20}$ heterohydrocarbylene group.

Statement 18. The method of any of Statements 16-17, wherein the n input variables $I^1, I^2, \ldots I^n$ comprise or are selected from any one of more of the following variables:
(a) the first, second, or third Cr—N distance (Å);
(b) the first, second, or third Cr—P distance (Å);
(c) the first or second Cr—S distance (Å);
(d) any one or more N—Cr—N angle (deg);
(e) any one or more P—Cr—P angle (deg);
(f) any one or more S—Cr—S angle (deg);
(g) any one or more S—Cr—N angle (deg);
(h) any one or more N—Cr—P angle (deg);
(i) the C—Cr—N angle (deg), wherein C is a non-heteroatomic ligand carbon atom bonded to or within bonding distance of the Cr atom;
(j) the C—Cr—P angle (deg);
(k) the C—Cr—S angle (deg);
(l) the Cr—N—C angle (deg);
(m) the Cr—P—C angle (deg);
(n) the Cr—S—C angle (deg);
(o) the Cr—P—C angle (deg);
(p) the Cr - - - R on α-C distance (Å);
(q) the distance out of pocket (Å);
(r) the Cr - - - α-C distance (Å);
(s) the Cr CHELPG (atomic charge);
(t) any P CHELPG (atomic charge);
(u) any N CHELPG (atomic charge);
(v) any chelate Cr—N—C—C Dihedral angle (deg);
(w) any chelate Cr—P—C—C Dihedral angle (deg);
(x) any chelate Cr—S—C—C Dihedral angle (deg); or
(y) the percent volume buried.

Statement 19. The method of any of Statements 1-18, wherein the one or more performance parameters associated with the olefin oligomerization reaction are selected from: (a) an olefin oligomer purity; (b) an olefin oligomer selectivity; (c) a heteroatomic ligand-metal compound complex productivity ("productivity"); or (d) any combination thereof.

Statement 20. The method of any of Statements 1-19, wherein the one or more performance parameters associated with the olefin oligomerization reaction are selected from: (a) 1-hexene purity; (b) 1-octene purity; (c) 1-hexene:1-octene ratio ($C_6/C_8$ ratio); (d) 1-hexene productivity; (e) 1-octene productivity; (f) the total 1-hexene plus 1-octene productivity; or any combination thereof.

Statement 21. The method of any of Statements 9-20, wherein:
a) the one or more ground state model structures $GS^{A1}, \ldots GS^{Ap}$ derived from one or more first training heteroatomic ligand-metal compound complexes comprise or are selected independently from $GS^I$-I, $GS^I$-II, $GS^I$-III, $GS^I$-IV, $GS^I$-V, $GS^I$-VI, $GS^I$-VII, or any combination thereof; and
b) the performance parameter associated with the olefin oligomerization reaction is a heteroatomic ligand-metal compound complex 1-hexene productivity, 1-octene productivity, or a total 1-hexene and 1-octene productivity.

Statement 22. The method of any of Statements 9-21, wherein:
a) the plurality of transition state model structures $TS^{A1}$, $TS^{A2}$, ... $TS^{Am}$ derived from one or more first training heteroatomic ligand-metal compound complexes comprise or are selected independently from $TS^I$-I, $TS^I$-II, $TS^I$-III, $TS^I$-IV, $TS^I$-V, or any combination thereof; and
b) the performance parameter associated with the olefin oligomerization reaction is a heteroatomic ligand-metal compound complex 1-hexene productivity, 1-octene productivity, or a total 1-hexene and 1-octene productivity.

Statement 23. The method of any of Statements 9-22, wherein:
a) the one or more ground state model structures $GS^{B1}$, ... $GS^{Bp}$ derived from the first target heteroatomic ligand-metal compound complex comprise or are selected independently from $GS^T$-I, $GS^T$-II, $GS^T$-III, $GS^T$-IV, $GS^T$-V, $GS^T$-VI, $GS^T$-VII, or any combination thereof; and
b) the performance parameter associated with the olefin oligomerization reaction is a heteroatomic ligand-metal compound complex 1-hexene productivity, 1-octene productivity, or a total 1-hexene and 1-octene productivity.

Statement 24. The method of any of Statements 9-23, wherein:
a) the plurality of transition state model structures $TS^{B1}$, $TS^{B2}$, ... $TS^{Bm}$ derived from the first target heteroatomic ligand-metal compound complex comprise or are selected independently from $TS^T$-I, $TS^T$-II, $TS^T$-III, $TS^T$-IV, $TS^T$-V, or any combination thereof; and
b) the performance parameter associated with the olefin oligomerization reaction is a heteroatomic ligand-metal compound complex 1-hexene productivity, 1-octene productivity, or a total 1-hexene and 1-octene productivity.

Statement 25. The method of any of Statements 9-20, wherein:
a) the one or more ground state model structures $GS^{A1}$, ... $GS^{Ap}$ derived from one or more first training heteroatomic ligand-metal compound complexes comprise $GS^I$-VI; and
b) the performance parameter associated with the olefin oligomerization reaction is the $C_6/C_8$ ratio.

Statement 26. The method of any of Statements 9-20 and 25, wherein:
a) the plurality of transition state model structures $TS^{A1}$, $TS^{A2}$, ... $TS^{Am}$ derived from one or more first training heteroatomic ligand-metal compound complexes comprise $TS^I$-III and $TS^I$-IV; and
b) the performance parameter associated with the olefin oligomerization reaction is the $C_6/C_8$ ratio.

Statement 27. The method of any of Statements 9-20 and 25-26, wherein:
a) the one or more ground state model structures $GS^{B1}$, ... $GS^{Bp}$ derived from the first target heteroatomic ligand-metal compound complex comprise $GS^T$-VI; and
b) the performance parameter associated with the olefin oligomerization reaction is the $C_6/C_8$ ratio.

Statement 28. The method of any of Statements 9-20 and 25-27, wherein:

a) the plurality of transition state model structures $TS^{B1}$, $TS^{B2}$, ... $TS^{Bm}$ derived from the first target heteroatomic ligand-metal compound complex comprise $TS^T$-III and $TS^T$-IV; and
b) the performance parameter associated with the olefin oligomerization reaction is the $C_6/C_8$ ratio.

Statement 29. The method of any of Statements 9-20, wherein:
a) the one or more ground state model structures $GS^{A1}$, ... $GS^{Ap}$ derived from one or more first training heteroatomic ligand-metal compound complexes comprise or are selected independently from $GS^I$-VI, $GS^I$-VIII, $GS^I$-IX, $GS^I$-X, $GS^I$-XI, or any combination thereof; and
b) the performance parameter associated with the olefin oligomerization reaction is 1-hexene purity.

Statement 30. The method of any of Statements 9-20 and 29, wherein:
a) the plurality of transition state model structures $TS^{A1}$, $TS^{A2}$, ... $TS^{Am}$ derived from one or more first training heteroatomic ligand-metal compound complexes comprise or are selected independently from $TS^I$-III, $TS^I$-VI, $TS^I$-VII, $TS^I$-VIII, $TS^I$-IX, $TS^I$-X, $TS^I$-XI, $TS^I$-XII, $TS^I$-XIII, $TS^I$-XIV, $TS^I$-XV, or any combination thereof;
b) the performance parameter associated with the olefin oligomerization reaction is 1-hexene purity.

Statement 31. The method of any of Statements 9-20 and 29-30, wherein:
a) the one or more ground state model structures $GS^{B1}$, ... $GS^{Bp}$ derived from the first target heteroatomic ligand-metal compound complex comprise or are selected independently from $GS^I$-VI, $GS^I$-VIII, $GS^I$-IX, $GS^I$-X, $GS^I$-XI, or any combination thereof, and
b) the performance parameter associated with the olefin oligomerization reaction is 1-hexene purity.

Statement 32. The method of any of Statements 9-20 and 29-31, wherein:
a) the plurality of transition state model structures $TS^{B1}$, $TS^{B2}$, ... $TS^{Bm}$ derived from the first target heteroatomic ligand-metal compound complex comprise or are selected from $TS^I$-III, $TS^I$-VI, $TS^I$-VII, $TS^I$-VIII, $TS^I$-IX, $TS^I$-X, $TS^I$-XI, $TS^I$-XII, $TS^I$-XIII, $TS^I$-XIV, $TS^I$-XV, or any combination thereof, and
b) the performance parameter associated with the olefin oligomerization reaction is 1-hexene purity.

Statement 33. The method of any of Statements 9-20, wherein:
a) the one or more ground state model structures $GS^{A1}$, ... $GS^{Ap}$ derived from one or more first training heteroatomic ligand-metal compound complexes comprise or are selected independently from $GS^I$-VII, $GS^I$-XII, $GS^I$-XIII, or any combination thereof, and
b) the performance parameter associated with the olefin oligomerization reaction is 1-octene purity.

Statement 34. The method of any of Statements 9-20 and 33, wherein:
a) the one or more ground state model structures $GS^{B1}$, ... $GS^{Bp}$ derived from the first target heteroatomic ligand-metal compound complex comprise or are selected independently from $GS^T$-VII, $GS^T$-XII, $GS^T$-XIII, or any combination thereof, and
b) the performance parameter associated with the olefin oligomerization reaction is 1-octene purity.

Statement 35. The method of any of Statements 9-20, wherein:

a) the plurality of transition state model structures $TS^{A1}$, $TS^{A2}$, ... $TS^{Am}$ derived from one or more first training heteroatomic ligand-metal compound complexes comprise a transition state for the addition of the olefin to ground state model structure $GS^I$-VI to form ground state model structure $GS^I$-VII; and/or b) the plurality of transition state model structures $TS^{B1}$, $TS^{B2}$, ... $TS^{Bm}$ derived from one or more first target heteroatomic ligand-metal compound complexes comprise a transition state for the addition of the olefin to ground state model structure $GS^T$-VI to form ground state model structure $GS^T$-VII.

Statement 36. The method of any of Statements 9-20 and 35, wherein:

a) the plurality of transition state model structures $TS^{A1}$, $TS^{A2}$, ... $TS^{Am}$ derived from the first training heteroatomic ligand-metal compound complex comprise the transition state $TS^I$-IV; and/or b) the plurality of transition state model structures $TS^{B1}$, $TS^{B2}$, ... $TS^{Bm}$ derived from the first target heteroatomic ligand-metal compound complex comprise the transition state $TS^T$-IV.

Statement 37. The method of any of Statements 9-20, wherein:

a) the plurality of transition state model structures $TS^{A1}$, $TS^{A2}$, ... $TS^{Am}$ derived from one or more first training heteroatomic ligand-metal compound complexes comprise a transition state for β-H extraction from ground state model structure $GS^I$-VI leading to 1-hexene production and/or a transition state for β-H extraction from ground state model structure $GS^I$-VII leading to 1-octene production; and/or b) the plurality of transition state model structures $TS^{B1}$, $TS^{B2}$, ... $TS^{Bm}$ derived from one or more first target heteroatomic ligand-metal compound complexes comprise a transition state for β-H extraction from ground state model structure $GS^T$-VI leading to 1-hexene production and/or a transition state for β-H extraction from ground state model structure $GS^T$-VII leading to 1-octene production.

Statement 38. The method of any of Statements 37, wherein:

a) the plurality of transition state model structures $TS^{A1}$, $TS^{A2}$, ... $TS^{Am}$ derived from the first training heteroatomic ligand-metal compound complex comprise $TS^I$-III; and/or b) the plurality of transition state model structures $TS^{B1}$, $TS^{B2}$, ... $TS^{Bm}$ derived from the first target heteroatomic ligand-metal compound complex comprise $TS^T$-III.

Statement 39. The method of any of Statements 37-38, wherein:

a) the plurality of transition state model structures $TS^{A1}$, $TS^{A2}$, ... $TS^{Am}$ derived from the first training heteroatomic ligand-metal compound complex comprise $TS^I$-V; and/or b) the plurality of transition state model structures $TS^{B1}$, $TS^{B2}$, ... $TS^{Bm}$ derived from the first target heteroatomic ligand-metal compound complex comprise $TS^T$-V.

Statement 40. The method of any of Statements 37-39, wherein the transition state model for β-H extraction from ground state model structure $GS^I$-VI and/or $GS^T$-VI leading to 1-hexene production is $TS^I$-III and/or $TS^T$-III, respectively.

Statement 41. The method of any of Statements 37-40, wherein the transition state model for β-H extraction from ground state model structure $GS^I$-VII and/or $GS^T$-VII leading to 1-octene production is $TS^I$-V and/or $TS^T$-V, respectively.

Statement 42. The method of any of Statements 1-41, wherein the one or more performance parameters comprises olefin oligomer purity, based upon the mass ratio of 1-hexene to the total of other (non-1-hexene) $C_6$ products calculated as ln[(weight 1-hexene)/(weight non-1-hexene $C_6$)] versus ΔG[TS(1-hexene)-TS(non-1-hexene $C_6$)], or based upon the mass ratio of 1-octene to the total of other (non-1-octene) $C_8$ products and calculated as ln[(weight 1-octene)/(weight non-1-octene $C_8$)] versus ΔG[TS(1-octene)-TS(non-1-octene $C_8$)].

Statement 43. The method of any of Statements 1-41, wherein the one or more performance parameters comprises olefin oligomer selectivity, based upon the mass ratio of 1-hexene to 1-octene and calculated as ln[(weight 1-hexene)/(weight 1-octene)] versus ΔG[TS(1-hexene)-TS(1-octene)].

Statement 44. The method of any of Statements 1-43, wherein the one or more performance parameters associated with the olefin oligomerization comprises heteroatomic ligand-metal compound complex productivity, based upon the grams of olefin oligomer(s) (grams 1-hexene, grams 1-octene, or the total grams of 1-hexene and 1-octene) per grams of the heteroatomic ligand-metal compound complex per hour.

Statement 45. The method of any of Statements 1-44, wherein the quantitative value assigned to each n input variable $I^1, I^2, \ldots I^n$, for each of the one or more ground state model structures $GS^{A1}, \ldots GS^{Ap}$ and each of the plurality of transition state model structures $TS^{A1}, TS^{A2}, \ldots TS^{Am}$ derived from the one or more first training heteroatomic ligand-metal compound complexes are assigned on the basis of calculated, measured, or estimated values, or any combination thereof.

Statement 46. The method of any of Statements 1-45, wherein the one or more of the n input variables $I^1, I^2, \ldots I^n$ identified in step (e) are identified based upon the greater percentage changes in [1] the difference in energies between any of the one or more ground state model structures $GS^{A1}, \ldots GS^{Ap}$ and at least one of the plurality of transition state model structures $TS^{A1}, TS^{A2}, \ldots TS^{Am}$ [ΔG(TS-GS) or ΔΔG(TS-GS)] or [2] the difference in energies between any two or more of the plurality of transition state model structures $TS^{A1}, TS^{A2}, \ldots TS^{Am}$ [ΔG(TS-TS) or ΔΔG(TS-TS)], for each percentage change in the one or more of the n input variables $I^1, I^2, \ldots I^n$ which influence ΔG(TS-GS), ΔΔG(TS-GS), or ΔΔG(TS-TS).

Statement 47. The method of any of Statements 1-46, wherein the step of generating the second target heteroatomic ligand-metal compound complex comprises:

(a) adjusting the quantitative value of one or more n input variables $I^1, I^2, \ldots I^n$ or $I^{1.1}, I^{2.1}, \ldots I^{n.1}$ to approach the value of the corresponding n output variables $O^1, O^2, \ldots O^n$ or $O^{1.1}, O^{2.1}, \ldots O^{n.1}$ in any first training heteroatomic ligand-metal compound complex comprising a chromium heteroatomic ligand moiety independently selected from NPFCrM-1, NPACrM-1, GuCrM-1, GuCrM-2, GuCrM-3, GuCrM-4, GuCrM-5, or HCPACrM-1, by:

[1] independently increasing or decreasing the steric bulk of one or more of the groups $R^1, R^2, L^{12r}, R^{2a}, R^{2b}, L^{12}, L^{23}, L^{22}, R^3, R^4, R^5$, and $L^{45}$;

[2] independently changing the inductive electronic effects of one or more of the groups $R^1, R^2, L^{12r}, R^{2a}$, $R^{2b}$, $L^{12}$, $L^{23}$, $L^{22}$, $R^3$, $R^4$, $R^5$, and $L^{45}$ with one or more +I substituent or one or more −I substituent;

[3] independently increasing or decreasing the saturation in one or more of the organyl groups or organylene groups;

[4] increasing or decreasing the polarity of a solvent used for olefin oligomerization; or

[5] any combination thereof;

and (b) generating, based upon the at least one adjusted n input variable from step (a) a second target heteroatomic ligand-metal compound complex for olefin oligomerization and comprising a second target heteroatomic ligand.

Statement 48. The method of any of Statements 1-46, wherein the step of generating the second target heteroatomic ligand-metal compound complex comprises:

(a) adjusting the quantitative value of one or more n input variables $I^1$, $I^2$, ... $I^n$ or $I^{1.1}$, $I^{2.1}$, ... $I^{n.1}$ to approach the value of the corresponding n output variables $O^1$, $O^2$, ... $O^n$ or $O^{1.1}$, $O^{2.1}$, ... $O^{n.1}$ in any first training heteroatomic ligand-metal compound complex comprising a chromium heteroatomic ligand moiety independently selected from NRNCrM-1, PRPCrM-1, SRSCrM-1, PNPCrM-1, NRNRNCrM-1, PRPRPCrM-1, SRNRSCrM-1, PRNRPCrM-1, or NRPRNCrM-1, by:

[1] independently increasing or decreasing the steric bulk of one or more of the groups $R^{1s}$, $R^{2s}$, $R^{5s}$, $R^{11s}$, $R^{12s}$, $R^{13s}$, $R^{14s}$, $L^{1s}$, $L^{3s}$, $L^{4s}$, $L^{1sr}$, $L^{1sr}$, $L^{12sr}$, and $L^{34sr}$

[2] independently changing the inductive electronic effects of one or more of the groups $R^{1s}$, $R^{2s}$, $R^{5s}$, $R^{11s}$, $R^{12s}$, $R^{13s}$, $R^{14s}$, $L^{1s}$, $L^{3s}$, $L^{4s}$, $L^{1sr}$, $L^{1sr}$, $L^{12sr}$, and $L^{34sr}$ with one or more +I substituent or one or more −I substituent;

[3] independently increasing or decreasing the saturation in one or more of the organyl groups or organylene groups;

[4] increasing or decreasing the polarity of a solvent used for olefin oligomerization; or

[5] any combination thereof;

and (b) generating, based upon the at least one adjusted n input variable from step (a) a second target heteroatomic ligand-metal compound complex for olefin oligomerization and comprising a second target heteroatomic ligand.

Statement 49. The method of any of Statements 1-48, wherein any of the ground state model structures $GS^{A1}$, ... $GS^{Ap}$ or any of the plurality of transition state model structures $TS^{A1}$, $TS^{A2}$, ... $TS^{Am}$ derived from the one or more first training heteroatomic ligand-metal compound complexes are calculated using a density functional theory (DFT) calculations.

Statement 50. The method of any of Statements 1-49, wherein generating the machine learning model comprises a Gaussian Process Algorithm or a Random Forest Algorithm.

Statement 51. A method for designing a heteroatomic ligand-metal compound complex for olefin oligomerization, the method comprising:

(a) selecting n input variables $I^1$, $I^2$, ... $I^n$ (n is an integer), each input variable corresponding to a structural property or an electronic property of one or more ground state model structures $GS^{A1}$, ... $GS^{Ap}$ (p is an integer) and a plurality of transition state model structures $TS^{A1}$, $TS^{A2}$, ... $TS^{Am}$ (m is an integer) associated with the one or more ground state model structures, wherein each of the one or more ground state model structures $GS^{A1}$, ... $GS^{Ap}$ and each of the plurality of transition state model structures $TS^{A1}$, $TS^{A2}$, ... $TS^{Am}$ are generated from one or more first training heteroatomic ligand-metal compound complexes, each complex comprising a first training heteroatomic ligand;

(b) assigning a quantitative value to each n input variable $I^1$, $I^2$, ... $I^n$, for each of the ground state model structures $GS^{A1}$, ... $GS^{Ap}$ and each of the transition state model structures $TSA^1$, $TS^{A2}$, ... $TS^{Am}$;

(c) determining, by at least one processor of a device, the relative energies of each of the ground state model structures $GS^{A1}$, ... $GS^{Ap}$ and each of the transition state model structures $TS^{A1}$, $TS^{A2}$, ... $TS^{Am}$;

(d) generating a machine learning model to correlate the quantitative value of each n input variable $I^1$, $I^2$, ... $I^n$ and the relative energies of each of the ground state model structures $GS^{A1}$, ... $GS^{Ap}$ and each of the transition state model structures $TS^{A1}$, $TS^{A2}$, ... $TS^{Am}$;

(e) determining, using the machine learning model, a relationship between one or more of the n input variables $I^1$, $I^2$, ... $I^n$ and [1] the difference in energies between one of the ground state model structures $GS^{A1}$, ... $GS^{Ap}$ and at least one of the plurality of transition state model structures $TS^{A1}$, $TS^{A2}$, ... $TS^{Am}$ [$\Delta G$(TS-GS) or $\Delta\Delta G$(TS-GS)] or [2] the difference in energies between any two or more of the plurality of transition state model structures $TS^{A1}$, $TS^{A2}$, ... $TS^{Am}$ [$\Delta G$(TS-TS) or $\Delta\Delta G$(TS-TS)];

(f) generating, based upon the relationship identified from step (e), an output of the machine learning model comprising a first target heteroatomic ligand-metal compound complex for olefin oligomerization and comprising a first target heteroatomic ligand, wherein the first target heteroatomic ligand-metal compound complex is characterized by n output variables $O^1$, $O^2$, ... $O^n$, each having a quantitative value corresponding to a structural property or an electronic property of one or more ground state model structures $GS^{B1}$, ... $GS^{Bx}$ (x is an integer) or any of a plurality of transition state model structures $TS^{B1}$, $TS^{B2}$, ... $TS^{By}$ (y is an integer) associated with the one or more ground state model structures, wherein each of the one or more ground state model structures $GS^{B1}$, ... $GS^{Bx}$ and each of the plurality of transition state model structures $TS^{B1}$, $TS^{B2}$, ... $TS^{By}$ are generated from the first target heteroatomic ligand-metal compound complex, each complex comprising a first target heteroatomic ligand, and wherein the n output variables $O^1$, $O^2$ ... $O^n$ are reused as new n input variables $I^{1.1}$, $I^{2.1}$, ... $I^{n.1}$ to the machine learning model;

(g) identifying one or more performance parameters associated with an olefin oligomerization reaction and the value of the performance parameters for the one or more first training heteroatomic ligand-metal compound complexes and the first target heteroatomic ligand-metal compound complex; and (h) repeating steps (a)-(f) one or more times using the quantitative values of the n output variables $O^1$, $O^2$, ... $O^n$ of the first target heteroatomic ligand-metal compound complex as an input dataset of the new n input variables $I^{1.1}$, $I^{2.1}$, ... $I^{n.1}$, the new n input variables $I^{1.1}$, $I^{2.1}$, ... $I^{n.1}$ derived from one or more second training heteroatomic ligand-metal compound complexes for olefin oligomerization and comprising a second training heteroatomic ligand, which is input into the machine learning model to generate a second target heteroatomic ligand-metal compound complex comprising a second target heteroatomic ligand, wherein the second target heteroatomic ligand-metal compound complex is characterized by quantitative values of an output dataset of new n output variables $O^{1.1}$, $O^{2.1}$, ... $O^{n.1}$, and having one or more second target heteroatomic ligand-metal compound complex performance parameter values.

Statement 52. The method of Statement 51, further comprising the step of:
(i) [1] synthesizing the first target heteroatomic ligand and/or the second target heteroatomic ligand; or [2] synthesizing the first target heteroatomic ligand and/or the second target heteroatomic ligand, followed by synthesizing the first target heteroatomic ligand-metal compound complex or the second target heteroatomic ligand-metal compound complex.

Statement 53. The method of Statement 52, further comprising the step of:
(j) performing the olefin oligomerization reaction by: [1] contacting the first target heteroatomic ligand or the second target heteroatomic ligand, a metal compound, an organometal compound, and an olefin; or [2] contacting the first target heteroatomic ligand-metal compound complex or the second target heteroatomic ligand-metal compound complex, an organometal compound, and an olefin.

Statement 54. The method of any of Statements 51-53, wherein at least one input variable $I^1, I^2, \ldots I^n$ corresponds to a structural property or an electronic property of at least one of the one or more ground state model structures $GS^{A1}, \ldots GS^{Ap}$.

Statement 55. The method of any of Statements 51-54, wherein at least one input variable $I^1, I^2, \ldots I^n$ corresponds to a structural property or an electronic property of at least one of the plurality of transition state model structures $TS^{A1}, TS^{A2}, \ldots TS^{Am}$.

Statement 56. The method of any of Statements 51-55, wherein step (e) identifies, based on the machine learning model, one or more of the n input variables $I^1, I^2, \ldots I^n$ associated with the difference in energies between any of the one or more ground state model structures $GS^{A1}, \ldots GS^{Ap}$ and at least one of the plurality of transition state model structures $TS^{A1}, TS^{A2}, \ldots TS^{Am}$ [ΔG(TS-GS) or ΔΔG(TS-GS)].

Statement 57. The method of any of Statements 51-56, wherein step (e) identifies, based on the machine learning model, one or more of the n input variables $I^1, I^2, \ldots I^n$ associated with the difference in energies between any two or more of the plurality of transition state model structures $TS^{A1}, TS^{A2}, \ldots TS^{Am}$ [ΔΔG(TS-TS)].

Statement 58. The method of any of Statements 51-57, wherein the one or more first training heteroatomic ligand-metal compound complexes have a formula independently selected from:

[(HetLig)CrX$_q$L$_r$]$^{3-q}$(A); wherein:

HetLig represents the one or more first training heteroatomic ligands;
X is an anionic ligand, and q is an integer;
L is a neutral ligand, and r is an integer,
wherein any two or more of the X and L ligands may be linked to form a multidentate ligand; and
wherein each selected n input variable $I^1, I^2, \ldots I^n$, corresponds to a structural property or an electronic property of any of the one or more ground state model structures $GS^{A1}, \ldots GS^{Ap}$ or any of the plurality of transition state model structures $TS^{A1}, TS^{A2}, \ldots TS^{Am}$ associated with the one or more ground state model structures of formula (A).

Statement 59. The method of any of Statements 51-58, wherein the one or more ground state model structures $GS^{A1}, \ldots GS^{Ap}$ derived from the one or more first training heteroatomic ligand-metal compound complexes are selected independently from:

(GS$^I$-I)

(GS$^I$-II)

(GS$^I$-III)

(GS$^I$-IV)

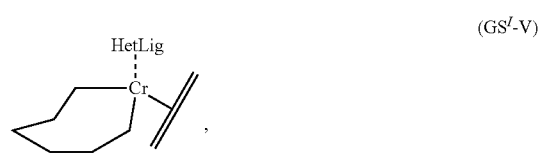
(GS$^I$-V)

(GS$^I$-VI)

(GS$^I$-VII)

(GS$^I$-VIII)

-continued

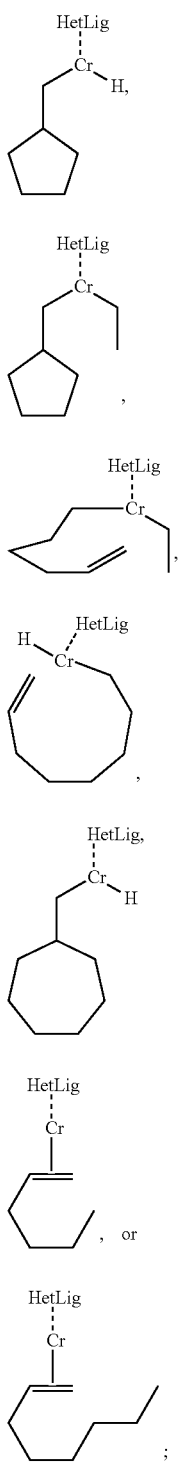

(GS$^I$-IX), (GS$^I$-X), (GS$^I$-XI), (GS$^I$-XII), (GS$^I$-XIII), (GS$^I$-XIV), (GS$^I$-XV)

wherein HetLig represents the one or more first training heteroatomic ligands.

Statement 60. The method of any of Statements 51-59, wherein the plurality of transition state model structures $TS^{A1}$, $TS^{A2}$, ... $TS^{Am}$ derived from the one or more first training heteroatomic ligand-metal compound complexes are selected independently from:

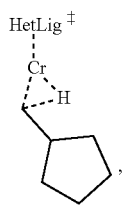

(TS$^I$-I), (TS$^I$-II), (TS$^I$-III), (TS$^I$-IV), (TS$^I$-V), (TS$^I$-VI), (TS$^I$-VII), (TS$^I$-VIII), (TS$^I$-IX)

(TS$^I$-X)

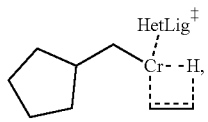

(TS$^I$-XI)

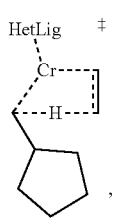

(TS$^I$-XII)

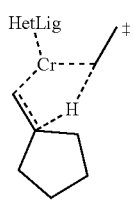

(TS$^I$-XIII)

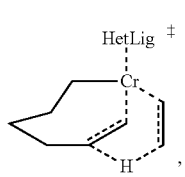

(TS$^I$-XIV)

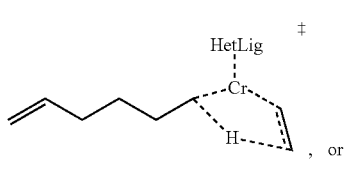, or (TS$^I$-XV)

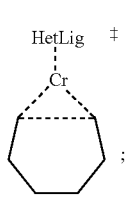;

wherein HetLig represents the one or more first training heteroatomic ligands.

Statement 61. The method of any of Statements 51-60, wherein the one or more ground state model structures GS$^{B1}$, ... GS$^{Bx}$ derived from the one or more first target heteroatomic ligand-metal compound complexes are selected independently from:

(GS$^T$-I)

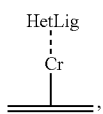

(GS$^T$-II)

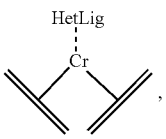

(GS$^T$-III)

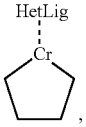

(GS$^T$-IV)

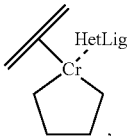

(GS$^T$-V)

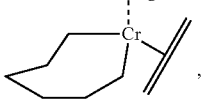

(GS$^T$-VI)

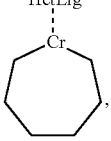

(GS$^T$-VII)

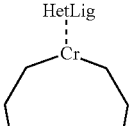

(GS$^T$-VIII)

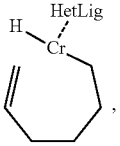

(GS$^T$-IX)

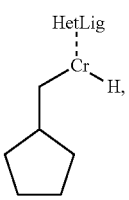

(GS$^T$-X)

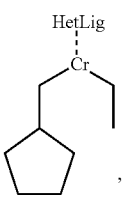

-continued (GS^T-XI)
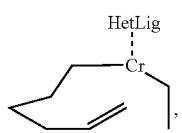,

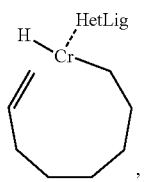, (GS^T-XII)

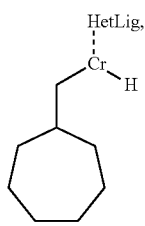, (GS^T-XIII)

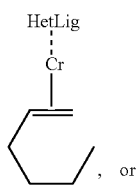, or

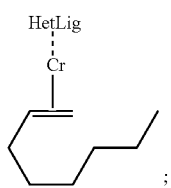;

wherein HetLig represents the one or more first target heteroatomic ligands.

Statement 62. The method of any of Statements 51-61, wherein the plurality of transition state model structures $TS^{A1}, TS^{A2}, \ldots TS^{Am}$ derived from the one or more first target heteroatomic ligand-metal compound complexes are selected independently from:

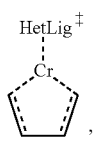, (TS^T-I)

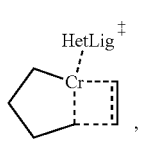, (TS^T-II)

-continued (TS^T-III)
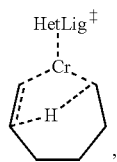, (TS^L-IV)
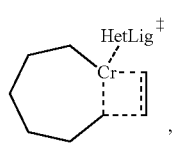, (TS^T-V)
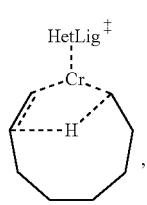, (TS^T-VI)
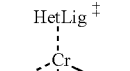, (TS^T-VII)
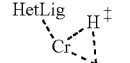, (TS^T-VIII)
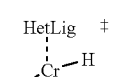, (TS^T-IX)
,

, (TS^T-X)
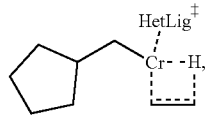,

-continued

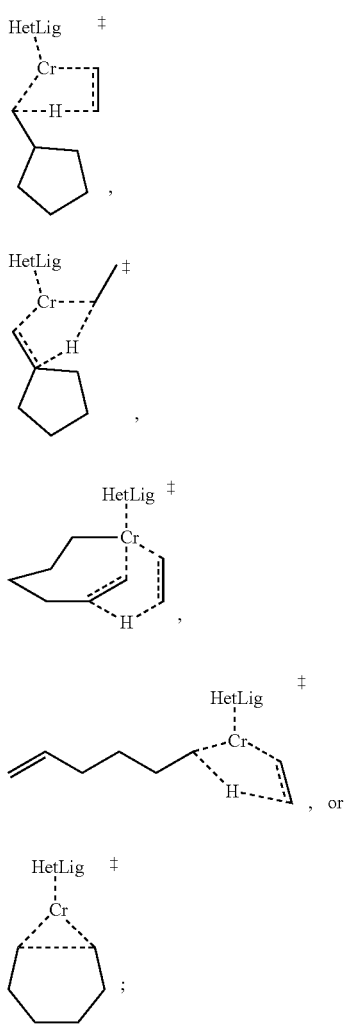

(TS$^T$-XI), (TS$^T$-XII), (TS$^T$-XIII), (TS$^T$-XIV), or (TS$^T$-XV);

wherein HetLig represents the one or more first target heteroatomic ligands.

Statement 63. The method of any of Statements 51-62, wherein the one or more ground state model structures and any of the plurality of transition state model structures comprise a chromium heteroatomic ligand moiety independently selected from:

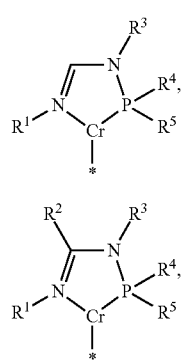

NPFCrM-1

NPACrM-1

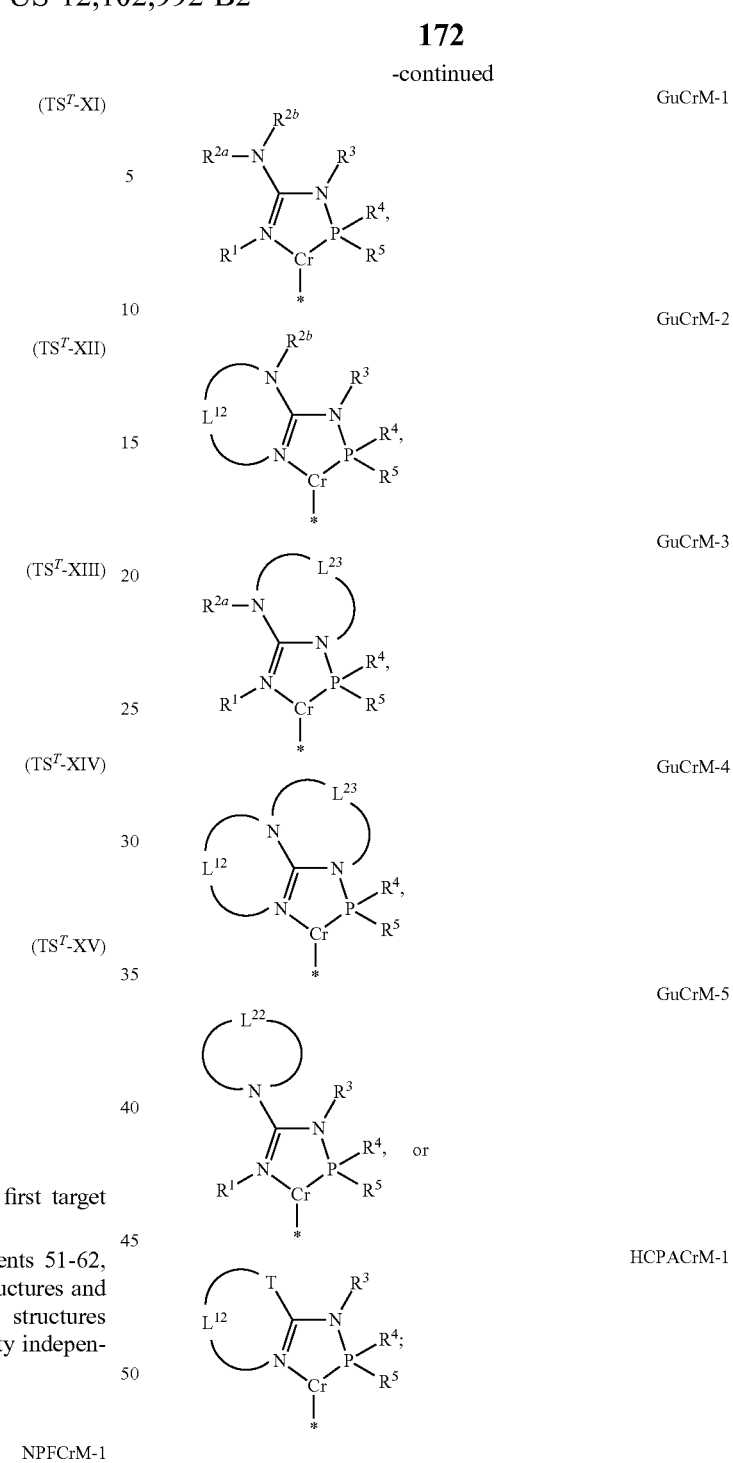

GuCrM-1

GuCrM-2

GuCrM-3

GuCrM-4

GuCrM-5 or

HCPACrM-1 wherein:
  $R^1$ is a hydrogen or a $C_1$ to $C_{20}$ organyl group;
  $R^2$ is a $C_1$ to $C_{20}$ organyl group;
  T is oxygen or sulfur;
  $R^{2a}$ and $R^{2b}$ independently are $C_1$ to $C_{20}$ organyl groups;
  $L^{12}$ and $L^{23}$ independently are $C_2$ to $C_{20}$ organylene groups;
  $L^{22}$ is a $C_3$ to $C_{20}$ organylene groups;
  $R^3$ is hydrogen or a $C_1$ to $C_{20}$ organyl group; and
  $R^4$ and $R^5$ independently are hydrogen or a $C_1$ to $C_{20}$ organyl groups;
  where $R^1$ and $R^2$ are optionally joined to form $L^{12r}$, and $L^{12r}$ is a $C_3$ to $C_{30}$ organylene group;

where R⁴ and R⁵ are optionally joined to form L⁴⁵, and L⁴⁵ is a C₄ to C₃₀ organylene group; and where "*" represents any additional bonding required in [1] any of the one or more ground state model structures or any of the plurality of transition state model structures derived from the one or more first training heteroatomic ligand-metal compound complexes, or [2] any of the one or more ground state model structures or any of the plurality of transition state model structures derived from the one or more first target heteroatomic ligand-metal compound complexes.

Statement 64. The method of Statement 63, wherein:

R¹ is hydrogen, a C₁ to C₂₀ hydrocarbyl group, or a C₁ to C₂₀ heterohydrocarbyl group;

R² is a C₁ to C₂₀ hydrocarbyl group or a C₁ to C₂₀ heterohydrocarbyl group;

R²ᵃ and R²ᵇ are independently selected from a C₁ to C₂₀ hydrocarbyl group or a C₁ to C₂₀ heterohydrocarbyl group;

L¹² and L²³ are independently selected from a C₂ to C₂₀ hydrocarbylene group or a C₂ to C₂₀ heterohydrocarbylene group;

L²² is a C₃ to C₂₀ hydrocarbylene group or a C₃ to C₂₀ heterohydrocarbylene group;

R³ is hydrogen, a C₁ to C₂₀ hydrocarbyl group, or a C₁ to C₂₀ heterohydrocarbyl group; and R⁴ and R⁵ are independently selected from a C₁ to C₂₀ hydrocarbyl group or a C₁ to C₂₀ heterohydrocarbyl group;

where R¹ and R² are optionally joined to form L¹²ʳ, and L¹²ʳ is a C₃ to C₂₀ hydrocarbylene group or a C₃ to C₂₀ heterohydrocarbylene group; and where R⁴ and R⁵ are optionally joined to form L⁴⁵, and L⁴⁵ is a C₄ to C₂₀ hydrocarbylene group or a C₄ to C₂₀ heterohydrocarbylene group.

Statement 65. The method of any of Statements 63-64, wherein the n input variables I¹, I², ... Iⁿ comprise or are selected from any one of more of the following variables:

(a) the Cr—P distance (Å);
(b) the Cr—N distance (Å);
(c) the Cr - - - R on α-C distance (Å);
(d) the P—Cr—N angle (deg);
(e) the C—Cr—N angle (deg), wherein C is a non-heteroatomic ligand carbon atom bonded to or within bonding distance of the Cr atom;
(f) the Cr—N—C angle (deg);
(g) the distance out of pocket (Å);
(h) the Cr - - - α-C distance (Å);
(i) the Cr CHELPG (atomic charge);
(j) the P CHELPG (atomic charge);
(k) the N CHELPG (atomic charge);
(l) the Cr—N—C—N Dihedral angle (deg);
(m) the Cr—P—N—C Dihedral angle (deg);
(n) the P—Cr—N—C Dihedral angle (deg);
(o) the P—N—C—N Dihedral angle (deg);
(p) the C—C—N—C Dihedral angle (deg); or
(q) the percent volume buried.

Statement 66. The method of any of Statements 51-62, wherein the one or more ground state model structures and any of the plurality of transition state model structures comprise a chromium heteroatomic ligand moiety independently selected from:

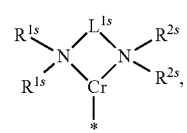
NRNCrM-1

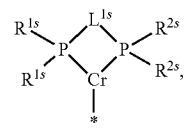
PRPCrM-1

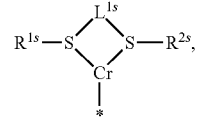
SRSCrM-1

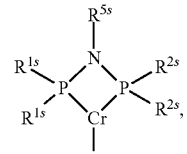
PNPCrM-1

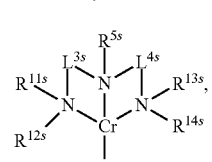
NRNRNCrM-1

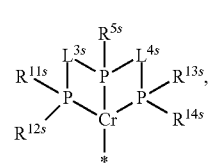
PRPRPCrM-1

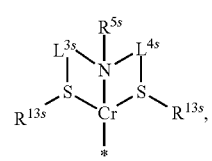
SRSNSCrM-1

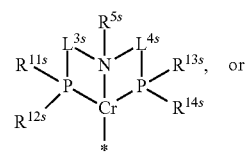
PRNRPCrM-1, or

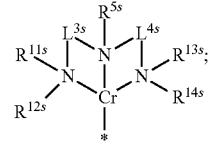
NRPRNCrM-1 wherein:
each R¹ˢ, R²ˢ, R⁵ˢ, R¹¹ˢ, R¹²ˢ, R¹³ˢ, and R¹⁴ˢ, independently, is selected from a hydrogen or a C₁ to C₂₀ organyl group;

each L¹ˢ, L³ˢ, and L⁴ˢ, independently, is selected from a C₂ to C₂₀ organylene group; and any two geminal R¹ˢ are optionally joined to form L¹ˢʳ, and L¹ˢʳ is a C₃ to C₃₀ organylene group;

any two geminal R²ˢ are optionally joined to form L²ˢʳ, and L²ˢʳ is a C₃ to C₃₀ organylene group;

any germinal $R^{11s}$ and $R^{12s}$ are optionally joined to form $L^{1112sr}$, and $L^{1112sr}$ is a $C_3$ to $C_{30}$ organylene group;

any germinal $R^{13s}$ and $R^{14s}$ are optionally joined to form $L^{1314sr}$, and $L^{1314sr}$ is a $C_3$ to $C_{30}$ organylene group;

where "*" represents any additional bonding required in [1] any of the one or more ground state model structures or any of the plurality of transition state model structures derived from the one or more first training heteroatomic ligand-metal compound complexes, or [2] any of the one or more ground state model structures or any of the plurality of transition state model structures derived from the one or more first target heteroatomic ligand-metal compound complexes.

Statement 67. The method of Statement 66, wherein:
each $R^{1s}$, $R^{2s}$, $R^{5s}$, $R^{11s}$, $R^{12s}$, $R^{13s}$, and $R^{14s}$, independently, is selected from hydrogen, a $C_1$ to $C_{20}$ hydrocarbyl group, or a $C_1$ to $C_{20}$ heterohydrocarbyl group;
each $L^{1s}$, $L^{3s}$, and $L^{4s}$, independently, is selected from a $C_2$ to $C_{20}$ hydrocarbylene group or a $C_2$ to $C_{20}$ heterohydrocarbylene group;
any two geminal $R^{1s}$ are optionally joined to form $L^{1s}$, and $L^{1sr}$ is a $C_2$ to $C_{20}$ hydrocarbylene group or a $C_2$ to $C_{20}$ heterohydrocarbylene group;
any two geminal $R^{2s}$ are optionally joined to form $L^{2sr}$, and $L^{2sr}$ is a $C_2$ to $C_{20}$ hydrocarbylene group or a $C_2$ to $C_{20}$ heterohydrocarbylene group;
any germinal $R^{11s}$ and $R^{12s}$ are optionally joined to form $L^{12sr}$, and $L^{12sr}$ is a $C_2$ to $C_{20}$ hydrocarbylene group or a $C_2$ to $C_{20}$ heterohydrocarbylene group; and
any germinal $R^{13s}$ and $R^{14s}$ are optionally joined to form $L^{34sr}$, and $L^{34sr}$ is a $C_2$ to $C_{20}$ hydrocarbylene group or a $C_2$ to $C_{20}$ heterohydrocarbylene group.

Statement 68. The method of any of Statements 66-67, wherein the n input variables $I^1$, $I^2$, ... $I^n$ comprise or are selected from any one of more of the following variables:
(a) the first, second, or third Cr—N distance (Å);
(b) the first, second, or third Cr—P distance (Å);
(c) the first or second Cr—S distance (Å);
(d) any one or more N—Cr—N angle (deg);
(e) any one or more P—Cr—P angle (deg);
(f) any one or more S—Cr—S angle (deg);
(g) any one or more S—Cr—N angle (deg);
(h) any one or more N—Cr—P angle (deg);
(i) the C—Cr—N angle (deg), wherein C is a non-heteroatomic ligand carbon atom bonded to or within bonding distance of the Cr atom;
(j) the C—Cr—P angle (deg);
(k) the C—Cr—S angle (deg);
(l) the Cr—N—C angle (deg);
(m) the Cr—P—C angle (deg);
(n) the Cr—S—C angle (deg);
(o) the Cr—P—C angle (deg);
(p) the Cr - - - R on α-C distance (Å);
(q) the distance out of pocket (Å);
(r) the Cr - - - α-C distance (Å);
(s) the Cr CHELPG (atomic charge);
(t) any P CHELPG (atomic charge);
(u) any N CHELPG (atomic charge);
(v) any chelate Cr—N—C—C Dihedral angle (deg);
(w) any chelate Cr—P—C—C Dihedral angle (deg);
(x) any chelate Cr—S—C—C Dihedral angle (deg); or
(y) the percent volume buried.

Statement 69. The method of any of Statements 51-68, wherein the one or more performance parameters associated with the olefin oligomerization reaction are selected from: (a) an olefin oligomer purity; (b) an olefin oligomer selectivity; (c) a heteroatomic ligand-metal compound complex productivity ("productivity"); or (d) any combination thereof.

Statement 70. The method of any of Statements 51-69, wherein the one or more performance parameters associated with the olefin oligomerization reaction are selected from: (a) 1-hexene purity; (b) 1-octene purity; (c) 1-hexene:1-octene ratio ($C_6/C_8$ ratio); (d) 1-hexene productivity; (e) 1-octene productivity; (f) the total 1-hexene plus 1-octene productivity; (g) trimerization selectivity to 1-hexene; (h) tetramerization selectivity to 1-octene; (i) 1-octene efficiency of fourth ethylene addition; or any combination thereof.

Statement 71. The method of any of Statements 59-70, wherein:
a) the one or more ground state model structures $GS^{A1}$, ... $GS^{Ap}$ derived from one or more first training heteroatomic ligand-metal compound complexes comprise or are selected independently from $GS^I$-I, $GS^I$-II, $GS^I$-III, $GS^I$-IV, $GS^I$-V, $GS^I$-VI, $GS^I$-VII, or any combination thereof; and
b) the performance parameter associated with the olefin oligomerization reaction is a heteroatomic ligand-metal compound complex 1-hexene productivity, 1-octene productivity, or a total 1-hexene and 1-octene productivity.

Statement 72. The method of any of Statements 59-71, wherein:
a) the plurality of transition state model structures $TS^{A1}$, $TS^{A2}$, ... $TS^{Am}$ derived from one or more first training heteroatomic ligand-metal compound complexes comprise or are selected independently from $TS^I$-I, $TS^I$-II, $TS^I$-III, $TS^I$-IV, $TS^I$-V, or any combination thereof; and
b) the performance parameter associated with the olefin oligomerization reaction is a heteroatomic ligand-metal compound complex 1-hexene productivity, 1-octene productivity, or a total 1-hexene and 1-octene productivity.

Statement 73. The method of any of Statements 59-72, wherein:
a) the one or more ground state model structures $GS^{B1}$, ... $GS^{Bp}$ derived from the first target heteroatomic ligand-metal compound complex comprise or are selected independently from $GS^T$-I, $GS^T$-II, $GS^T$-III, $GS^T$-IV, $GS^T$-V, $GS^T$-VI, $GS^T$-VII, or any combination thereof; and
b) the performance parameter associated with the olefin oligomerization reaction is a heteroatomic ligand-metal compound complex 1-hexene productivity, 1-octene productivity, or a total 1-hexene and 1-octene productivity.

Statement 74. The method of any of Statements 59-73, wherein:
a) the plurality of transition state model structures $TS^{B1}$, $TS^{B2}$, ... $TS^{Bm}$ derived from the first target heteroatomic ligand-metal compound complex comprise or are selected independently from $TS^T$-I, $TS^T$-II, $TS^T$-III, $TS^T$-IV, $TS^T$-V, or any combination thereof; and
b) the performance parameter associated with the olefin oligomerization reaction is a heteroatomic ligand-metal compound complex 1-hexene productivity, 1-octene productivity, or a total 1-hexene and 1-octene productivity.

Statement 75. The method of any of Statements 59-70, wherein:

a) the one or more ground state model structures $GS^{A1}, \ldots GS^{Ap}$ derived from one or more first training heteroatomic ligand-metal compound complexes comprise $GS^I$-VI; and
b) the performance parameter associated with the olefin oligomerization reaction is the $C_6/C_8$ ratio.

Statement 76. The method of any of Statements 59-70 and 75, wherein:
a) the plurality of transition state model structures $TS^{A1}, TS^{A2}, \ldots TS^{Am}$ derived from one or more first training heteroatomic ligand-metal compound complexes comprise $TS^I$-III and $TS^I$-IV; and
b) the performance parameter associated with the olefin oligomerization reaction is the $C_6/C_8$ ratio.

Statement 77. The method of any of Statements 59-70 and 75-76, wherein:
a) the one or more ground state model structures $GS^{B1}, \ldots GS^{Bp}$ derived from the first target heteroatomic ligand-metal compound complex comprise $GS^T$-VI; and
b) the performance parameter associated with the olefin oligomerization reaction is the $C_6/C_8$ ratio.

Statement 78. The method of any of Statements 59-70 and 75-77, wherein:
a) the plurality of transition state model structures $TS^{B1}, TS^{B2}, \ldots TS^{Bm}$ derived from the first target heteroatomic ligand-metal compound complex comprise $TS^T$-III and $TS^T$-IV; and
b) the performance parameter associated with the olefin oligomerization reaction is the $C_6/C_8$ ratio.

Statement 79. The method of any of Statements 59-70, wherein:
a) the one or more ground state model structures $GS^{A1}, \ldots GS^{Ap}$ derived from one or more first training heteroatomic ligand-metal compound complexes comprise or are selected independently from $GS^I$-VI, $GS^I$-VIII, $GS^I$-IX, $GS^I$-X, $GS^I$-XI, or any combination thereof; and
b) the performance parameter associated with the olefin oligomerization reaction is 1-hexene purity.

Statement 80. The method of any of Statements 59-70 and 79, wherein:
a) the plurality of transition state model structures $TS^{A1}, TS^{A2}, \ldots TS^{Am}$ derived from one or more first training heteroatomic ligand-metal compound complexes comprise or are selected independently from $TS^I$-III, $TS^I$-VI, $TS^I$-VII, $TS^I$-VIII, $TS^I$-IX, $TS^I$-X, $TS^I$-XI, $TS^I$-XII, $TS^I$-XIII, $TS^I$-XIV, $TS^I$-XV, or any combination thereof;
b) the performance parameter associated with the olefin oligomerization reaction is 1-hexene purity.

Statement 81. The method of any of Statements 59-70 and 79-80, wherein:
a) the one or more ground state model structures $GS^{B1}, \ldots GS^{Bp}$ derived from the first target heteroatomic ligand-metal compound complex comprise or are selected independently from $GS^I$-VI, $GS^I$-VIII, $GS^I$-IX, $GS^I$-X, $GS^I$-XI, or any combination thereof; and
b) the performance parameter associated with the olefin oligomerization reaction is 1-hexene purity.

Statement 82. The method of any of Statements 59-70 and 79-81, wherein:
a) the plurality of transition state model structures $TS^{B1}, TS^{B2}, \ldots TS^{Bm}$ derived from the first target heteroatomic ligand-metal compound complex comprise or are selected from $TS^I$-III, $TS^I$-VI, $TS^I$-VII, $TS^I$-VIII, $TS^I$-IX, $TS^I$-X, $TS^I$-XI, $TS^I$-XII, $TS^I$-XIII, $TS^I$-XIV, $TS^I$-XV, or any combination thereof; and
b) the performance parameter associated with the olefin oligomerization reaction is 1-hexene purity.

Statement 83. The method of any of Statements 59-70, wherein:
a) the one or more ground state model structures $GS^{A1}, \ldots GS^{Ap}$ derived from one or more first training heteroatomic ligand-metal compound complexes comprise or are selected independently from $GS^I$-VII, $GS^I$-XII, $GS^I$-XIII, or any combination thereof; and
b) the performance parameter associated with the olefin oligomerization reaction is 1-octene purity.

Statement 84. The method of any of Statements 59-70 and 83, wherein:
a) the one or more ground state model structures $GS^{B1}, \ldots GS^{Bp}$ derived from the first target heteroatomic ligand-metal compound complex comprise or are selected independently from $GS^T$-VII, $GS^T$-XII, $GS^T$-XIII, or any combination thereof; and
b) the performance parameter associated with the olefin oligomerization reaction is 1-octene purity.

Statement 85. The method of any of Statements 59-70, wherein:
a) the plurality of transition state model structures $TS^{A1}, TS^{A2}, \ldots TS^{Am}$ derived from one or more first training heteroatomic ligand-metal compound complexes comprise a transition state for the addition of the olefin to ground state model structure $GS^I$-VI to form ground state model structure $GS^I$-VII; and/or
b) the plurality of transition state model structures $TS^{B1}, TS^{B2}, \ldots TS^{Bm}$ derived from one or more first target heteroatomic ligand-metal compound complexes comprise a transition state for the addition of the olefin to ground state model structure $GS^T$-VI to form ground state model structure $GS^T$-VII.

Statement 86. The method of any of Statements 59-70 and 85, wherein:
a) the plurality of transition state model structures $TS^{A1}, TS^{A2}, \ldots TS^{Am}$ derived from the first training heteroatomic ligand-metal compound complex comprise the transition state $TS^I$-IV; and/or
b) the plurality of transition state model structures $TS^{B1}, TS^{B2}, \ldots TS^{Bm}$ derived from the first target heteroatomic ligand-metal compound complex comprise the transition state $TS^T$-IV.

Statement 87. The method of any of Statements 59-70, wherein:
a) the plurality of transition state model structures $TS^{A1}, TS^{A2}, \ldots TS^{Am}$ derived from one or more first training heteroatomic ligand-metal compound complexes comprise a transition state for β-H extraction from ground state model structure $GS^I$-VI leading to 1-hexene production and/or a transition state for β-H extraction from ground state model structure $GS^I$-VII leading to 1-octene production; and/or
b) the plurality of transition state model structures $TS^{B1}, TS^{B2}, \ldots TS^{Bm}$ derived from one or more first target heteroatomic ligand-metal compound complexes comprise a transition state for β-H extraction from ground state model structure $GS^T$-VI leading to 1-hexene production and/or a transition state for β-H extraction from ground state model structure $GS^T$-VII leading to 1-octene production.

Statement 88. The method of any of Statements 87, wherein:

a) the plurality of transition state model structures $TS^{A1}$, $TS^{A2}$, ... $TS^{Am}$ derived from the first training heteroatomic ligand-metal compound complex comprise $TS^I$-III; and/or b) the plurality of transition state model structures $TS^{B1}$, $TS^{B2}$, ... $TS^{Bm}$ derived from the first target heteroatomic ligand-metal compound complex comprise $TS^T$-III.

Statement 89. The method of any of Statements 87-88, wherein:

a) the plurality of transition state model structures $TS^{A1}$, $TS^{A2}$, ... $TS^{Am}$ derived from the first training heteroatomic ligand-metal compound complex comprise $TS^I$-V; and/or b) the plurality of transition state model structures $TS^{B1}$, $TS^{B2}$, ... $TS^{Bm}$ derived from the first target heteroatomic ligand-metal compound complex comprise $TS^T$-V.

Statement 90. The method of any of Statements 87-89, wherein the transition state model for β-H extraction from ground state model structure $GS^I$-VI and/or $GS^T$-VI leading to 1-hexene production is $TS^I$-III and/or $TS^T$-III, respectively.

Statement 91. The method of any of Statements 87-90, wherein the transition state model for β-H extraction from ground state model structure $GS^I$-VII and/or $GS^T$-VII leading to 1-octene production is $TS^I$-V and/or $TS^T$-V, respectively.

Statement 92. The method of any of Statements 51-91, wherein the one or more performance parameters comprises olefin oligomer purity, based upon the mass ratio of 1-hexene to the total of other (non-1-hexene) $C_6$ products calculated as ln[(weight 1-hexene)/(weight non-1-hexene $C_6$)] versus ΔG[TS(1-hexene)-TS(non-1-hexene $C_6$)], or based upon the mass ratio of 1-octene to the total of other (non-1-octene) $C_8$ products and calculated as ln[(weight 1-octene)/(weight non-1-octene $C_8$)] versus ΔG[TS(1-octene)-TS(non-1-octene $C_8$)].

Statement 93. The method of any of Statements 51-91, wherein the one or more performance parameters comprises olefin oligomer selectivity, based upon the mass ratio of 1-hexene to 1-octene and calculated as ln[(weight 1-hexene)/(weight 1-octene)] versus ΔG[TS(1-hexene)-TS(1-octene)].

Statement 94. The method of any of Statements 51-93, wherein the one or more performance parameters associated with the olefin oligomerization comprises heteroatomic ligand-metal compound complex productivity, based upon the grams of olefin oligomer(s) (grams 1-hexene, grams 1-octene, or the total grams of 1-hexene and 1-octene) per grams of the heteroatomic ligand-metal compound complex per hour.

Statement 95. The method of any of Statements 51-94, wherein the quantitative value assigned to each n input variable $I^1, I^2, \ldots I^n$, for each of the one or more ground state model structures $GS^{A1}, \ldots GS^{Ap}$ and each of the plurality of transition state model structures $TS^{A1}, TS^{A2}, \ldots TS^{Am}$ derived from the one or more first training heteroatomic ligand-metal compound complexes are assigned on the basis of calculated, measured, or estimated values, or any combination thereof.

Statement 96. The method of any of Statements 51-95, wherein the one or more of the n input variables $I^1, I^2, \ldots I^n$ identified in step (e) are identified based upon the greater percentage changes in [1] the difference in energies between any of the one or more ground state model structures $GS^{A1}, \ldots GS^{Ap}$ and at least one of the plurality of transition state model structures $TS^{A1}, TS^{A2}, \ldots TS^{Am}$ [ΔG(TS-GS) or ΔΔG(TS-GS)] or [2] the difference in energies between any two or more of the plurality of transition state model structures $TS^{A1}, TS^{A2}, \ldots TS^{Am}$ [ΔG(TS-TS) or ΔΔG(TS-TS)], for each percentage change in the one or more of the n input variables $I^1, I^2, \ldots I^n$ which influence ΔG(TS-GS), ΔΔG(TS-GS), or ΔΔG(TS-TS).

Statement 97. The method of any of Statements 51-96, wherein the step of generating the second target heteroatomic ligand-metal compound complex comprises:

(a) adjusting the quantitative value of one or more n input variables $I^1, I^2, \ldots I^n$ or $I^{1.1}, I^{2.1}, \ldots I^{n.1}$ to approach the value of the corresponding n output variables $O^1, O^2, \ldots O^n$ or $O^{1.1}, O^{2.1}, \ldots O^{n.1}$ in any first training heteroatomic ligand-metal compound complex comprising a chromium heteroatomic ligand moiety independently selected from NPFCrM-1, NPACrM-1, GuCrM-1, GuCrM-2, GuCrM-3, GuCrM-4, GuCrM-5, or HCPACrM-1, by:

[1] independently increasing or decreasing the steric bulk of one or more of the groups $R^1, R^2, L^{12r}, R^{2a}, R^{2b}, L^{12}, L^{23}, L^{22}, R^3, R^4, R^5$, and $L^{45}$;

[2] independently changing the inductive electronic effects of one or more of the groups $R^1, R^2, L^{12r}, R^{2a}, R^{2b}, L^{12}, L^{23}, L^{22}, R^3, R^4, R^5$, and $L^{45}$ with one or more +I substituent or one or more −I substituent;

[3] independently increasing or decreasing the saturation in one or more of the organyl groups or organylene groups;

[4] increasing or decreasing the polarity of a solvent used for olefin oligomerization; or

[5] any combination thereof;

and (b) generating, based upon the at least one adjusted n input variable from step (a) a second target heteroatomic ligand-metal compound complex for olefin oligomerization and comprising a second target heteroatomic ligand.

Statement 98. The method of any of Statements 51-96, wherein the step of generating the second target heteroatomic ligand-metal compound complex comprises:

(a) adjusting the quantitative value of one or more n input variables $I^1, I^2, \ldots I^n$ or $I^{1.1}, I^{2.1}, \ldots I^{n.1}$ to approach the value of the corresponding n output variables $O^1, O^2, \ldots O^n$ or $O^{1.1}, O^{2.1}, \ldots O^{n.1}$ in any first training heteroatomic ligand-metal compound complex comprising a chromium heteroatomic ligand moiety independently selected from NRNCrM-1, PRPCrM-1, SRSCrM-1, PNPCrM-1, NRNRNCrM-1, PRPRPCrM-1, SRNRSCrM-1, PRNRPCrM-1, or NRPRNCrM-1, by:

[1] independently increasing or decreasing the steric bulk of one or more of the groups $R^{1s}, R^{2s}, R^{5s}, R^{11s}, R^{12s}, R^{13s}, R^{14s}, L^{1s}, L^{3s}, L^{4s}, L^{1sr}, L^{1sr}, L^{12sr}$, and $L^{34sr}$.

[2] independently changing the inductive electronic effects of one or more of the groups $R^{1s}, R^{2s}, R^{5s}, R^{11s}, R^{12s}, R^{13s}, R^{14s}, L^{1s}, L^{3s}, L^{4s}, L^{1sr}, L^{1sr}, L^{12sr}$, and $L^{34sr}$ with one or more +I substituent or one or more −I substituent;

[3] independently increasing or decreasing the saturation in one or more of the organyl groups or organylene groups;

[4] increasing or decreasing the polarity of a solvent used for olefin oligomerization; or

[5] any combination thereof;
and
(b) generating, based upon the at least one adjusted n input variable from step (a) a second target heteroatomic ligand-metal compound complex for olefin oligomerization and comprising a second target heteroatomic ligand.

Statement 99. The method of any of Statements 51-98, wherein any of the ground state model structures $GS^{A1}$, ... $GS^{Ap}$ or any of the plurality of transition state model structures $TS^{A1}$, $TS^{A2}$, ... $TS^{Am}$ derived from the one or more first training heteroatomic ligand-metal compound complexes are calculated using a density functional theory (DFT) calculations.

Statement 100. The method of any of Statements 51-99, wherein generating the machine learning model comprises a Gaussian Process Algorithm or a Random Forest Algorithm.

We claim:

1. A method for designing a heteroatomic ligand-metal compound complex for olefin oligomerization, the method comprising:
   (a) selecting n input variables $I^1, I^2, \ldots I^n$ (n is an integer), each input variable corresponding to a structural property or an electronic property of one or more ground state model structures $GS^{A1}, \ldots GS^{Ap}$ (p is an integer) and a plurality of transition state model structures $TS^{A1}, TS^{A2}, \ldots TS^{Am}$ (m is an integer) associated with the one or more ground state model structures,
   wherein each of the one or more ground state model structures $GS^{A1}, \ldots GS^{Ap}$ and each of the plurality of transition state model structures $TS^{A1}, TS^{A2}, \ldots TS^{Am}$ are derived from one or more first training heteroatomic ligand-metal compound complexes, each complex comprising a first training heteroatomic ligand;
   (b) assigning a quantitative value to each n input variable $I^1, I^2, \ldots I^n$, for each of the ground state model structures $GS^{A1}, \ldots GS^{Ap}$ and each of the transition state model structures $TS^{A1}, TS^{A2}, \ldots TS^{Am}$,
   (c) determining, by at least one processor of a device, the relative energies of each of the ground state model structures $GS^{A1}, \ldots GS^{Ap}$ and each of the transition state model structures $TS^{A1}, TS^{A2}, \ldots TS^{Am}$;
   (d) generating a machine learning model based upon correlating the quantitative value of each n input variable $I^1, I^2, \ldots I^n$ with the relative energies of each of the ground state model structures $GS^{A1}, \ldots GS^{Ap}$ and each of the transition state model structures $TS^{A1}, TS^{A2}, \ldots TS^{Am}$,
   (e) identifying, based on the machine learning model, one or more of the n input variables $I^1, I^2, \ldots I^n$ associated with [1] the difference in energies between one of the ground state model structures $GS^{A1}, \ldots GS^{Ap}$ and at least one of the plurality of transition state model structures $TS^{A1}, TS^{A2}, \ldots TS^{Am}$ [$\Delta G(TS-GS)$ or $\Delta\Delta G(TS-GS)$] or [2] the difference in energies between any two or more of the plurality of transition state model structures $TS^{A1}, TS^{A2}, \ldots TS^{Am}$ [$\Delta G(TS-TS)$ or $\Delta\Delta G(TS-TS)$];
   (f) generating, based upon the one or more n input variables $I^1, I^2, \ldots I^n$ identified from step (e), a first target heteroatomic ligand-metal compound complex for olefin oligomerization and comprising a first target heteroatomic ligand, wherein the first target heteroatomic ligand-metal compound complex is characterized by n output variables $O^1, O^2, \ldots O^n$, each having a quantitative value corresponding to a structural property or an electronic property of one or more ground state model structures $GS^{B1}, \ldots GS^{Bx}$ (x is an integer) or any of a plurality of transition state model structures $TS^{B1}, TS^{B2}, \ldots TS^{By}$ (y is an integer) associated with the one or more ground state model structures,
   wherein each of the one or more ground state model structures $GS^{B1}, \ldots GS^{Bx}$ and each of the plurality of transition state model structures $TS^{B1}, TS^{B2}, \ldots TS^{By}$ are derived from the first target heteroatomic ligand-metal compound complex, each complex comprising a first target heteroatomic ligand;
   (g) identifying one or more performance parameters associated with an olefin oligomerization reaction and the value of the performance parameters for the one or more first training heteroatomic ligand-metal compound complexes and the first target heteroatomic ligand-metal compound complex; and
   (h) repeating steps (a)-(f) one or more times using the quantitative values of the n output variables $O^1, O^2, \ldots O^n$ of the first target heteroatomic ligand-metal compound complex as an input dataset of new n input variables $I^{1.1}, I^{2.1}, \ldots I^{n.1}$ derived from one or more second training heteroatomic ligand-metal compound complexes for olefin oligomerization and comprising a second training heteroatomic ligand, which is computationally evaluated against the machine learning model to generate a second target heteroatomic ligand-metal compound complex comprising a second target heteroatomic ligand, wherein the second target heteroatomic ligand-metal compound complex is characterized by quantitative values of an output dataset of new n output variables $O^{1.1}, O^{2.1}, \ldots O^{n.1}$, and having one or more second target heteroatomic ligand-metal compound complex performance parameter values.

2. The method of claim 1, further comprising the step of:
   (i) [1] synthesizing the first target heteroatomic ligand and/or the second target heteroatomic ligand; or [2] synthesizing the first target heteroatomic ligand and/or the second target heteroatomic ligand, followed by synthesizing the first target heteroatomic ligand-metal compound complex or the second target heteroatomic ligand-metal compound complex.

3. The method of claim 2, further comprising the step of:
   (j) performing the olefin oligomerization reaction by: [1] contacting the first target heteroatomic ligand or the second target heteroatomic ligand, a metal compound, an organometal compound, and an olefin; or [2] contacting the first target heteroatomic ligand-metal compound complex or the second target heteroatomic ligand-metal compound complex, an organometal compound, and an olefin.

4. The method of claim 1, wherein the one or more of the n input variables $I^1, I^2, \ldots I^n$ identified in step (e) are identified based upon the greater percentage changes in [1] the difference in energies between any of the one or more ground state model structures $GS^{A1}, \ldots GS^{AP}$ and at least one of the plurality of transition state model structures $TS^{A1}, TS^{A2}, \ldots TS^{Am}$ [$\Delta G(TS-GS)$ or $\Delta\Delta G(TS-GS)$] or [2] the difference in energies between any two or more of the plurality of transition state model structures $TS^{A1}, TS^{A2}, \ldots TS^{Am}$ [$\Delta G(TS-TS)$ or $\Delta\Delta G(TS-TS)$], for each percentage change in the one or more of the n input variables $I^1, I^2, \ldots I^n$ which influence $\Delta G(TS-GS)$, $\Delta\Delta G(TS-GS)$, or $\Delta\Delta G(TS-TS)$.

5. The method of claim 1, wherein the one or more first training heteroatomic ligand-metal compound complexes have a formula independently selected from:

$$[(HetLig)CrX_qL_r]^{3-q} \text{ (A); wherein:}$$

HetLig represents the one or more first training heteroatomic ligands;

X is an anionic ligand, and q is an integer;

L is a neutral ligand, and r is an integer, wherein any two or more of the X and L ligands may be linked to form a multidentate ligand; and wherein each selected n input variable $I^1, I^2, \ldots I^n$, corresponds to a structural property or an electronic property of any of the one or more ground state model structures $GS^{A1}, \ldots GS^{Ap}$ or any of the plurality of transition state model structures $TS^{A1}, TS^{A2}, \ldots TS^{Am}$ associated with the one or more ground state model structures of formula (A).

6. The method of claim 1, wherein the one or more ground state model structures $GS^{A1}, \ldots GS^{Ap}$ derived from the one or more first training heteroatomic ligand-metal compound complexes ($GS^1$), and the one or more ground state model structures $GS^{B1}, \ldots GS^{Bx}$ derived from the one or more first target heteroatomic ligand-metal compound complexes ($GS^T$) are selected independently from:

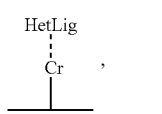

(GS$^X$-I)

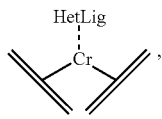

(GS$^X$-II)

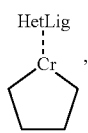

(GS$^X$-III)

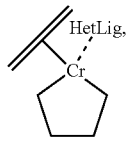

(GS$^X$-IV)

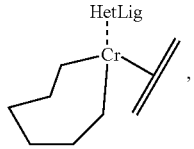

(GS$^X$-V)

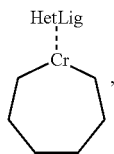

(GS$^X$-VI)

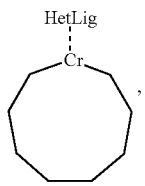

(GS$^X$-VII)

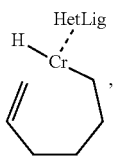

(GS$^X$-VIII)

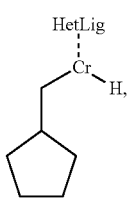

(GS$^X$-IX)

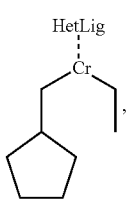

(GS$^X$-X)

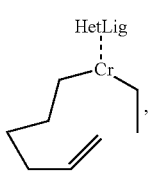

(GS$^X$-XI)

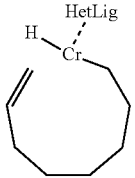

(GS$^X$-XII)

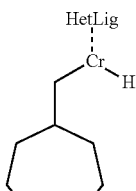

(GS$^X$-XIII)

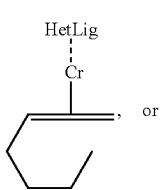

, or (GS$^X$-XIV)

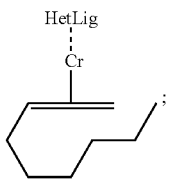

;

(GS$^X$-XV)

wherein:
HetLig represents the one or more first training heteroatomic ligands or the one or more first target heteroatomic ligands, and
$GS^X$ is the first training heteroatomic ligand-metal compound complex ($GS^1$) or the first target heteroatomic ligand-metal compound complexes ($GS^T$).

7. The method of claim 6, wherein the plurality of transition state model structures $TS^{A1}$, $TS^{A2}$, ... $TS^{Am}$ derived from the one or more first training heteroatomic ligand-metal compound complexes ($TS^1$) and the plurality of transition state model structures $TS^{B1}$, $TS^{B2}$, ... $TS^{By}$ derived from the one or more first target heteroatomic ligand-metal compound complexes ($TS^T$) are selected independently from:

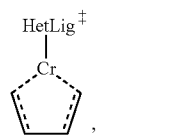
($TS^Y$-I)

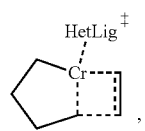
($TS^Y$-II)

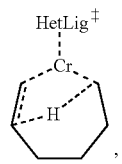
($TS^Y$-III)

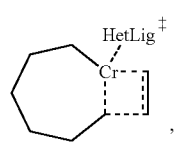
($TS^Y$-IV)

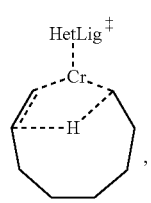
($TS^Y$-V)

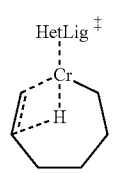
($TS^Y$-VI)

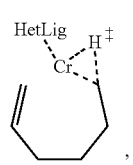
($TS^Y$-VII)

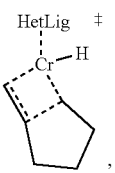
($TS^Y$-VIII)

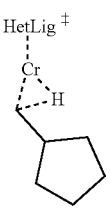
($TS^Y$-IX)

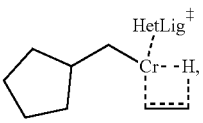
($TS^Y$-X)

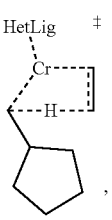
($TS^Y$-XI)

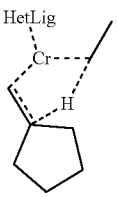
($TS^Y$-XII)

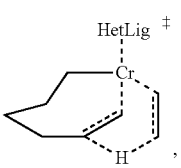
($TS^Y$-XIII)

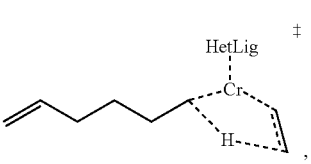
($TS^Y$-XIV)

($TS^Y$-XV)

wherein:
HetLig represents the one or more first training heteroatomic ligands or the one or more first target heteroatomic ligands, and TS$^Y$ is the first training heteroatomic ligand-metal compound complex (TS$^1$) or the first target heteroatomic ligand-metal compound complexes (TS$^T$).

8. The method of claim 1, wherein the one or more ground state model structures and any of the plurality of transition state model structures comprise a chromium heteroatomic ligand moiety independently selected from:

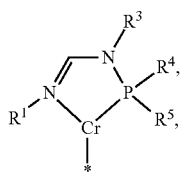

NPFCrM-1

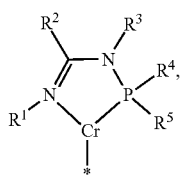

NPACrM-1

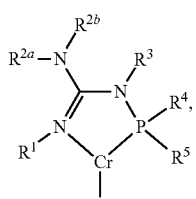

GuCrM-1

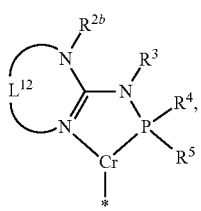

GuCrM-2

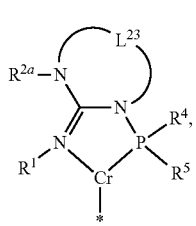

GuCrM-3

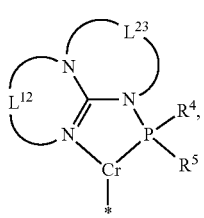

GuCrM-4

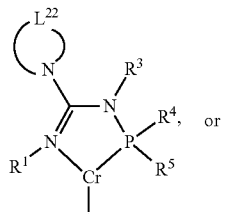

GuCrM-5

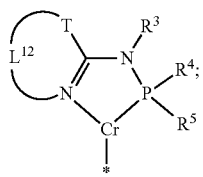

HCPACrM-1 wherein:
R$^1$ is a hydrogen or a C$_1$ to C$_{20}$ organyl group;
R$^2$ is a C$_1$ to C$_{20}$ organyl group;
T is oxygen or sulfur;
R$^{2a}$ and R$^{2b}$ independently are C$_1$ to C$_{20}$ organyl groups;
L$^{12}$ and L$^{23}$ independently are C$_2$ to C$_{20}$ organylene groups;
L$^{22}$ is a C$_3$ to C$_{20}$ organylene groups;
R$^3$ is hydrogen or a C$_1$ to C$_{20}$ organyl group; and
R$^4$ and R$^5$ independently are hydrogen or a C$_1$ to C$_{20}$ organyl groups;
where R$^1$ and R$^2$ are optionally joined to form L$^{12r}$, and L$^{12r}$ is a C$_3$ to C$_{30}$ organylene group;
where R$^4$ and R$^5$ are optionally joined to form L$^{45}$, and L$^{45}$ is a C$_4$ to C$_{30}$ organylene group; and
where "*" represents any additional bonding required in [1] any of the one or more ground state model structures or any of the plurality of transition state model structures derived from the one or more first training heteroatomic ligand-metal compound complexes, or [2] any of the one or more ground state model structures or any of the plurality of transition state model structures derived from the one or more first target heteroatomic ligand-metal compound complexes.

9. The method of claim 8, wherein:
R$^1$ is hydrogen, a C$_1$ to C$_{20}$ hydrocarbyl group, or a C$_1$ to C$_{20}$ heterohydrocarbyl group;
R$^2$ is a C$_1$ to C$_{20}$ hydrocarbyl group or a C$_1$ to C$_{20}$ heterohydrocarbyl group;
R$^{2a}$ and R$^{2b}$ are independently selected from a C$_1$ to C$_{20}$ hydrocarbyl group or a C$_1$ to C$_{20}$ heterohydrocarbyl group;
L$^{12}$ and L$^{23}$ are independently selected from a C$_2$ to C$_{20}$ hydrocarbylene group or a C$_2$ to C$_{20}$ heterohydrocarbylene group;
L$^{22}$ is a C$_3$ to C$_{20}$ hydrocarbylene group or a C$_3$ to C$_{20}$ heterohydrocarbylene group;
R$^3$ is hydrogen, a C$_1$ to C$_{20}$ hydrocarbyl group, or a C$_1$ to C$_{20}$ heterohydrocarbyl group; and
R$^4$ and R$^5$ are independently selected from a C$_1$ to C$_{20}$ hydrocarbyl group or a C$_1$ to C$_{20}$ heterohydrocarbyl group;
where R$^1$ and R$^2$ are optionally joined to form L$^{12r}$, and L$^{12r}$ is a C$_3$ to C$_{20}$ hydrocarbylene group or a C$_3$ to C$_{20}$ heterohydrocarbylene group; and where $R^4$ and $R^5$ are optionally joined to form $L^{45}$, and $L^{45}$ is a $C_4$ to $C_{20}$ hydrocarbylene group or a $C_4$ to $C_{20}$ heterohydrocarbylene group.

10. The method of claim 8, wherein the n input variables $I^1, I^2, \ldots I^n$ comprise or are selected from any one of more of the following variables:
   (a) the Cr—P distance (Å);
   (b) the Cr—N distance (Å);
   (c) the Cr - - - R on α-C distance (Å);
   (d) the P—Cr—N angle (deg);
   (e) the C—Cr—N angle (deg), wherein C is a non-heteroatomic ligand carbon atom bonded to or within bonding distance of the Cr atom;
   (f) the Cr—N—C angle (deg);
   (g) the distance out of pocket (Å);
   (h) the Cr - - - α-C distance (Å);
   (i) the Cr CHELPG (atomic charge);
   (j) the P CHELPG (atomic charge);
   (k) the N CHELPG (atomic charge);
   (l) the Cr—N—C—N Dihedral angle (deg);
   (m) the Cr—P—N—C Dihedral angle (deg);
   (n) the P—Cr—N—C Dihedral angle (deg);
   (o) the P—N—C—N Dihedral angle (deg);
   (p) the C—C—N—C Dihedral angle (deg); or
   (q) the percent volume buried.

11. The method of claim 1, wherein the one or more ground state model structures and any of the plurality of transition state model structures comprise a chromium heteroatomic ligand moiety independently selected from:

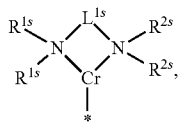
NRNCrM-1

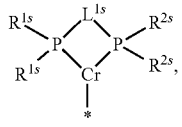
PRPCrM-1

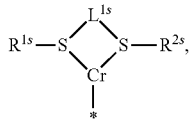
SRSCrM-1

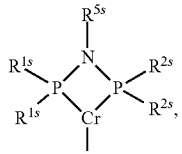
PNPCrM-1

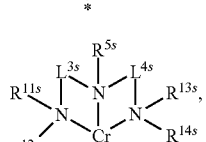
NRNRNCrM-1

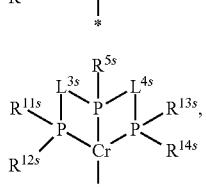
PRPRPCrM-1

-continued

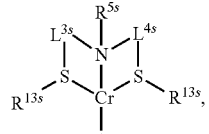
SRNRSCrM-1

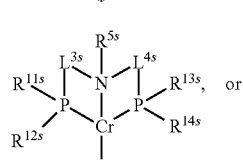
PRNRPCrM-1, or

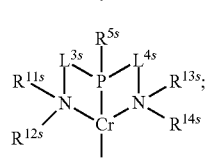
NRPRNCrM-1 wherein:
each $R^{1s}$, $R^{2s}$, $R^{5s}$, $R^{11s}$, $R^{12s}$, $R^{13s}$, and $R^{14s}$, independently, is selected from a hydrogen or a $C_1$ to $C_{20}$ organyl group;
each $L^{1s}$, $L^{3s}$, and $L^{4s}$, independently, is selected from a $C_2$ to $C_{20}$ organylene group; and
any two geminal $R^{1s}$ are optionally joined to form $L^{11s}$, and $L^{11s}$ is a $C_3$ to $C_{30}$ organylene group;
any two geminal $R^{2s}$ are optionally joined to form $L^{22s}$, and $L^{22s}$ is a $C_3$ to $C_{30}$ organylene group;
any germinal $R^{11s}$ and $R^{12s}$ are optionally joined to form $L^{12s}$, and $L^{12s}$ is a $C_3$ to $C_{30}$ organylene group;
any germinal $R^{13s}$ and $R^{14s}$ are optionally joined to form $L^{34s}$, and $L^{34s}$ is a $C_3$ to $C_{30}$ organylene group;
where "*" represents any additional bonding required in [1] any of the one or more ground state model structures or any of the plurality of transition state model structures derived from the one or more first training heteroatomic ligand-metal compound complexes, or [2] any of the one or more ground state model structures or any of the plurality of transition state model structures derived from the one or more first target heteroatomic ligand-metal compound complexes.

12. The method of claim 11, wherein:
each $R^{1s}$, $R^{2s}$, $R^{5s}$, $R^{11s}$, $R^{12s}$, $R^{13s}$, and $R^{14s}$, independently, is selected from hydrogen, a $C_1$ to $C_{20}$ hydrocarbyl group, or a $C_1$ to $C_{20}$ heterohydrocarbyl group;
each $L^{1s}$, $L^{3s}$, and $L^{4s}$, independently, is selected from a $C_2$ to $C_{20}$ hydrocarbylene group or a $C_2$ to $C_{20}$ heterohydrocarbylene group;
any two geminal $R^{1s}$ are optionally joined to form $L^{11s}$, and $L^{11s}$ is a $C_2$ to $C_{20}$ hydrocarbylene group or a $C_2$ to $C_{20}$ heterohydrocarbylene group;
any two geminal $R^{2s}$ are optionally joined to form $L^{22s}$, and $L^{22s}$ is a $C_2$ to $C_{20}$ hydrocarbylene group or a $C_2$ to $C_{20}$ heterohydrocarbylene group;
any germinal $R^{11s}$ and $R^{12s}$ are optionally joined to form $L^{12s}$, and $L^{12s}$ is a $C_2$ to $C_{20}$ hydrocarbylene group or a $C_2$ to $C_{20}$ heterohydrocarbylene group; and
any germinal $R^{13s}$ and $R^{14s}$ are optionally joined to form $L^{34s}$, and $L^{34s}$ $L^{22s}$, and
$L^{22sF}$ is a $C_2$ to $C_{20}$ hydrocarbylene group or a $C_2$ to $C_{20}$ heterohydrocarbylene group.

13. The method of claim 11, wherein the n input variables $I^1, I^2, \ldots I^n$ comprise or are selected from any one of more of the following variables:
(a) the first, second, or third Cr—N distance (Å);
(b) the first, second, or third Cr—P distance (Å);
(c) the first or second Cr—S distance (Å);
(d) any one or more N—Cr—N angle (deg);
(e) any one or more P—Cr—P angle (deg);
(f) any one or more S—Cr—S angle (deg);
(g) any one or more S—Cr—N angle (deg);
(h) any one or more N—Cr—P angle (deg);
(i) the C—Cr—N angle (deg), wherein C is a non-heteroatomic ligand carbon atom bonded to or within bonding distance of the Cr atom;
(j) the C—Cr—P angle (deg);
(k) the C—Cr—S angle (deg);
(l) the Cr—N—C angle (deg);
(m) the Cr—P—C angle (deg);
(n) the Cr—S—C angle (deg);
(o) the Cr—P—C angle (deg);
(p) the Cr - - - R on α-C distance (Å);
(q) the distance out of pocket (Å);
(r) the Cr - - - α-C distance (Å);
(s) the Cr CHELPG (atomic charge);
(t) any P CHELPG (atomic charge);
(u) any N CHELPG (atomic charge);
(v) any chelate Cr—N—C—C Dihedral angle (deg);
(w) any chelate Cr—P—C—C Dihedral angle (deg);
(x) any chelate Cr—S—C—C Dihedral angle (deg); or
(y) the percent volume buried.

14. The method of claim 1, wherein the one or more performance parameters associated with the olefin oligomerization reaction are selected from: (a) 1-hexene purity; (b) 1-octene purity; (c) 1-hexene:1-octene ratio ($C_6/C_8$ ratio); (d) 1-hexene productivity; (e) 1-octene productivity; (f) the total 1-hexene plus 1-octene productivity; or any combination thereof.

15. The method of claim 7, wherein:
(a) [1] the one or more ground state model structures $GS^{A1}, \ldots GS^{Ap}$ derived from one or more first training heteroatomic ligand-metal compound complexes comprise or are selected independently from $GS^1$-I, $GS^1$-II, $GS^1$-III, $GS^1$-IV, $GS^1$-V, $GS^1$-VI, $GS^1$-VII, or any combination thereof, and [2] the plurality of transition state model structures $TS^{A1}, TS^{A2}, \ldots TS^{Am}$ derived from one or more first training heteroatomic ligand-metal compound complexes comprise or are selected independently from $TS^1$-I, $TS^1$-II, $TS^1$-III, $TS^1$-IV, $TS^1$-V, or any combination thereof;
(b) [1] the one or more ground state model structures $GS^{B1}, \ldots GS^{Bp}$ derived from the first target heteroatomic ligand-metal compound complex comprise or are selected independently from $GS^T$-I, $GS^T$-II, $GS^T$-III, $GS^T$-IV, $GS^T$-V, $GS^T$-VI, $GS^T$-VII, or any combination thereof, and [2] the plurality of transition state model structures $TS^{B1}, TS^{B2}, \ldots TS^{Bm}$ derived from the first target heteroatomic ligand-metal compound complex comprise or are selected independently from $TS^T$-I, $TS^T$-II, $TS^T$-III, $TS^T$-IV, $TS^T$-V, or any combination thereof; and
(c) the performance parameter associated with the olefin oligomerization reaction is a heteroatomic ligand-metal compound complex 1-hexene productivity, 1-octene productivity, or a total 1-hexene and 1-octene productivity.

16. The method of claim 7, wherein:
(a) [1] the one or more ground state model structures $GS^{A1}, \ldots GS^{Ap}$ derived from one or more first training heteroatomic ligand-metal compound complexes comprise $GS^1$-VI and [2] the plurality of transition state model structures $TS^{A1}, TS^{A2}, \ldots TS^{Am}$ derived from one or more first training heteroatomic ligand-metal compound complexes comprise $TS^1$-III and $TS^1$-IV,
(b) [1] the one or more ground state model structures $GS^{B1}, \ldots GS^{Bp}$ derived from the first target heteroatomic ligand-metal compound complex comprise $GS^T$-VI, and [2] the plurality of transition state model structures $TS^{B1}, TS^{B2}, \ldots TS^{Bm}$ derived from the first target heteroatomic ligand-metal compound complex comprise $TS^T$-III and $TS^T$-IV; and
(c) the performance parameter associated with the olefin oligomerization reaction is the C6/C8 ratio.

17. The method of claim 7, wherein:
(a) [1] the one or more ground state model structures $GS^{A1}, \ldots GS^{Ap}$ derived from one or more first training heteroatomic ligand-metal compound complexes comprise or are selected independently from $GS^1$-VI, $GS^1$-VIII, $GS^1$-IX, $GS^1$-X, $GS^1$-XI, or any combination thereof, and [2] the plurality of transition state model structures $TS^{A1}, TS^{A2}, \ldots TS^{Am}$ derived from one or more first training heteroatomic ligand-metal compound complexes comprise or are selected independently from $TS^1$-III, $TS^1$-VI, $TS^1$-VII, $TS^1$-VIII, $TS^1$-IX, $TS^1$-X, $TS^1$-XI, $TS^1$-XII, $TS^1$-XIII, $TS^1$-XIV, $TS^1$-XV, or any combination thereof;
(b) [1] the one or more ground state model structures $GS^{B1}, \ldots GS^{Bp}$ derived from the first target heteroatomic ligand-metal compound complex comprise or are selected independently from $GS^1$-VI, $GS^1$-VIII, $GS^1$-IX, $GS^1$-X, $GS^1$-XI, or any combination thereof, and [2] the plurality of transition state model structures $TS^{B1}, TS^{B2}, \ldots TS^{Bm}$ derived from the first target heteroatomic ligand-metal compound complex comprise or are selected from $TS^1$-III, $TS^1$-VI, $TS^1$-VII, $TS^1$-VIII, $TS^1$-IX, $TS^1$-X, $TS^1$-XI, $TS^1$-XII, $TS^1$-XIII, $TS^1$-XIV, $TS^1$-XV, or any combination thereof; and
(c) the performance parameter associated with the olefin oligomerization reaction is 1-hexene purity.

18. The method of claim 7, wherein:
(a) [1] the one or more ground state model structures $GS^{A1}, \ldots GS^{Ap}$ derived from one or more first training heteroatomic ligand-metal compound complexes comprise or are selected independently from $GS^1$-VII, $GS^1$-XII, $GS^1$-XIII, or any combination thereof, and [2] the one or more ground state model structures $GS^{B1}, \ldots GS^{Bp}$ derived from the first target heteroatomic ligand-metal compound complex comprise or are selected independently from $GS^T$-VII, $GS^T$-XII, $GS^T$-XIII, or any combination thereof; and
(b) the performance parameter associated with the olefin oligomerization reaction is 1-octene purity.

19. The method of claim 7, wherein:
(a) [1] the plurality of transition state model structures $TS^{A1}, TS^{A2}, \ldots TS^{Am}$ derived from one or more first training heteroatomic ligand-metal compound complexes comprise a transition state for the addition of the olefin to ground state model structure $GS^1$-VI to form ground state model structure $GS^1$-VII; and/or [2] the plurality of transition state model structures $TS^{B1}, TS^{B2}, \ldots TS^{Bm}$ derived from one or more first target heteroatomic ligand-metal compound complexes comprise a transition state for the addition of the olefin to ground state model structure $GS^T$-VI to form ground state model structure $GS^T$-VII; or
- (b) [1] the plurality of transition state model structures $TS^{A1}, TS^{A2}, \ldots TS^{Am}$ derived from the first training heteroatomic ligand-metal compound complex comprise the transition state $TS^I$-IV; and/or [2] the plurality of transition state model structures $TS^{B1}, TS^{B2}, \ldots TS^{Bm}$ derived from the first target heteroatomic ligand-metal compound complex comprise the transition state $TS^T$-IV.

20. The method of claim 7, wherein:
- (a) [1] the plurality of transition state model structures $TS^{A1}, TS^{A2}, \ldots TS^{Am}$ derived from one or more first training heteroatomic ligand-metal compound complexes comprise a transition state for β-H extraction from ground state model structure $GS^I$-VI leading to 1-hexene production and/or a transition state for β-H extraction from ground state model structure $GS^I$-VII leading to 1-octene production; and/or [2] the plurality of transition state model structures $TS^{B1} TS^{B2}, \ldots TS^{Bm}$ derived from one or more first target heteroatomic ligand-metal compound complexes comprise a transition state for β-H extraction from ground state model structure $GS^T$-VI leading to 1-hexene production and/or a transition state for β-H extraction from ground state model structure $GS^T$-VII leading to 1-octene production; and
- (b) [1] the plurality of transition state model structures $TS^{A1}, TS^{A2}, \ldots TS^{Am}$ derived from the first training heteroatomic ligand-metal compound complex comprise $TS^I$-III or $TS^I$-V; and/or [2] the plurality of transition state model structures $TS^{B1}, TS^{B2}, \ldots TS^{Bm}$ derived from the first target heteroatomic ligand-metal compound complex comprise $TS^T$-III or $TS^T$-V.

21. The method of claim 1, wherein the quantitative value assigned to each n input variable $I^1, I^2, \ldots I^n$, for each of the one or more ground state model structures $GS^{A1}, \ldots GS^{AP}$ and each of the plurality of transition state model structures $TS^{A1}, TS^{A2}, \ldots TS^{Am}$ derived from the one or more first training heteroatomic ligand-metal compound complexes are assigned on the basis of calculated, measured, or estimated values, or any combination thereof.

22. The method of claim 1, wherein the step of generating the second target heteroatomic ligand-metal compound complex comprises:
- (a) adjusting the quantitative value of one or more n input variables $I^1, I^2, \ldots I^n$ or $I^{1.1}, I^{2.1}, \ldots I^{n.1}$ to approach the value of the corresponding n output variables $O^1, O^2, \ldots O^n$ or $O^{1.1}, O^{2.1}, \ldots O^{n.1}$ in any first training heteroatomic ligand-metal compound complex comprising a chromium heteroatomic ligand moiety independently selected from NPFCrM-1, NPACrM-1, GuCrM-1, GuCrM-2, GuCrM-3, GuCrM-4, GuCrM-5, or HCPACrM-1, by:
  - [1] independently increasing or decreasing the steric bulk of one or more of the groups $R^1, R^2, L^{12r}, R^{2a}, R^{2b}, L^{12}, L^{23}, L^{22}, R^3, R^4, R^5$, and $L^{45}$;
  - [2] independently changing the inductive electronic effects of one or more of the groups $R^1, R^2, L^{12r}, R^{2a}, R^{2b}, L^{12}, L^{23}, L^{22}, R^3, R^4, R^5$, and $L^{45}$ with one or more +I substituent or one or more −I substituent;
  - [3] independently increasing or decreasing the saturation in one or more of the organyl groups or organylene groups;
  - [4] increasing or decreasing the polarity of a solvent used for olefin oligomerization; or
  - [5] any combination thereof;
  and
- (b) generating, based upon the at least one adjusted n input variable from step (a) a second target heteroatomic ligand-metal compound complex for olefin oligomerization and comprising a second target heteroatomic ligand.

23. The method of claim 1, wherein the step of generating the second target heteroatomic ligand-metal compound complex comprises:
- (a) adjusting the quantitative value of one or more n input variables $I^1, I^2, \ldots I^n$ or $I^{1.1}, I^{2.1}, \ldots I^{n.1}$ to approach the value of the corresponding n output variables $O^1, O^2, \ldots O^n$ or $O^{1.1}, O^{2.1}, \ldots O^{n.1}$ in any first training heteroatomic ligand-metal compound complex comprising a chromium heteroatomic ligand moiety independently selected from NRNCrM-1, PRPCrM-1, SRSCrM-1, PNPCrM-1, NRNRNCrM-1, PRPRPCrM-1, SRNRSCrM-1, PRNRPCrM-1, or NRPRNCrM-1, by:
  - [1] independently increasing or decreasing the steric bulk of one or more of the groups $R^{1s}, R^{2s}, R^{5s}, R^{11s}, R^{12s}, R^{13s}, R^{14s}, L^{1s}, L^{3s}, L^{4s}, L^{1sr}, L^{1sr}, L^{12sr}$, and $L^{34sr}$;
  - [2] independently changing the inductive electronic effects of one or more of the groups $R^{1s}, R^{2s}, R^{5s}, R^{11s}, R^{12s}, R^{13s}, R^{14s}, L^{1s}, L^{3s}, L^{4s}, L^{1sr}, L^{1sr}, L^{12sr}$, and $L^{34sr}$ with one or more +I substituent or one or more −I substituent;
  - [3] independently increasing or decreasing the saturation in one or more of the organyl groups or organylene groups;
  - [4] increasing or decreasing the polarity of a solvent used for olefin oligomerization; or
  - [5] any combination thereof;
  and
- (b) generating, based upon the at least one adjusted n input variable from step (a) a second target heteroatomic ligand-metal compound complex for olefin oligomerization and comprising a second target heteroatomic ligand.

24. A method for designing a heteroatomic ligand-metal compound complex for olefin oligomerization, the method comprising:
- (a) selecting n input variables $I^1, I^2, \ldots I^n$ (n is an integer), each input variable corresponding to a structural property or an electronic property of one or more ground state model structures $GS^{A1}, \ldots GS^{Ap}$ (p is an integer) and a plurality of transition state model structures $TS^{A1}, TS^{A2}, \ldots TS^{Am}$ (m is an integer) associated with the one or more ground state model structures,
  wherein each of the one or more ground state model structures $GS^{A1}, \ldots GS^{Ap}$ and each of the plurality of transition state model structures $TS^{A1}, TS^{A2}, \ldots TS^{Am}$ are generated from one or more first training heteroatomic ligand-metal compound complexes, each complex comprising a first training heteroatomic ligand;
- (b) assigning a quantitative value to each n input variable $I^1, I^2, \ldots I^n$, for each of the ground state model structures $GS^{A1}, \ldots GS^{Ap}$ and each of the transition state model structures $TS^{A1}, TS^{A2}, \ldots TS^{Am}$,
- (c) determining, by at least one processor of a device, the relative energies of each of the ground state model structures $GS^{A1}, \ldots GS^{Ap}$ and each of the transition state model structures $TS^{A1}, TS^{A2}, \ldots TS^{Am}$,
- (d) generating a machine learning model to correlate the quantitative value of each n input variable $I^1, I^2, \ldots I^n$ and the relative energies of each of the ground state model structures $GS^{A1}, \ldots GS^{Ap}$ and each of the transition state model structures $TS^{A1}, TS^{A2}, \ldots TS^{Am}$;

(e) determining, using the machine learning model, a relationship between one or more of the n input variables $I^1, I^2, \ldots I^n$ and [1] the difference in energies between one of the ground state model structures $GS^{A1}, \ldots GS^{Ap}$ and at least one of the plurality of transition state model structures $TS^{A1}, TS^{A2}, \ldots TS^{Am}$ [$\Delta G(TS\text{-}GS)$ or $\Delta\Delta G(TS\text{-}GS)$] or [2] the difference in energies between any two or more of the plurality of transition state model structures $TS^{A1}, TS^{A2}, \ldots TS^{Am}$ [$\Delta G(TS\text{-}TS)$ or $\Delta\Delta G(TS\text{-}TS)$];

(f) generating, based upon the relationship identified from step (e), an output of the machine learning model comprising a first target heteroatomic ligand-metal compound complex for olefin oligomerization and comprising a first target heteroatomic ligand, wherein the first target heteroatomic ligand-metal compound complex is characterized by n output variables $O^1, O^2, \ldots O^n$, each having a quantitative value corresponding to a structural property or an electronic property of one or more ground state model structures $GS^{B1}, \ldots GS^{Bx}$ (x is an integer) or any of a plurality of transition state model structures $TS^{B1}, TS^{B2}, \ldots TS^{By}$ (y is an integer) associated with the one or more ground state model structures, wherein each of the one or more ground state model structures $GS^{B1}, \ldots GS^{Bx}$ and each of the plurality of transition state model structures $TS^{B1}, TS^{B2}, \ldots TS^{By}$ are generated from the first target heteroatomic ligand-metal compound complex, each complex comprising a first target heteroatomic ligand, and wherein the n output variables $O^1, O^2, \ldots O^n$ are reused as new n input variables $I^{1.1}, I^{2.1}, \ldots I^{n.1}$ to the machine learning model;

(g) identifying one or more performance parameters associated with an olefin oligomerization reaction and the value of the performance parameters for the one or more first training heteroatomic ligand-metal compound complexes and the first target heteroatomic ligand-metal compound complex; and (h) repeating steps (a)-(f) one or more times using the quantitative values of the n output variables $O^1, O^2, \ldots O^n$ of the first target heteroatomic ligand-metal compound complex as an input dataset of the new n input variables $I^{1.1}, I^{2.1}, \ldots I^{n.1}$, the new n input variables $I^{1.1}, I^{2.1}, \ldots I^{n.1}$ derived from one or more second training heteroatomic ligand-metal compound complexes for olefin oligomerization and comprising a second training heteroatomic ligand, which is input into the machine learning model to generate a second target heteroatomic ligand-metal compound complex comprising a second target heteroatomic ligand, wherein the second target heteroatomic ligand-metal compound complex is characterized by quantitative values of an output dataset of new n output variables $O^{1.1}, O^{2.1}, \ldots O^{n.1}$, and having one or more second target heteroatomic ligand-metal compound complex performance parameter values.

25. The method of claim 24, further comprising the step of:

(i) [1] synthesizing the first target heteroatomic ligand and/or the second target heteroatomic ligand; or [2] synthesizing the first target heteroatomic ligand and/or the second target heteroatomic ligand, followed by synthesizing the first target heteroatomic ligand-metal compound complex or the second target heteroatomic ligand-metal compound complex.

26. The method of claim 25, further comprising the step of:

(j) performing the olefin oligomerization reaction by: [1] contacting the first target heteroatomic ligand or the second target heteroatomic ligand, a metal compound, an organometal compound, and an olefin; or [2] contacting the first target heteroatomic ligand-metal compound complex or the second target heteroatomic ligand-metal compound complex, an organometal compound, and an olefin.

27. The method of claim 24, wherein the one or more of the n input variables $I^1, I^2, \ldots I^n$ identified in step (e) are identified based upon the greater percentage changes in [1] the difference in energies between any of the one or more ground state model structures $GS^{A1}, \ldots GS^{Ap}$ and at least one of the plurality of transition state model structures $TS^{A1}, TS^{A2}, \ldots TS^{Am}$ [$\Delta G(TS\text{-}GS)$ or $\Delta\Delta G(TS\text{-}GS)$] or [2] the difference in energies between any two or more of the plurality of transition state model structures $TS^{A1}, TS^{A2}, \ldots TS^{Am}$ [$\Delta G(TS\text{-}TS)$ or $\Delta\Delta G(TS\text{-}TS)$], for each percentage change in the one or more of the n input variables $I^1, I^2, \ldots I^n$ which influence $\Delta G(TS\text{-}GS)$, $\Delta\Delta G(TS\text{-}GS)$, or $\Delta\Delta G(TS\text{-}TS)$.

28. The method of claim 24, wherein the one or more first training heteroatomic ligand-metal compound complexes have a formula independently selected from:

[(HetLig)CrX$_q$L$_r$]$^{3-q}$(A); wherein:

HetLig represents the one or more first training heteroatomic ligands;

X is an anionic ligand, and q is an integer;

L is a neutral ligand, and r is an integer, wherein any two or more of the X and L ligands may be linked to form a multidentate ligand; and wherein each selected n input variable $I^1, I^2, \ldots I^n$, corresponds to a structural property or an electronic property of any of the one or more ground state model structures $GS^{A1}, \ldots GS^{Ap}$ or any of the plurality of transition state model structures $TS^{A1}, TS^{A2}, \ldots TS^{Am}$ associated with the one or more ground state model structures of formula (A).

29. The method of claim 24, wherein the one or more ground state model structures $GS^{A1}, \ldots GS^{Ap}$ derived from the one or more first training heteroatomic ligand-metal compound complexes $(GS^I)$, and the one or more ground state model structures $GS^{B1}, \ldots GS^{Bx}$ derived from the one or more first target heteroatomic ligand-metal compound complexes $(GS^T)$ are selected independently from:

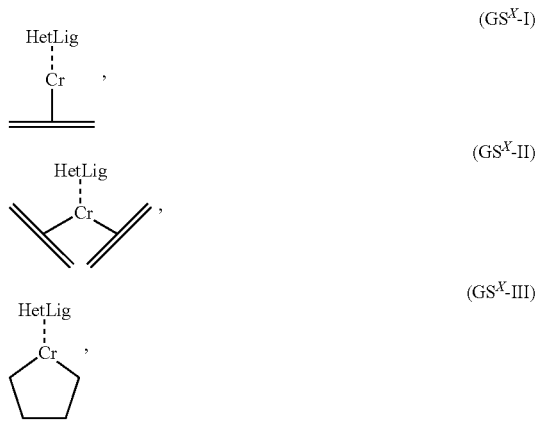

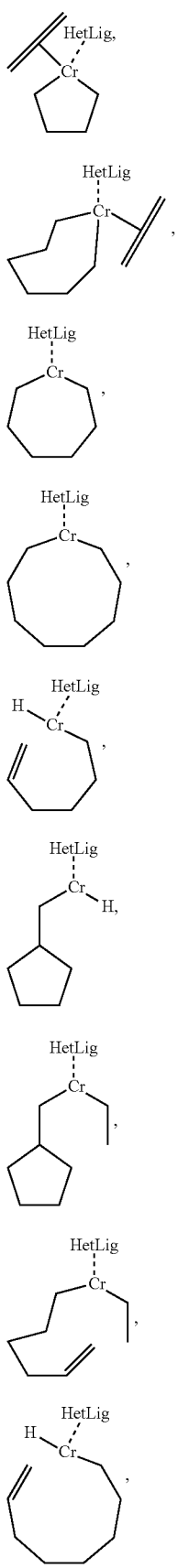

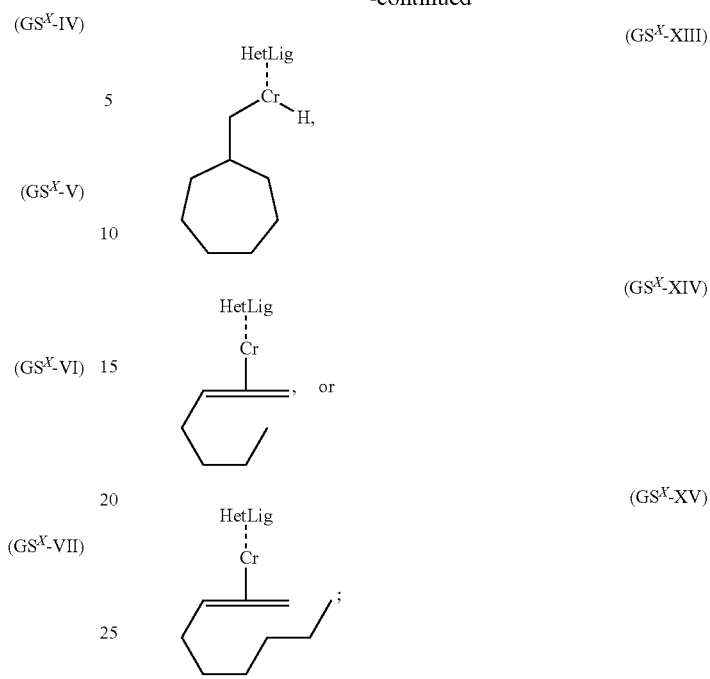

wherein:

HetLig represents the one or more first training heteroatomic ligands or the one or more first target heteroatomic ligands, and $GS^X$ is the first training heteroatomic ligand-metal compound complex ($GS^I$) or the first target heteroatomic ligand-metal compound complexes ($GS^T$).

30. The method of claim 29, wherein the plurality of transition state model structures $TS^{A1}, TS^{A2}, \ldots TS^{Am}$ derived from the one or more first training heteroatomic ligand-metal compound complexes ($TS^I$) and the plurality of transition state model structures $TS^{B1}, TS^{B2}, \ldots TS^{By}$ derived from the one or more first target heteroatomic ligand-metal compound complexes ($TS^T$) are selected independently from:

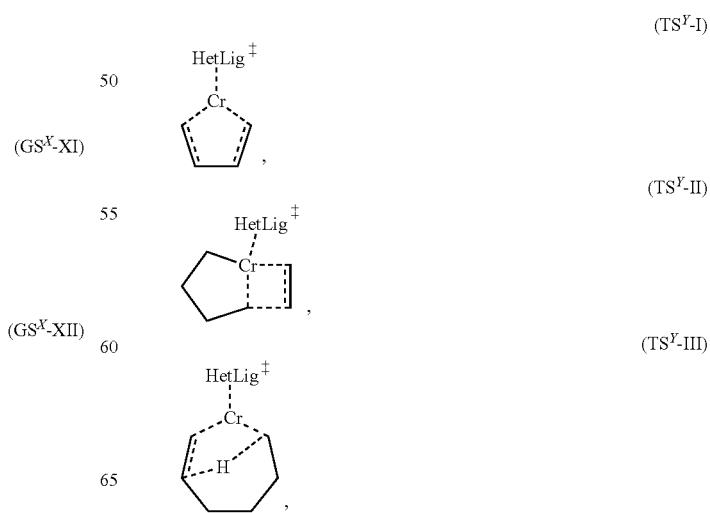

-continued (TS$^Y$-IV) 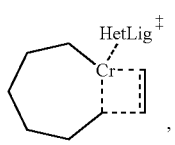

(TS$^Y$-V) 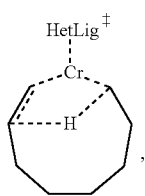

(TS$^Y$-VI) 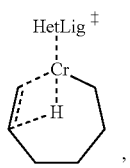

(TS$^Y$-VII) 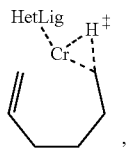

(TS$^Y$-VIII) 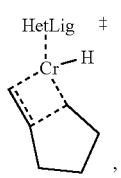

(TS$^Y$-IX) 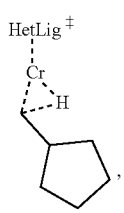

(TS$^Y$-X) 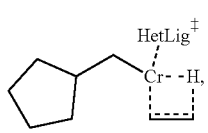

(TS$^Y$-XI) 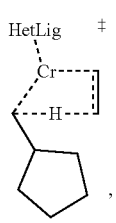

-continued (TS$^Y$-XII) 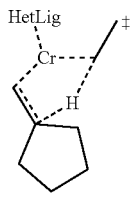

(TS$^Y$-XIII) 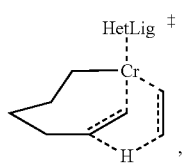

(TS$^Y$-XIV) 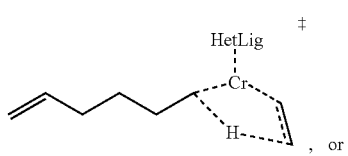, or (TS$^Y$-XV) 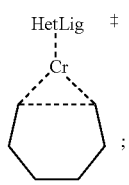;

wherein:

HetLig represents the one or more first training heteroatomic ligands or the one or more first target heteroatomic ligands, and TS$^Y$ is the first training heteroatomic ligand-metal compound complex (TS$^I$) or the first target heteroatomic ligand-metal compound complexes (TS$^T$).

31. The method of claim 24, wherein the one or more ground state model structures and any of the plurality of transition state model structures comprise a chromium heteroatomic ligand moiety independently selected from:

NPFCrM-1
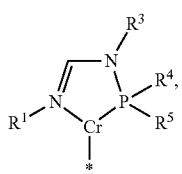

NPACrM-1
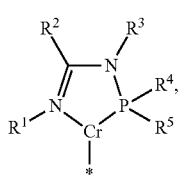

-continued

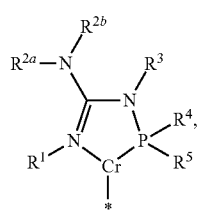

GuCrM-1

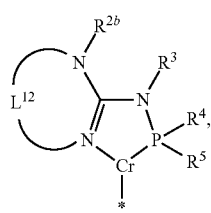

GuCrM-2

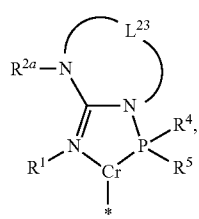

GuCrM-3

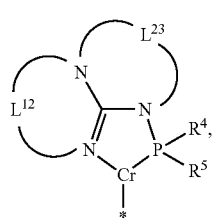

GuCrM-4

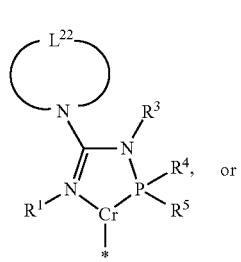

GuCrM-5 or

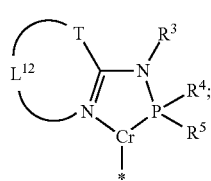

HCPACrM-1 wherein:
$R^1$ is a hydrogen or a $C_1$ to $C_{20}$ organyl group;
$R^2$ is a $C_1$ to $C_{20}$ organyl group;
T is oxygen or sulfur;
$R^{2a}$ and $R^{2b}$ independently are $C_1$ to $C_{20}$ organyl groups;
$L^{12}$ and $L^{23}$ independently are $C_2$ to $C_{20}$ organylene groups;
$L^{22}$ is a $C_3$ to $C_{20}$ organylene groups;
$R^3$ is hydrogen or a $C_1$ to $C_{20}$ organyl group; and
$R^4$ and $R^5$ independently are hydrogen or a $C_1$ to $C_{20}$ organyl groups;
where $R^1$ and $R^2$ are optionally joined to form $L^{12r}$, and $L^{12r}$ is a $C_3$ to $C_{30}$ organylene group;

where $R^4$ and $R^5$ are optionally joined to form $L^{45}$, and $L^{45}$ is a $C_4$ to $C_{30}$ organylene group; and
where "*" represents any additional bonding required in [1] any of the one or more ground state model structures or any of the plurality of transition state model structures derived from the one or more first training heteroatomic ligand-metal compound complexes, or [2] any of the one or more ground state model structures or any of the plurality of transition state model structures derived from the one or more first target heteroatomic ligand-metal compound complexes.

32. The method of claim 31, wherein:
$R^1$ is hydrogen, a $C_1$ to $C_{20}$ hydrocarbyl group, or a $C_1$ to $C_{20}$ heterohydrocarbyl group;
$R^2$ is a $C_1$ to $C_{20}$ hydrocarbyl group or a $C_1$ to $C_{20}$ heterohydrocarbyl group;
$R^{2a}$ and $R^{2b}$ are independently selected from a $C_1$ to $C_{20}$ hydrocarbyl group or a $C_1$ to $C_{20}$ heterohydrocarbyl group;
$L^{12}$ and $L^{23}$ are independently selected from a $C_2$ to $C_{20}$ hydrocarbylene group or a $C_2$ to $C_{20}$ heterohydrocarbylene group;
$L^{22}$ is a $C_3$ to $C_{20}$ hydrocarbylene group or a $C_3$ to $C_{20}$ heterohydrocarbylene group;
$R^3$ is hydrogen, a $C_1$ to $C_{20}$ hydrocarbyl group, or a $C_1$ to $C_{20}$ heterohydrocarbyl group; and
$R^4$ and $R^5$ are independently selected from a $C_1$ to $C_{20}$ hydrocarbyl group or a $C_1$ to $C_{20}$ heterohydrocarbyl group;
where $R^1$ and $R^2$ are optionally joined to form $L^{12r}$, and $L^{12r}$ is a $C_3$ to $C_{20}$ hydrocarbylene group or a $C_3$ to $C_{20}$ heterohydrocarbylene group; and
where $R^4$ and $R^5$ are optionally joined to form $L^{45}$, and $L^{45}$ is a $C_4$ to $C_{20}$ hydrocarbylene group or a $C_4$ to $C_{20}$ heterohydrocarbylene group.

33. The method of claim 31, wherein the n input variables $I1, I2, \ldots I^n$ comprise or are selected from any one of more of the following variables:
(a) the Cr—P distance (Å);
(b) the Cr—N distance (Å);
(c) the Cr - - - R on α-C distance (Å);
(d) the P—Cr—N angle (deg);
(e) the C—Cr—N angle (deg), wherein C is a non-heteroatomic ligand carbon atom bonded to or within bonding distance of the Cr atom;
(f) the Cr—N—C angle (deg);
(g) the distance out of pocket (Å);
(h) the Cr - - - α-C distance (Å);
(i) the Cr CHELPG (atomic charge);
(j) the P CHELPG (atomic charge);
(k) the N CHELPG (atomic charge);
(l) the Cr—N—C—N Dihedral angle (deg);
(m) the Cr—P—N—C Dihedral angle (deg);
(n) the P—Cr—N—C Dihedral angle (deg);
(o) the P—N—C—N Dihedral angle (deg);
(p) the C—C—N—C Dihedral angle (deg); or
(q) the percent volume buried.

34. The method of claim 24, wherein the one or more ground state model structures and any of the plurality of transition state model structures comprise a chromium heteroatomic ligand moiety independently selected from:

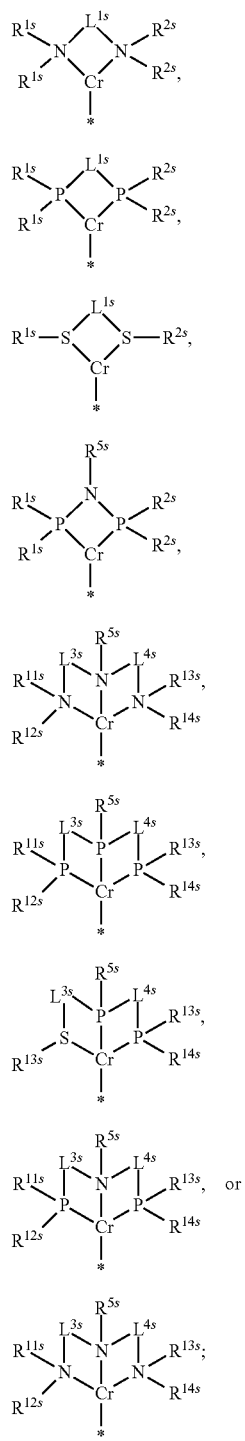

NRNCrM-1
PRPCrM-1
SRSCrM-1
PNPCrM-1
NRNRNCrM-1
PRPRPCrM-1
SRSNSCrM-1
PRNRPCrM-1
NRPRNCrM-1 wherein:
each $R^{1s}$, $R^{2s}$, $R^{5s}$, $R^{11s}$, $R^{12s}$, $R^{13s}$, and $R^{14s}$, independently, is selected from a hydrogen or a $C_1$ to $C_{20}$ organyl group;
each $L^{1s}$, $L^{3s}$, and $L^{4s}$, independently, is selected from a $C_2$ to $C_{20}$ organylene group; and
any two geminal $R^{1s}$ are optionally joined to form $L^{11s}$, and $L^{11s}$ is a $C_3$ to $C_{30}$ organylene group;
any two geminal $R^{2s}$ are optionally joined to form $L^{22s}$, and $L^{22s}$ is a $C_3$ to $C_{30}$ organylene group;
any germinal $R^{11s}$ and $R^{12s}$ are optionally joined to form $L^{12s}$, and $L^{12s}$ is a $C_3$ to $C_{30}$ organylene group;
any germinal $R^{13s}$ and $R^{14s}$ are optionally joined to form $L^{34s}$, and $L^{34s}$ is a $C_3$ to $C_{30}$ organylene group;
where "*" represents any additional bonding required in [1] any of the one or more ground state model structures or any of the plurality of transition state model structures derived from the one or more first training heteroatomic ligand-metal compound complexes, or [2] any of the one or more ground state model structures or any of the plurality of transition state model structures derived from the one or more first target heteroatomic ligand-metal compound complexes.

35. The method of claim 34, wherein:
each $R^{1s}$, $R^{2s}$, $R^{5s}$, $R^{11s}$, $R^{12s}$, $R^{13s}$, and $R^{14s}$, independently, is selected from hydrogen, a $C_1$ to $C_{20}$ hydrocarbyl group, or a $C_1$ to $C_{20}$ heterohydrocarbyl group;
each $L^{1s}$, $L^{3s}$, and $L^{4s}$, independently, is selected from a $C_2$ to $C_{20}$ hydrocarbylene group or a $C_2$ to $C_{20}$ heterohydrocarbylene group;
any two geminal $R^{1s}$ are optionally joined to form $L^{11s}$, and $L^{11s}$ is a $C_2$ to $C_{20}$ hydrocarbylene group or a $C_2$ to $C_{20}$ heterohydrocarbylene group;
any two geminal $R^{2s}$ are optionally joined to form $L^{22s}$, and $L^{22s}$ is a $C_2$ to $C_{20}$ hydrocarbylene group or a $C_2$ to $C_{20}$ heterohydrocarbylene group;
any germinal $R^{11s}$ and $R^{12s}$ are optionally joined to form $L^{12s}$, and $L^{12s}$ is a $C_2$ to $C_{20}$ hydrocarbylene group or a $C_2$ to $C_{20}$ heterohydrocarbylene group; and
any germinal $R^{13s}$ and $R^{14s}$ are optionally joined to form $L^{34s}$, and $L^{34s}$ $L^{22s}$, and $L^{22sF}$ is a $C_2$ to $C_{20}$ hydrocarbylene group or a $C_2$ to $C_{20}$ heterohydrocarbylene group.

36. The method of claim 34, wherein the n input variables $I^1, I^2, \ldots I^n$ comprise or are selected from any one of more of the following variables:
(a) the first, second, or third Cr—N distance (Å);
(b) the first, second, or third Cr—P distance (Å);
(c) the first or second Cr—S distance (Å);
(d) any one or more N—Cr—N angle (deg);
(e) any one or more P—Cr—P angle (deg);
(f) any one or more S—Cr—S angle (deg);
(g) any one or more S—Cr—N angle (deg);
(h) any one or more N—Cr—P angle (deg);
(i) the C—Cr—N angle (deg), wherein C is a non-heteroatomic ligand carbon atom bonded to or within bonding distance of the Cr atom;
(j) the C—Cr—P angle (deg);
(k) the C—Cr—S angle (deg);
(l) the Cr—N—C angle (deg);
(m) the Cr—P—C angle (deg);
(n) the Cr—S—C angle (deg);
(o) the Cr—P—C angle (deg);
(p) the Cr - - - R on α-C distance (Å);
(q) the distance out of pocket (Å);
(r) the Cr - - - α-C distance (Å);
(s) the Cr CHELPG (atomic charge);
(t) any P CHELPG (atomic charge);
(u) any N CHELPG (atomic charge);
(v) any chelate Cr—N—C—C Dihedral angle (deg);
(w) any chelate Cr—P—C—C Dihedral angle (deg);
(x) any chelate Cr—S—C—C Dihedral angle (deg); or
(y) the percent volume buried.

37. The method of claim 24, wherein the one or more performance parameters associated with the olefin oligomerization reaction are selected from: (a) 1-hexene purity; (b)

1-octene purity; (c) 1-hexene: 1-octene ratio ($C_6/C_8$ ratio); (d) 1-hexene productivity; (e) 1-octene productivity; (f) the total 1-hexene plus 1-octene productivity; (g) trimerization selectivity to 1-hexene; (h) tetramerization selectivity to 1-octene; (i) 1-octene efficiency of fourth ethylene addition; or any combination thereof.

38. The method of claim 30, wherein:
  (a) [1] the one or more ground state model structures $GS^{A1}, \ldots GS^{Ap}$ derived from one or more first training heteroatomic ligand-metal compound complexes comprise or are selected independently from $GS^I$-I, $GS^I$-II, $GS^I$-III, $GS^I$-IV, $GS^I$-V, $GS^I$-VI, $GS^I$-VII, or any combination thereof, and [2] the plurality of transition state model structures $TS^{A1}, TS^{A2}, \ldots TS^{Am}$ derived from one or more first training heteroatomic ligand-metal compound complexes comprise or are selected independently from $TS^I$-I, $TS^I$-II, $TS^I$-III, $TS^I$-IV, $TS^I$-V, or any combination thereof;
  (b) [1] the one or more ground state model structures $GS^{B1}, \ldots GS^{Bp}$ derived from the first target heteroatomic ligand-metal compound complex comprise or are selected independently from $GS^T$-I, $GS^T$-II, $GS^T$-III, $GS^T$-IV, $GS^T$-V, $GS^T$-VI, $GS^T$-VII, or any combination thereof, and [2] the plurality of transition state model structures $TS^{B1}, TS^{B2}, \ldots TS^{Bm}$ derived from the first target heteroatomic ligand-metal compound complex comprise or are selected independently from $TS^T$-I, $TS^T$-II, $TS^T$-III, $TS^T$-IV, $TS^T$-V, or any combination thereof, and
  (c) the performance parameter associated with the olefin oligomerization reaction is a heteroatomic ligand-metal compound complex 1-hexene productivity, 1-octene productivity, or a total 1-hexene and 1-octene productivity.

39. The method of claim 30, wherein:
  (a) [1] the one or more ground state model structures $GS^{A1}, \ldots GS^{Ap}$ derived from one or more first training heteroatomic ligand-metal compound complexes comprise $GS^I$-VI and [2] the plurality of transition state model structures $TS^{A1}, TS^{A2}, \ldots TS^{Am}$ derived from one or more first training heteroatomic ligand-metal compound complexes comprise $TS^I$-III and $TS^I$-IV,
  (b) [1] the one or more ground state model structures $GS^{B1}, \ldots GS^{Bp}$ derived from the first target heteroatomic ligand-metal compound complex comprise $GS^T$-VI, and [2] the plurality of transition state model structures $TS^{B1}, TS^{B2}, \ldots TS^{Bm}$ derived from the first target heteroatomic ligand-metal compound complex comprise $TS^T$-III and $TS^T$-IV; and
  (c) the performance parameter associated with the olefin oligomerization reaction is the $C_6/C_8$ ratio.

40. The method of claim 30, wherein:
  (a) [1] the one or more ground state model structures $GS^{A1}, \ldots GS^{Ap}$ derived from one or more first training heteroatomic ligand-metal compound complexes comprise or are selected independently from $GS^I$-VI, $GS^I$-VIII, $GS^I$-IX, $GS^I$-X, $GS^I$-XI, or any combination thereof, and [2] the plurality of transition state model structures $TS^{A1}, TS^{A2}, \ldots TS^{Am}$ derived from one or more first training heteroatomic ligand-metal compound complexes comprise or are selected independently from $TS^I$-III, $TS^I$-VI, $TS^I$-VII, $TS^I$-VIII, $TS^I$-IX, $TS^I$-X, $TS^I$-XI, $TS^I$-XII, $TS^I$-XIII, $TS^I$-XIV, $TS^I$-XV, or any combination thereof;
  (b) [1] the one or more ground state model structures $GS^{B1}, \ldots GS^{Bp}$ derived from the first target heteroatomic ligand-metal compound complex comprise or are selected independently from $GS^I$-VI, $GS^I$-VIII, $GS^I$-IX, $GS^I$-X, $GS^I$-XI, or any combination thereof, and [2] the plurality of transition state model structures $TS^{B1}, TS^{B2}, \ldots TS^{Bm}$ derived from the first target heteroatomic ligand-metal compound complex comprise or are selected from $TS^I$-III, $TS^I$-VI, $TS^I$-VII, $TS^I$-VIII, $TS^I$-IX, $TS^I$-X, $TS^I$-XI, $TS^I$-XII, $TS^I$-XIII, $TS^I$-XIV, $TS^I$-XV, or any combination thereof; and
  (c) the performance parameter associated with the olefin oligomerization reaction is 1-hexene purity.

41. The method of claim 30, wherein:
  (a) [1] the one or more ground state model structures $GS^{A1}, \ldots GS^{Ap}$ derived from one or more first training heteroatomic ligand-metal compound complexes comprise or are selected independently from $GS^I$-VII, $GS^I$-XII, $GS^I$-XIII, or any combination thereof, and [2] the one or more ground state model structures $GS^{B1}, \ldots GS^{Bp}$ derived from the first target heteroatomic ligand-metal compound complex comprise or are selected independently from GST-VII, GST-XII, GST-XIII, or any combination thereof; and
  (b) the performance parameter associated with the olefin oligomerization reaction is 1-octene purity.

42. The method of claim 30, wherein:
  (a) [1] the plurality of transition state model structures $TS^{A1}, TS^{A2}, \ldots TS^{Am}$ derived from one or more first training heteroatomic ligand-metal compound complexes comprise a transition state for the addition of the olefin to ground state model structure $GS^I$-VI to form ground state model structure $GS^I$-VII; and/or [2] the plurality of transition state model structures $TS^{B1}, TS^{B2} TS^{Bm}$ derived from one or more first target heteroatomic ligand-metal compound complexes comprise a transition state for the addition of the olefin to ground state model structure GST-VI to form ground state model structure GST-VII; or
  (b) [1] the plurality of transition state model structures $TS^{A1}, TS^{A2}, \ldots TS^{Am}$ derived from the first training heteroatomic ligand-metal compound complex comprise the transition state $TS^I$-IV; and/or [2] the plurality of transition state model structures $TS^{B1}, TS^{B2}, \ldots TS^{Bm}$ derived from the first target heteroatomic ligand-metal compound complex comprise the transition state $TS^T$-IV.

43. The method of claim 30, wherein:
  (a) [1] the plurality of transition state model structures $TS^{A1}, TS^{A2}, \ldots TS^{Am}$ derived from one or more first training heteroatomic ligand-metal compound complexes comprise a transition state for β-H extraction from ground state model structure $GS^I$-VI leading to 1-hexene production and/or a transition state for β-H extraction from ground state model structure $GS^I$-VII leading to 1-octene production; and/or [2] the plurality of transition state model structures $TS^{B1} TS^{B2}, \ldots TS^{Bm}$ derived from one or more first target heteroatomic ligand-metal compound complexes comprise a transition state for β-H extraction from ground state model structure GST-VI leading to 1-hexene production and/or a transition state for β-H extraction from ground state model structure GST-VII leading to 1-octene production; and
  (b) [1] the plurality of transition state model structures $TS^{A1}, TS^{A2}, \ldots TS^{Am}$ derived from the first training heteroatomic ligand-metal compound complex comprise $TS^I$-III or $TS^I$-V; and/or [2] the plurality of transition state model structures $TS^{B1}, TS^{B2}, \ldots TS^{Bm}$ derived from the first target heteroatomic ligand-metal compound complex comprise $TS^T$-III or $TS^T$-V.

44. The method of claim 24, wherein the quantitative value assigned to each n input variable $I^1, I^2, \ldots I^n$, for each of the one or more ground state model structures $GS^{41}, \ldots GS^{4p}$ and each of the plurality of transition state model structures $TS^{41}, TS^{42}, \ldots TS^{4m}$ derived from the one or more first training heteroatomic ligand-metal compound complexes are assigned on the basis of calculated, measured, or estimated values, or any combination thereof.

45. The method of claim 24, wherein the step of generating the second target heteroatomic ligand-metal compound complex comprises:
   (a) adjusting the quantitative value of one or more n input variables $I^1, I^2, \ldots I^n$ or $I^{1.1}, I^{2.1}, \ldots I^{n.1}$ to approach the value of the corresponding n output variables $O^1, O^2, \ldots O^n$ or $O^{1.1}, O^{2.1}, \ldots O^{n.1}$ in any first training heteroatomic ligand-metal compound complex comprising a chromium heteroatomic ligand moiety independently selected from NPFCrM-1, NPACrM-1, GuCrM-1, GuCrM-2, GuCrM-3, GuCrM-4, GuCrM-5, or HCPACrM-1, by:
      [1] independently increasing or decreasing the steric bulk of one or more of the groups $R^1$, $R^2$, $L^{12r}$, $R^{2a}$, $R^{2b}$, $L^{12}$, $L^{23}$, $L^{22}$, $R^3$, $R^4$, $R^5$, and $L^{45}$;
      [2] independently changing the inductive electronic effects of one or more of the groups $R^1$, $R^2$, $L^{12r}$, $R^{2a}$, $R^{2b}$, $L^{12}$, $L^{23}$, $L^{22}$, $R^3$, $R^4$, $R^5$, and $L^{45}$ with one or more +I substituent or one or more −I substituent;
      [3] independently increasing or decreasing the saturation in one or more of the organyl groups or organylene groups;
      [4] increasing or decreasing the polarity of a solvent used for olefin oligomerization; or
      [5] any combination thereof;
   and
   (b) generating, based upon the at least one adjusted n input variable from step (a) a second target heteroatomic ligand-metal compound complex for olefin oligomerization and comprising a second target heteroatomic ligand.

46. The method of claim 24, wherein the step of generating the second target heteroatomic ligand-metal compound complex comprises:
   (a) adjusting the quantitative value of one or more n input variables $I^1, I^2, \ldots I^n$ or $I^{1.1}, I^{2.1}, \ldots I^{n.1}$ to approach the value of the corresponding n output variables $O^1, O^2, \ldots O^n$ or $O^{1.1}, O^{2.1}, \ldots O^{n.1}$ in any first training heteroatomic ligand-metal compound complex comprising a chromium heteroatomic ligand moiety independently selected from NRNCrM-1, PRPCrM-1, SRSCrM-1, PNPCrM-1, NRNRNCrM-1, PRPRPCrM-1, SRNRSCrM-1, PRNRPCrM-1, or NRPRNCrM-1, by:
      [1] independently increasing or decreasing the steric bulk of one or more of the groups $R^{1s}$, $R^{2s}$, $R^{5s}$, $R^{11s}$, $R^{12s}$, $R^{13s}$, $R^{14s}$, $L^{1s}$, $L^{3s}$, $L^{4s}$, $L^{1sr}$, $L^{1sr}$, $L^{12sr}$, and $L^{34sr}$;
      [2] independently changing the inductive electronic effects of one or more of the groups $R^{1s}$, $R^{2s}$, $R^{5s}$, $R^{11s}$, $R^{12s}$, $R^{13s}$, $R^{14s}$, $L^{1s}$, $L^{3s}$, $L^{4s}$, $L^{1sr}$, $L^{1sr}$, $L^{12sr}$, and $L^{34sr}$ with one or more +I substituent or one or more −I substituent;
      [3] independently increasing or decreasing the saturation in one or more of the organyl groups or organylene groups;
      [4] increasing or decreasing the polarity of a solvent used for olefin oligomerization; or
      [5] any combination thereof; and
   (b) generating, based upon the at least one adjusted n input variable from step (a) a second target heteroatomic ligand-metal compound complex for olefin oligomerization and comprising a second target heteroatomic ligand.

* * * * *